(12) United States Patent
La et al.

(10) Patent No.: US 11,552,255 B2
(45) Date of Patent: Jan. 10, 2023

(54) HETEROCYCLIC COMPOUND AND ORGANIC LIGHT-EMITTING ELEMENT USING SAME

(71) Applicant: LT MATERIALS CO., LTD., Yongin (KR)

(72) Inventors: Hyun-Ju La, Hwaseong-si (KR); Yu-Jin Heo, Osan-si (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin (KR)

( * ) Notice: Subject to any disclaimer, the term of this patent is extended or adjusted under 35 U.S.C. 154(b) by 600 days.

(21) Appl. No.: 16/348,733

(22) PCT Filed: Nov. 30, 2017

(86) PCT No.: PCT/KR2017/013906
§ 371 (c)(1),
(2) Date: May 9, 2019

(87) PCT Pub. No.: WO2018/101764
PCT Pub. Date: Jun. 7, 2018

(65) Prior Publication Data
US 2019/0288218 A1 Sep. 19, 2019

(30) Foreign Application Priority Data

Nov. 30, 2016 (KR) .................. 10-2016-0162219
Oct. 19, 2017 (KR) .................. 10-2017-0135667

(51) Int. Cl.
*H01L 51/52* (2006.01)
*H01L 51/50* (2006.01)
*H01L 27/32* (2006.01)
*C09K 11/06* (2006.01)
*C07F 9/6561* (2006.01)
*C07D 519/00* (2006.01)
*C07D 471/04* (2006.01)
*C07D 403/14* (2006.01)
*H01L 51/00* (2006.01)

(52) U.S. Cl.
CPC ........ *H01L 51/0072* (2013.01); *C07D 471/04* (2013.01); *C07D 519/00* (2013.01); *C07F 9/6561* (2013.01); *C09K 11/06* (2013.01); *H01L 51/0052* (2013.01); *H01L 51/0058* (2013.01); *H01L 51/0067* (2013.01); *H01L 51/0071* (2013.01); *C09K 2211/1018* (2013.01); *H01L 51/5012* (2013.01); *H01L 51/5016* (2013.01); *H01L 51/5072* (2013.01); *H01L 51/5092* (2013.01); *H01L 51/5096* (2013.01); *H01L 51/5278* (2013.01)

(58) Field of Classification Search
CPC ............ H01L 51/0072; H01L 51/0052; H01L 51/0058; H01L 51/0067; H01L 51/0071; C07D 471/04; C07D 519/00; C07F 9/6561; C09K 2211/1018
See application file for complete search history.

(56) References Cited

U.S. PATENT DOCUMENTS

| | | |
|---|---|---|
| 4,356,429 A | 10/1982 | Tang |
| 8,344,365 B2 | 1/2013 | Kim et al. |
| 8,889,267 B2 | 11/2014 | Kim et al. |
| 8,999,530 B2 | 4/2015 | Shin et al. |
| 9,728,731 B2 | 8/2017 | La et al. |
| 10,193,078 B2 | 1/2019 | Ito et al. |
| 2006/0040132 A1* | 2/2006 | Liao .............. H01L 51/5036 428/690 |
| 2016/0005980 A1* | 1/2016 | Ito ..................... C09B 1/00 257/40 |
| 2016/0072082 A1 | 3/2016 | Brooks et al. |
| 2017/0133602 A1 | 5/2017 | Lee et al. |

FOREIGN PATENT DOCUMENTS

| | | | |
|---|---|---|---|
| JP | 2014-523877 A | 9/2014 | |
| KR | 10-1117724 B1 | 3/2012 | |
| KR | 10-1182438 B1 | 9/2012 | |
| KR | 10-2015-0077383 A | 7/2015 | |
| KR | 20150124000 A * | 11/2015 | |
| KR | 10-2016-0002408 A | 1/2016 | |
| KR | 10-2016-0005196 A | 1/2016 | |
| WO | WO-2016074755 A1 * | 5/2016 | ......... H01L 51/0074 |

OTHER PUBLICATIONS

WO-2016074755-A1—translation (Year: 2016).*
KR-20150124000-A—translation (Year: 2015).*
International Search Report (PCT/ISA/210) issued in PCT/KR2017/013906, dated Mar. 12, 2018.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4'-Tris(3-methylphenylphenylamino)triphenylamine (m-MTDATA), as Hole-Transport Materials", Advanced Materials, vol. 6, No. 9, 1994, pp. 677-679.

* cited by examiner

*Primary Examiner* — Jennifer A Boyd
*Assistant Examiner* — Rachel Simbana
(74) *Attorney, Agent, or Firm* — Birch, Stewart, Kolasch & Birch, LLP

(57) ABSTRACT

The present application relates to a hetero-cyclic compound represented by Chemical Formula 1, and an organic light emitting device comprising the same.

12 Claims, 3 Drawing Sheets

[FIG. 1]
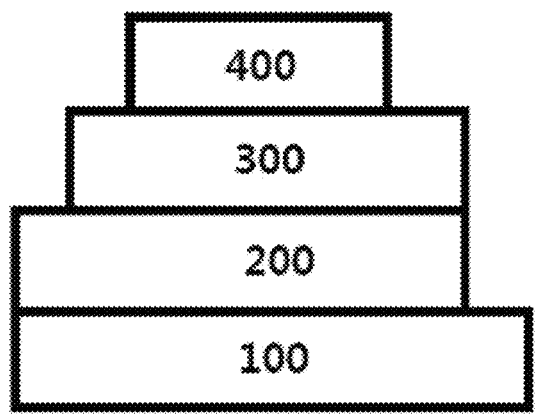
[FIG. 2]
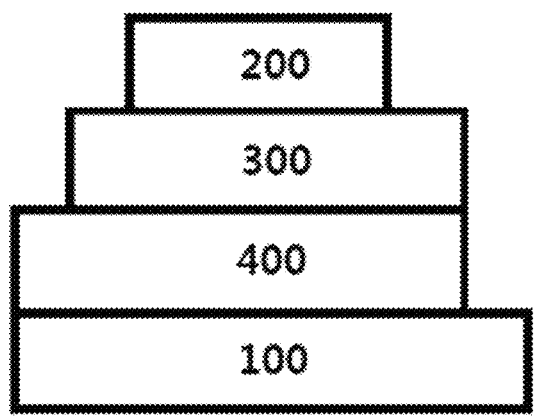

[FIG. 3]
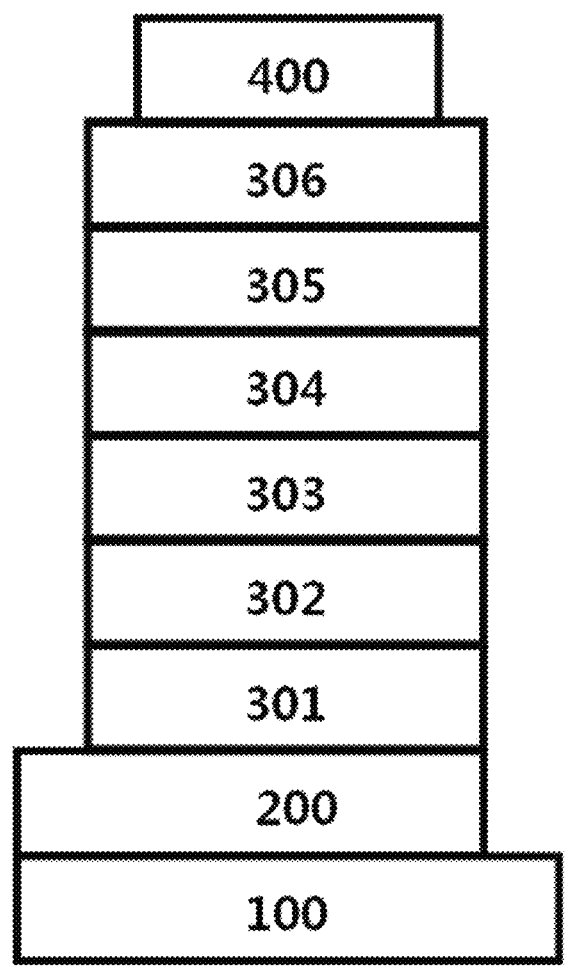

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT-EMITTING ELEMENT USING SAME

TECHNICAL FIELD

This application claims priority to and the benefits of Korean Patent Application No. 10-2016-0162219, filed with the Korean Intellectual Property Office on Nov. 30, 2016, and Korean Patent Application No. 10-2017-0135667, filed with the Korean Intellectual Property Office on Oct. 19, 2017, the entire contents of which are incorporated herein by reference.

The present application relates to a hetero-cyclic compound and an organic light emitting device using the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves may be used alone, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present application is directed to providing a novel hetero-cyclic compound and an organic light emitting device using the same.

Technical Solution

One embodiment of the present application provides a hetero-cyclic compound represented by the following Chemical Formula 1:

[Chemical Formula 1]

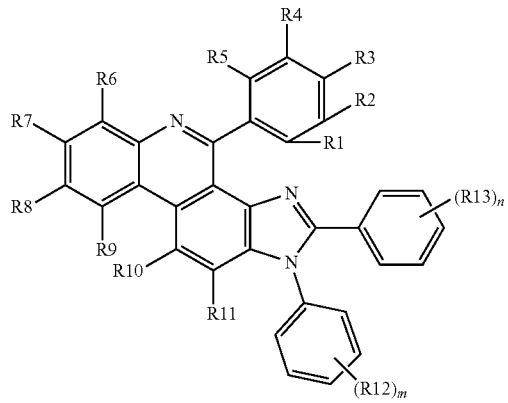

in Chemical Formula 1, at least one of R1 to R5 is represented by -(L1)p-(Z1)q, and the rest are hydrogen, a substituted or unsubstituted $C_6$ to $C_{60}$ aryl group, or a $C_2$ to $C_{60}$ heteroaryl group, L1 is a direct bond; a substituted or unsubstituted $C_6$ to $C_{60}$ arylene group; or a $C_2$ to $C_{60}$ heteroarylene group, Z1 is selected from the group consisting of a halogen group; —CN; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, p is an integer of 0 to 4, q is an integer of 1 to 4, R6 to R13 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, or two or more groups adjacent to each other bond to each other to form a substituted or unsubstituted aliphatic or aromatic hydrocarbon ring, m and n are each independently an integer of 0 to 5, and R, R' and R'' are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Another embodiment of the present application provides an organic light emitting device comprising an anode, a cathode, and one or more organic material layers provided between the anode and the cathode, wherein one or more layers of the organic material layers comprise the hetero-cyclic compound.

Advantageous Effects

A hetero-cyclic compound according to one embodiment of the present application can be used as an organic material layer material of an organic light emitting device. The hetero-cyclic compound can be used as a material of a hole injection layer, a hole transfer layer, a light emitting layer, an electron transfer layer, an electron injection layer, a charge generation layer or the like in an organic light emitting device. Particularly, the hetero-cyclic compound represented by Chemical Formula 1 can be used as a material of an electron transfer layer or a charge generation layer in an organic light emitting device. In addition, using the hetero-cyclic compound represented by Chemical Formula 1 in an organic light emitting device lowers a driving voltage of the device, enhances light efficiency, and can enhance a lifetime property of the device with thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

BEST MODE

Hereinafter, the present application will be described in detail.

A hetero-cyclic compound according to one embodiment of the present application is represented by Chemical Formula 1. More specifically, the hetero-cyclic compound represented by Chemical Formula 1 is capable of being used as a material of an organic material layer of an organic light emitting device with such a core structure and structural characteristics of substituents.

In one embodiment of the present application, when p of Chemical Formula 1 is 2 or greater, two or more L1s may be the same as or different from each other. In addition, when q of Chemical Formula 1 is 2 or greater, two or more Z1s may be the same as or different from each other.

In one embodiment of the present application, at least one of R1 to R5 of Chemical Formula 1 is represented by -(L1)p-(Z1)q, and the rest may be hydrogen.

In one embodiment of the present application, R3 of R1 to R5 of Chemical Formula 1 is represented by -(L1)p-(Z1)q, and the rest may be hydrogen.

In one embodiment of the present application, R4 of R1 to R5 of Chemical Formula 1 is represented by -(L1)p-(Z1)q, and the rest may be hydrogen.

Particularly, when the compound in which the position of R3 or R4 of R1 to R5 of Chemical Formula 1 is substituted with a substituent of -(L1)p-(Z1)q is used as a material of an electron transfer layer of an organic light emitting device later on, intermolecular interactions are smooth facilitating intermolecular electron migration.

The compound in which the position of R1 or R5 of Chemical Formula 1 is substituted with a substituent of -(L1)p-(Z1)q has a larger molecular size compared to the compound in which the position of R3 or R4 of R1 to R5 of Chemical Formula is substituted with a substituent of -(L1)p-(Z1)q, and therefore, the degree of electron migration is reduced due to decreased molecular interactions.

In one embodiment of the present application, L1 of Chemical Formula 1 may be a direct bond; a substituted or unsubstituted $C_6$ to $C_{60}$ arylene group; or a $C_2$ to $C_{60}$ heteroarylene group.

In another embodiment, L1 of Chemical Formula 1 may be a direct bond; a substituted or unsubstituted $C_6$ to $C_{40}$ arylene group; or a $C_2$ to $C_{40}$ heteroarylene group.

In another embodiment, L1 of Chemical Formula 1 may be a direct bond; a $C_6$ to $C_{40}$ arylene group; or a $C_2$ to $C_{40}$ heteroarylene group.

In another embodiment, L1 of Chemical Formula 1 may be a direct bond; a phenylene group; a biphenylene group; an anthracenylene group; a naphthylene group; a divalent imidazo[1,2-a]pyridine group; a divalent pyridine group; a divalent pyrimidine group; a divalent triazine group; a divalent quinazoline group; or a divalent benzimidazole group.

In one embodiment of the present application, Z1 of Chemical Formula 1 may be selected from the group consisting of a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —P(=O)RR'; —CN; and an amine group unsubstituted or substituted with a $C_6$ to $C_{60}$ aryl group or a $C_2$ to $C_{60}$ heteroaryl group.

In another embodiment, Z1 of Chemical Formula 1 may be selected from the group consisting of a substituted or unsubstituted $C_1$ to $C_{40}$ alkyl group; a substituted or unsubstituted $C_6$ to $C_{40}$ aryl group; a substituted or unsubstituted $C_2$ to $C_{40}$ heteroaryl group; —P(=O)RR'; —CN; and an amine group unsubstituted or substituted with a $C_6$ to $C_{40}$ aryl group or a $C_2$ to $C_{40}$ heteroaryl group.

In another embodiment, Z1 of Chemical Formula 1 may be selected from the group consisting of a $C_1$ to $C_{40}$ alkyl group; a $C_6$ to $C_{40}$ aryl group unsubstituted or substituted with one or more substituents selected from the group consisting of P(=O)RR', a $C_6$ to $C_{40}$ aryl group and a $C_2$ to $C_{40}$ heteroaryl group; a $C_2$ to $C_{40}$ heteroaryl group unsubstituted or substituted with one or more substituents selected from the group consisting of a $C_1$ to $C_{40}$ alkyl group, a $C_6$ to $C_{40}$ aryl group and a $C_2$ to $C_{40}$ heteroaryl group; —P(=O)RR'; and —CN.

In another embodiment, Z1 of Chemical Formula 1 may be selected from the group consisting of a $C_1$ to $C_{40}$ alkyl group; a $C_6$ to $C_{40}$ aryl group unsubstituted or substituted with one or more and three or less substituents selected from the group consisting of P(=O)RR', a $C_6$ to $C_{40}$ aryl group and a $C_2$ to $C_{40}$ heteroaryl group; a $C_2$ to $C_{40}$ heteroaryl group unsubstituted or substituted with one or more and three or less substituents selected from the group consisting of a $C_1$ to $C_{40}$ alkyl group, a $C_6$ to $C_{40}$ aryl group and a $C_2$ to $C_{40}$ heteroaryl group; —P(=O)RR'; and —CN.

In another embodiment, Z1 of Chemical Formula 1 may be selected from the group consisting of a phenyl group unsubstituted or substituted with one or more substituents selected from the group consisting of P(=O)RR', a phenyl group and a carbazole group; a naphthyl group unsubstituted or substituted with P(=O)RR'; an anthracene group unsubstituted or substituted with one or more substituents selected from the group consisting of P(=O)RR' and a naphthyl group; a biphenyl group; a triphenylene group; and a phenanthrene group.

In another embodiment, Z1 of Chemical Formula 1 may be selected from the group consisting of an ethyl group; P(=O)RR'; and —CN.

In another embodiment, Z1 of Chemical Formula 1 may be a $C_2$ to $C_{40}$ heteroaryl group unsubstituted or substituted with one or more substituents selected from the group consisting of a $C_1$ to $C_{40}$ alkyl group, a $C_6$ to $C_{40}$ aryl group and a $C_2$ to $C_{40}$ heteroaryl group, and the heteroaryl group may comprise at least one or more of N, O and S as a heteroatom.

In another embodiment, Z1 of Chemical Formula 1 may be selected from the group consisting of a pyridine group unsubstituted or substituted with one or more substituents selected from the group consisting of a phenyl group, a naphthyl group and a pyridine group; a pyrimidine group unsubstituted or substituted with one or more substituents selected from the group consisting of a phenyl group, a biphenyl group, a naphthyl group and a pyridine group; a triazine group unsubstituted or substituted with one or more substituents selected from the group consisting of a phenyl group, a biphenyl group, a naphthyl group and a pyridine group; a quinazoline group unsubstituted or substituted with one or more substituents selected from the group consisting of a phenyl group, a biphenyl group and a naphthyl group; a quinoline group; a carbazole group; a phenanthroline group unsubstituted or substituted with a phenyl group; an imidazo[1,2-a]pyridine group unsubstituted or substituted with a phenyl group; a benzimidazole group unsubstituted or substituted with an ethyl group; a benzothiazole group unsubstituted or substituted with a phenyl group; a pyrido[1,2-b]indazolyl group; an oxadiazolyl group unsubstituted or substituted with a phenyl group; a pyrazolo[1,5-c]quinazolinyl group unsubstituted or substituted with a phenyl group; and a 1,5-naphthyridyl group.

In one embodiment of the present application, R1, R2, R4, R5, and R6 to R13 of Chemical Formula 1 may be each independently hydrogen or deuterium.

In one embodiment of the present application, R1, R2, R3, R5, and R6 to R13 of Chemical Formula 1 may be each independently hydrogen or deuterium.

In one embodiment of the present application, R, R' and R'' of Chemical Formula 1 are the same as or different from each other, and may be each independently hydrogen; a substituted or unsubstituted $C_1$ to $C_{60}$ alkyl group; or a substituted or unsubstituted $C_6$ to $C_{60}$ aryl group.

In another embodiment, R, R' and R'' of Chemical Formula 1 are the same as or different from each other, and may be each independently a substituted or unsubstituted $C_1$ to $C_{40}$ alkyl group; or a substituted or unsubstituted $C_6$ to $C_{40}$ aryl group.

In another embodiment, R, R' and R'' of Chemical Formula 1 are the same as or different from each other, and may be each independently a $C_6$ to $C_{40}$ aryl group.

In another embodiment, R, R' and R'' of Chemical Formula 1 are the same as or different from each other, and may be each independently a phenyl group.

In the present specification, the term "substituted or unsubstituted" means being substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R''; —P(=O)RR'; a $C_1$ to $C_{20}$ alkylamine group; a $C_6$ to $C_{60}$ arylamine group; and a $C_2$ to $C_{60}$ heteroarylamine group, or being unsubstituted, or being substituted with a substituent bonding two or more of the above-mentioned substituents, or being substituted, or being substituted with a substituent linking two or more substituents selected from among the above-mentioned substituents, or being unsubstituted. For example, "a substituent linking two or more substituents" may comprise a biphenyl group. In other words, a biphenyl group may be an aryl group, or may be interpreted as a substituent linking two phenyl groups. The additional substituents may be further substituted. R, R' and R'' are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to one embodiment of the present application, the "substituted or unsubstituted" means being substituted with one or more substituents selected from the group consisting of deuterium, a halogen group, —CN, SiRR'R'', P(=O)RR', a $C_1$ to $C_{20}$ linear or branched alkyl group, a $C_6$ to $C_{60}$ aryl group, and a $C_2$ to $C_{60}$ heteroaryl group, or being unsubstituted, and R, R' and R'' are the same as or different from each other, and each independently hydrogen; deuterium; —CN; a $C_1$ to $C_{60}$ alkyl group unsubstituted or substituted with deuterium, a halogen group, —CN, a $C_1$ to $C_{20}$ alkyl group, a $C_6$ to $C_{60}$ aryl group and a $C_2$ to $C_{60}$ heteroaryl group; a $C_3$ to $C_{60}$ cycloalkyl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; a $C_6$ to $C_{60}$ aryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; or a $C_2$ to $C_{60}$ heteroaryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the spiro group is a group comprising a spiro structure, and may have 15 to 60 carbon atoms. For example, the spiro group may comprise a structure in which a 2,3-dihydro-1H-indene group or a cyclohexane group spiro bonds to a fluorenyl group. Specifically, the following spiro group may comprise any one of the groups having the following structural formulae.

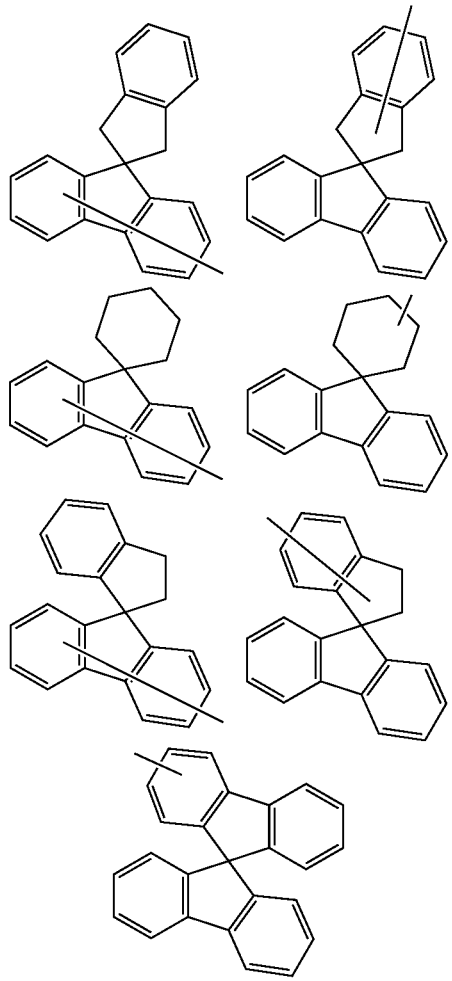

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, a thienyl group, an imidazo[1,2-a]pyridine group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

According to one embodiment of the present application, Chemical Formula 1 may be represented by any one of the following compounds, but is not limited thereto.

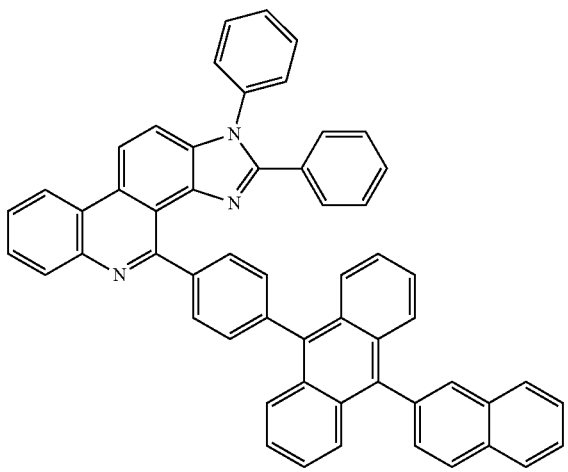

1

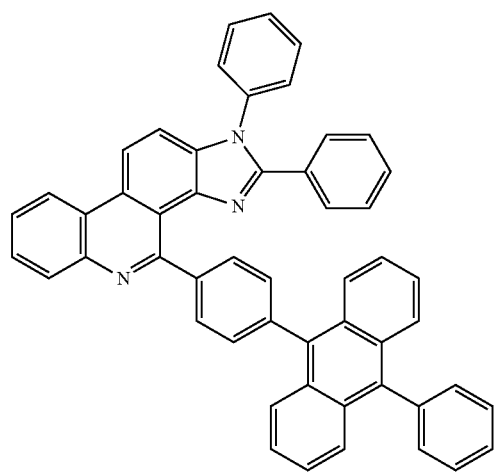

2

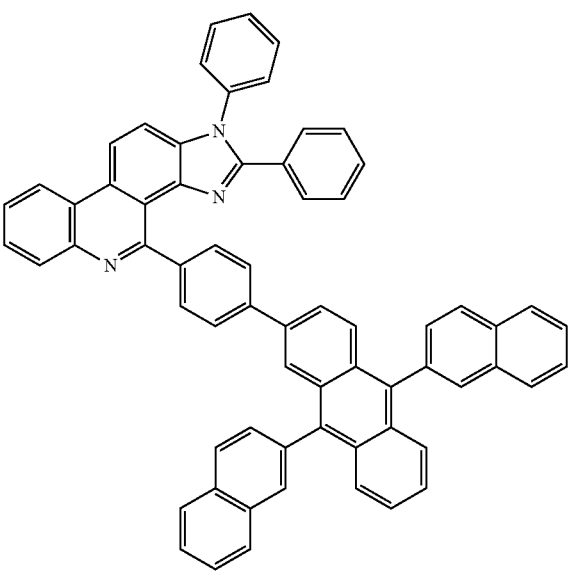

3

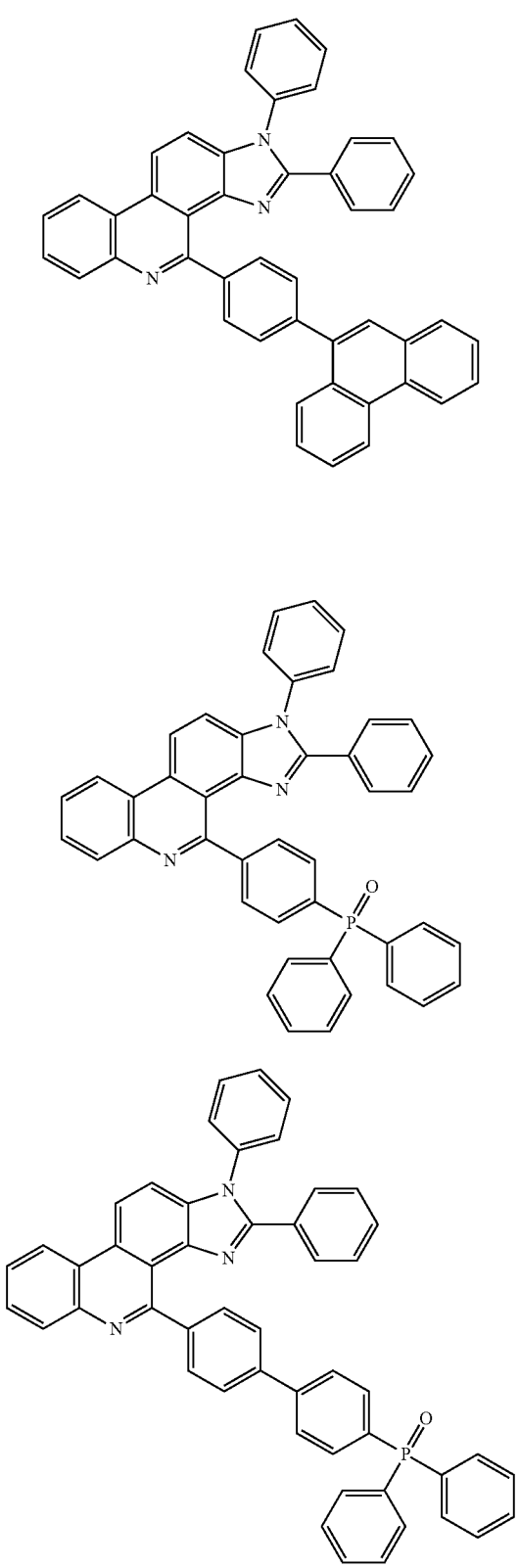
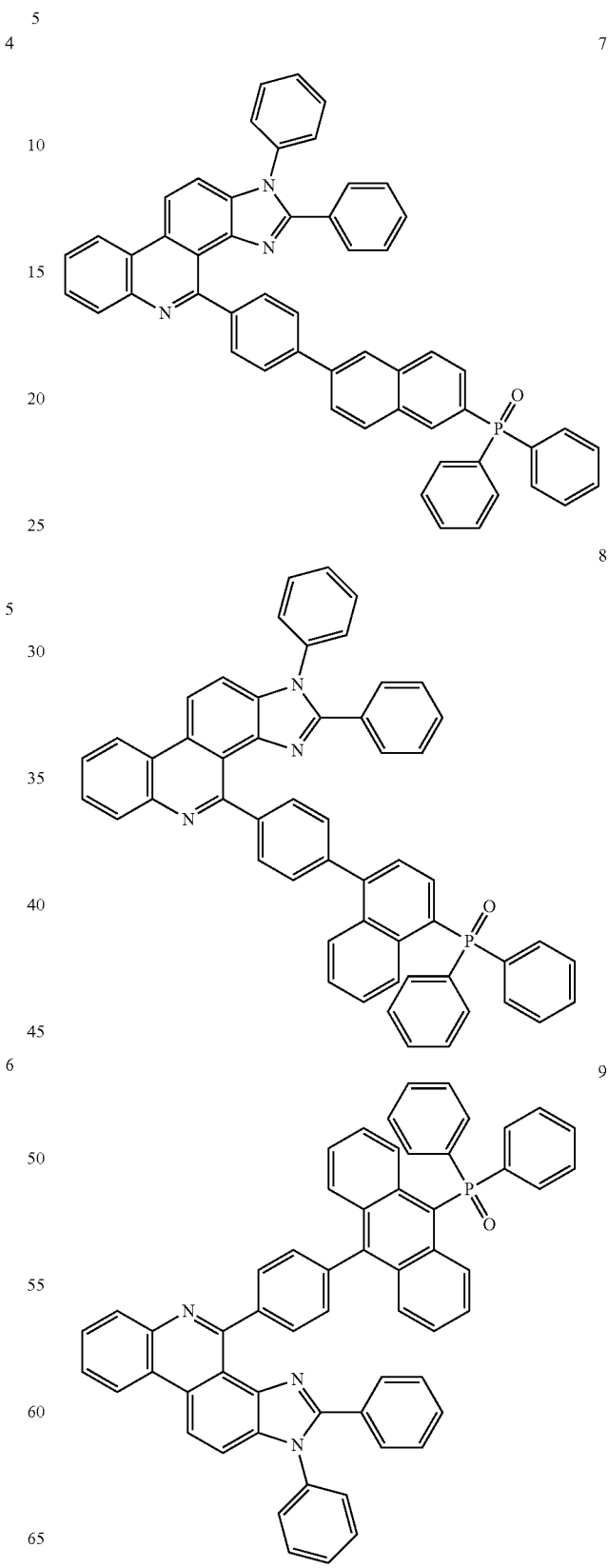

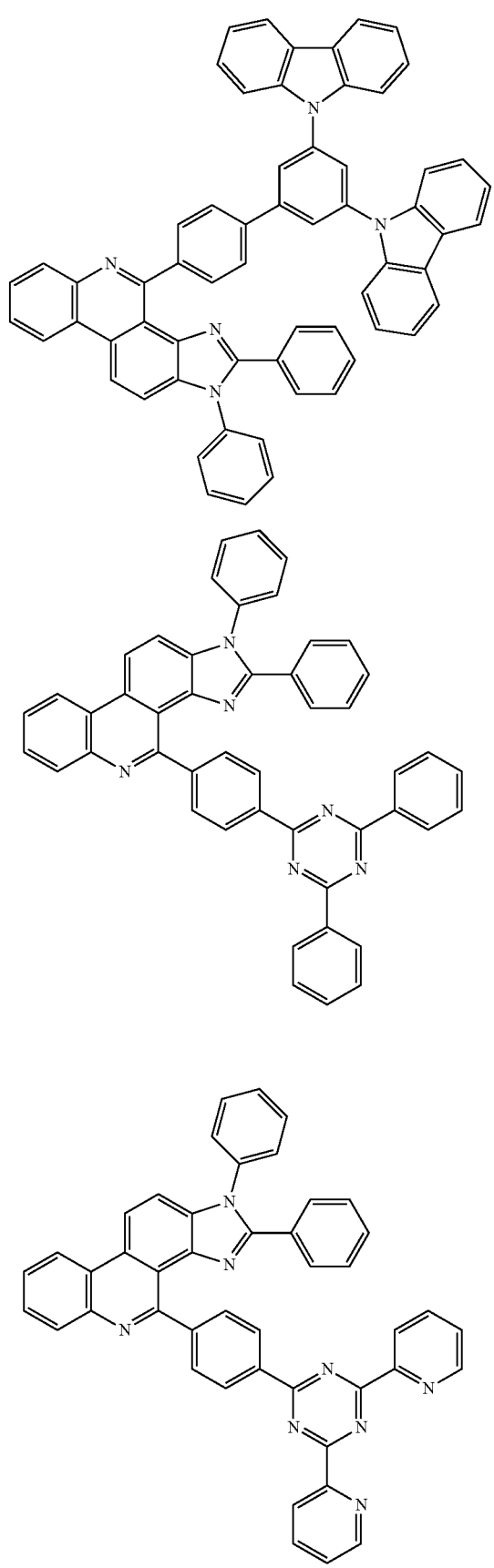
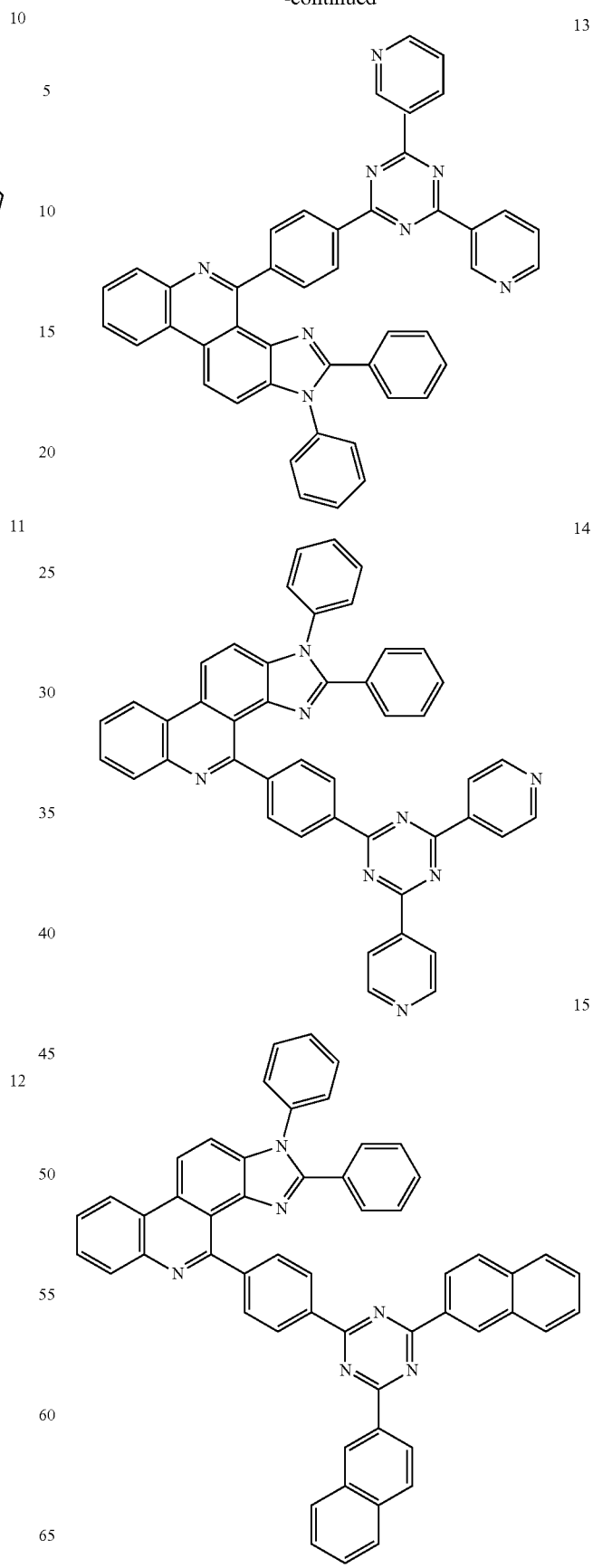

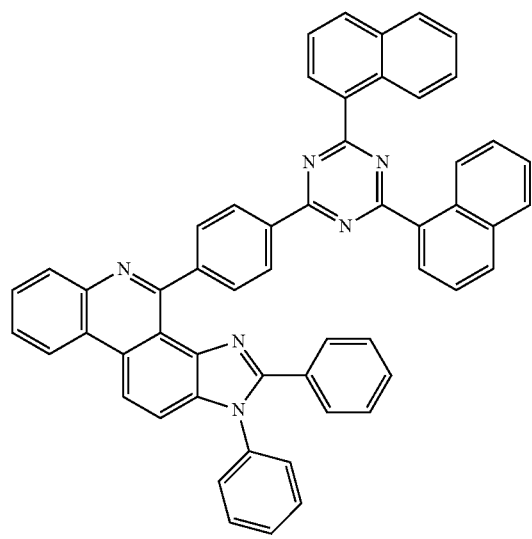
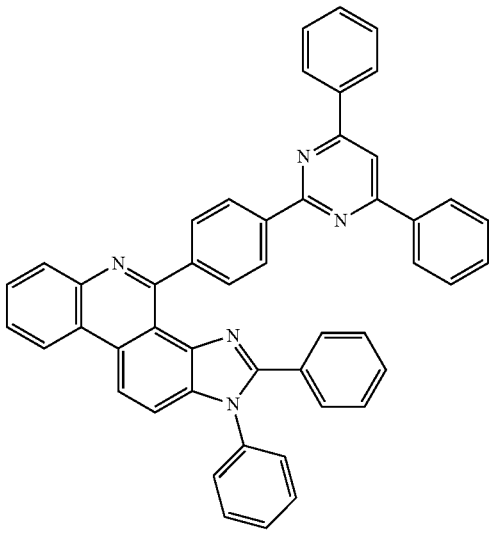
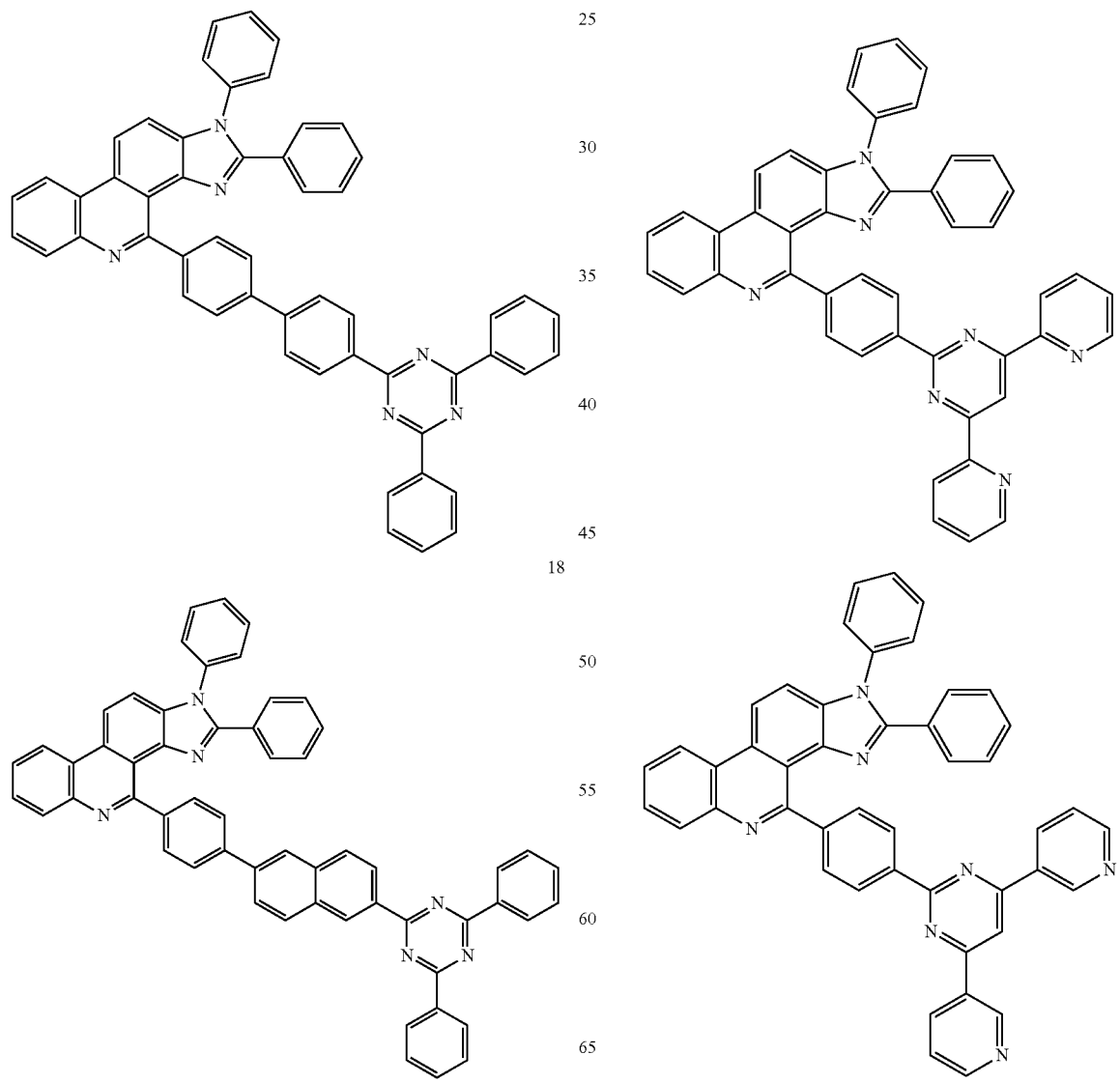

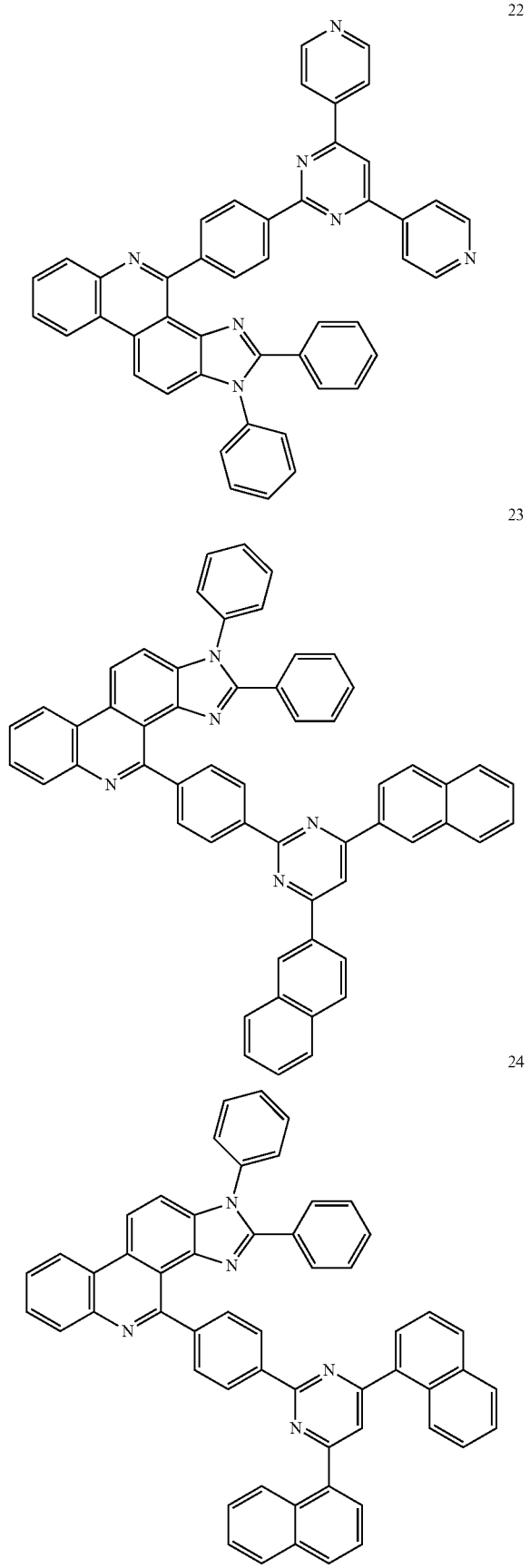
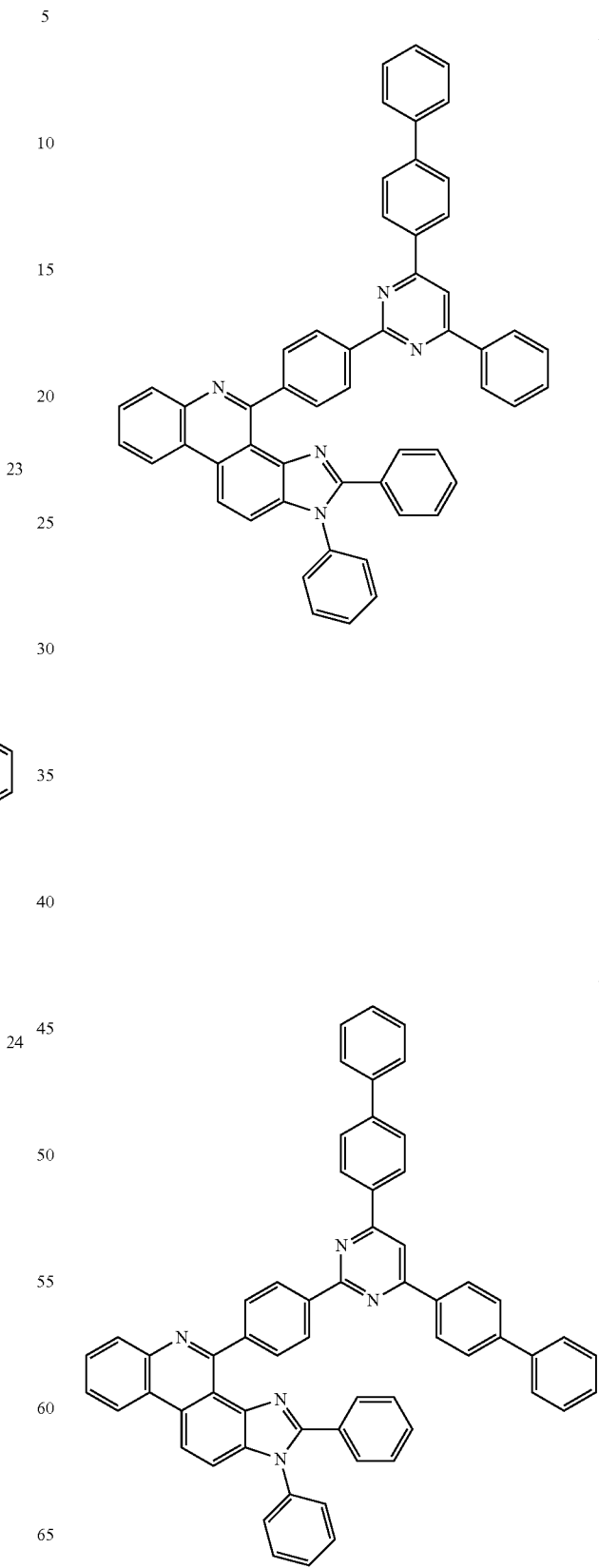

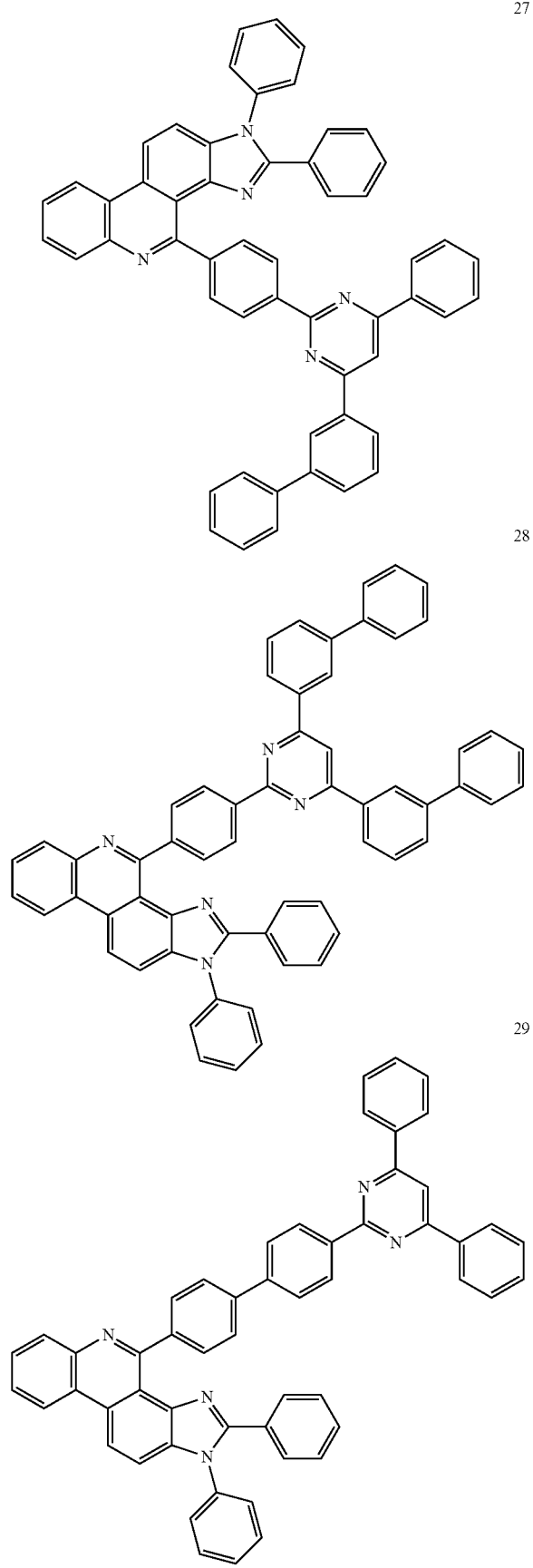
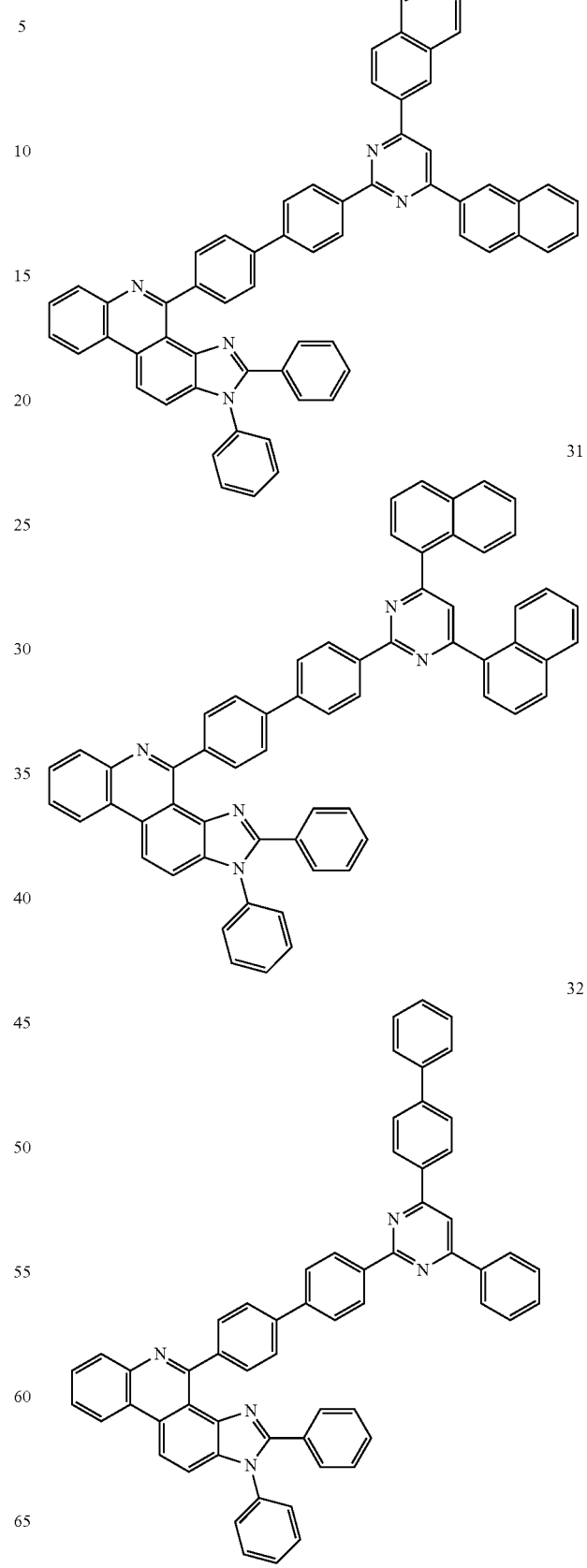

33
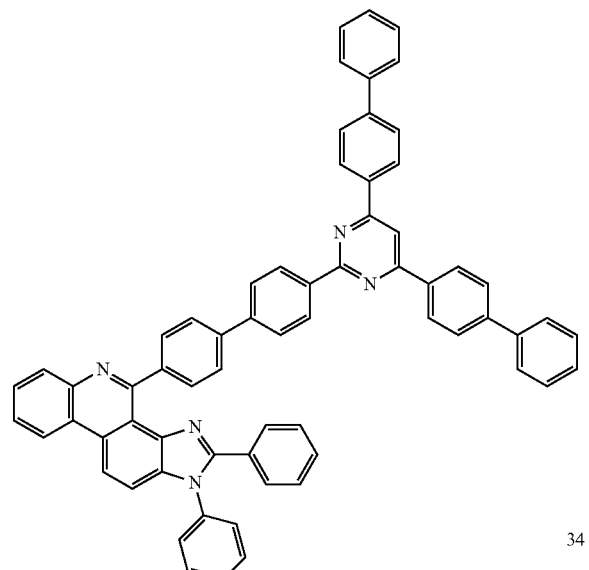
34
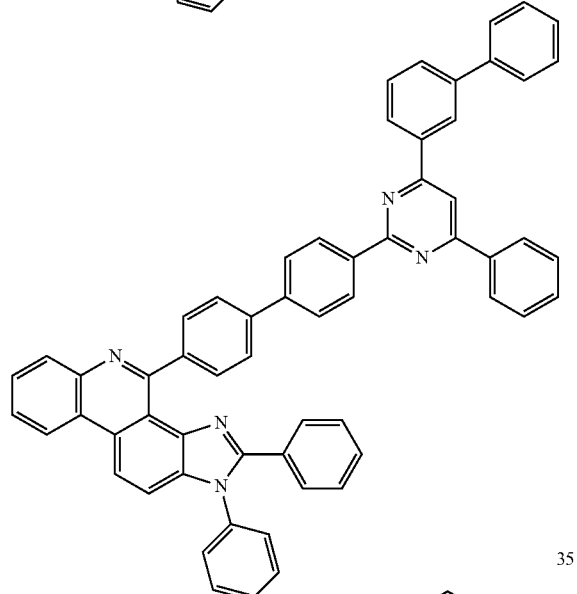
35
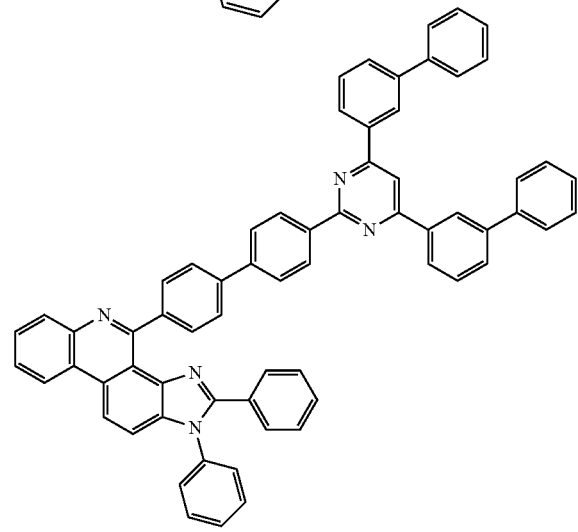
36
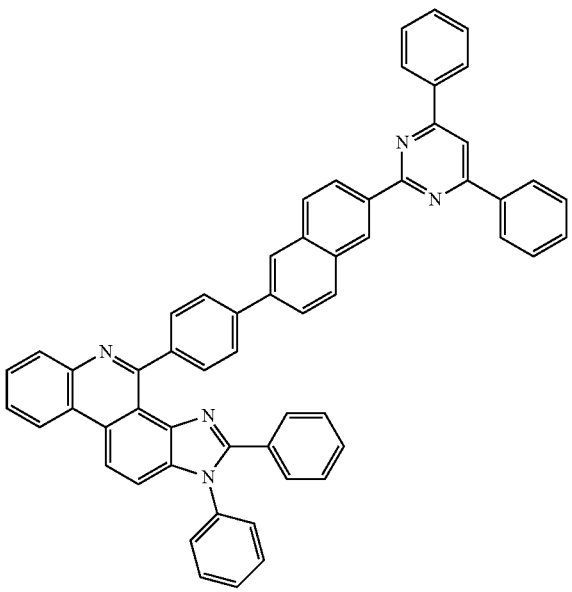
37
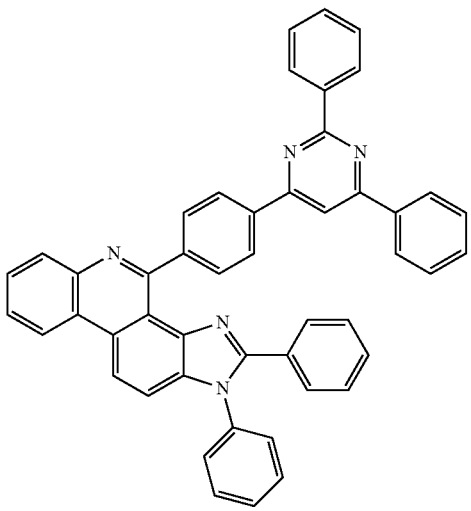
38
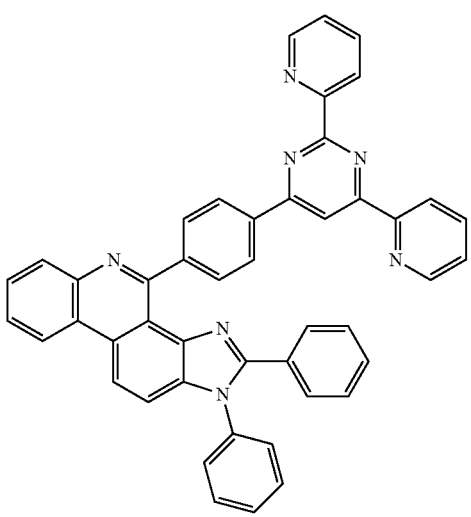

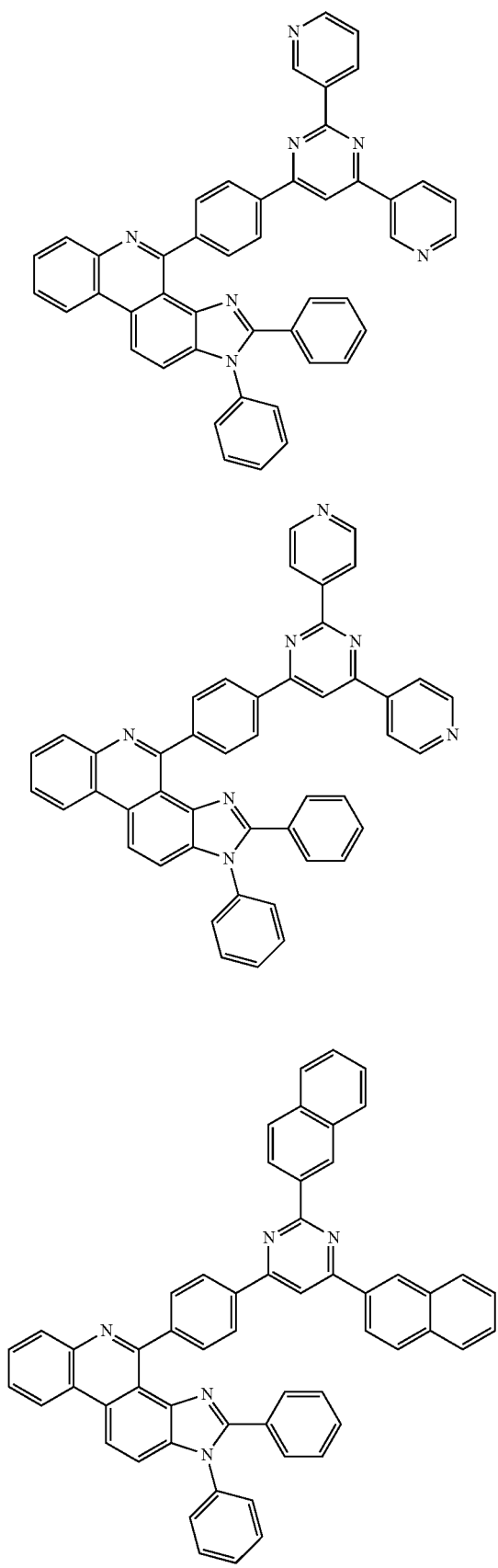
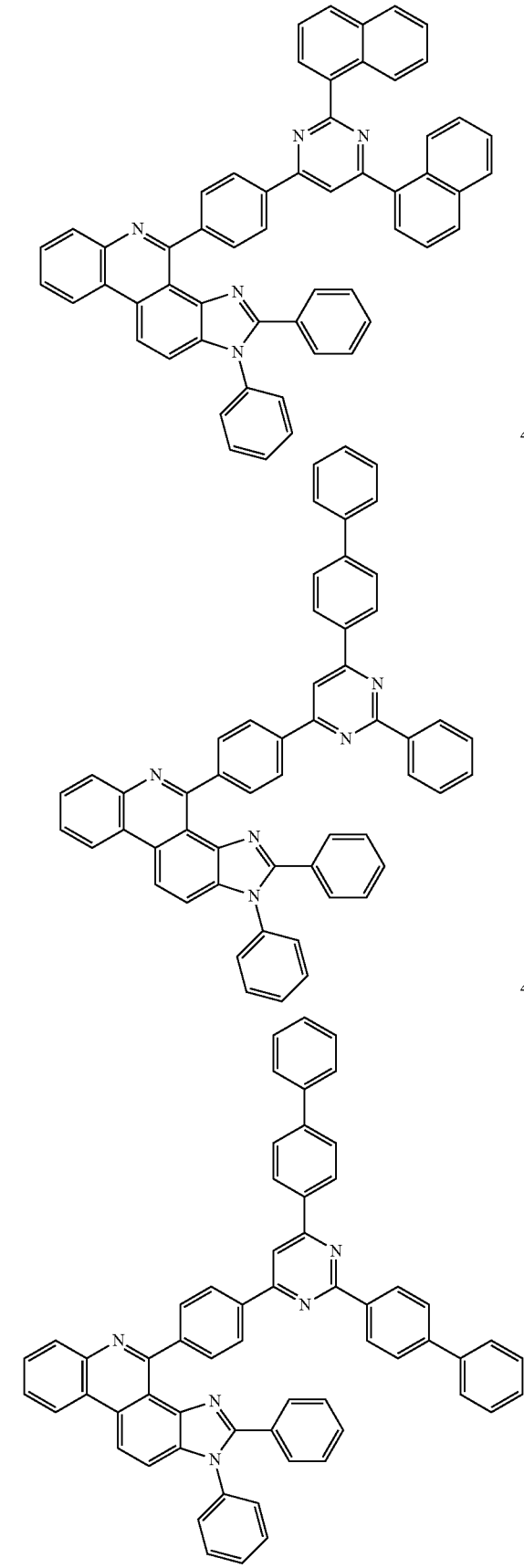

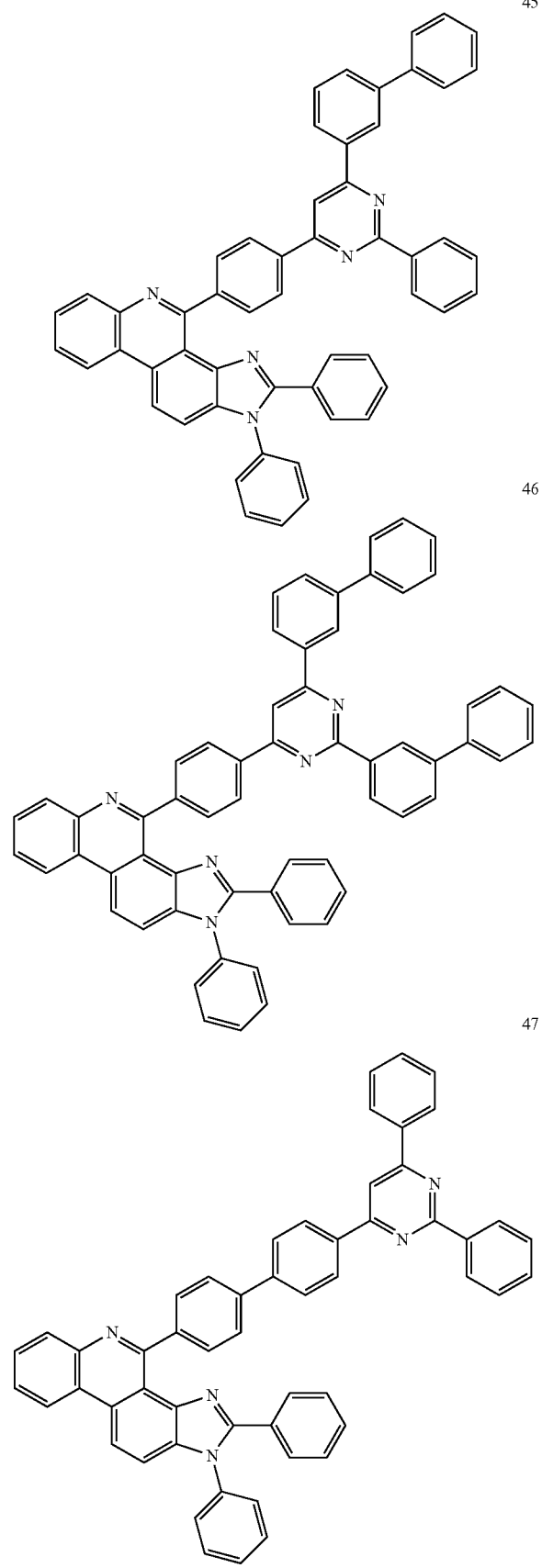
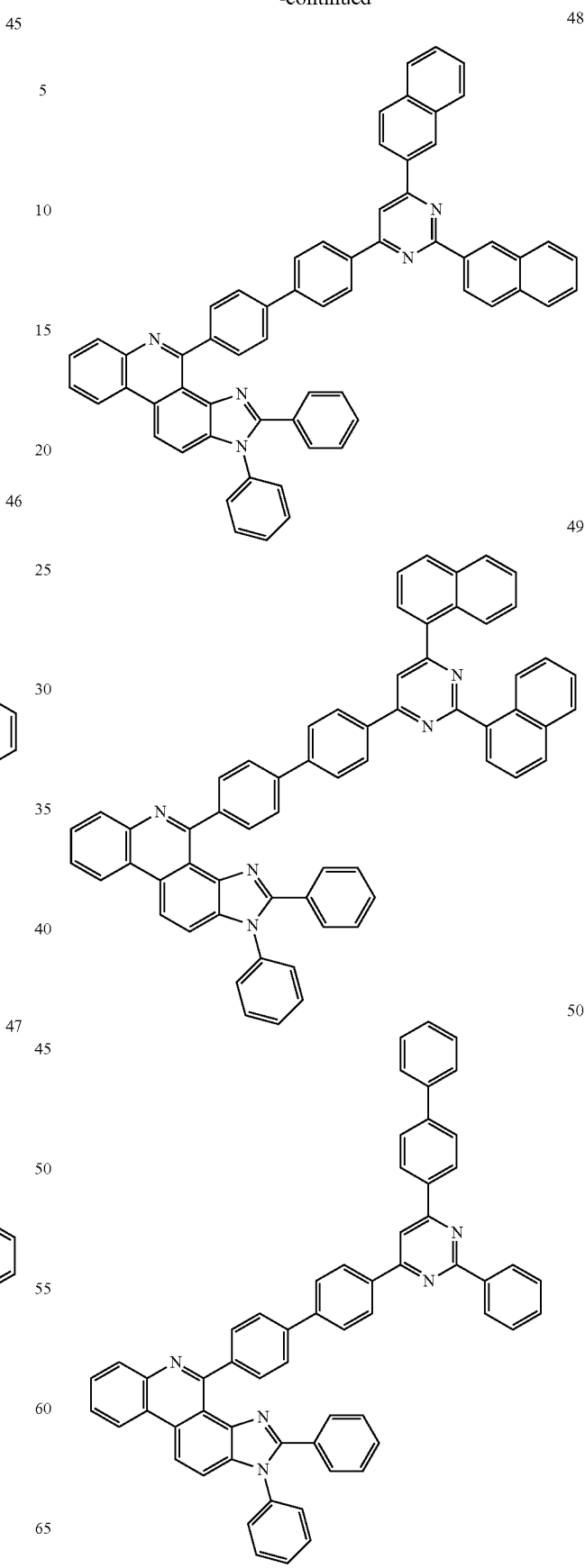

51
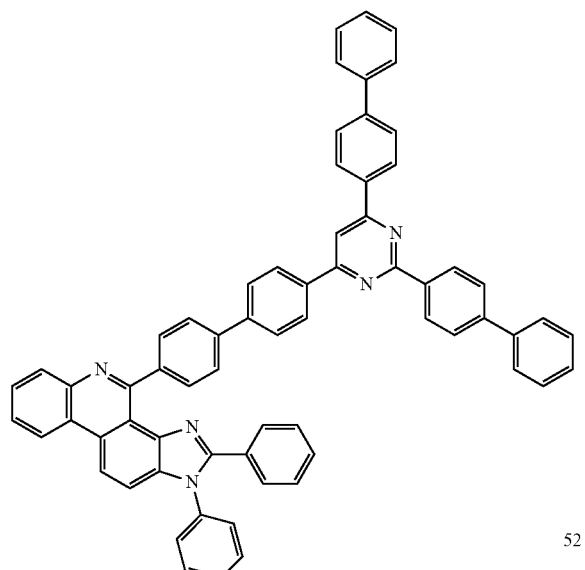
52
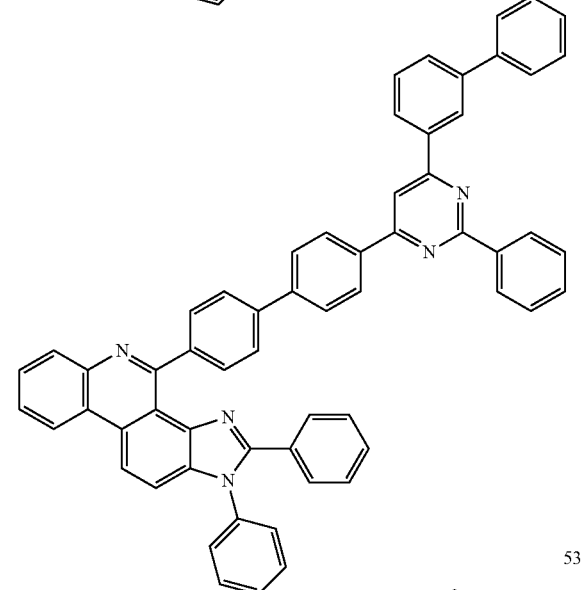
53
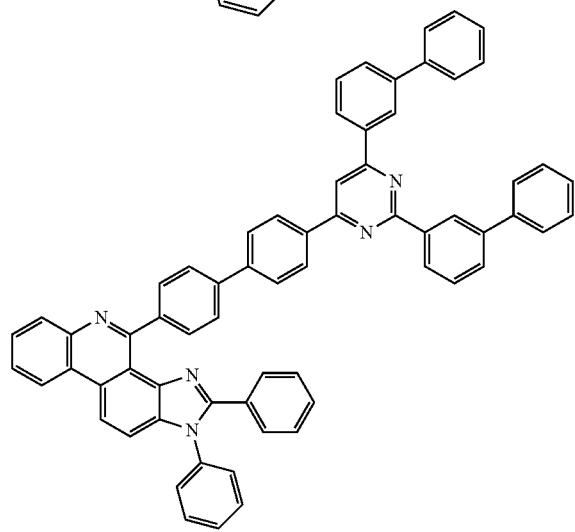
54
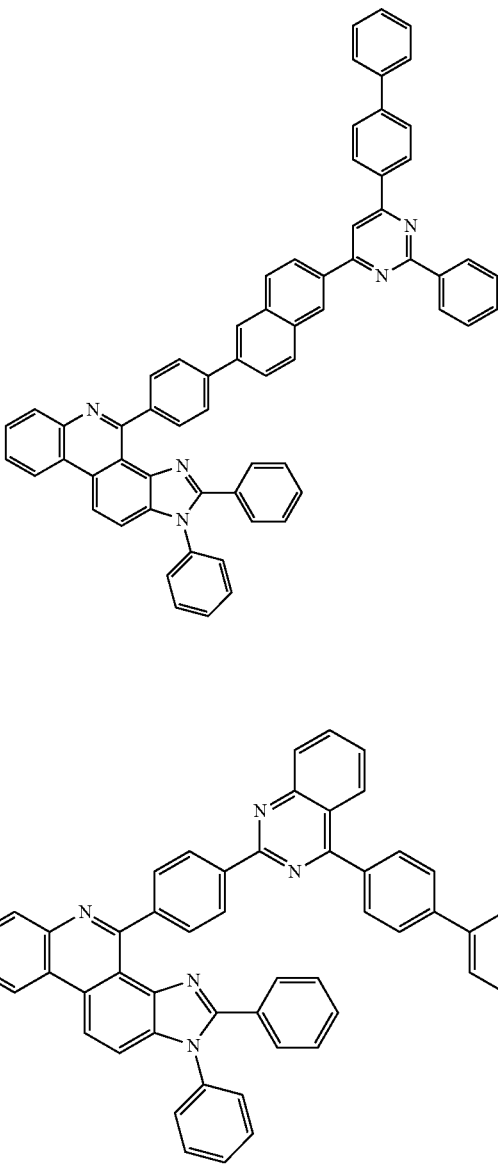
55
56
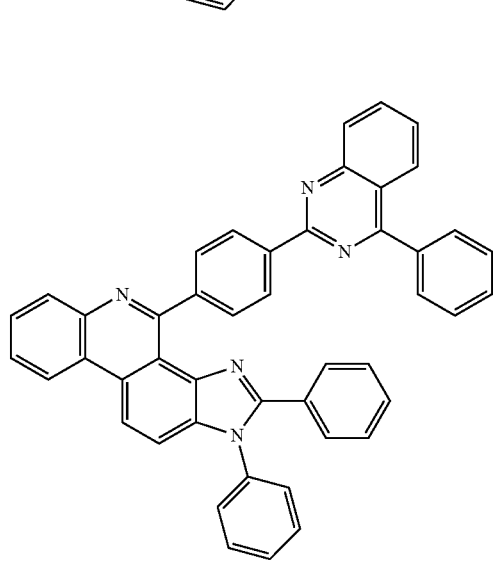

57
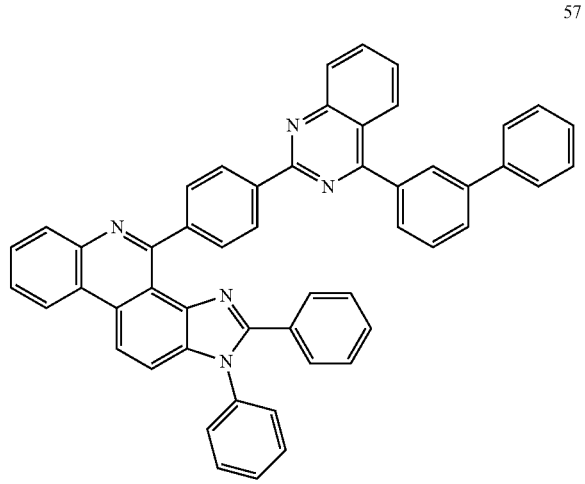
58
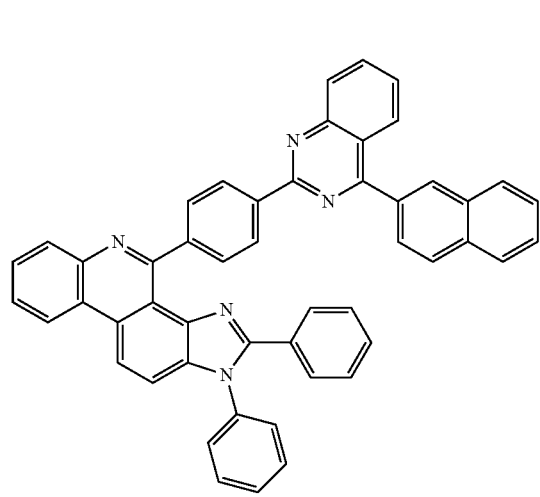
59
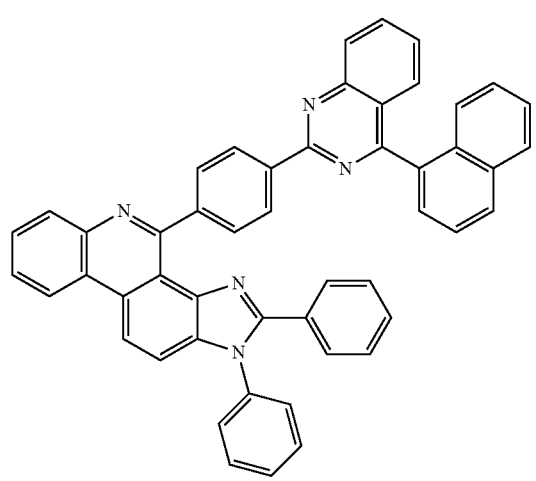
60
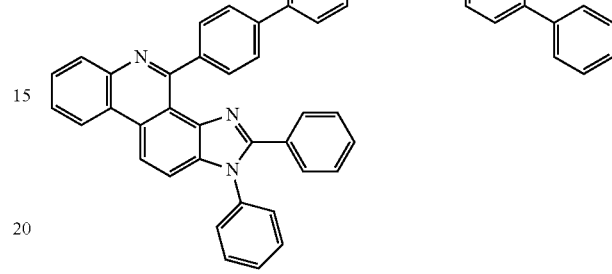
61
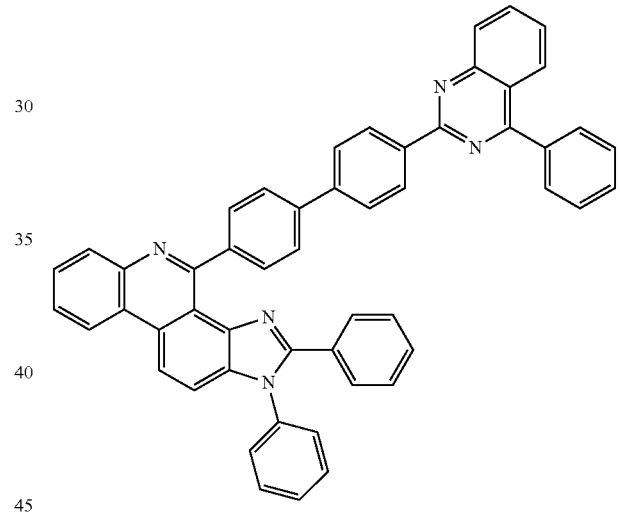
62
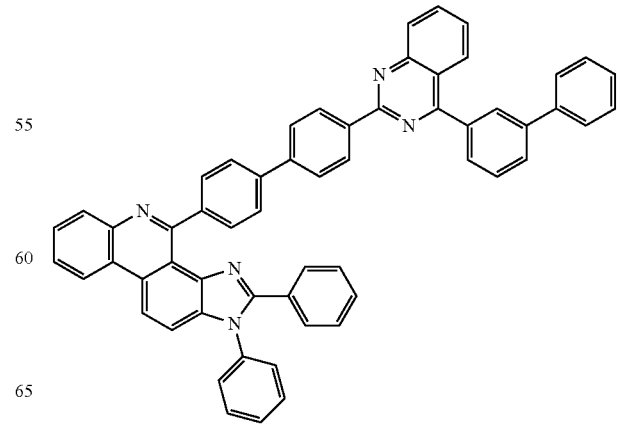

63
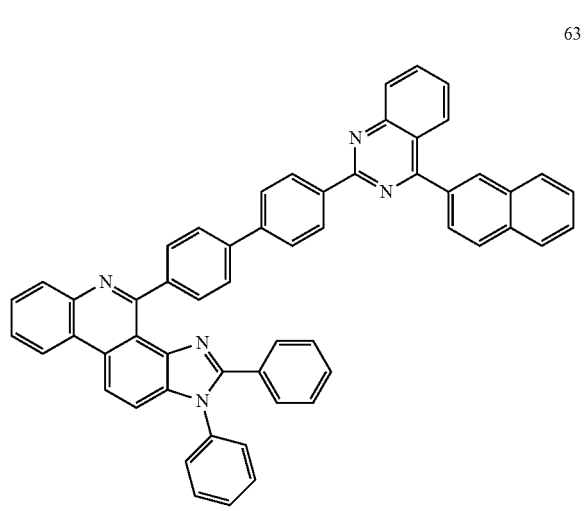
64
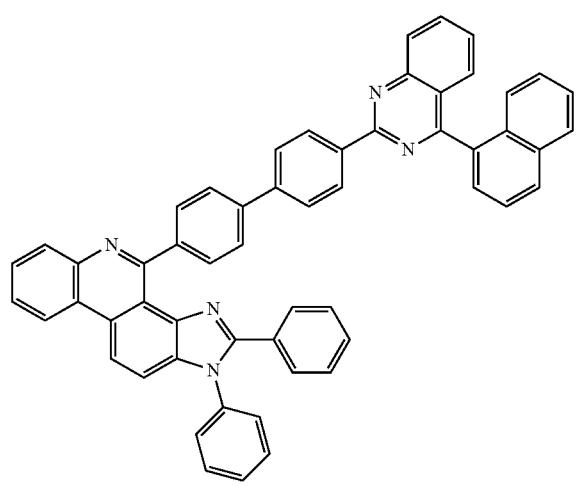
65
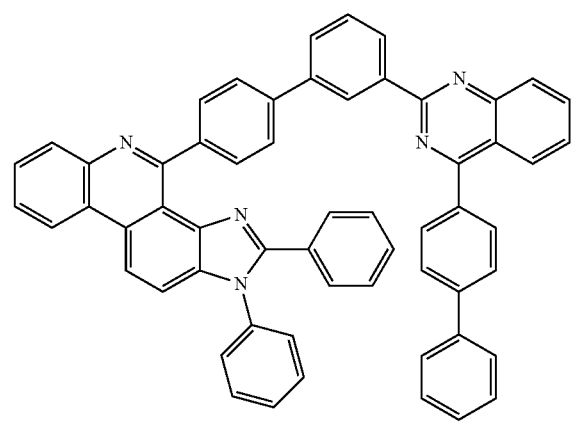
66
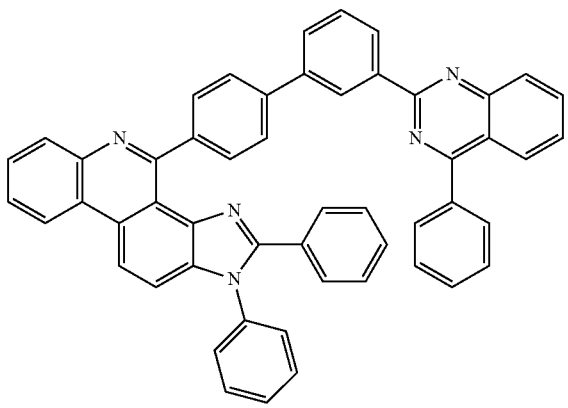
67
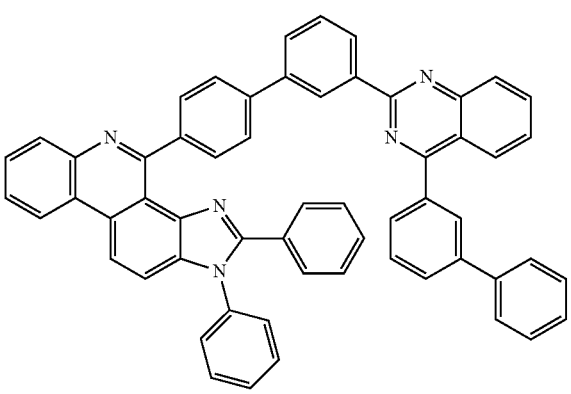
68
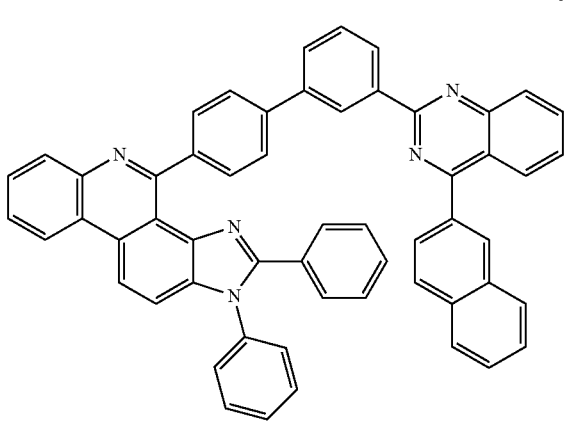

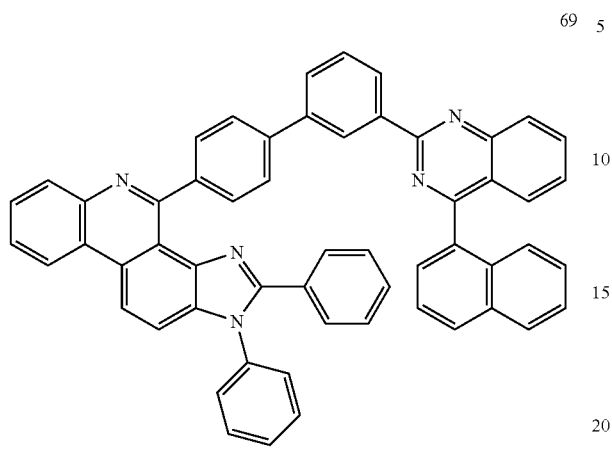
69
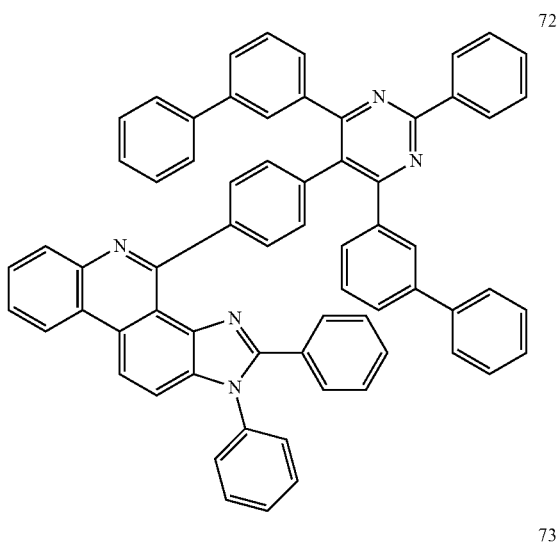
72
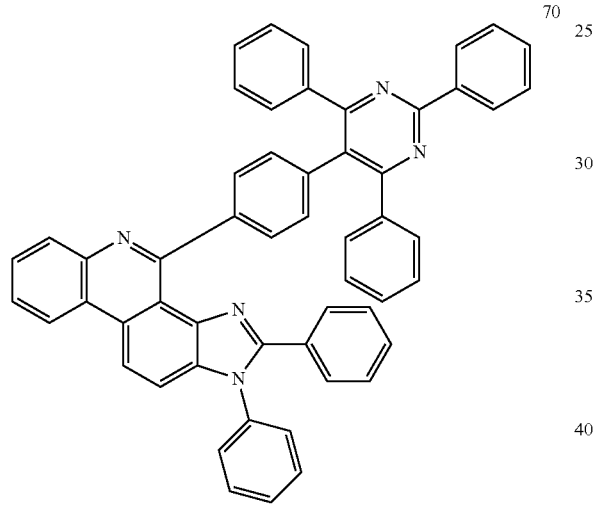
70
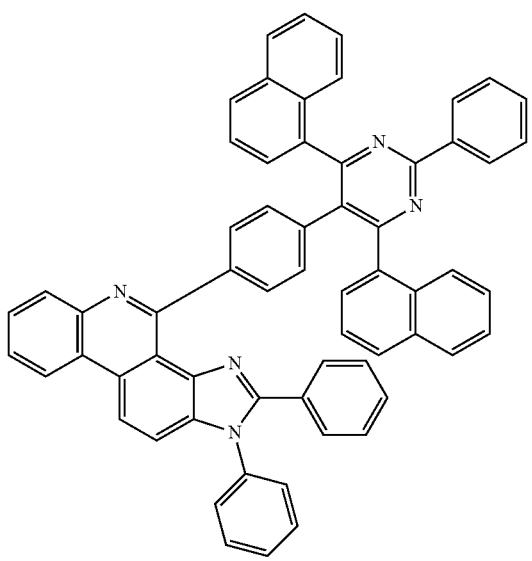
73
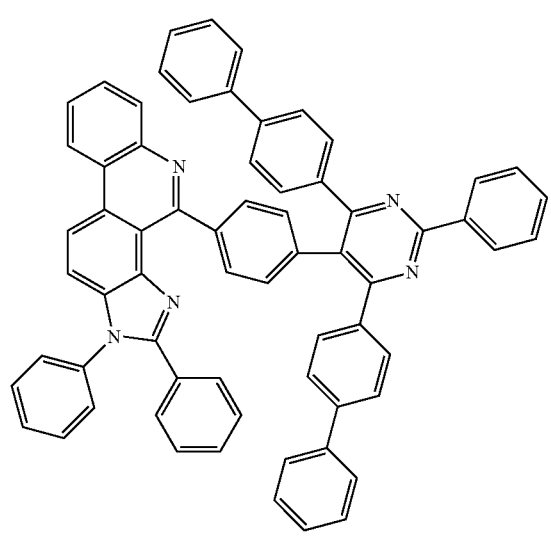
71
74

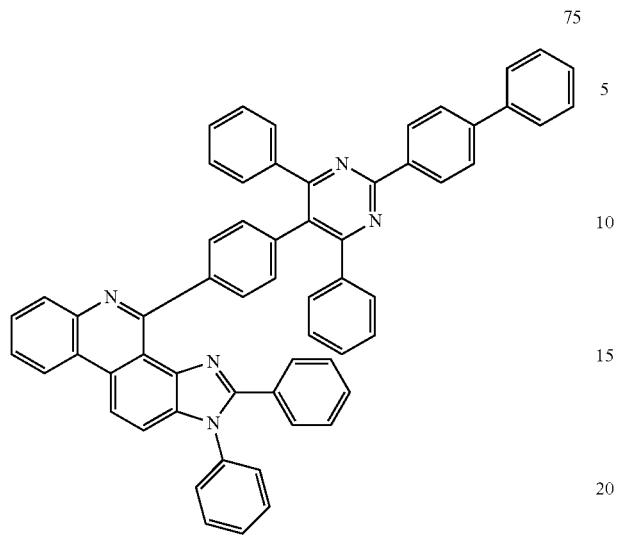
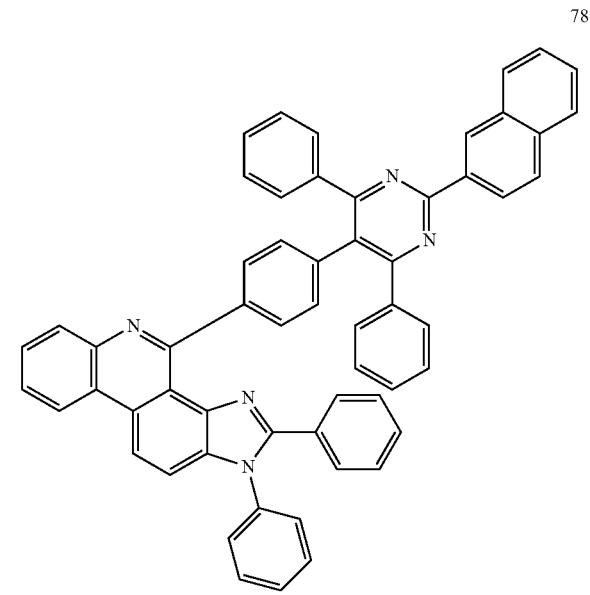
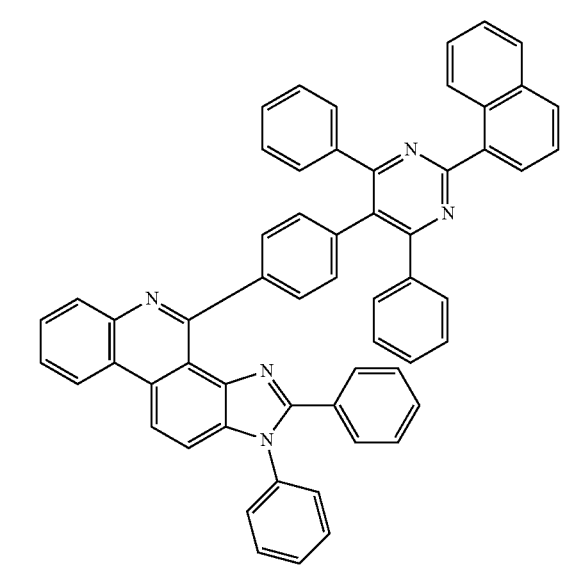
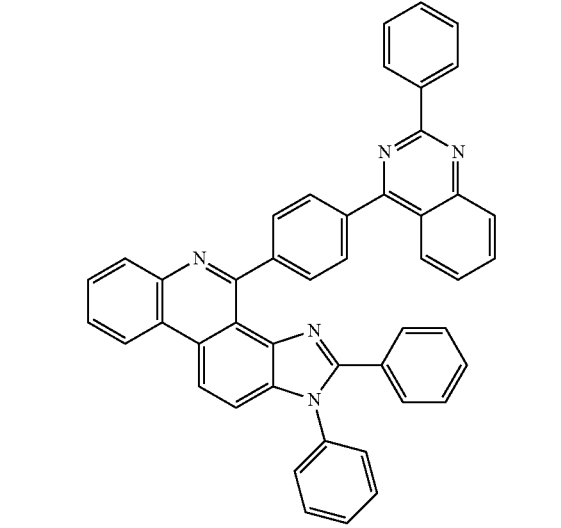

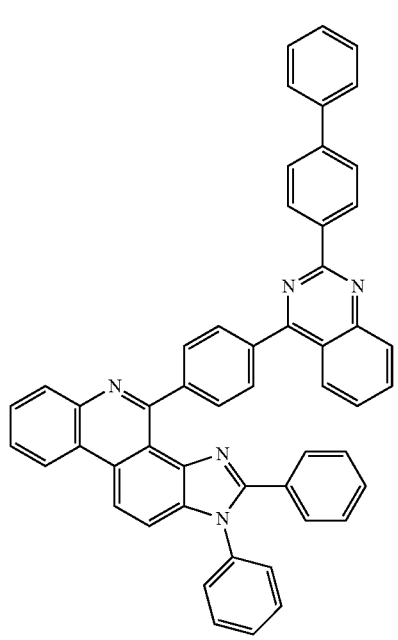
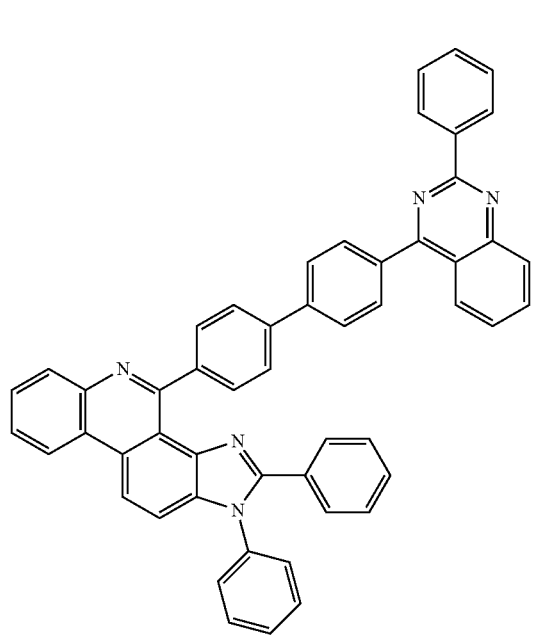

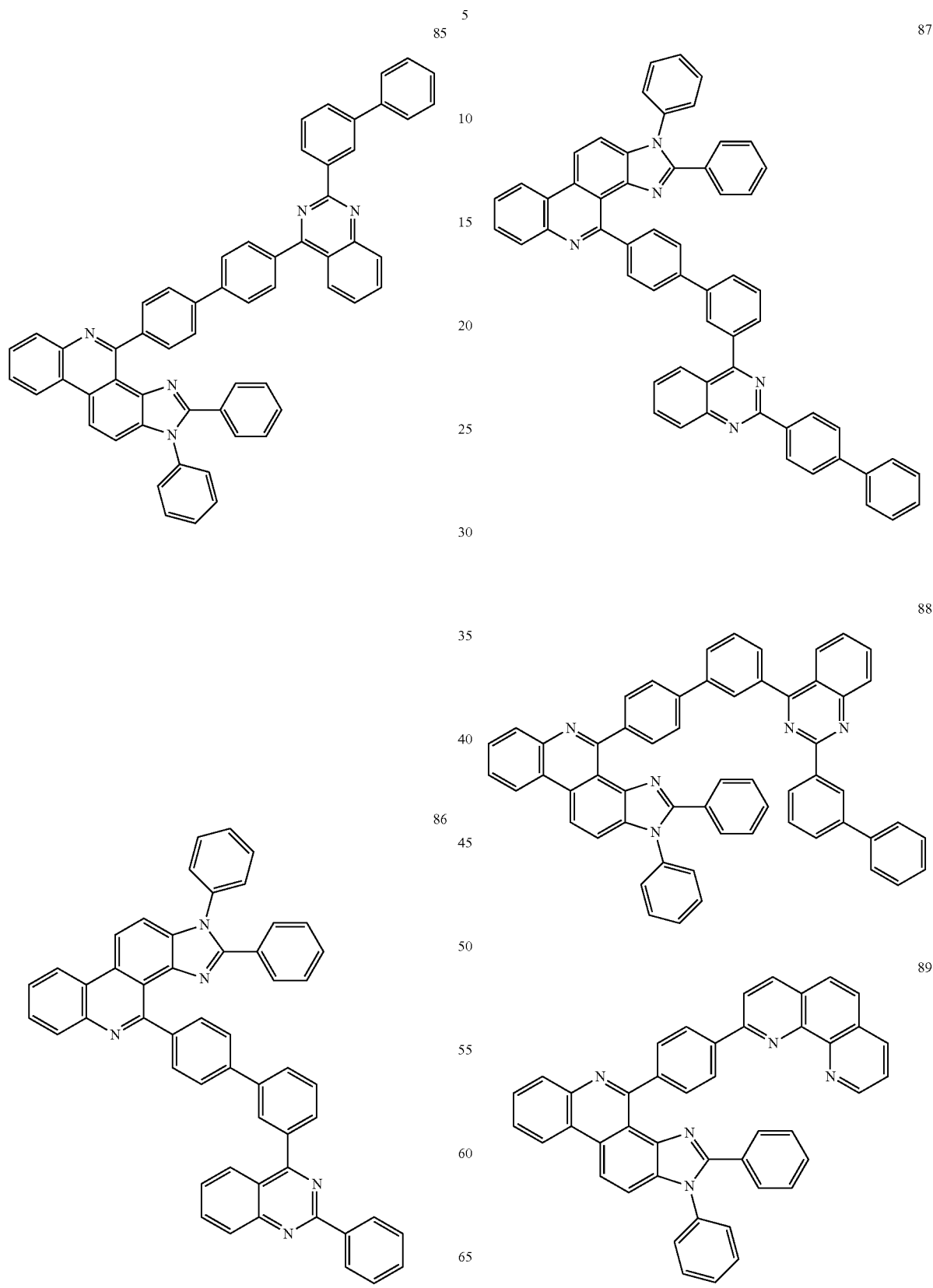

41
-continued
90
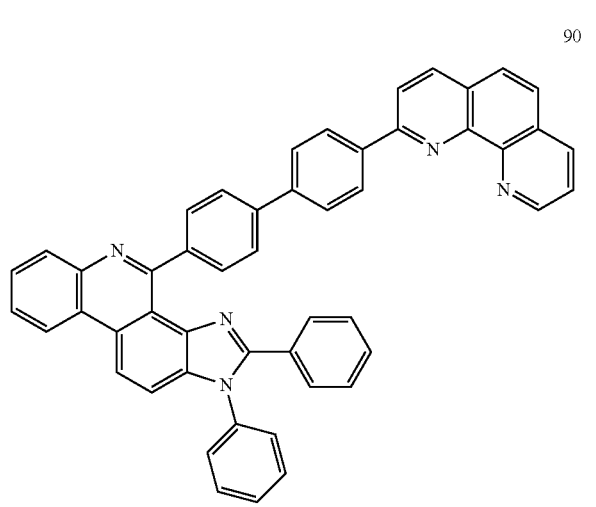
91
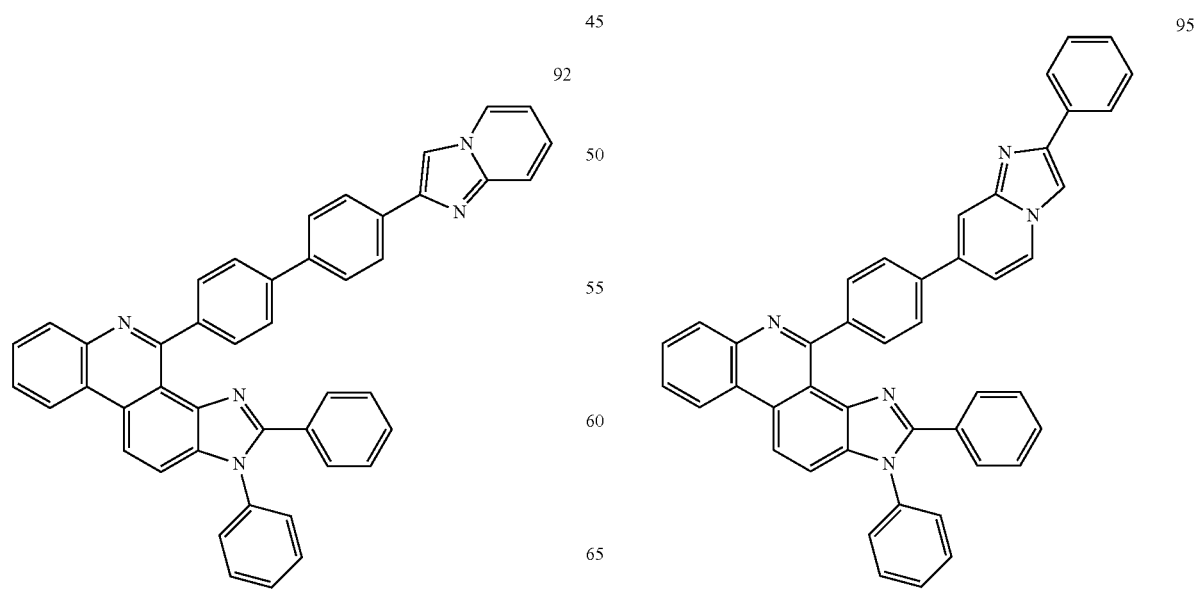
92
42
-continued
93
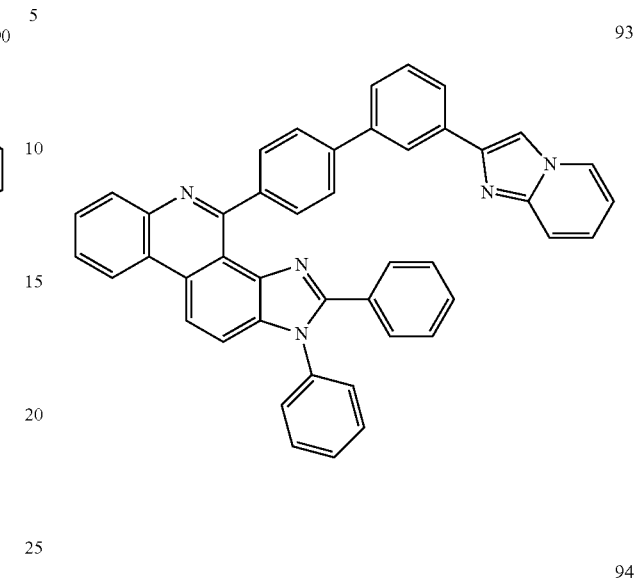
94
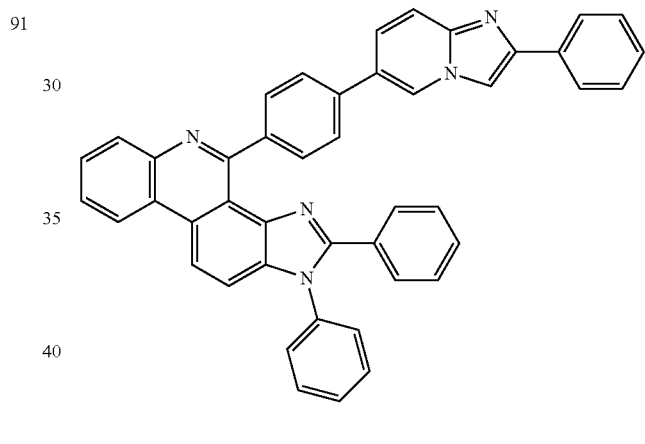
95

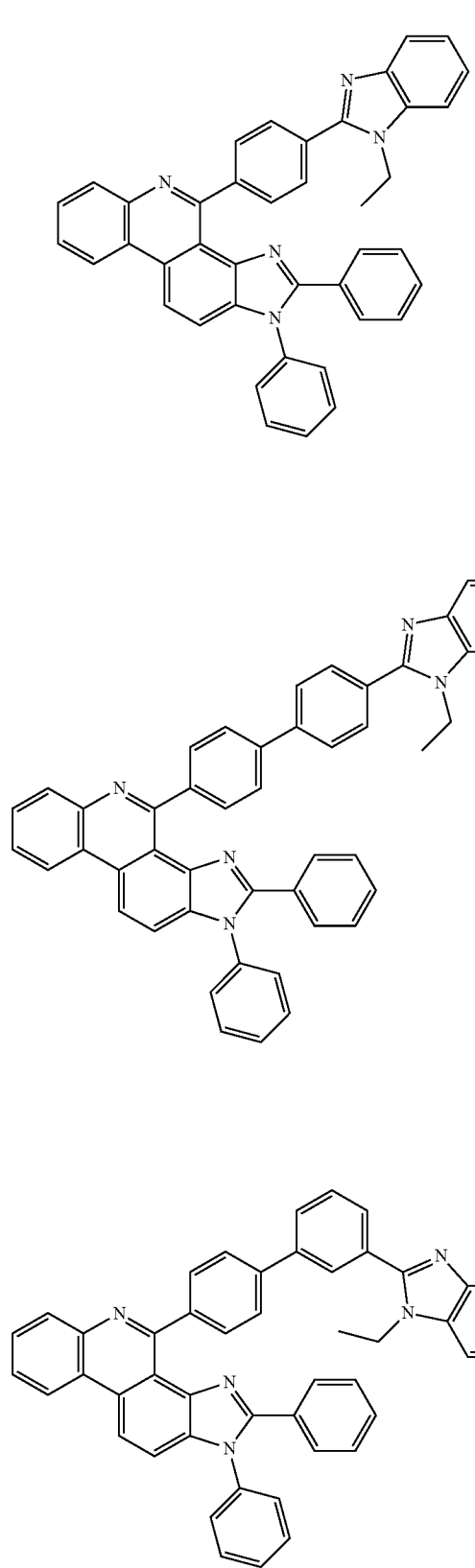
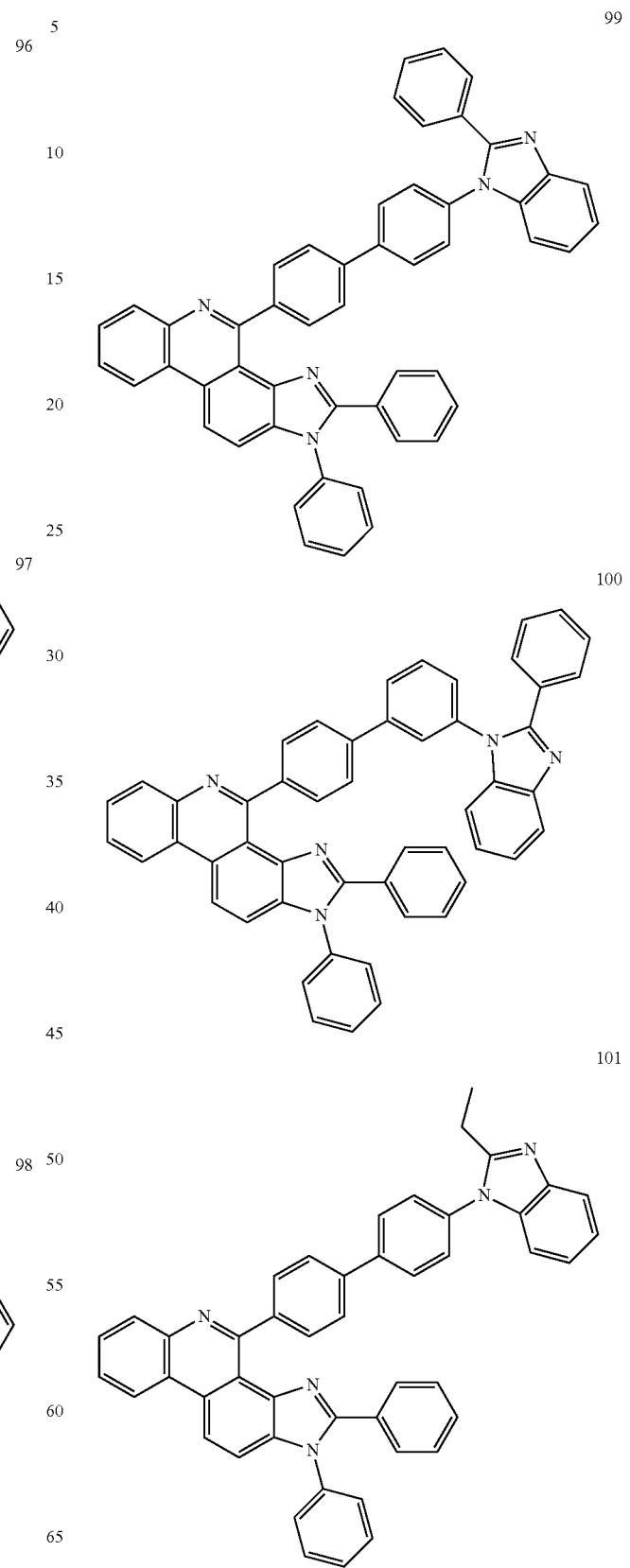

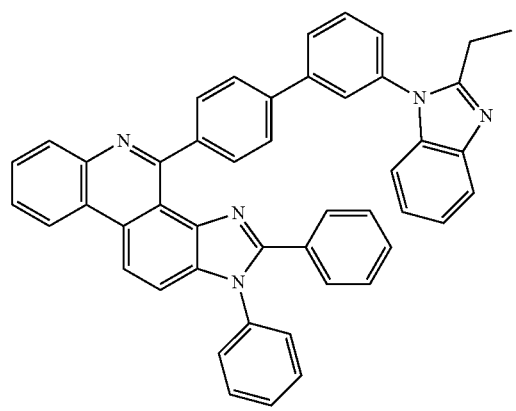
102
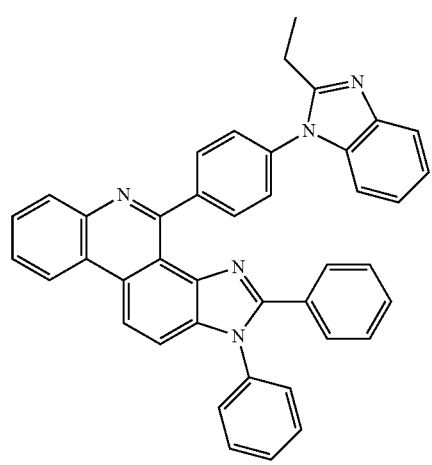
103
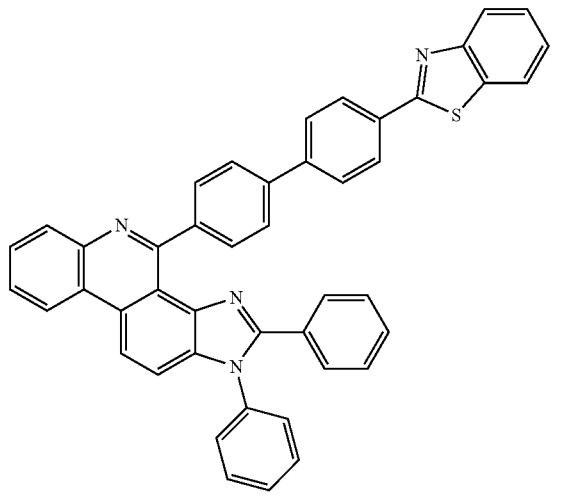
104
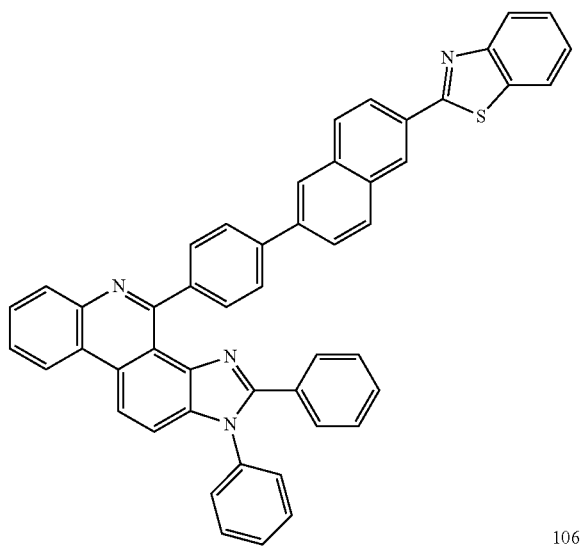
105
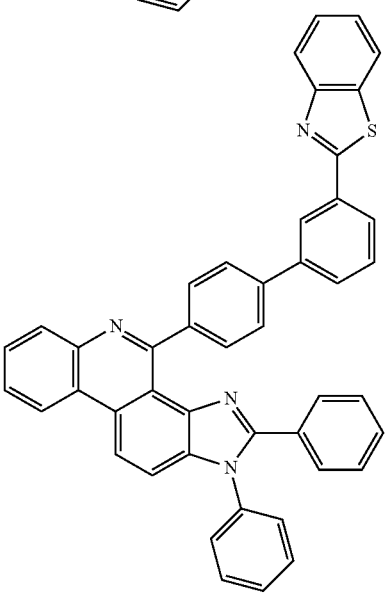
106
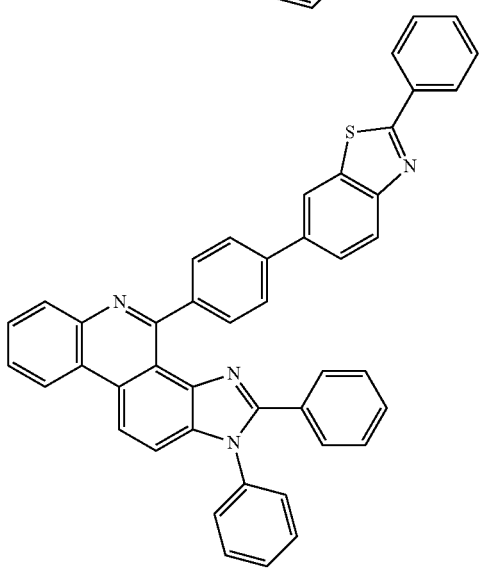
107

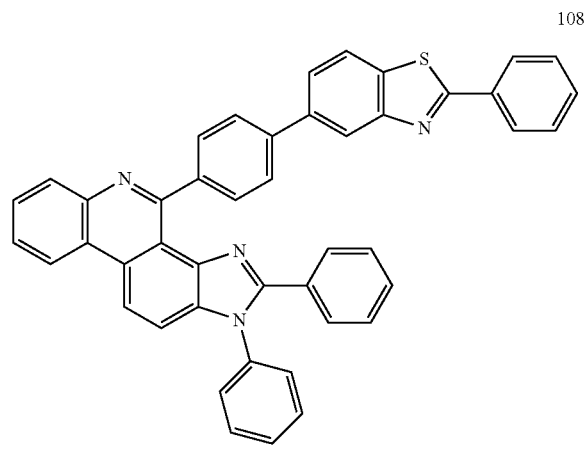
108
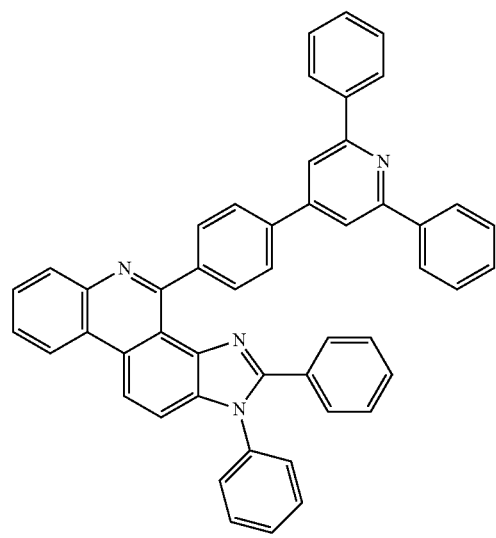
109
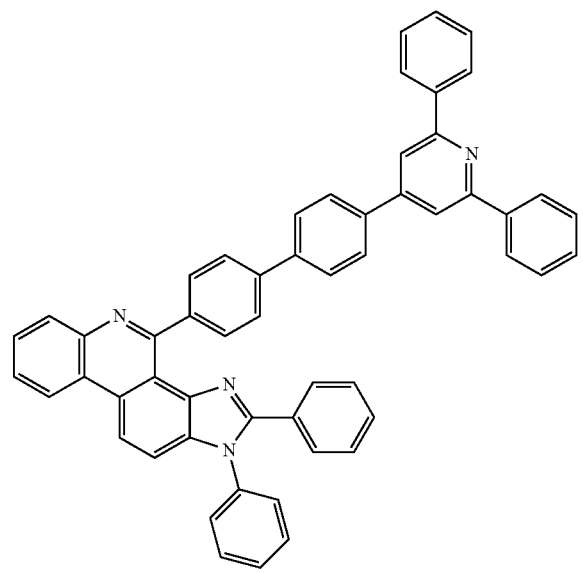
110
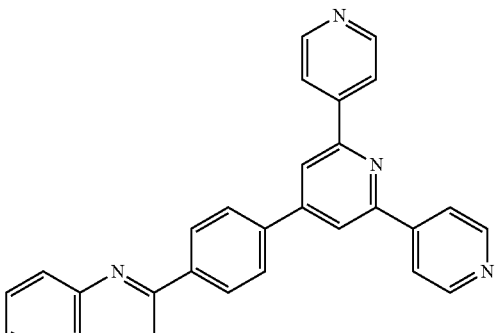
111
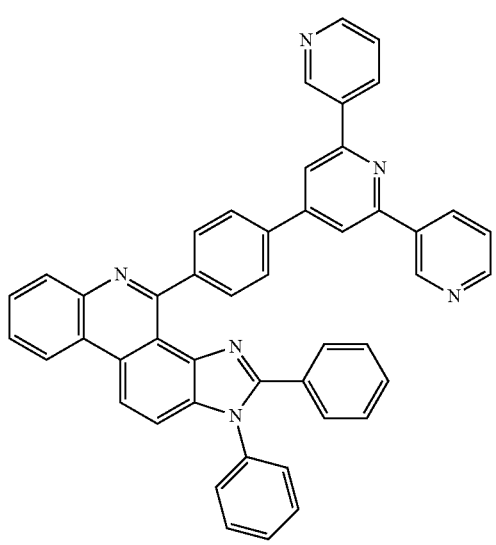
112
113

114
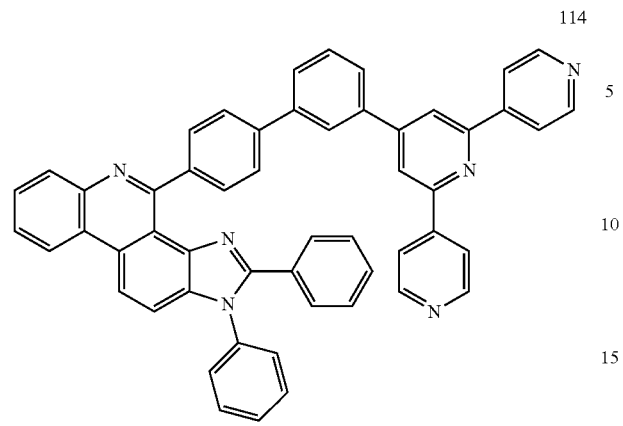
115
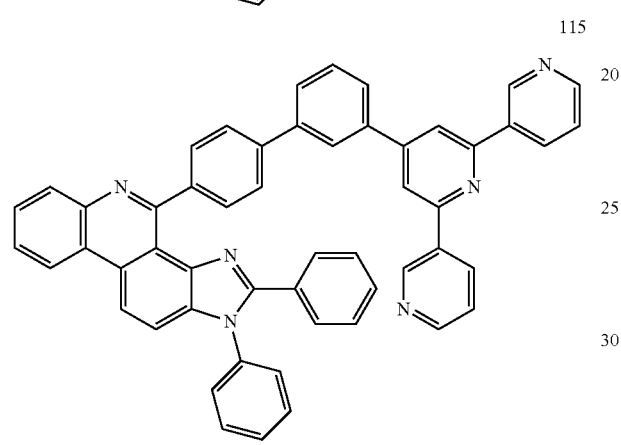
116
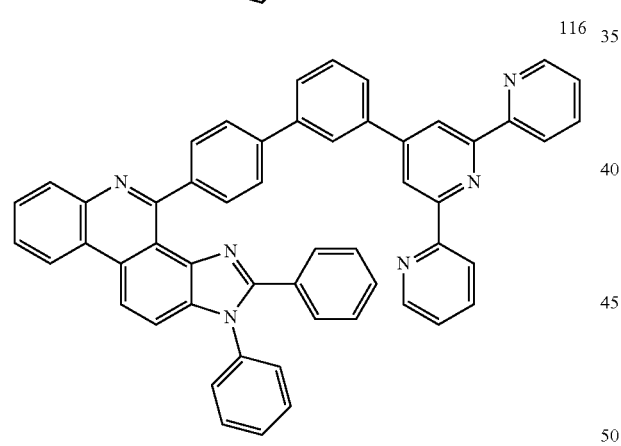
117
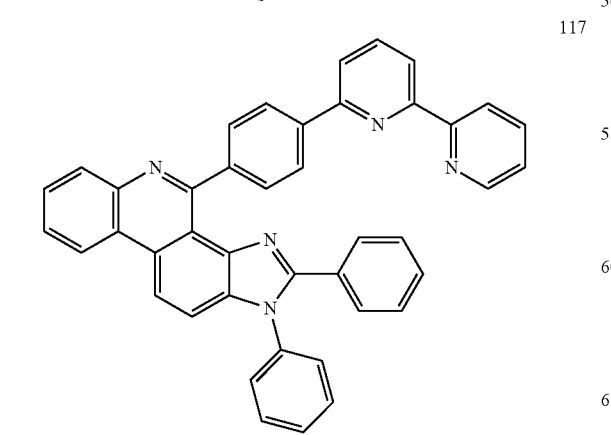
118
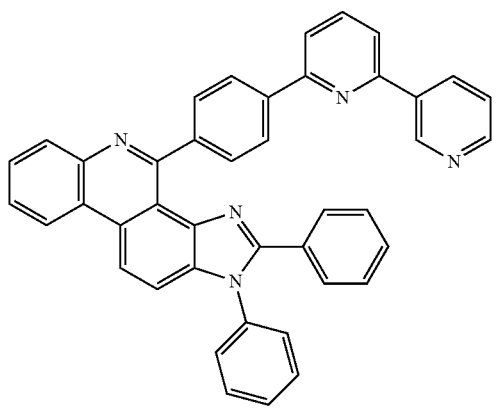
119
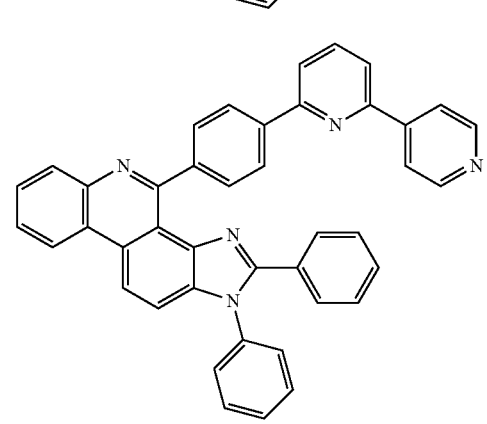
120
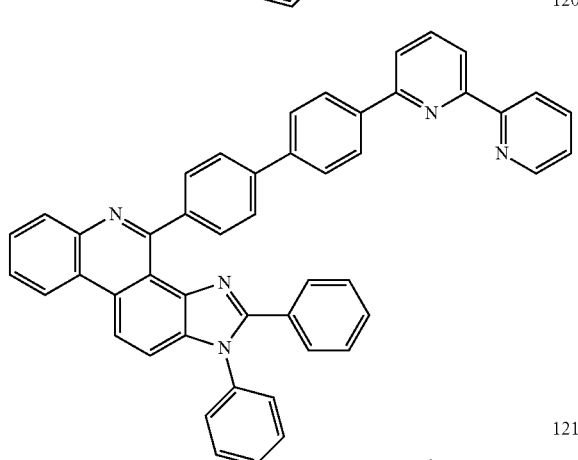
121
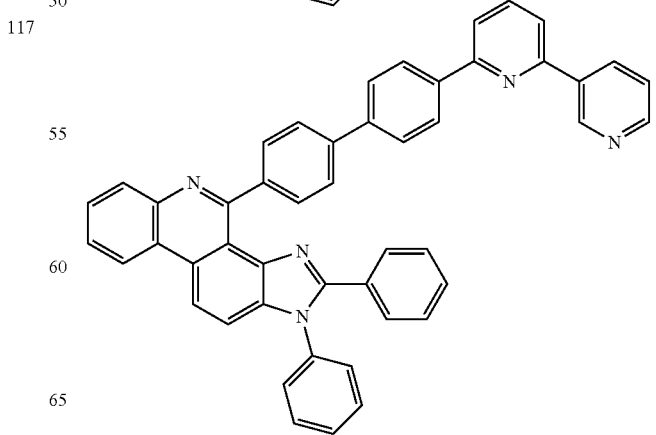

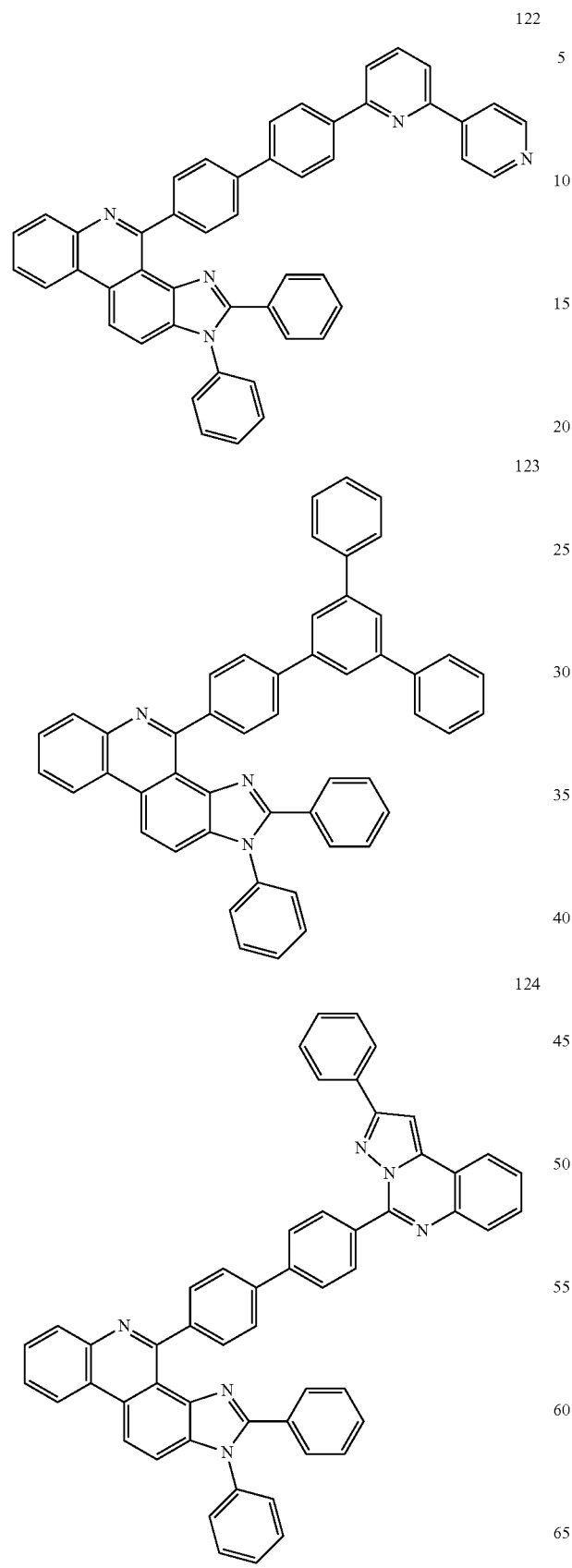
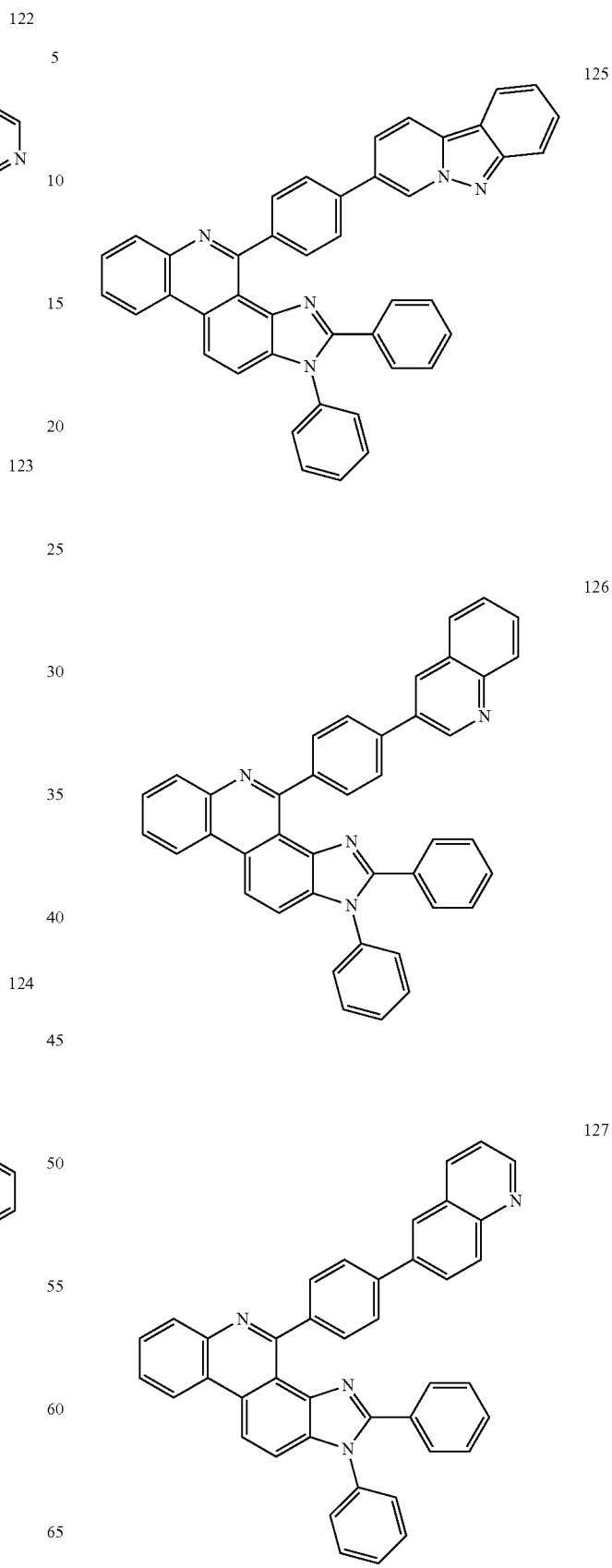

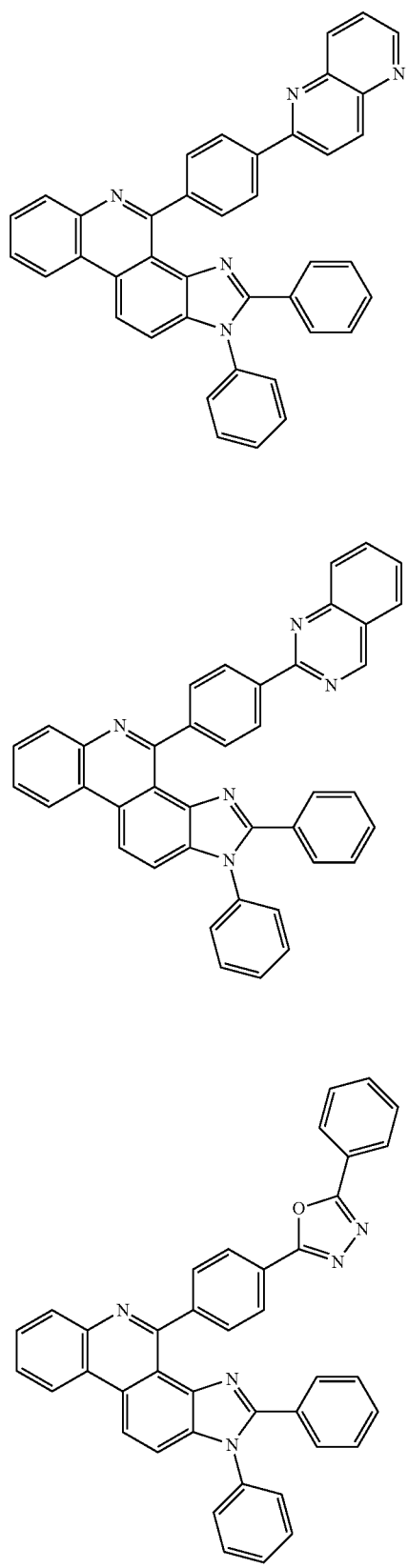
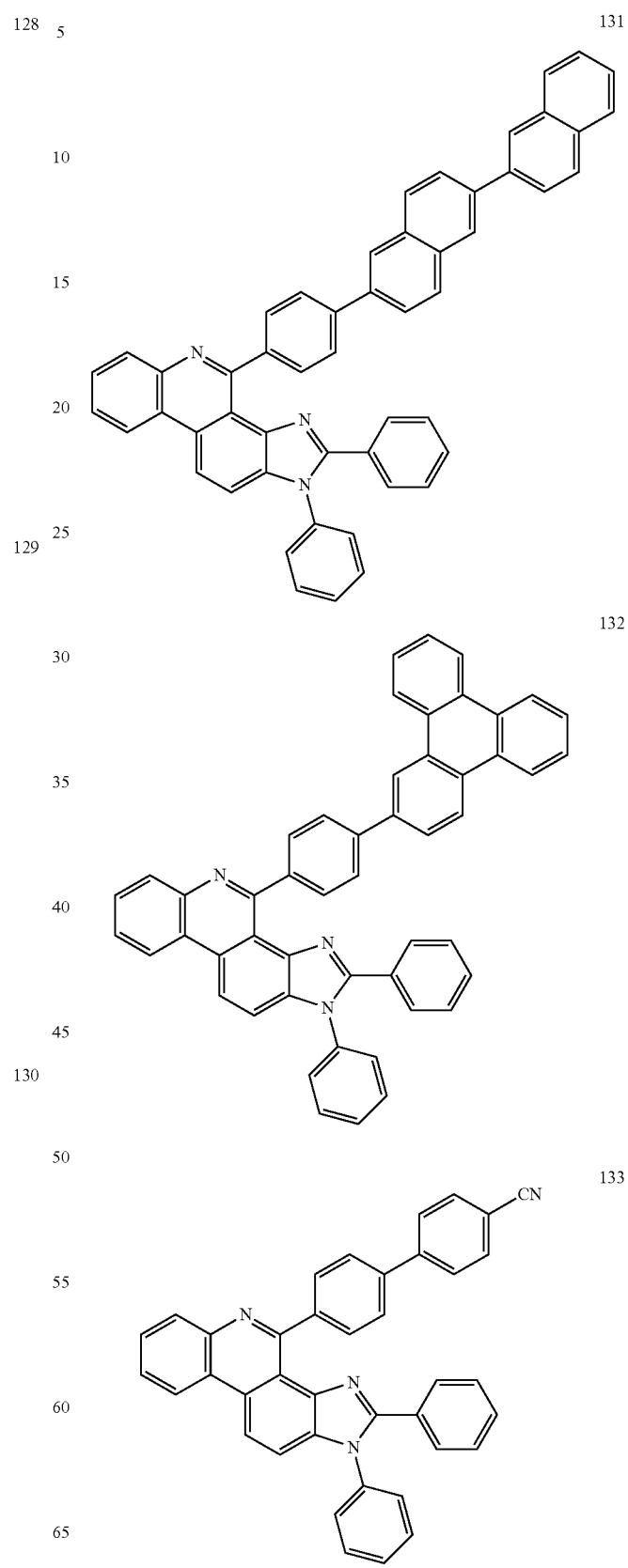

134
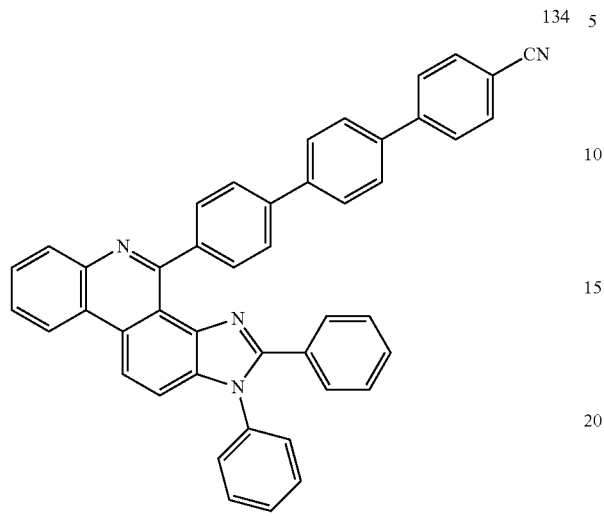
135
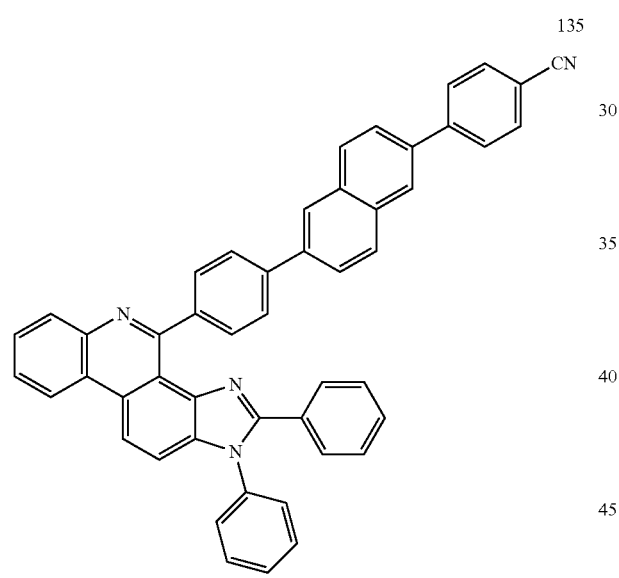
136
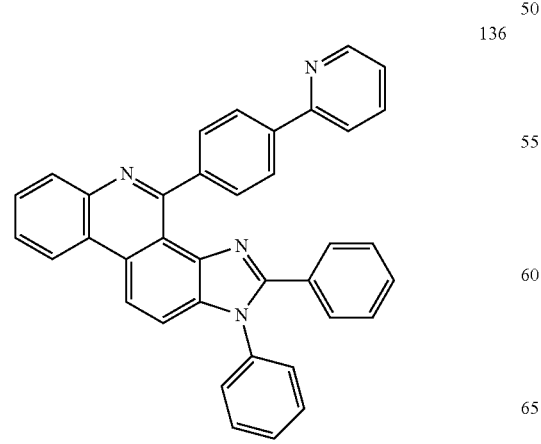
137
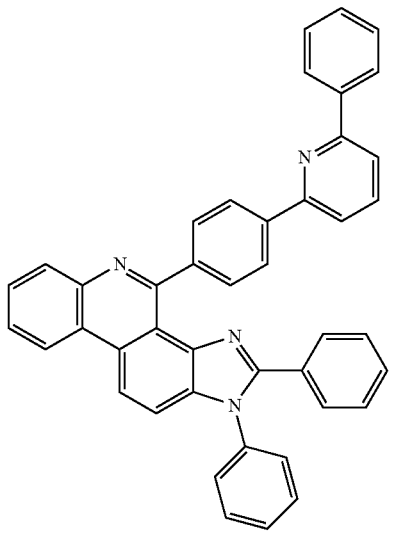
138
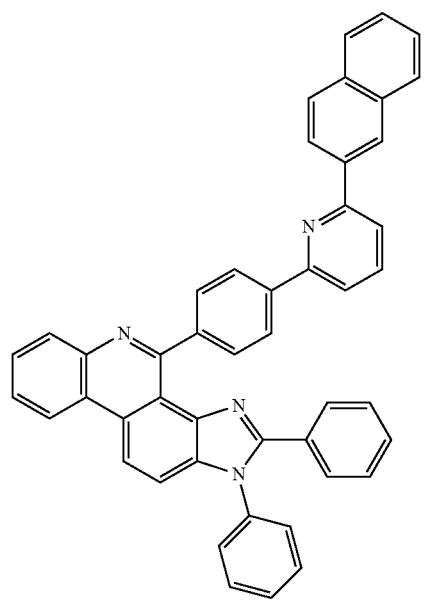
139
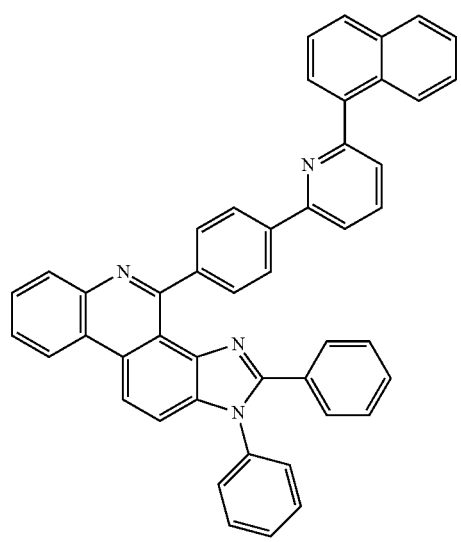

-continued
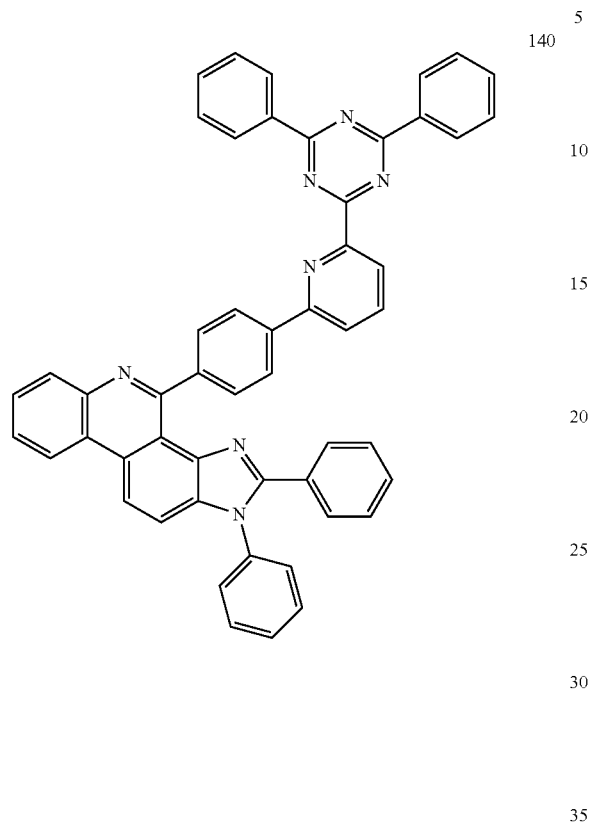
140
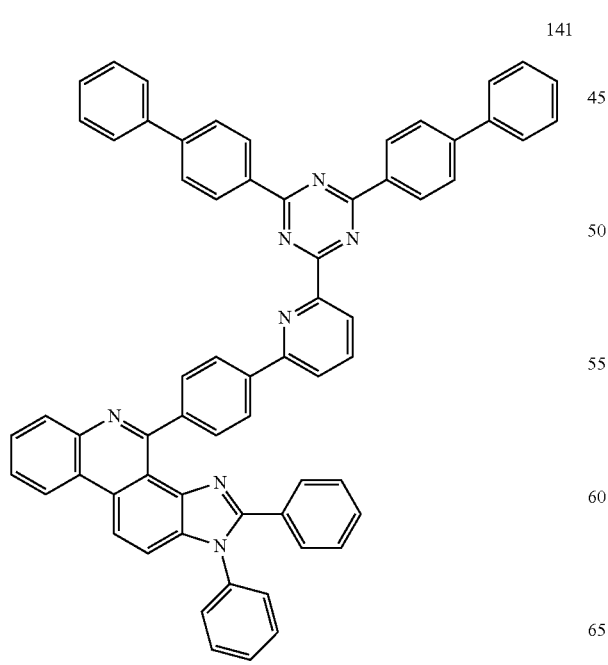
141
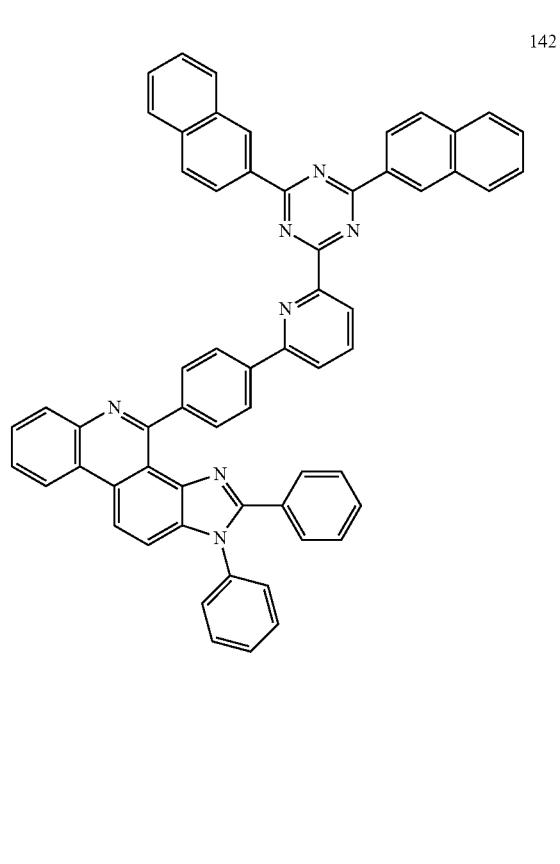
142
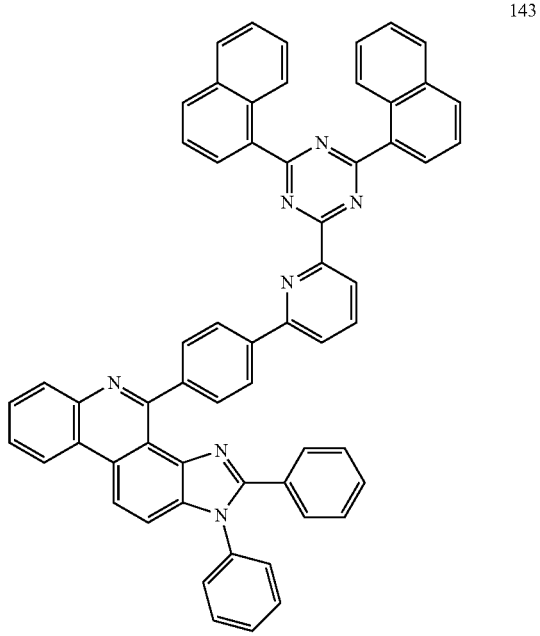
143

144
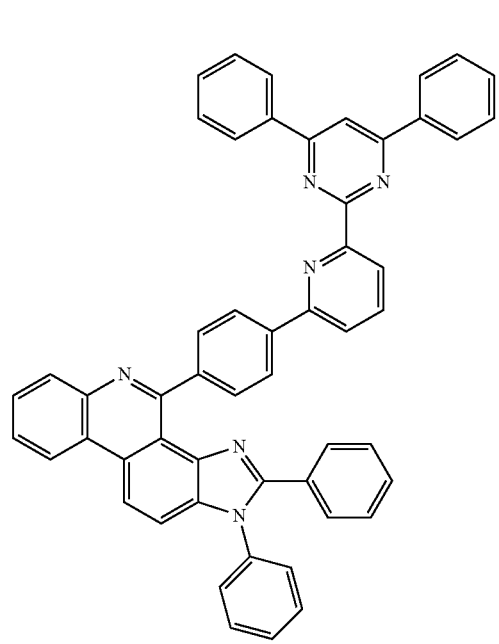
146
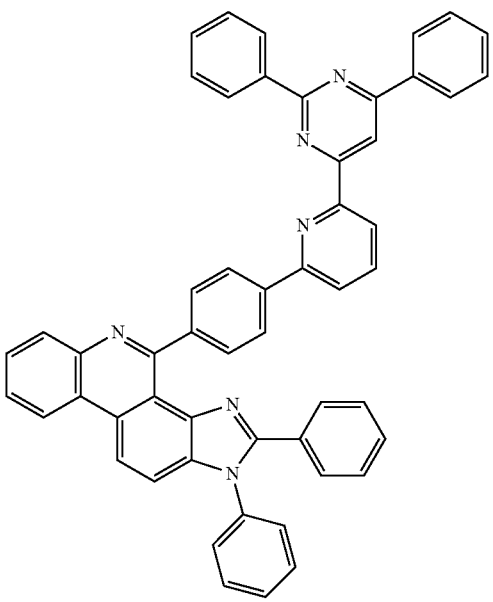
145
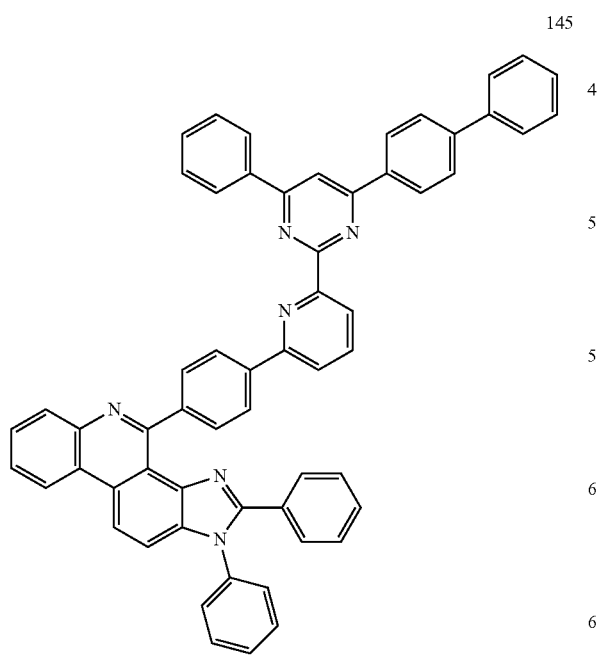
147
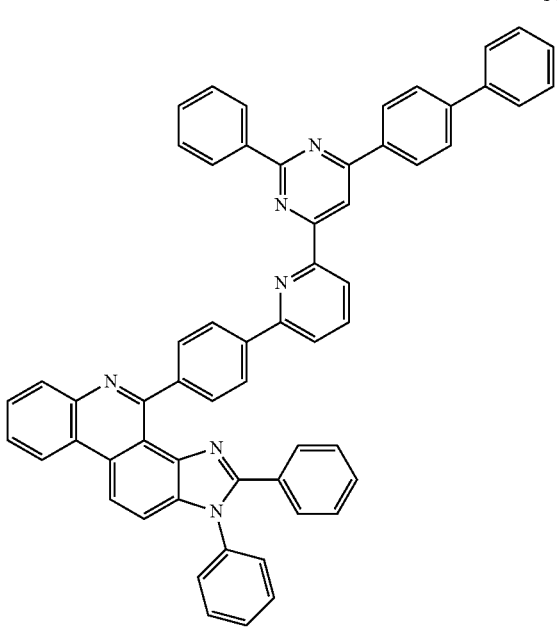

148
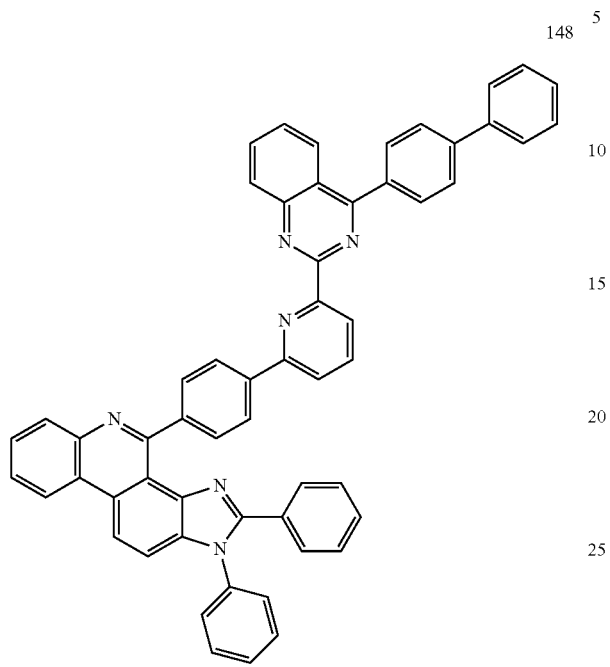
149
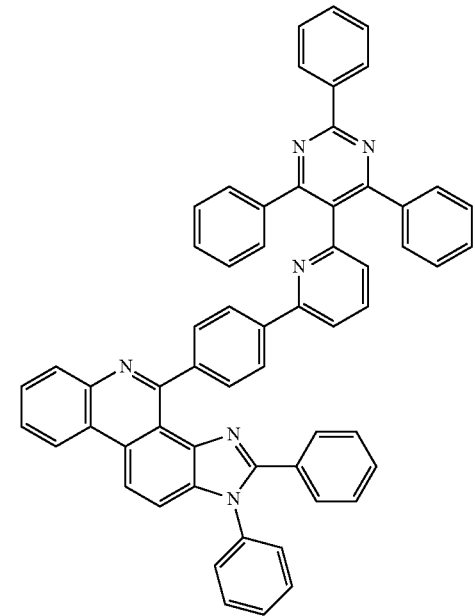
150
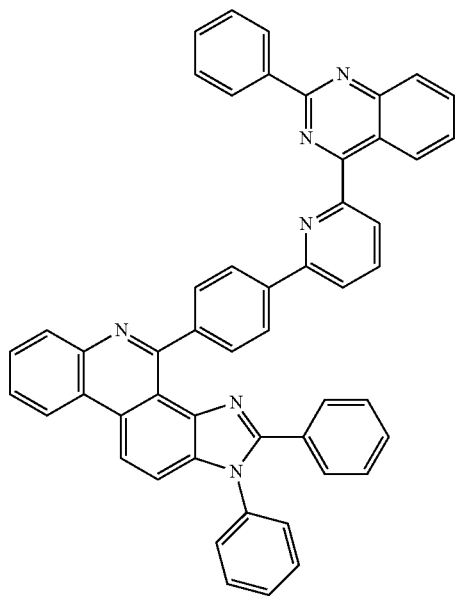
151
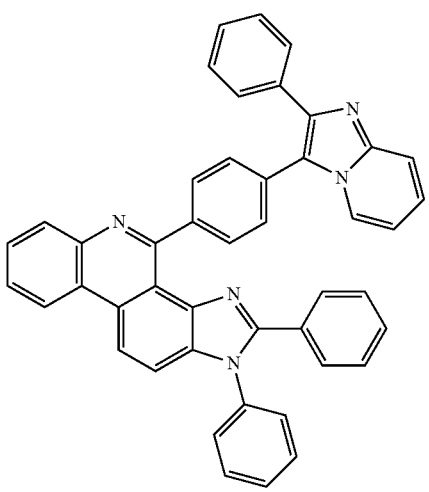
152
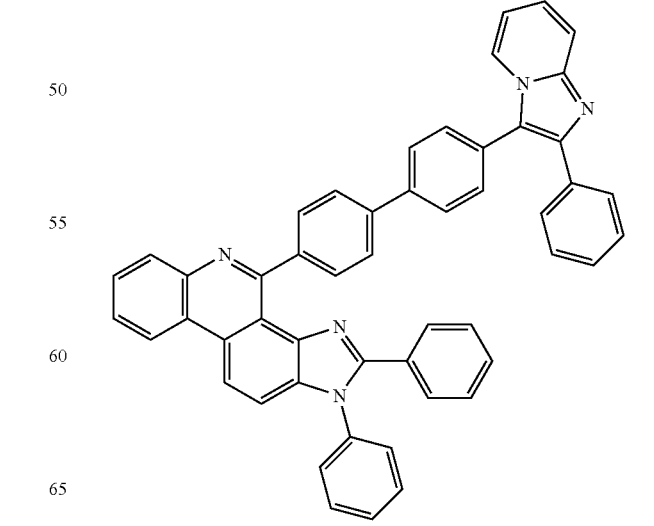

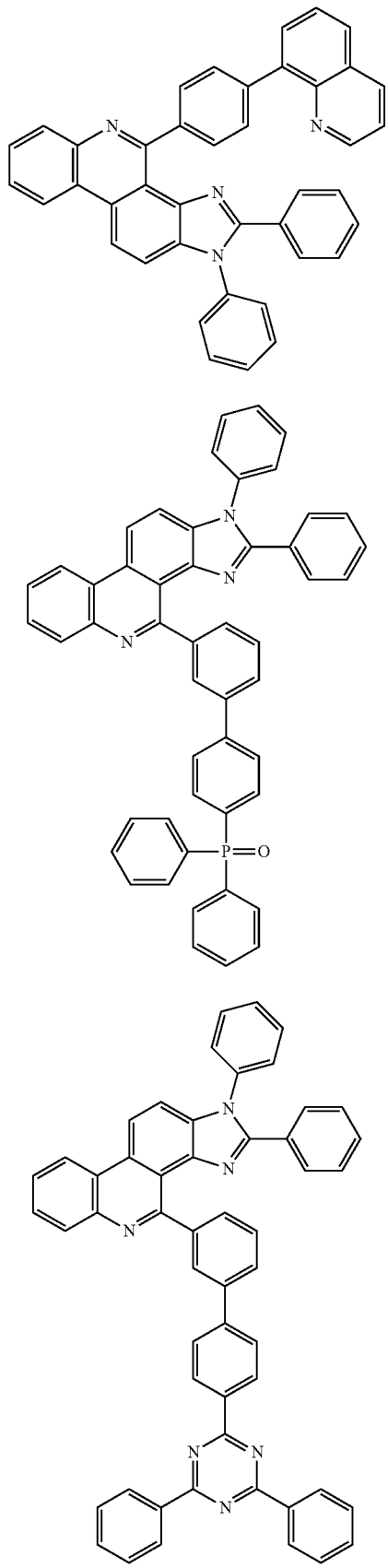
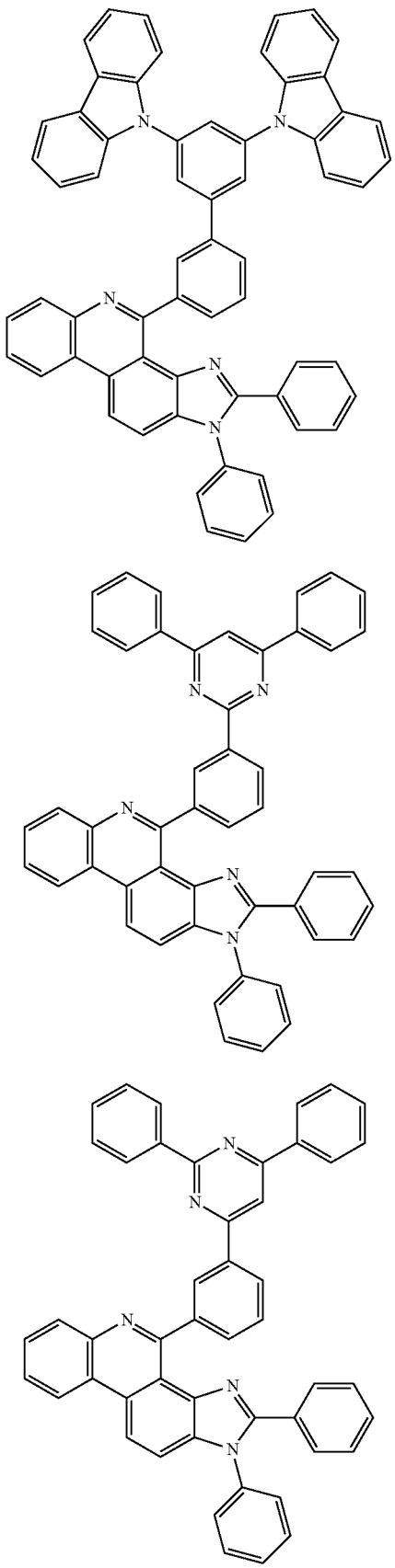

-continued
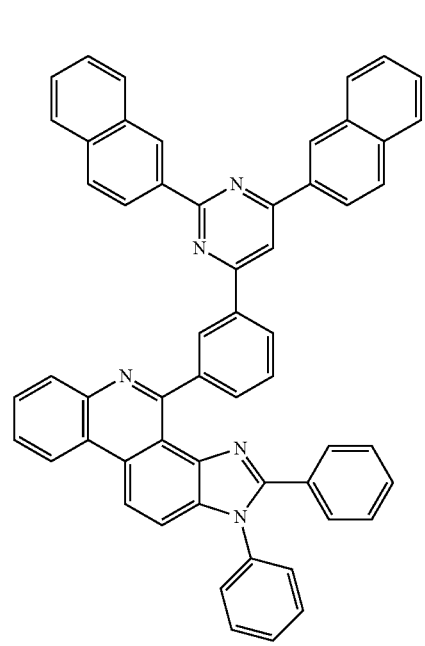
159
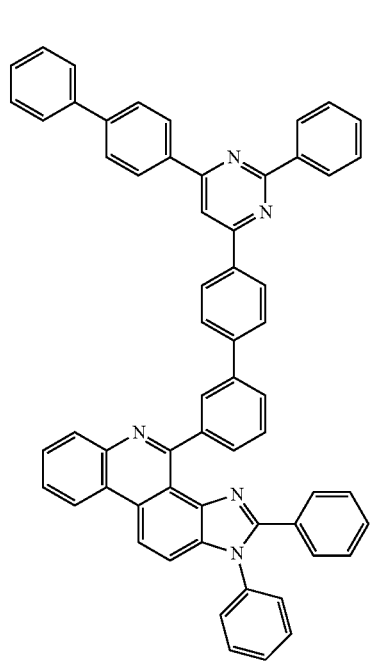
161
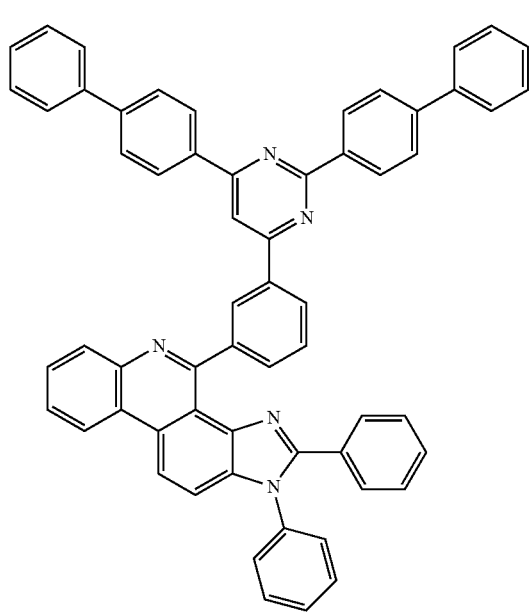
160
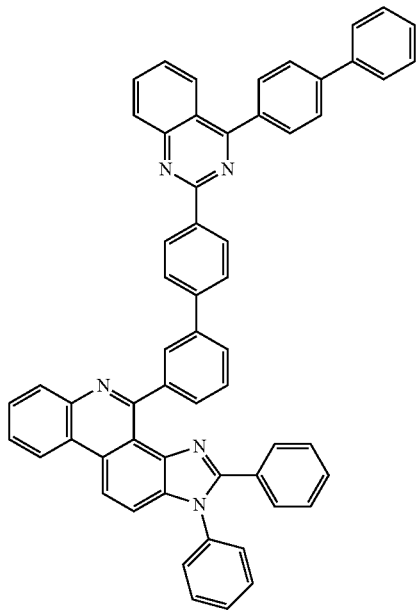
162

163 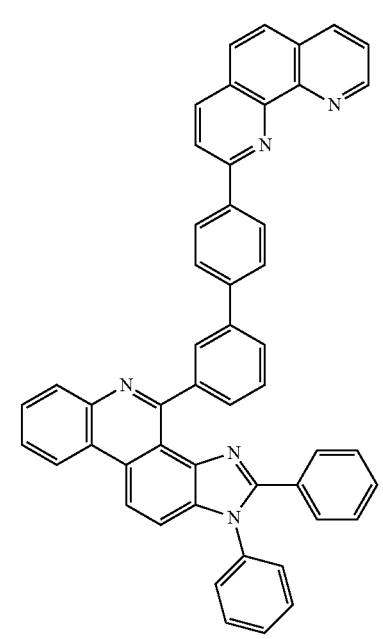
164 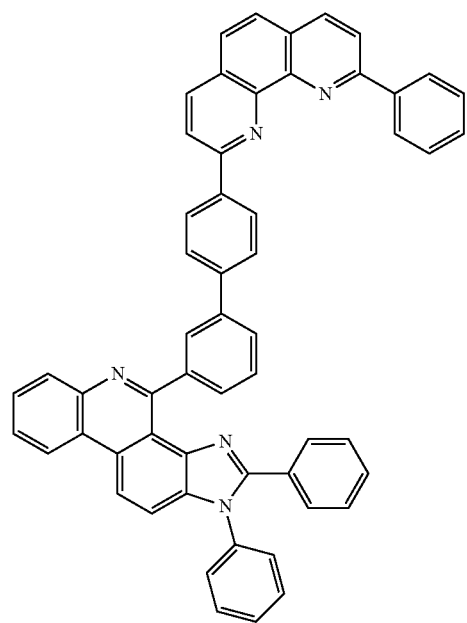
165 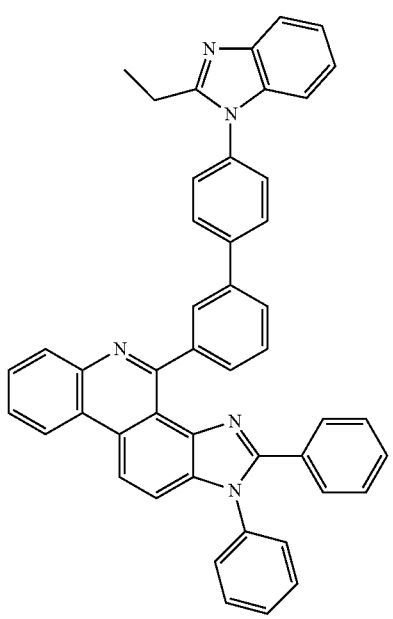
166 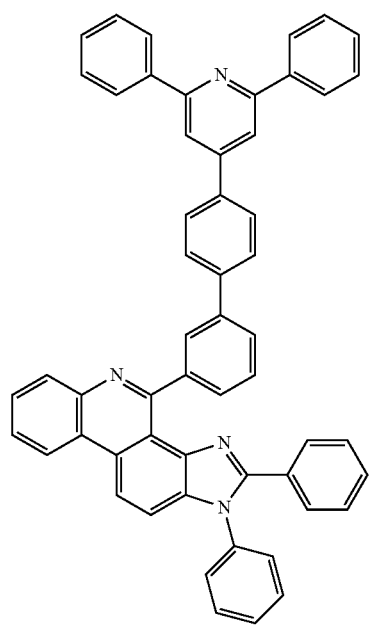

-continued

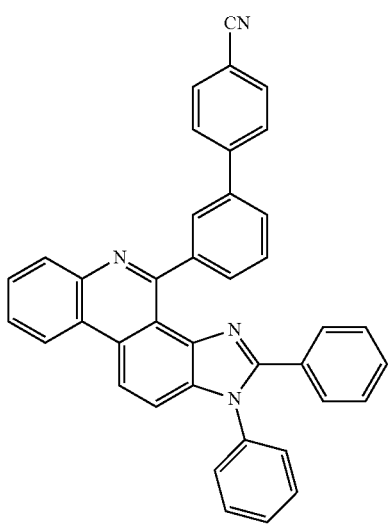

167

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the hetero-cyclic compound has excellent thermal stability with a high glass transition temperature (Tg). Such an increase in the thermal stability becomes an important factor in providing driving stability to a device.

The hetero-cyclic compound according to one embodiment of the present application may be prepared through a multistep chemical reaction. Some intermediate compounds are prepared first, and the compound of Chemical Formula 1 may be prepared from the intermediate compounds. More specifically, the hetero-cyclic compound according to one embodiment of the present application may be prepared based on preparation examples to be described below.

Another embodiment of the present application provides an organic light emitting device comprising the hetero-cyclic compound represented by Chemical Formula 1.

The organic light emitting device according to one embodiment of the present application may be manufactured using common organic light emitting device manufacturing methods and materials except that one or more organic material layers are formed using the hetero-cyclic compound described above.

The hetero-cyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

Specifically, the organic light emitting device according to one embodiment of the present application comprises an anode, a cathode, and one or more organic material layers provided between the anode and the cathode, wherein one or more layers of the organic material layers comprise the hetero-cyclic compound represented by Chemical Formula 1.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the hetero-cyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the hetero-cyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the hetero-cyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

The organic light emitting device according to the present specification may be manufactured using materials and methods known in the art except that one or more layers of the organic material layers comprise the hetero-cyclic compound represented by Chemical Formula 1.

The hetero-cyclic compound represented by Chemical Formula 1 may form one or more layers of the organic material layers of the organic light emitting device alone. However, as necessary, the hetero-cyclic compound represented by Chemical Formula 1 may be mixed with other materials to form the organic material layers.

The hetero-cyclic compound represented by Chemical Formula 1 may be used as a material of the charge generation layer in the organic light emitting device.

The hetero-cyclic compound represented by Chemical Formula 1 may be used as a material of the electron transfer layer, the hole blocking layer, the light emitting layer or the like in the organic light emitting device. As one example, the hetero-cyclic compound represented by Chemical Formula 1 may be used as a material of the electron transfer layer, the hole transfer layer or the light emitting layer in the organic light emitting device.

In addition, the hetero-cyclic compound represented by Chemical Formula 1 may be used as a material of the light emitting layer in the organic light emitting device. As one example, the hetero-cyclic compound represented by Chemical Formula 1 may be used as a phosphorescent host material of the light emitting layer in the organic light emitting device.

In the organic light emitting device according to one embodiment of the present application, materials other than the hetero-cyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly [3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

Mode for Disclosure

Hereinafter, the present specification will be described in more detail with reference to examples, however, these are for illustrative purposes only, and the scope of the present application is not limited thereto.

EXAMPLE

<Preparation Example 1> Preparation of Compound 2

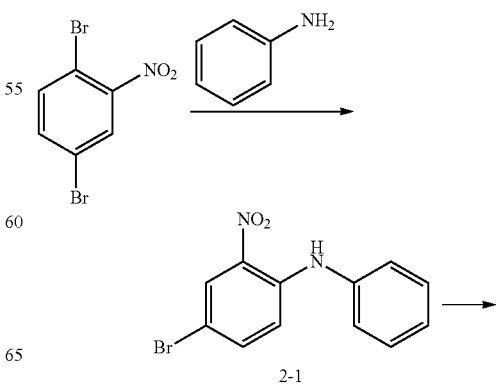

2-1

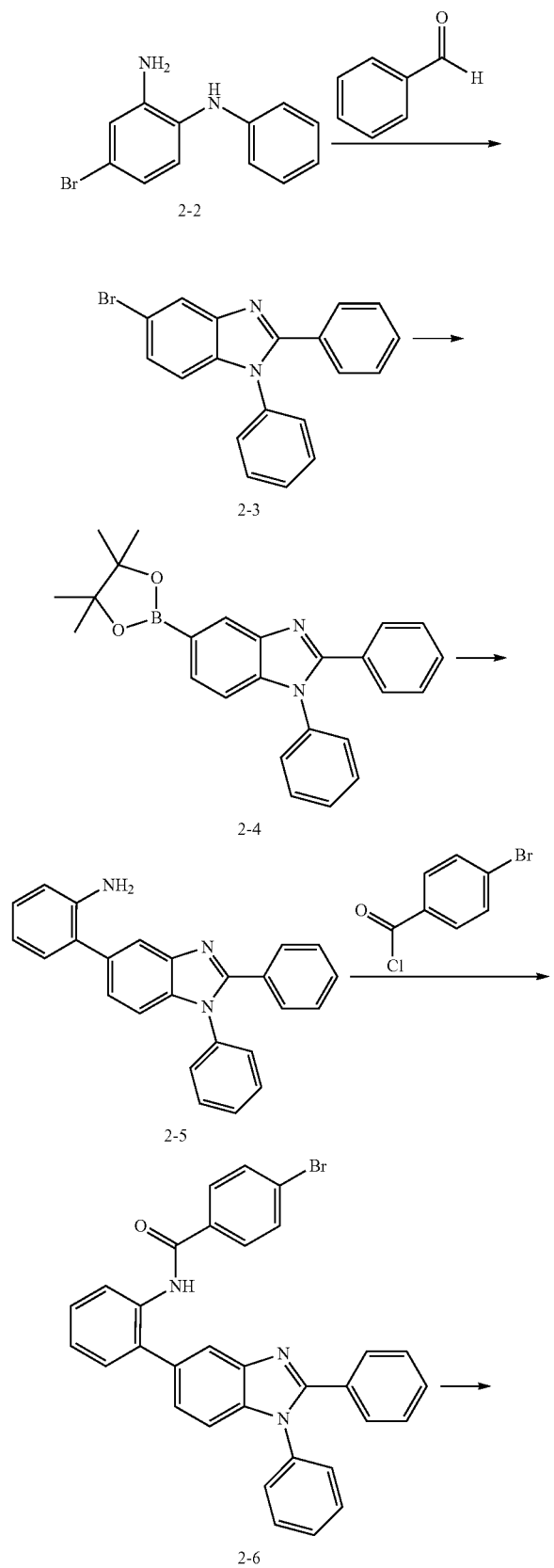
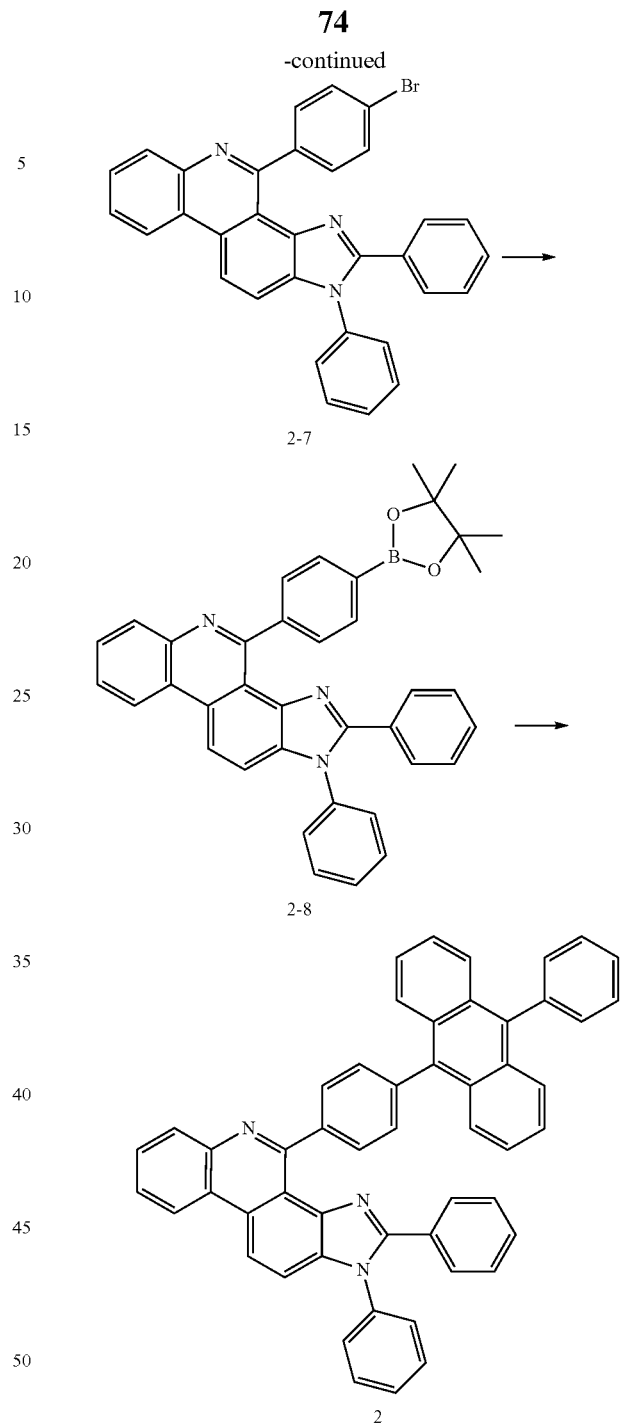

1) Preparation of Compound 2-1

After adding aniline (19.8 ml, 213 mmol) and sodium acetate trihydrate (26.4 g, 318 mol) to a compound 1,4-dibromo-2-nitrobenzene (30 g, 106 mmol), the result was stirred for 30 minutes at 80° C. and then refluxed for 72 hours at 160° C. After the reaction was completed, the result was cooled to room temperature, and extracted with distilled water and EA. The organic layer was dried with anhydrous $MgSO_4$, then the solvent was removed using a rotary evaporator, and the result was purified using column chromatography with dichloromethane and hexane as a developing solvent to obtain target Compound 2-1 (31 g, 99%).

2) Preparation of Compound 2-2

After dissolving Compound 2-1 (31 g, 105 mmol) in THF (210 ml), sodium dithionite (93 g, 525 mmol) dissolved in distilled water (370 ml) was added thereto, and the result was stirred for 12 hours at room temperature. After the reaction was completed, the result was extracted with distilled water and EA. The organic layer was dried with anhydrous $MgSO_4$, then the solvent was removed using a rotary evaporator, and target Compound 2-2 (28 g, 100%) was obtained without further purification.

3) Preparation of Compound 2-3

After dissolving Compound 2-2 (28 g, 106 mmol) in nitrobenzene, the result was refluxed for 6 hours at 180° C. After the reaction was completed, the result was vacuum distilled to remove nitrobenzene, and then extracted with distilled water and EA. The organic layer was dried with anhydrous $MgSO_4$, then the solvent was removed using a rotary evaporator, and the result was purified using column chromatography with dichloromethane and hexane as a developing solvent to obtain target Compound 2-3 (15 g, 40%).

4) Preparation of Compound 2-4

After dissolving Compound 2-3 (15 g, 43.0 mmol) in 1,4-dioxane, bis(pinacolato)diboron (21 g, 86.0 mmol), $Pd(dppf)Cl_2$ (1.6 g, 2.15 mmol) and potassium acetate (12.7 g, 129 mmol) were added thereto, and the result was stirred for 2 hours at 110° C. After the reaction was completed, the result was extracted with distilled water and EA. The organic layer was dried with anhydrous $MgSO_4$, then the solvent was removed using a rotary evaporator, and target Compound 2-4 (9.5 g, 56%) was obtained without further purification.

5) Preparation of Compound 2-5

After dissolving Compound 2-4 (9.5 g, 23.0 mmol) in toluene, EtOH and $H_2O$, 2-bromoaniline (4.9 g, 28.8 mmol), $Pd(PPh_3)_4$ (1.4 g, 1.2 mmol) and $K_2CO_3$ (10.0 g, 72.0 mmol) were added thereto, and the result was stirred for 6 hours at 110° C. After the reaction was completed, the result was cooled to room temperature, and extracted with distilled water and EA. The organic layer was dried with anhydrous $MgSO_4$, then the solvent was removed using a rotary evaporator, and the result was purified using column chromatography with ethyl acetate and hexane as a developing solvent to obtain target Compound 2-5 (7.1 g, 82%).

6) Preparation of Compound 2-6

After dissolving Compound 2-5 (7.1 g, 19.6 mmol) in THF, 4-bromobenzoyl chloride (3.8 ml, 29.4 mmol) and TEA (8.1 ml, 58.8 mmol) were added thereto at 0° C., and the result was stirred for 2 hours at room temperature. After the reaction was completed, EA and distilled water were added to the reactor for solidification, and the produced solids were collected to obtain target Compound 2-6 (11 g, 100%).

7) Preparation of Compound 2-7

After dissolving Compound 2-6 (11 g, 20.2 mmol) in nitrobenzene, $POCl_3$ (1.9 ml, 20.2 mmol) was added thereto, and the result was stirred for 18 hours at 150° C. After the reaction was completed, the result was vacuum distilled to remove nitrobenzene, then cooled to room temperature, and extracted with distilled water and EA. The organic layer was dried with anhydrous $MgSO_4$, then the solvent was removed using a rotary evaporator, and the result was purified using column chromatography with dichloromethane and hexane as a developing solvent to obtain target Compound 2-7 (7.4 g, 69%).

8) Preparation of Compound 2-8

After dissolving Compound 2-7 (7.4 g, 14.1 mmol) in 1,4-dioxane, bis(pinacolato)diboron, $Pd(dppf)Cl_2$ and potassium acetate were added thereto, and the result was stirred for 2 hours at 110° C. After the reaction was completed, the result was extracted with distilled water and EA. The organic layer was dried with anhydrous $MgSO_4$, then the solvent was removed using a rotary evaporator, and target Compound 2-8 (8.0 g, 100%) was obtained without further purification.

9) Preparation of Compound 2

After adding 9-bromo-10-phenylanthracene (5.6 g, 16.9 mmol), $Pd(PPh_3)_4$ (0.8 g, 0.71 mmol), $K_2CO_3$ (5.8 g, 42.3 mmol) and tolene/EtOH/$H_2O$ to Compound 2-8 (8.0 g, 14.1 mmol), the result was stirred for 2 hours at 110° C. After the reaction was completed, the result was cooled to room temperature, and extracted with distilled water and EA. The organic layer was dried with anhydrous $MgSO_4$, then the solvent was removed using a rotary evaporator, and the result was purified using column chromatography with dichloromethane and hexane as a developing solvent to obtain target Compound 2 (8.4 g, 86%).

<Preparation Example 2> Preparation of Compound 5

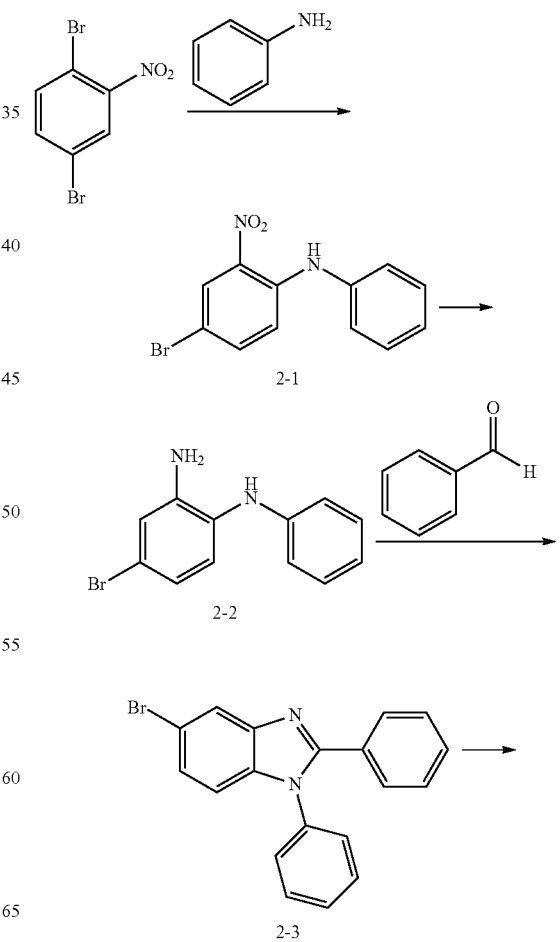

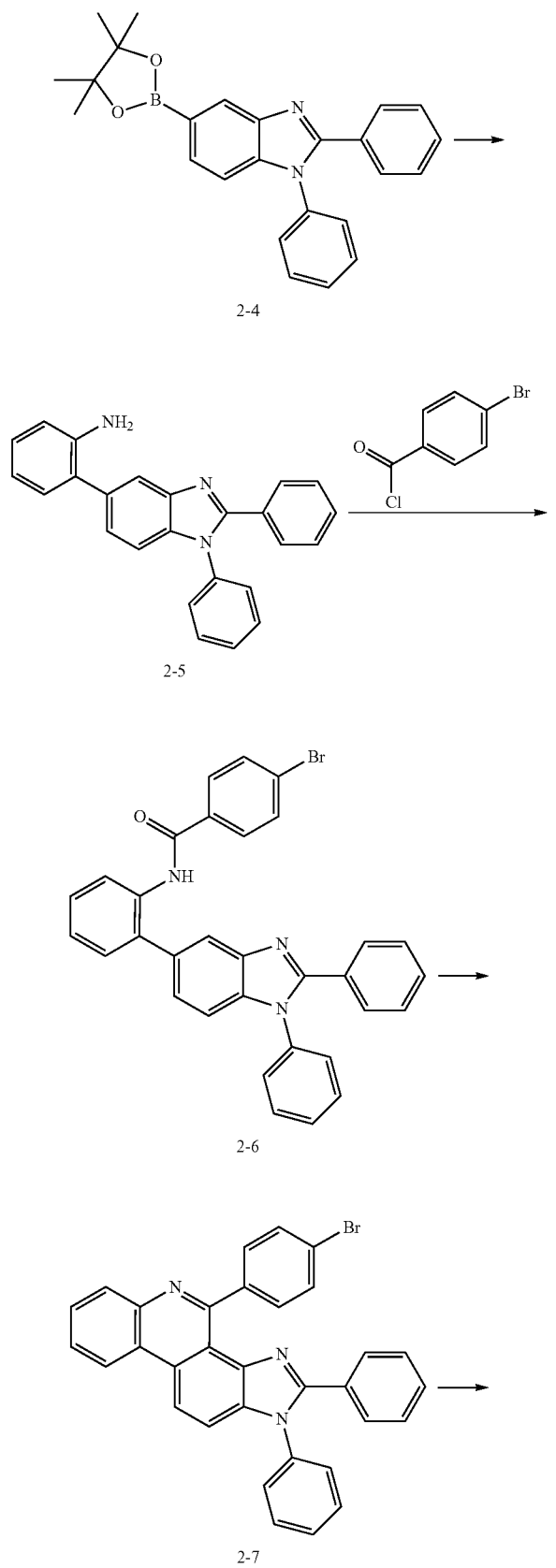

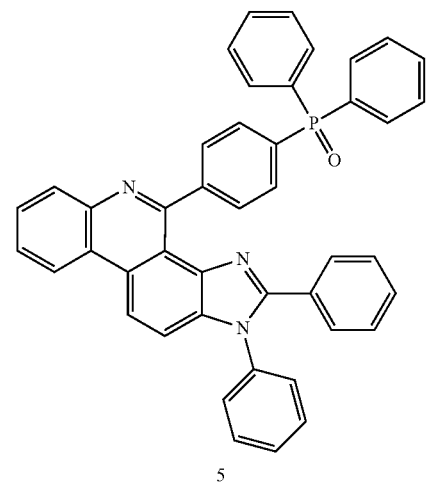

5

After dissolving Compound 2-7 (7.1 g, 13.5 mmol) in THF, 2.5 M n-BuLi (7.0 ml, 17.6 mmol) was slowly added dropwise thereto at −78° C., and the result was stirred for 30 minutes. Chlorodiphenylphosphine (3.3 ml, 17.6 mmol) was added thereto, and the result was stirred for 1 hour. After the reaction was completed, methanol was added thereto, and the result was stirred for 1 hour, and then extracted with distilled water and EA. The organic layer was dried with anhydrous MgSO$_4$, and then the solvent was removed using a rotary evaporator. The concentrated liquid was dissolved by adding dichloromethane (150 ml), then hydrogen peroxide (7.0 ml) was added thereto, and the result was stirred for 3 hours at room temperature. After the reaction was completed, the result was extracted with distilled water and EA. The organic layer was dried with anhydrous MgSO$_4$, and then the solvent was removed using a rotary evaporator. The result was dissolved by adding toluene and heating, and then recrystallized to obtain target Compound 5 (7.1 g, 81%).

<Preparation Example 3> Preparation of Compound 10

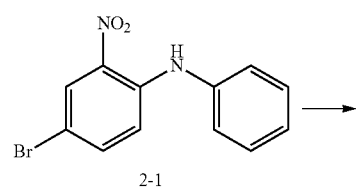

2-1

-continued

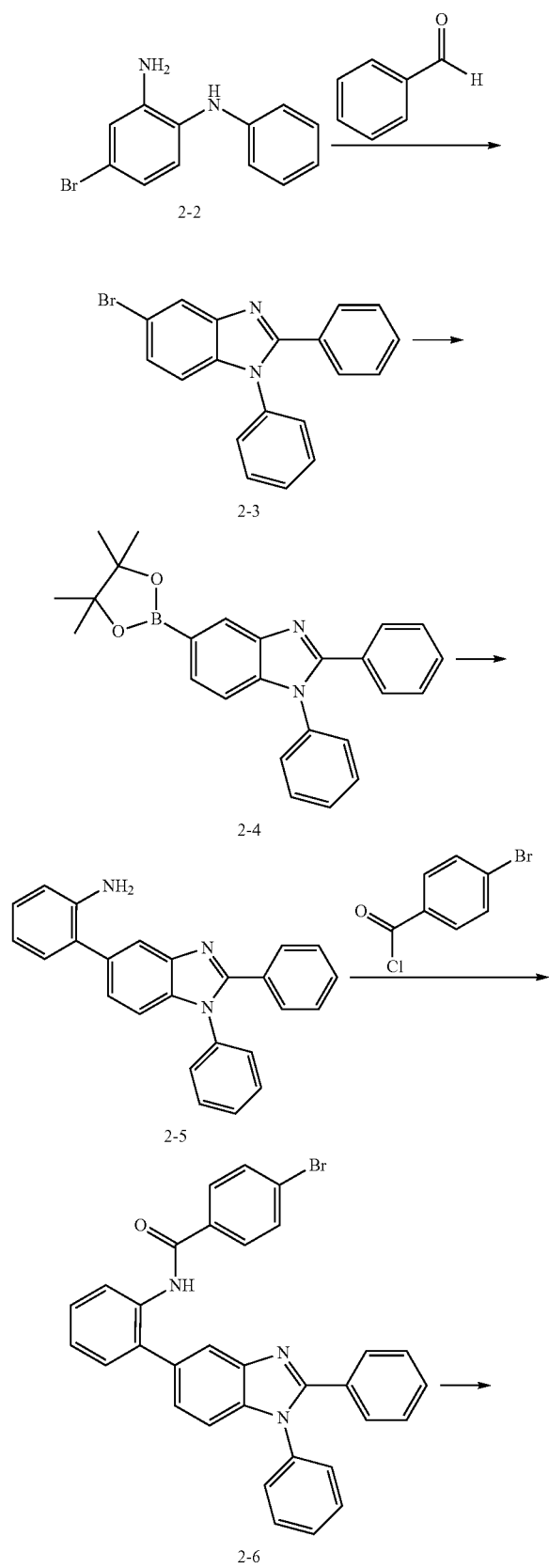

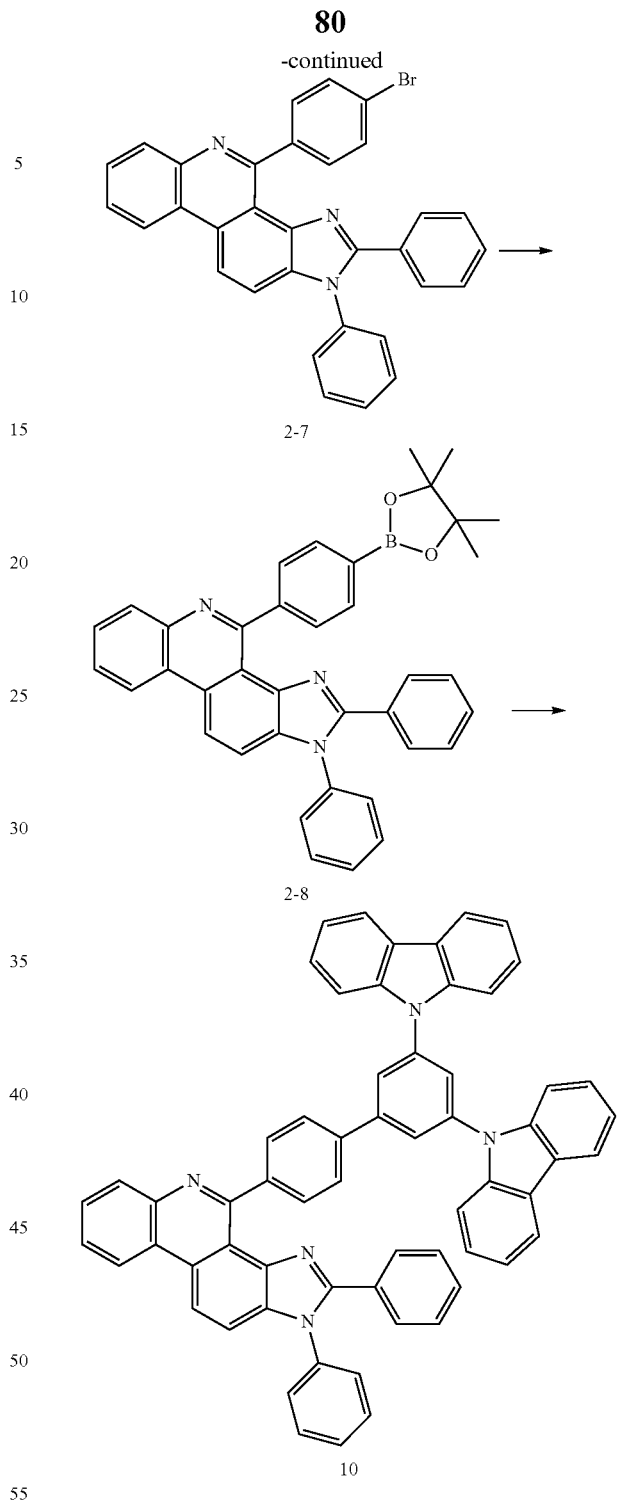

After adding 9-bromo-10-phenylanthracene (5.6 g, 16.9 mmol), Pd(PPh$_3$)$_4$ (0.8 g, 0.71 mmol), K$_2$CO$_3$ (5.8 g, 42.3 mmol) and tolene/EtOH/H$_2$O to Compound 2-8 (8.0 g, 14.1 mmol), the result was stirred for 2 hours at 110° C. After the reaction was completed, the result was cooled to room temperature, and extracted with distilled water and EA. The organic layer was dried with anhydrous MgSO$_4$, then the solvent was removed using a rotary evaporator, and the result was purified using column chromatography with dichloromethane and hexane as a developing solvent to obtain target Compound 10 (8.4 g, 86%).

<Preparation Example 4> Preparation of Compound 11
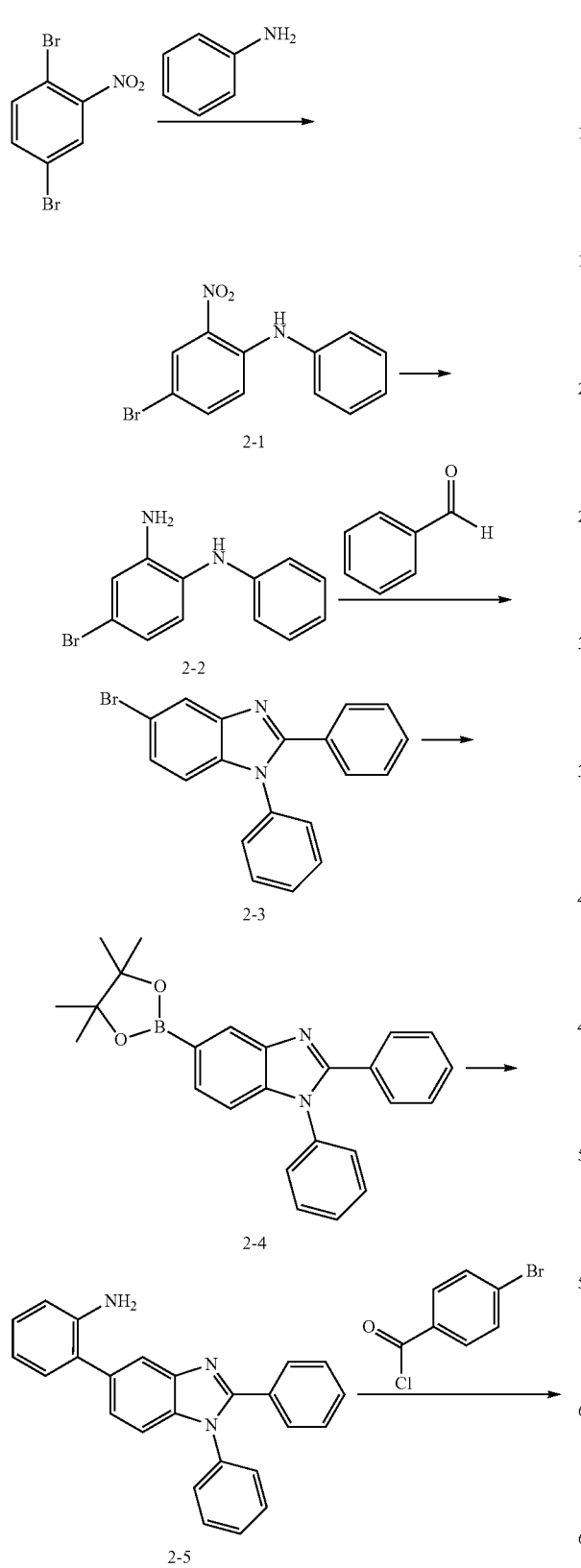
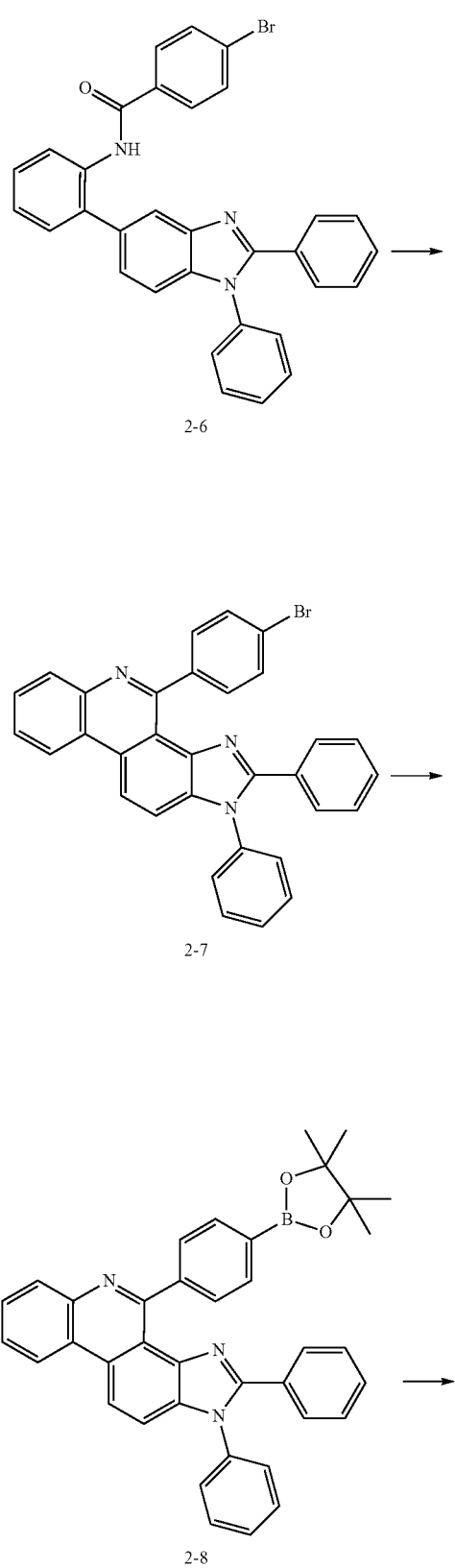

83
-continued
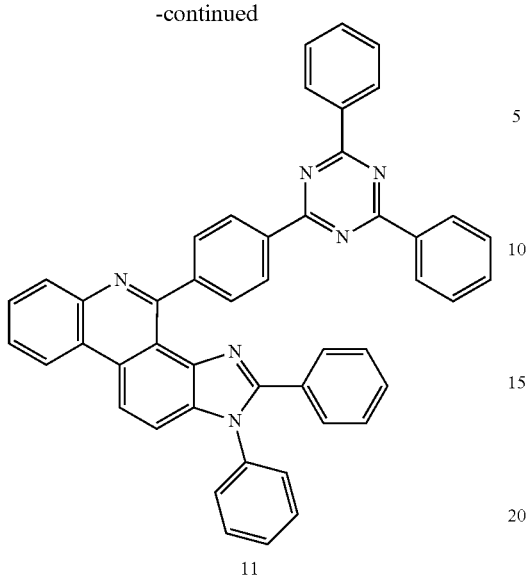
11
Target Compound 11 was obtained in the same manner as Compound 2 in Preparation Example 1, except that 2-bromo-4,6-diphenyl-1,3,5-triazine was used instead of 9-bromo-10-phenylanthracene.
<Preparation Example 5> Preparation of Compound 15
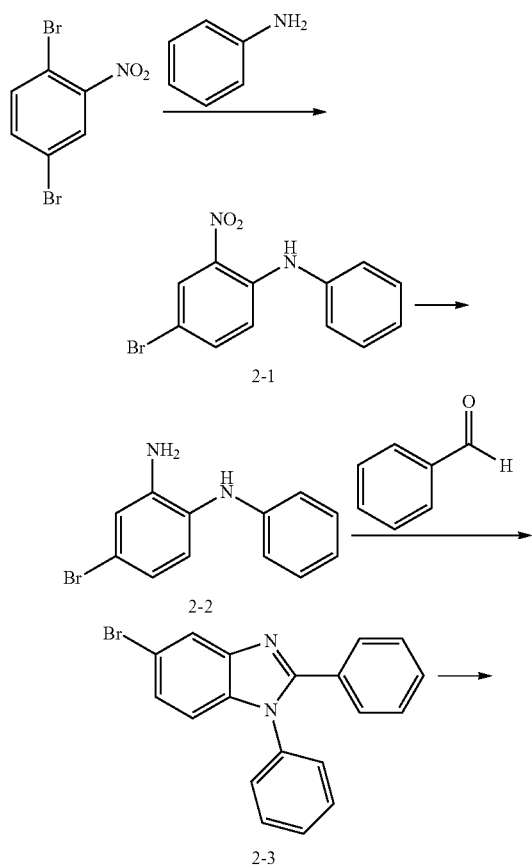
84
-continued
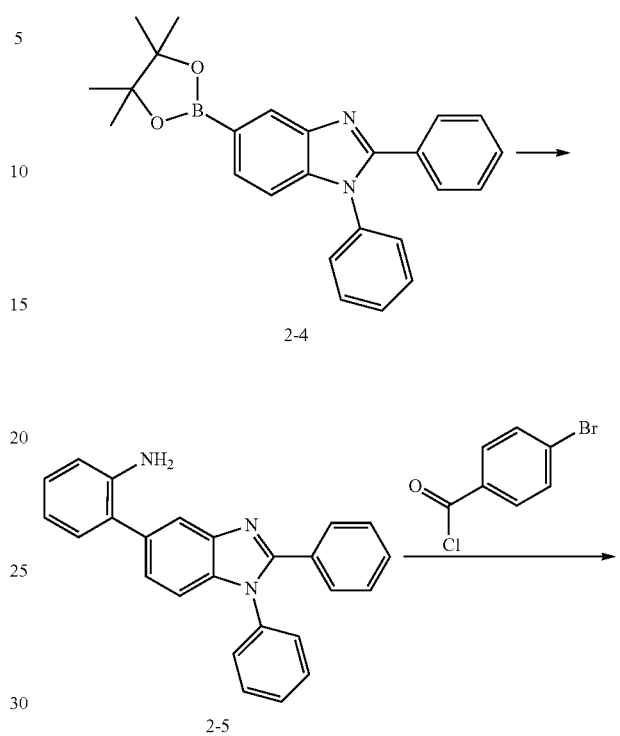
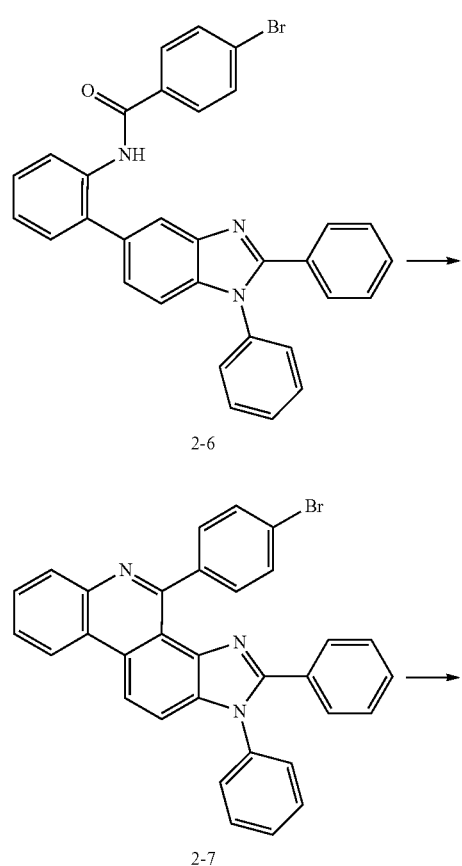

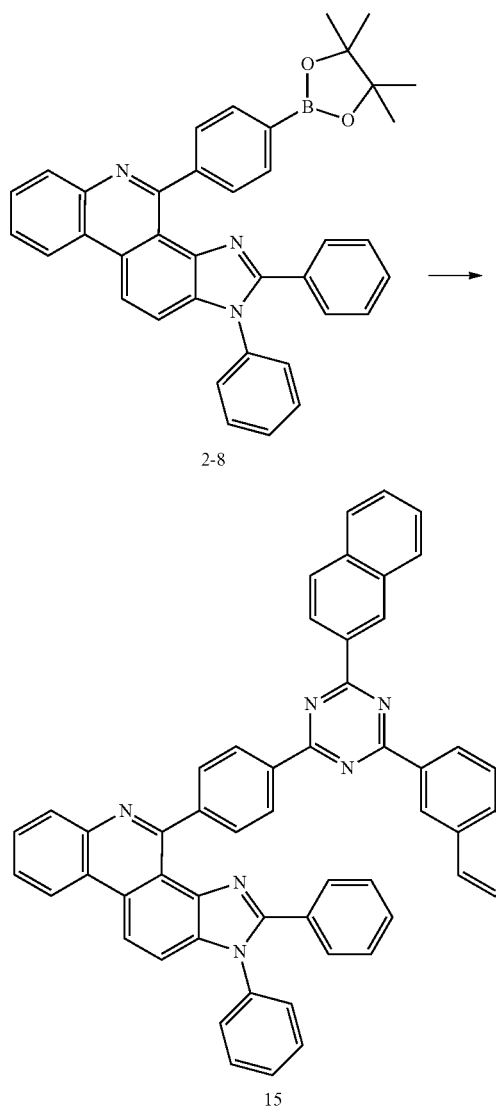
Target Compound 15 was obtained in the same manner as Compound 2 in Preparation Example 1, except that 2-bromo-4,6-di(naphthalen-2-yl)-1,3,5-triazine was used instead of 9-bromo-10-phenylanthracene.
<Preparation Example 6> Preparation of Compound 25
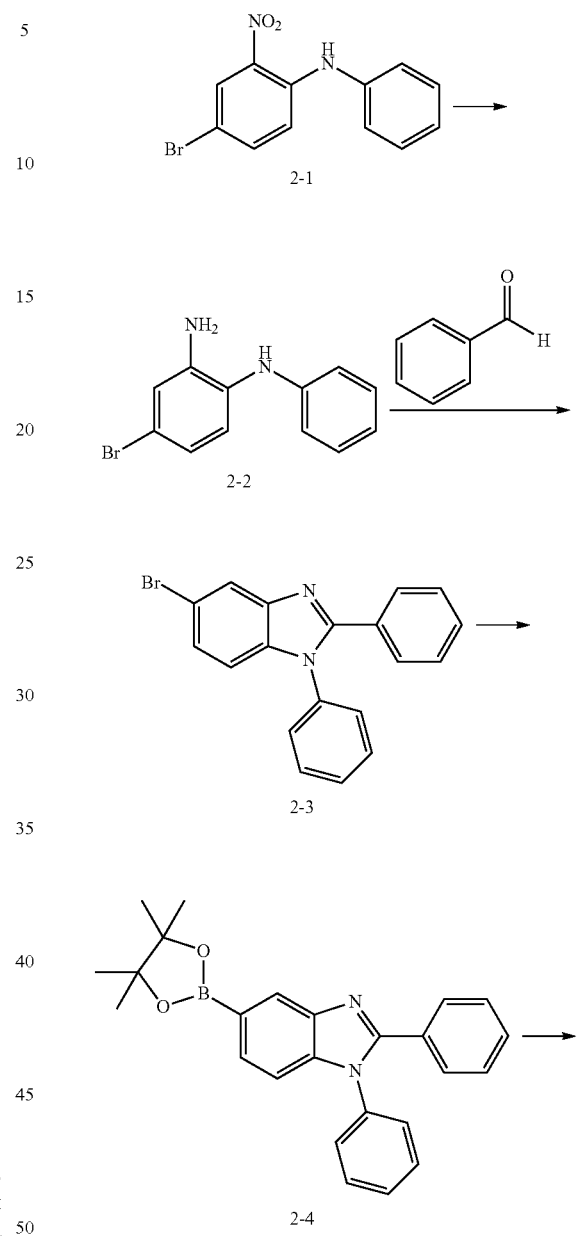

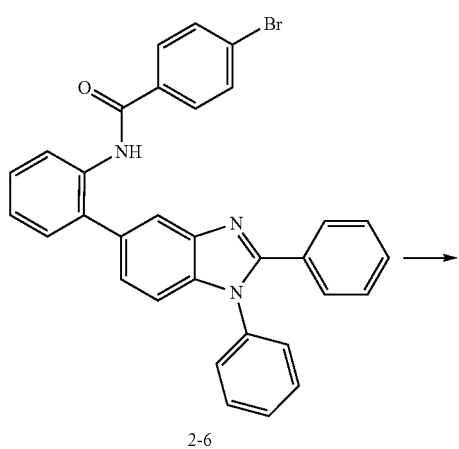
2-6
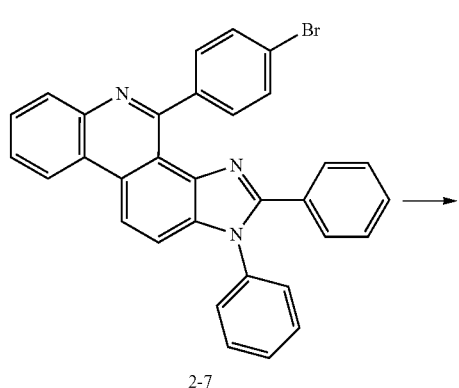
2-7
2-8
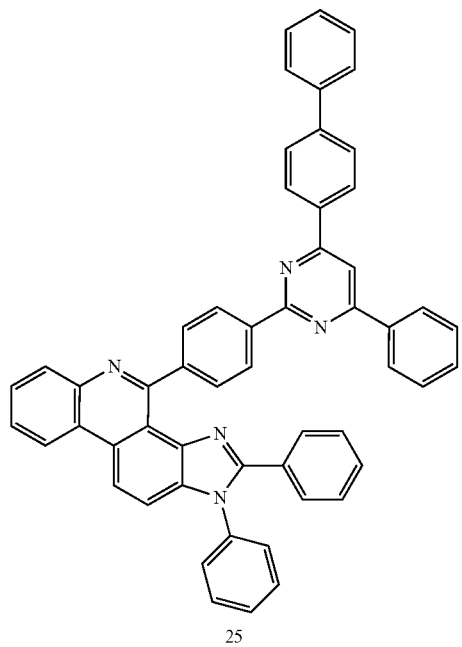 [SMILES: c1ccc(-c2ccc(-c3cc(-c4ccccc4)nc(-c4ccc(-c5nc6ccccc6c6ccc7c(nc(-c8ccccc8)n7-c7ccccc7)c56)cc4)n3)cc2)cc1]
25
Target Compound 25 was obtained in the same manner as Compound 2 in Preparation Example 1, except that 4-([1,1'-biphenyl]-4-yl)-2-bromo-6-phenylpyrimidine was used instead of 9-bromo-10-phenylanthracene.
<Preparation Example 7> Preparation of Compound 55
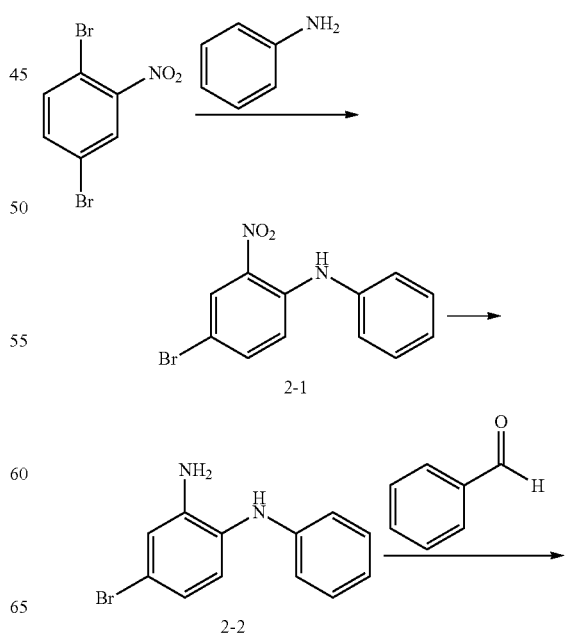

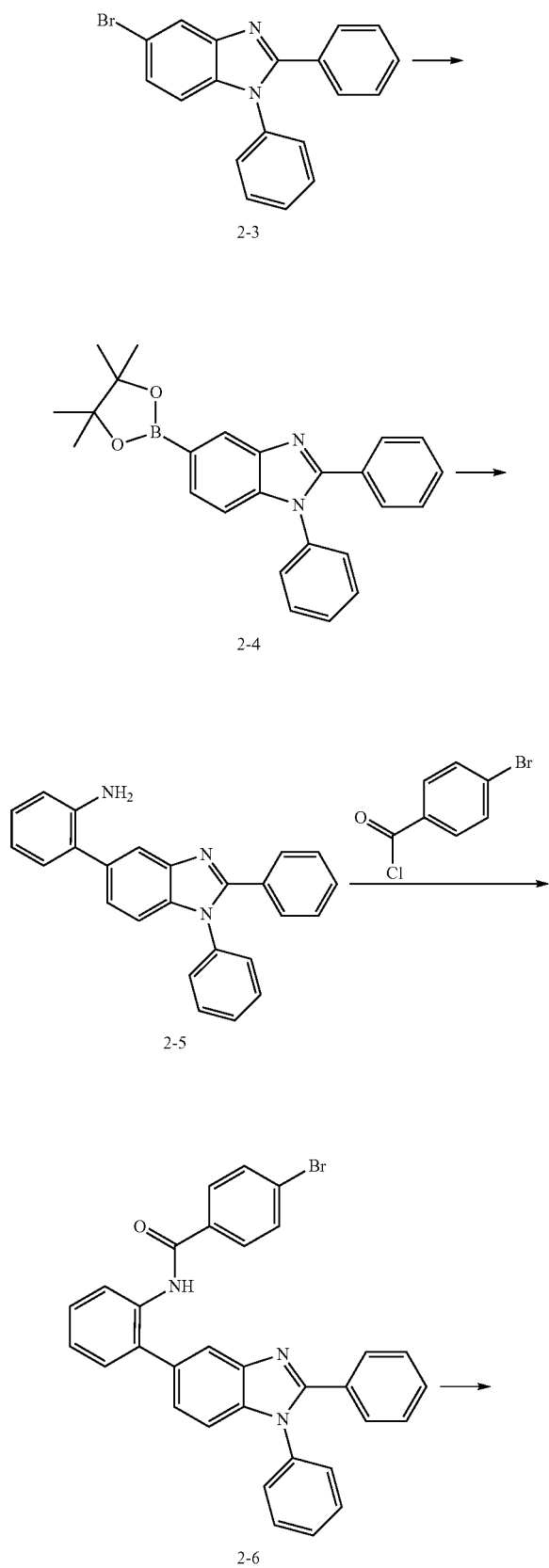
2-3
2-4
2-5
2-6
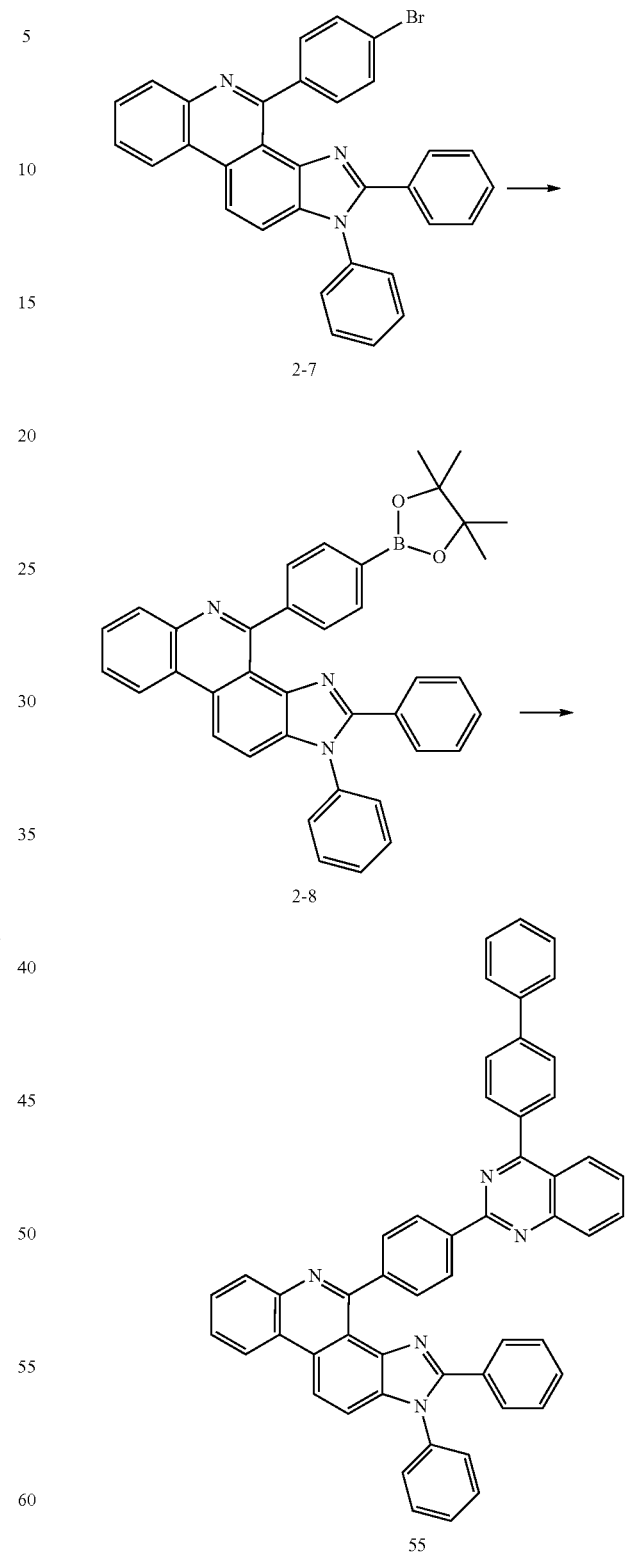
2-7
2-8
55
Target Compound 55 was obtained in the same manner as Compound 2 in Preparation Example 1, except that 4-([1,1'-biphenyl]-4-yl)-2-bromoquinazoline was used instead of 9-bromo-10-phenylanthracene.

<Preparation Example 8> Preparation of Compound 70
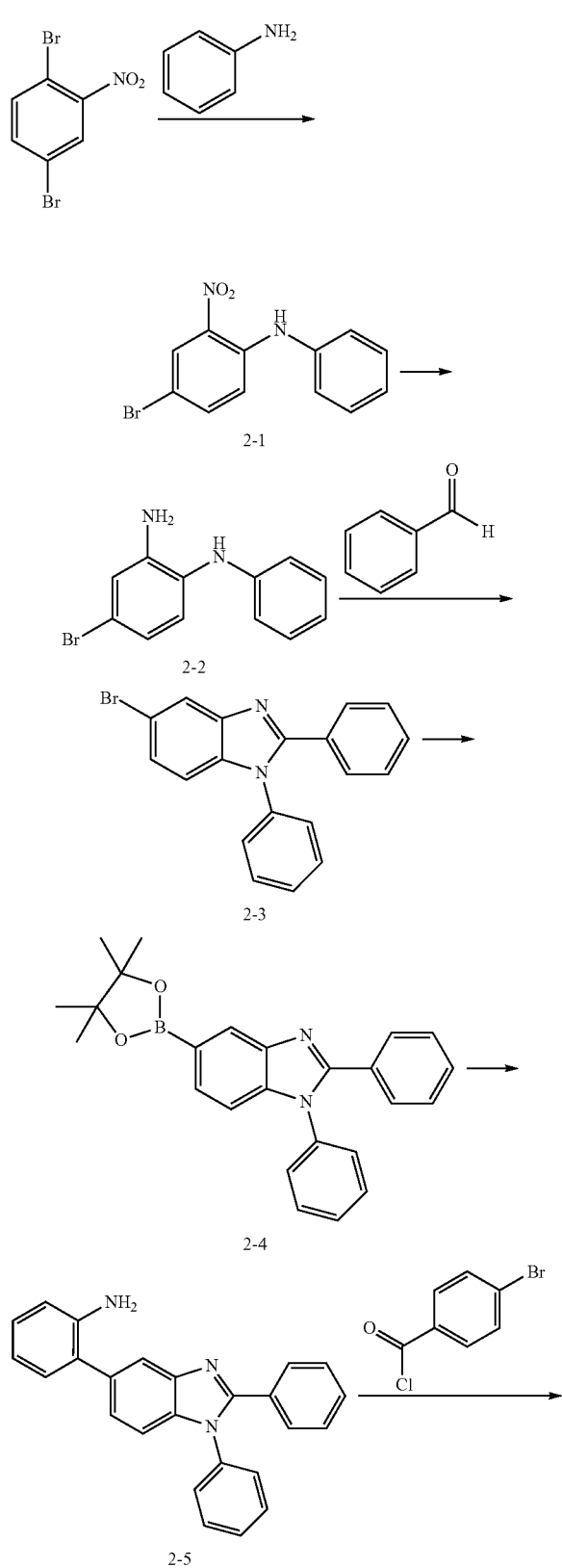
2-1
2-2
2-3
2-4
2-5
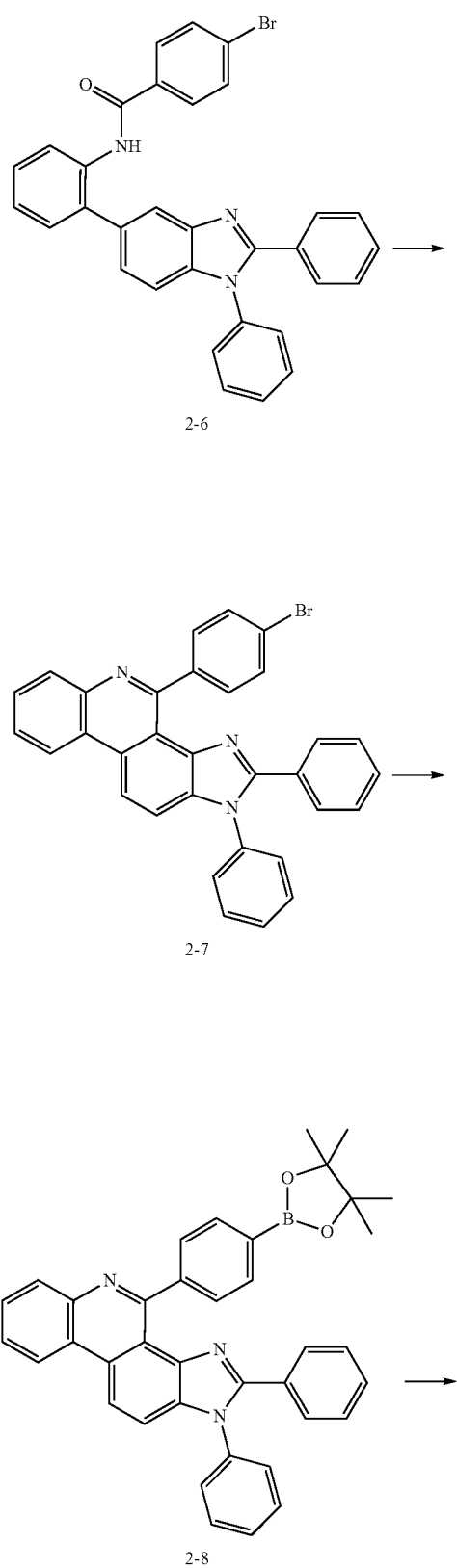
2-6
2-7
2-8

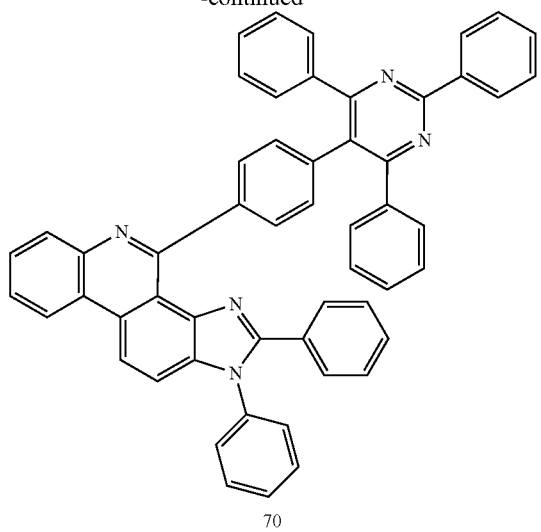
70
Target Compound 70 was obtained in the same manner as Compound 2 in Preparation Example 1, except that 5-bromo-2,4,6-triphenylpyrimidine was used instead of 9-bromo-10-phenylanthracene.
<Preparation Example 9> Preparation of Compound 89
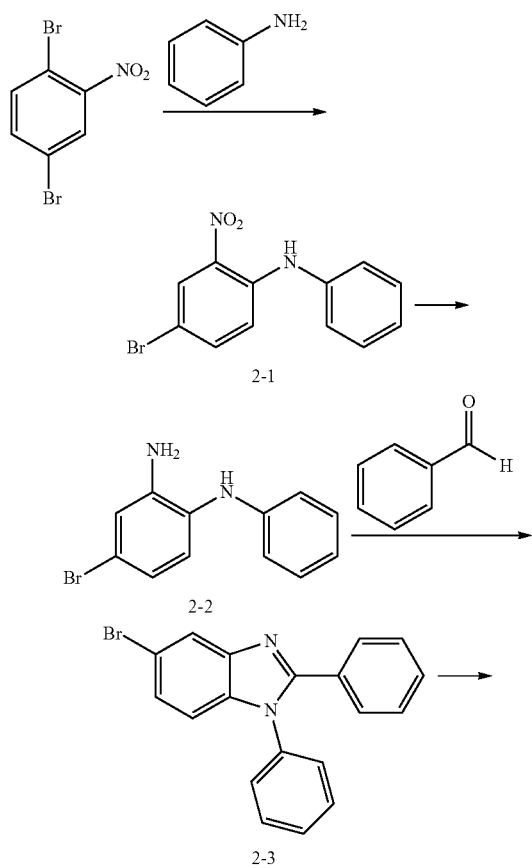
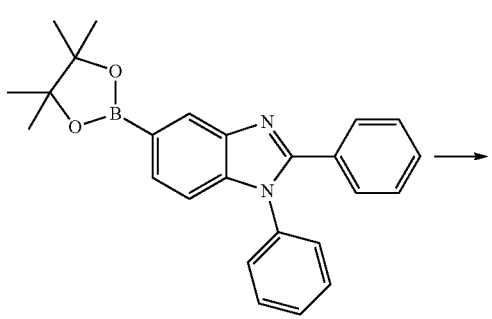
2-4
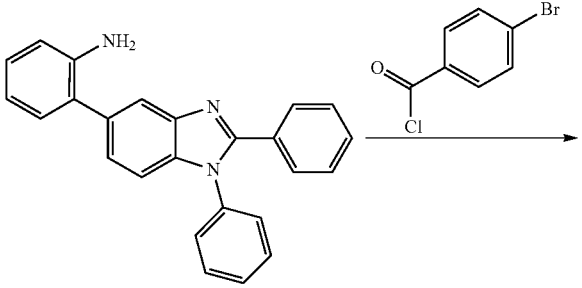
2-5
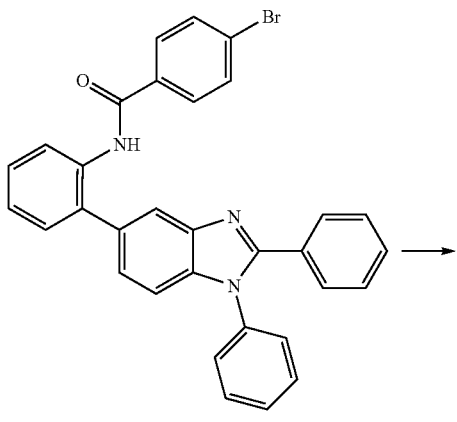
2-6
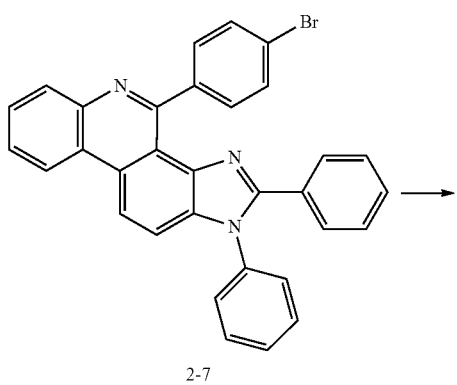
2-7

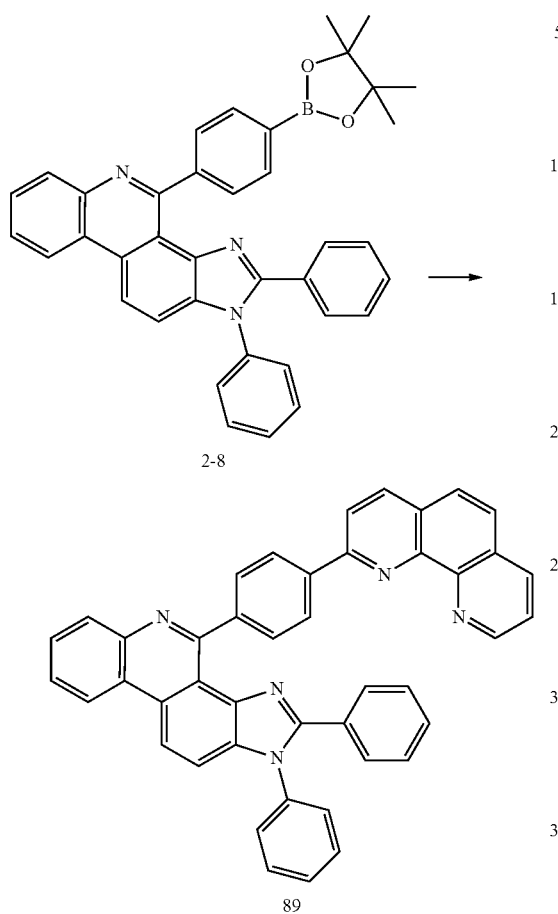
Target Compound 89 was obtained in the same manner as Compound 2 in Preparation Example 1, except that 2-bromo-1,10-phenanthroline was used instead of 9-bromo-10-phenylanthracene.
<Preparation Example 10> Preparation of Compound 94
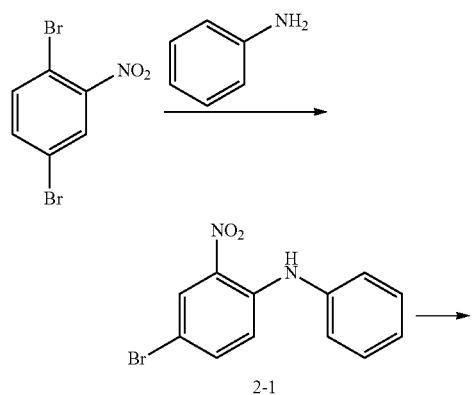
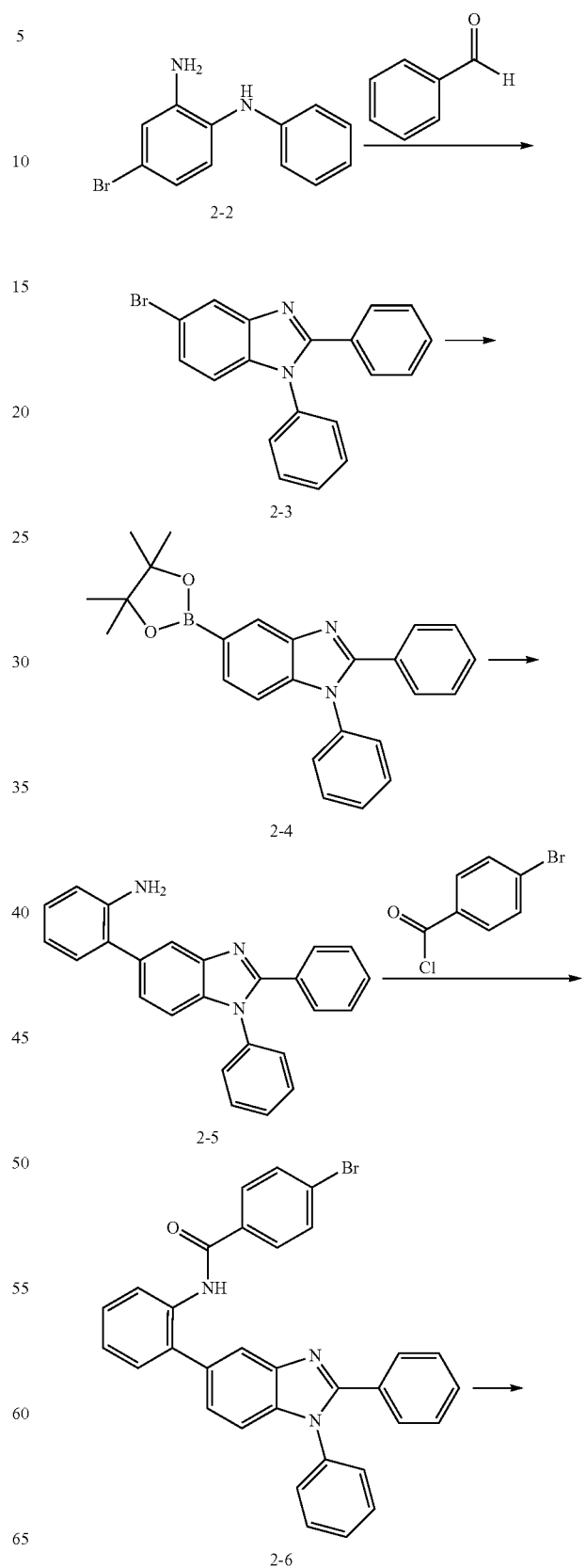

97
-continued
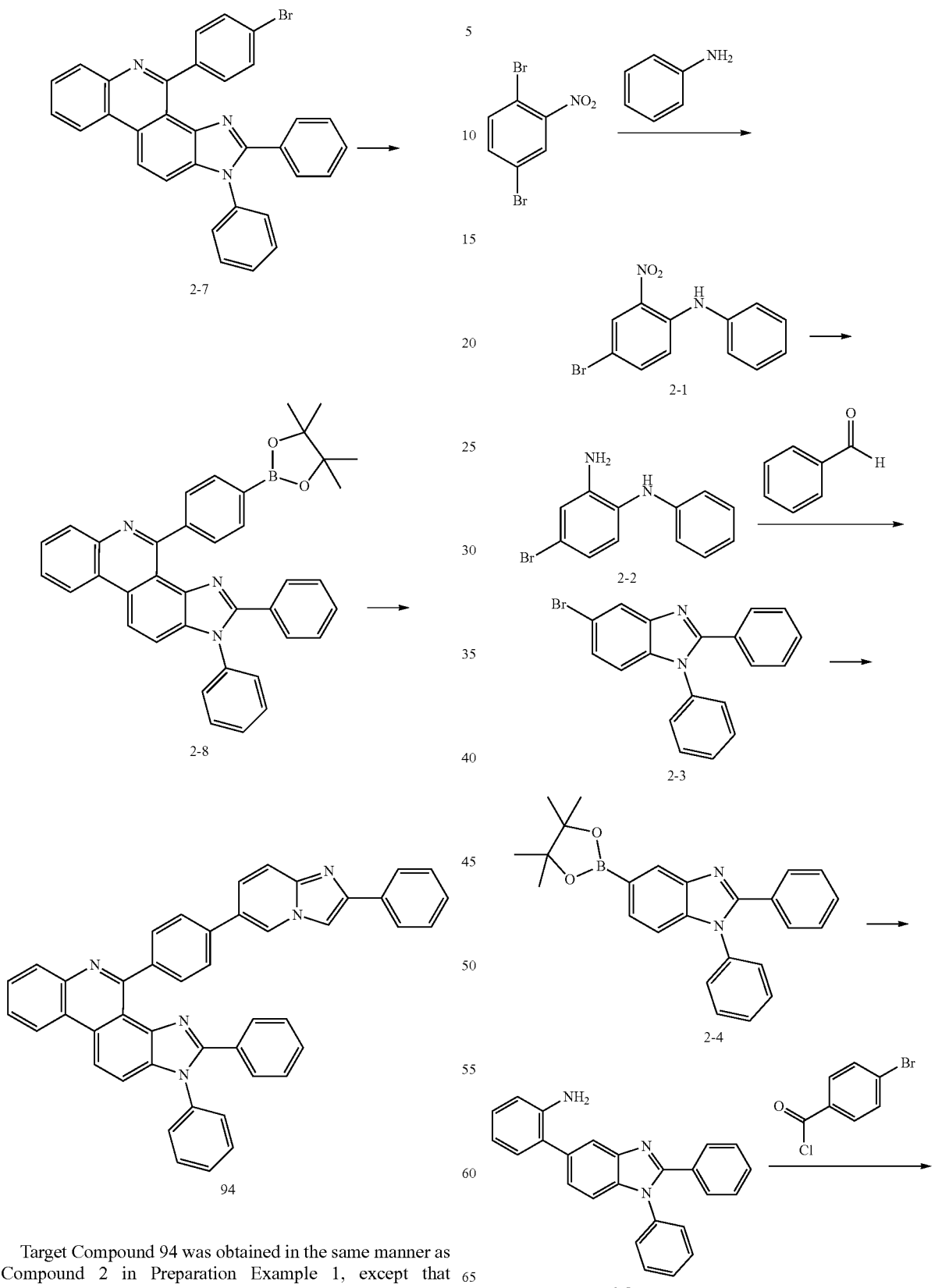
Target Compound 94 was obtained in the same manner as Compound 2 in Preparation Example 1, except that 6-bromo-2-phenylimidazo[1,2-a]pyridine was used instead of 9-bromo-10-phenylanthracene.
98
<Preparation Example 11> Preparation of Compound 101

-continued
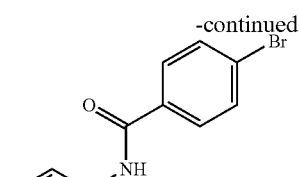
2-6
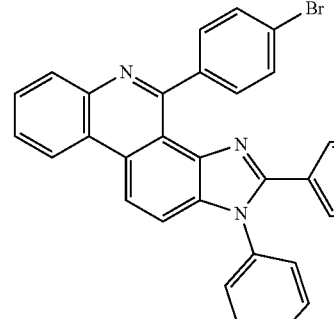
2-7
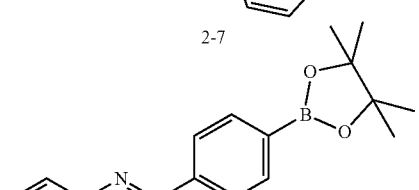
2-8
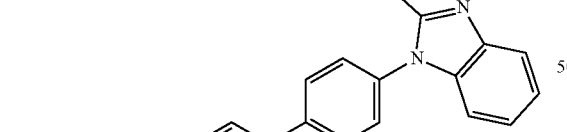
101
Target Compound 101 was obtained in the same manner as Compound 2 in Preparation Example 1, except that 1-(4-bromophenyl)-2-ethyl-1H-benzo[d]imidazole was used instead of 9-bromo-10-phenylanthracene.
<Preparation Example 12> Preparation of Compound 104
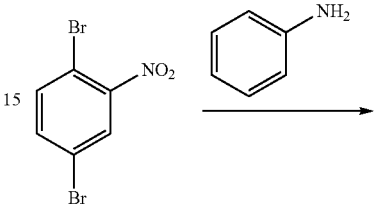
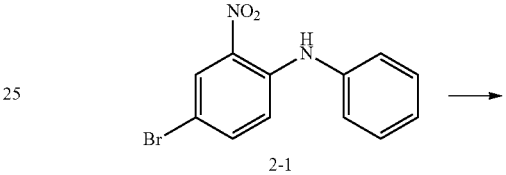
2-1
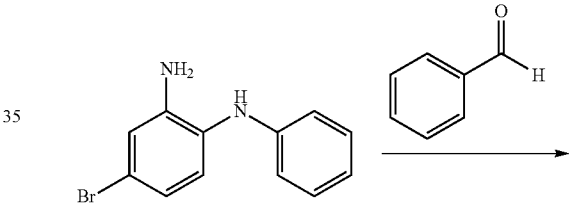
2-2
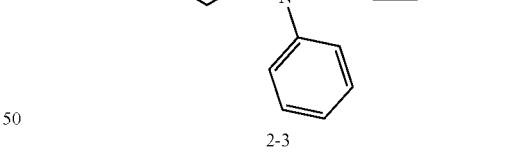
2-3
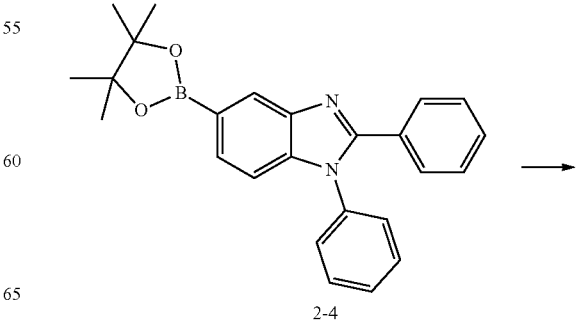
2-4

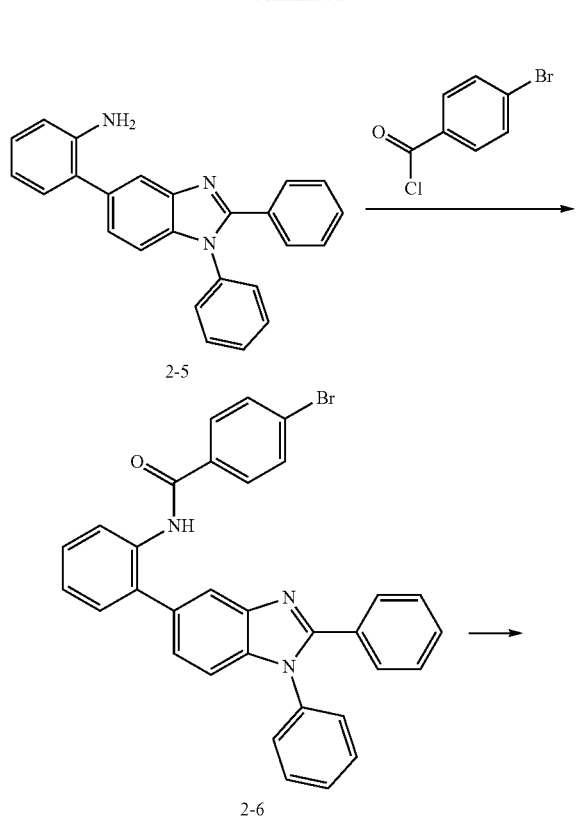
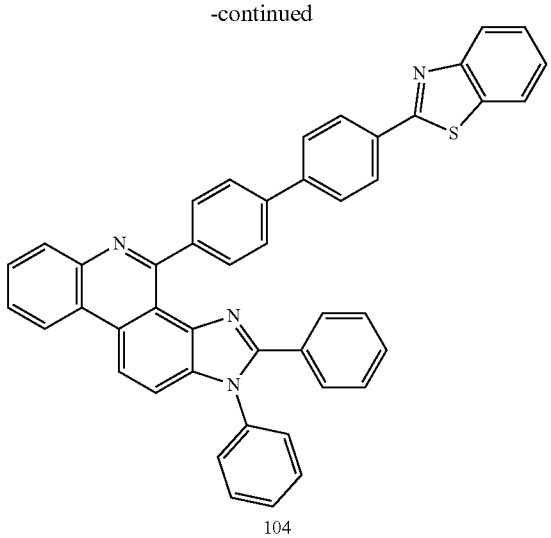
Target Compound 104 was obtained in the same manner as Compound 2 in Preparation Example 1, except that 2-(4-bromophenyl)benzo[d]thiazole was used instead of 9-bromo-10-phenylanthracene.
<Preparation Example 13> Preparation of Compound 126
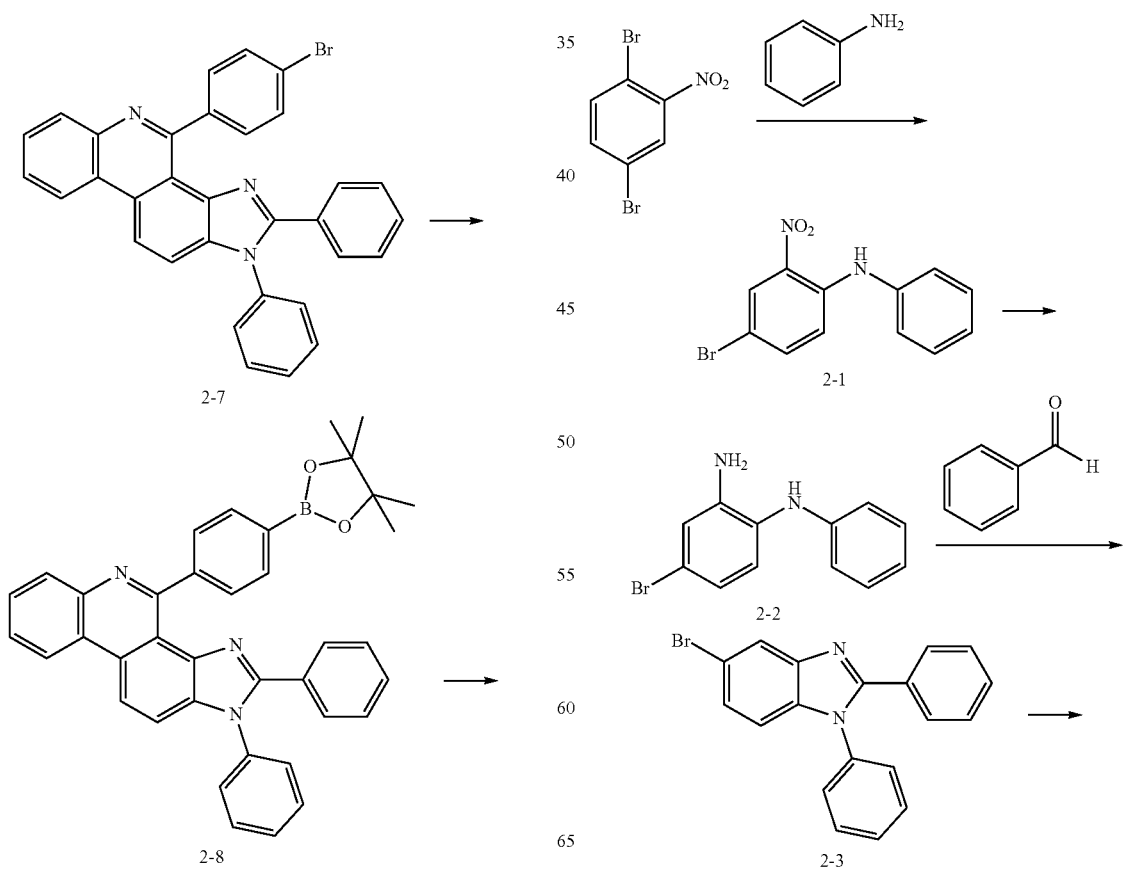

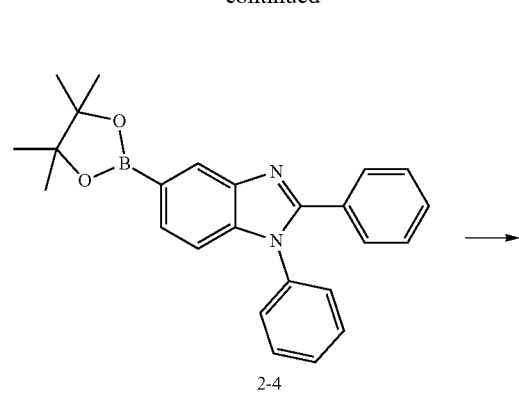
2-4
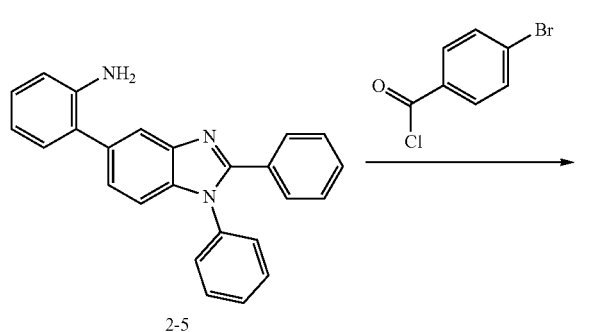
2-5
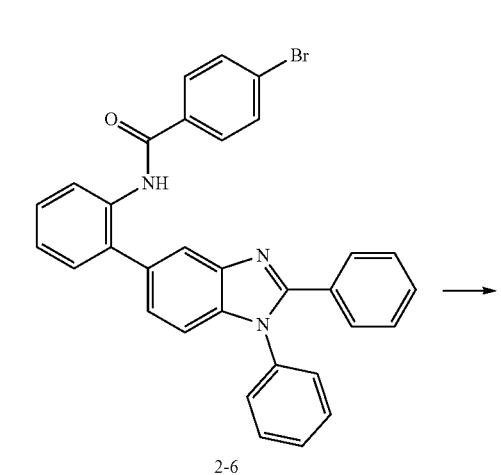
2-6
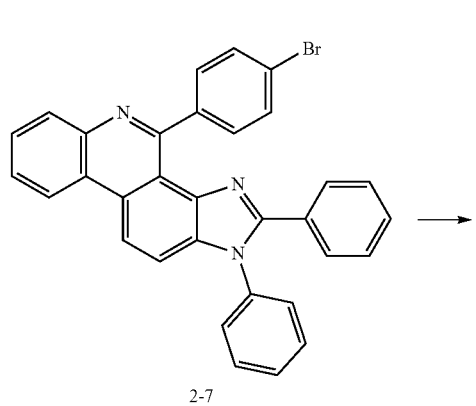
2-7
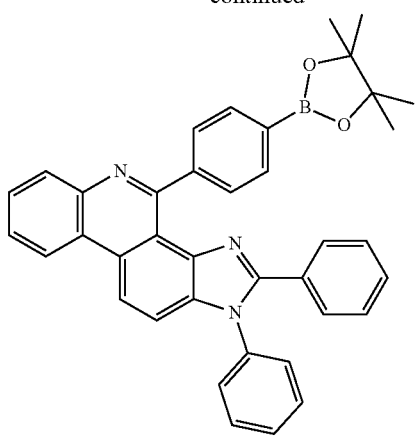
2-8
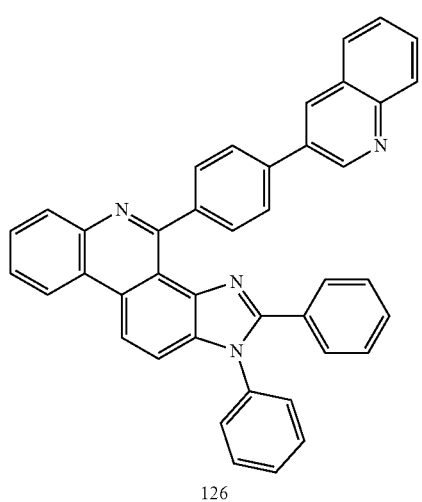
126
Target Compound 126 was obtained in the same manner as Compound 2 in Preparation Example 1, except that 3-bromoquinoline was used instead of 9-bromo-10-phenylanthracene.
<Preparation Example 14> Preparation of Compound 131
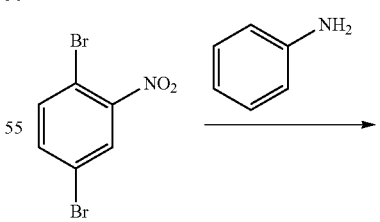
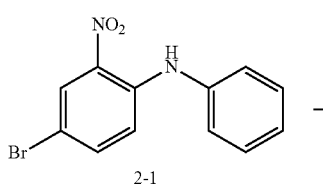
2-1

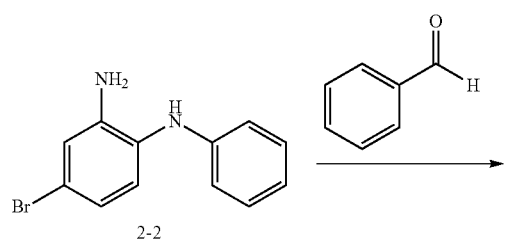
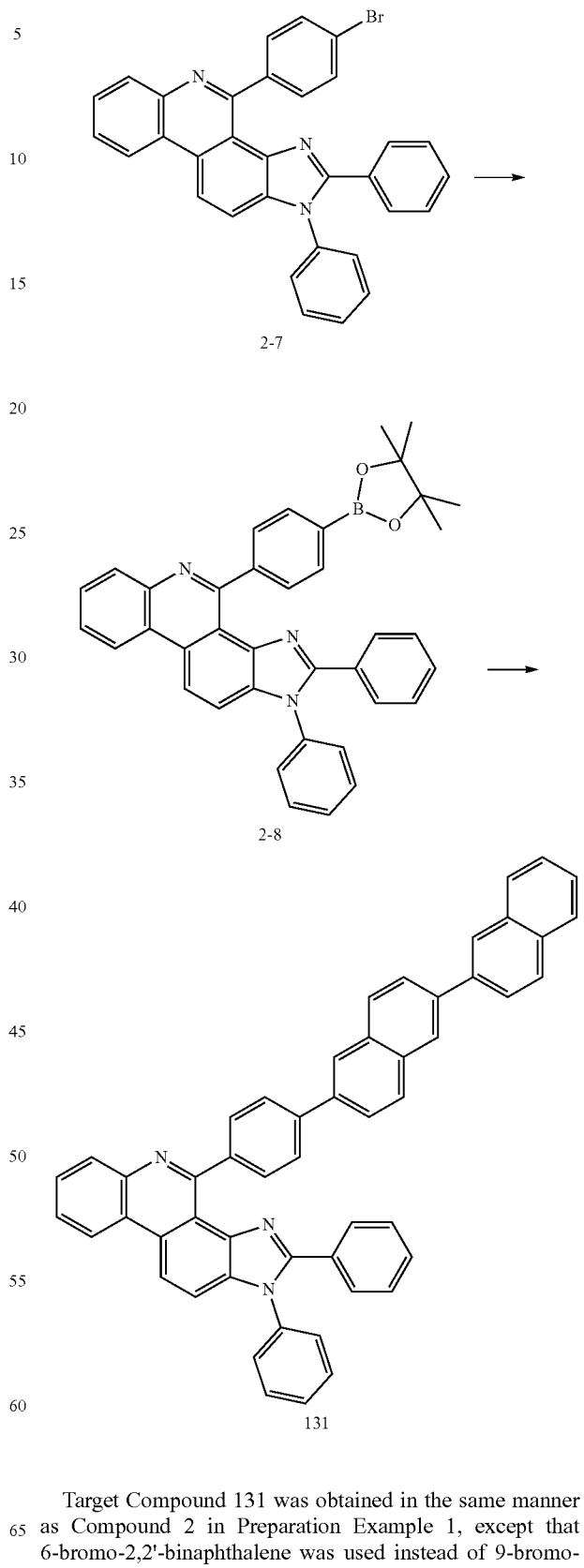
Target Compound 131 was obtained in the same manner as Compound 2 in Preparation Example 1, except that 6-bromo-2,2'-binaphthalene was used instead of 9-bromo-10-phenylanthracene.

107
<Preparation Example 15> Preparation of Compound 133
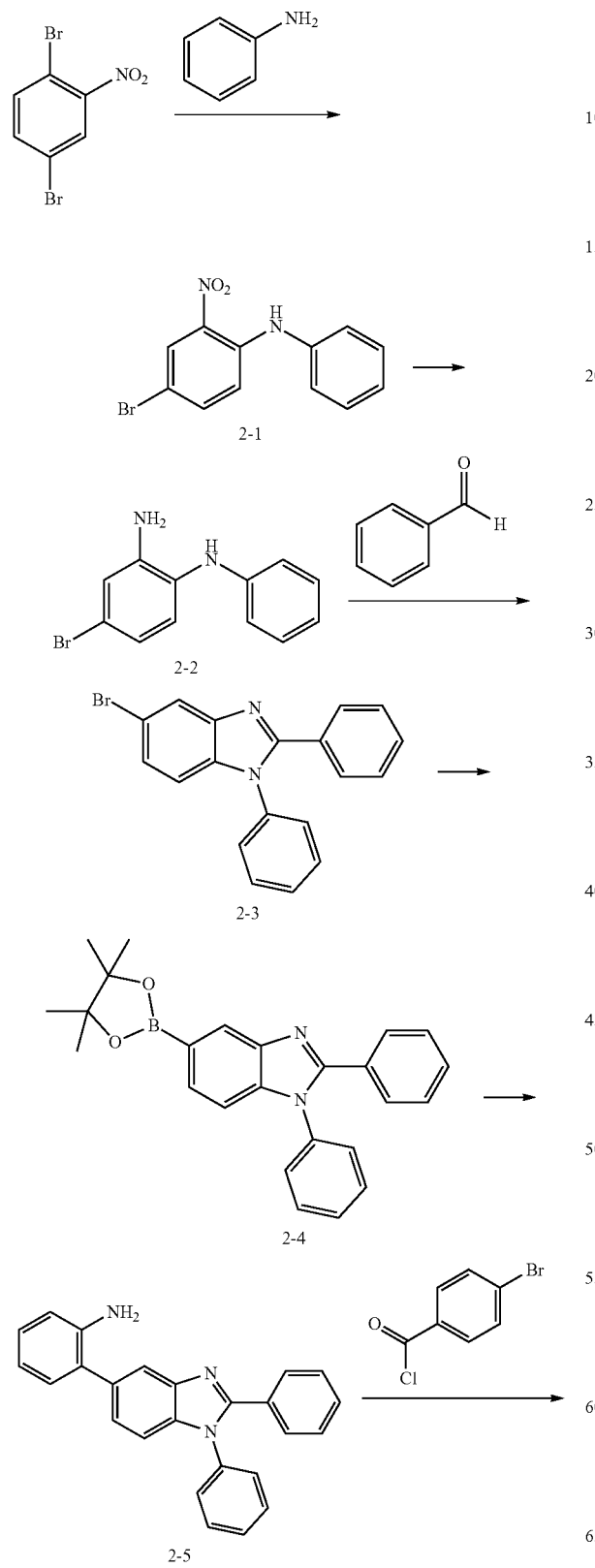
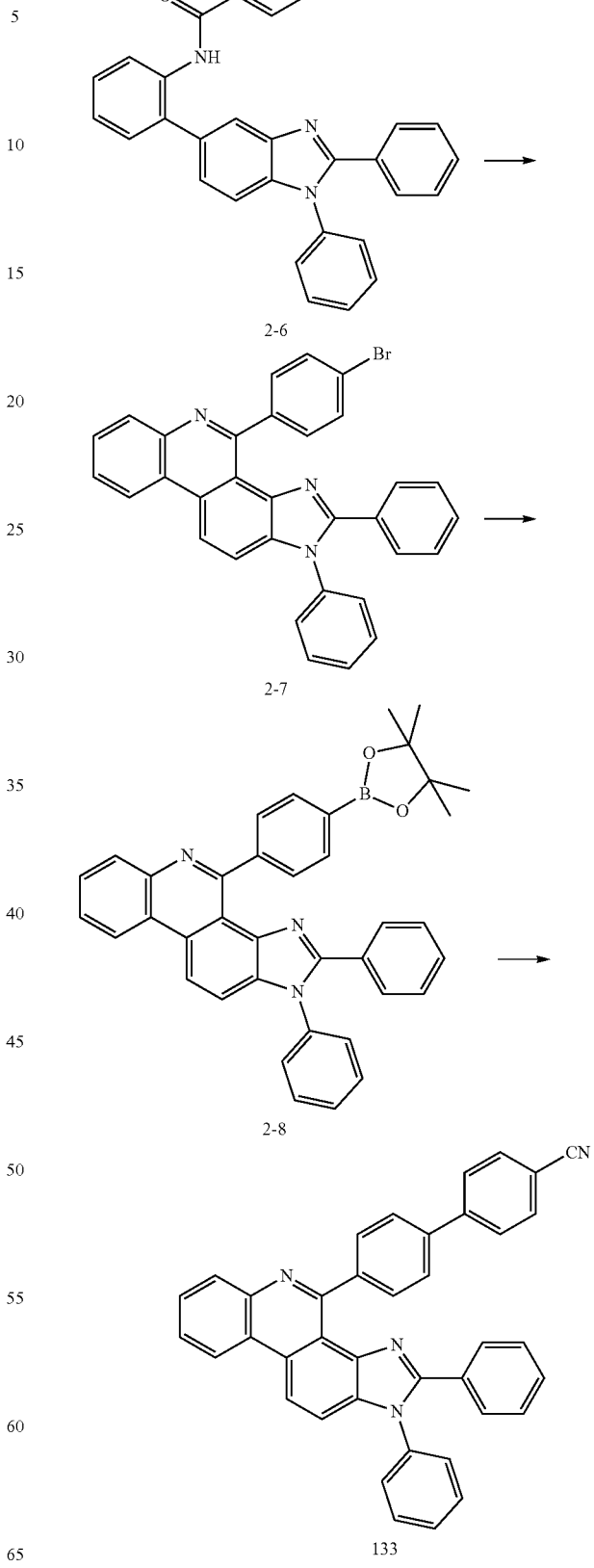

Target Compound 133 was obtained in the same manner as Compound 2 in Preparation Example 1, except that 4-bromobenzonitrile was used instead of 9-bromo-10-phenylanthracene.
<Preparation Example 16> Preparation of Compound 136
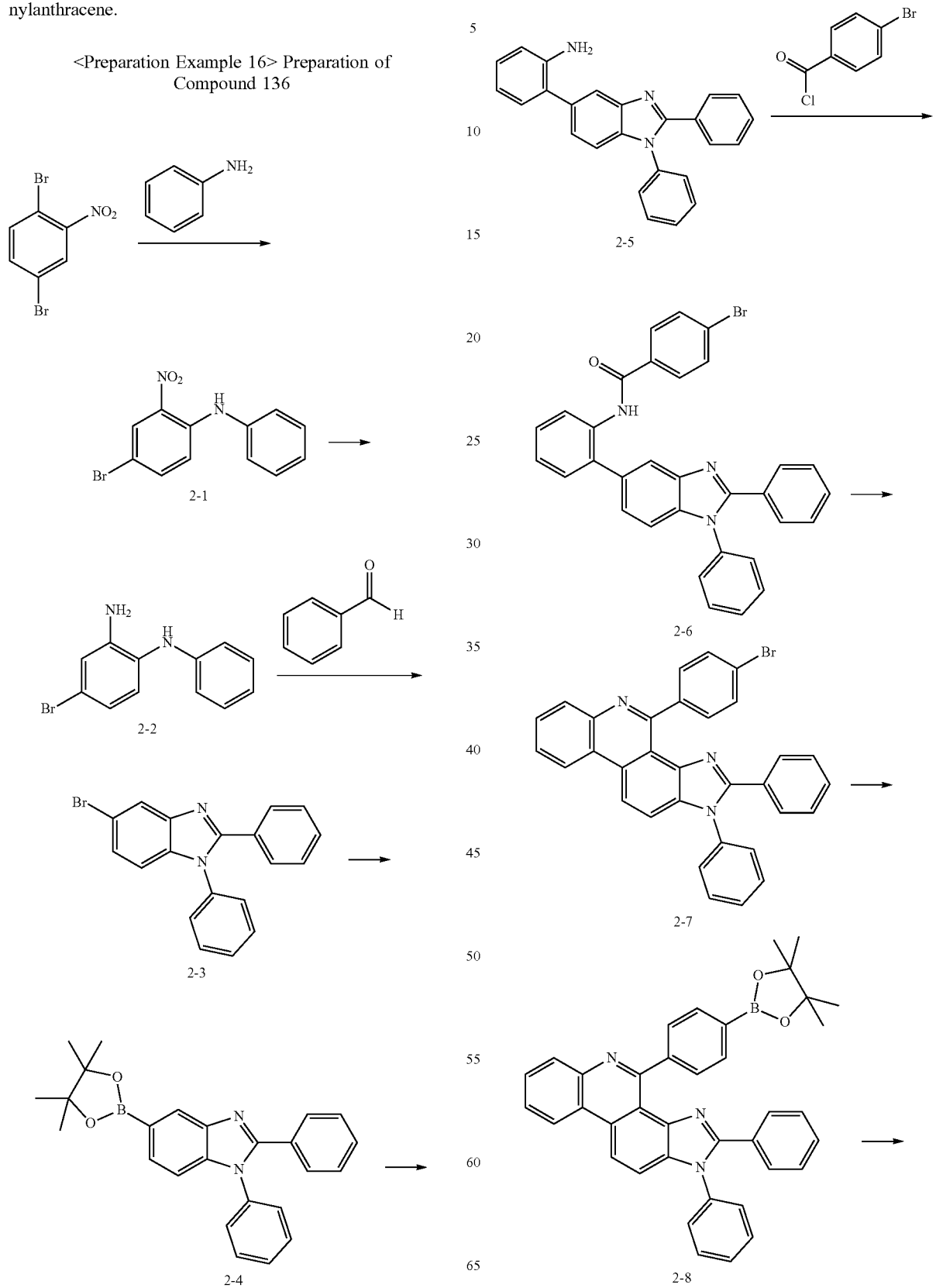

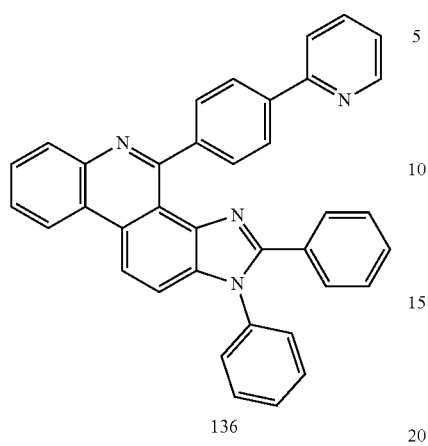
Target Compound 136 was obtained in the same manner as Compound 2 in Preparation Example 1, except that 2-bromopyridine was used instead of 9-bromo-10-phenylanthracene.
<Preparation Example 17> Preparation of Compound 152
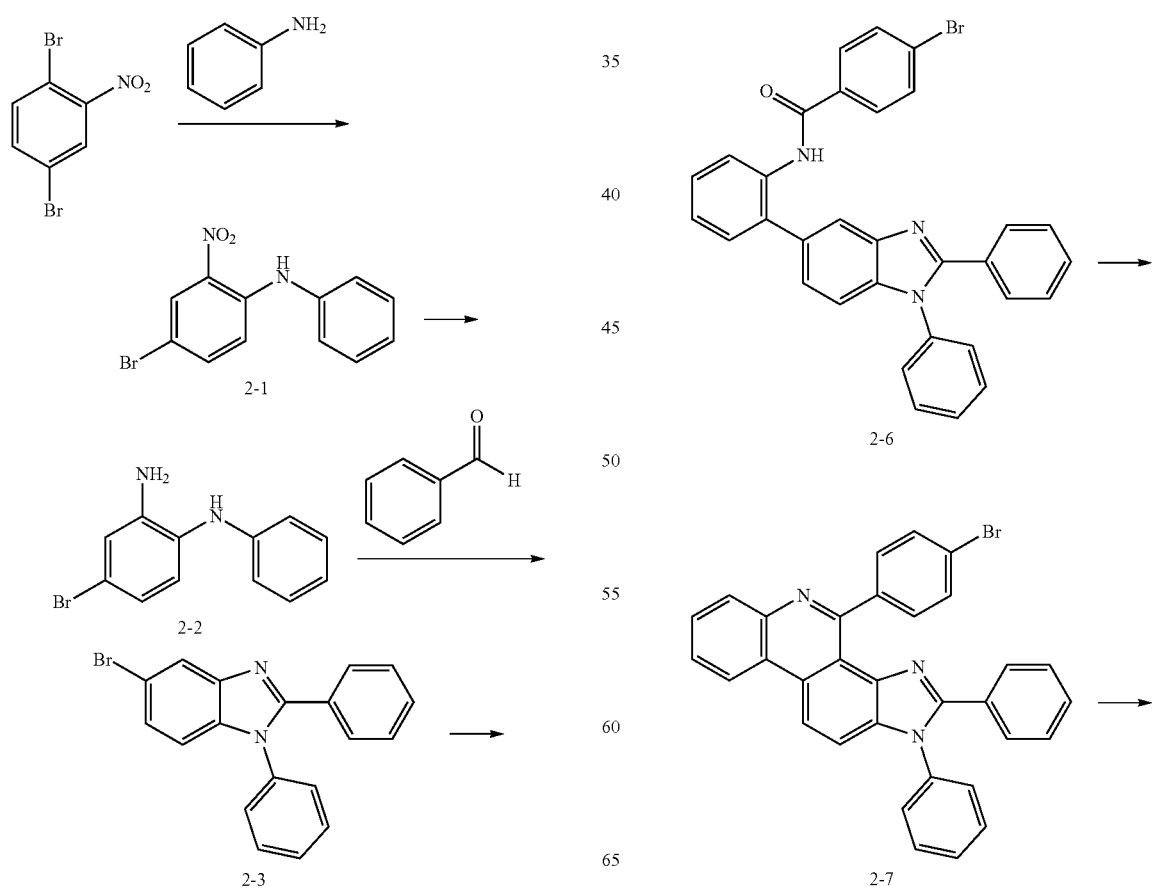
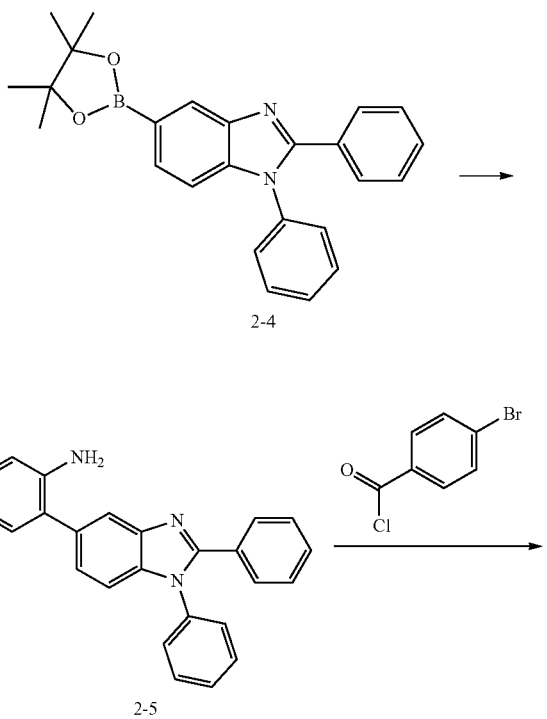

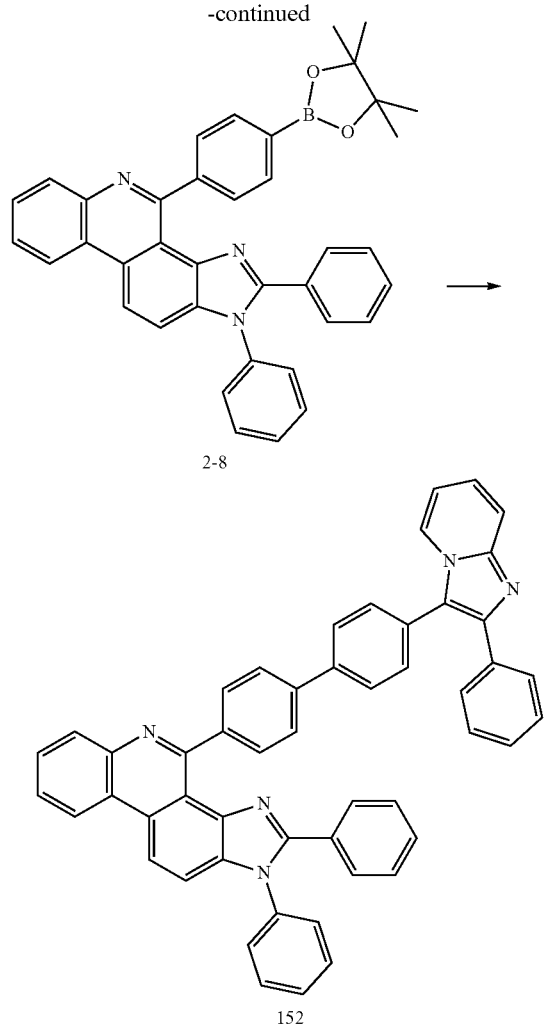
Target Compound 152 was obtained in the same manner as Compound 2 in Preparation Example 1, except that 3-(4-bromophenyl)-2-phenylimidazo[1,2-a]pyridine was used instead of 9-bromo-10-phenylanthracene.
<Preparation Example 18> Preparation of Compound 153
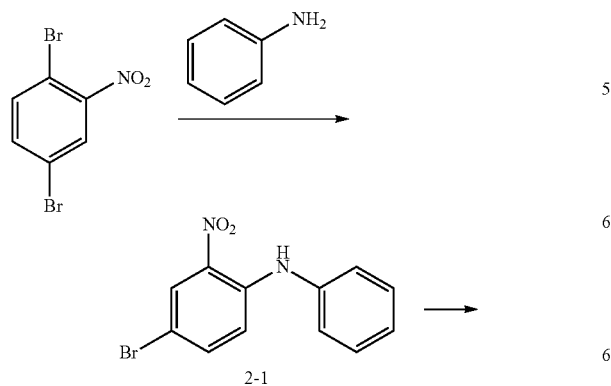
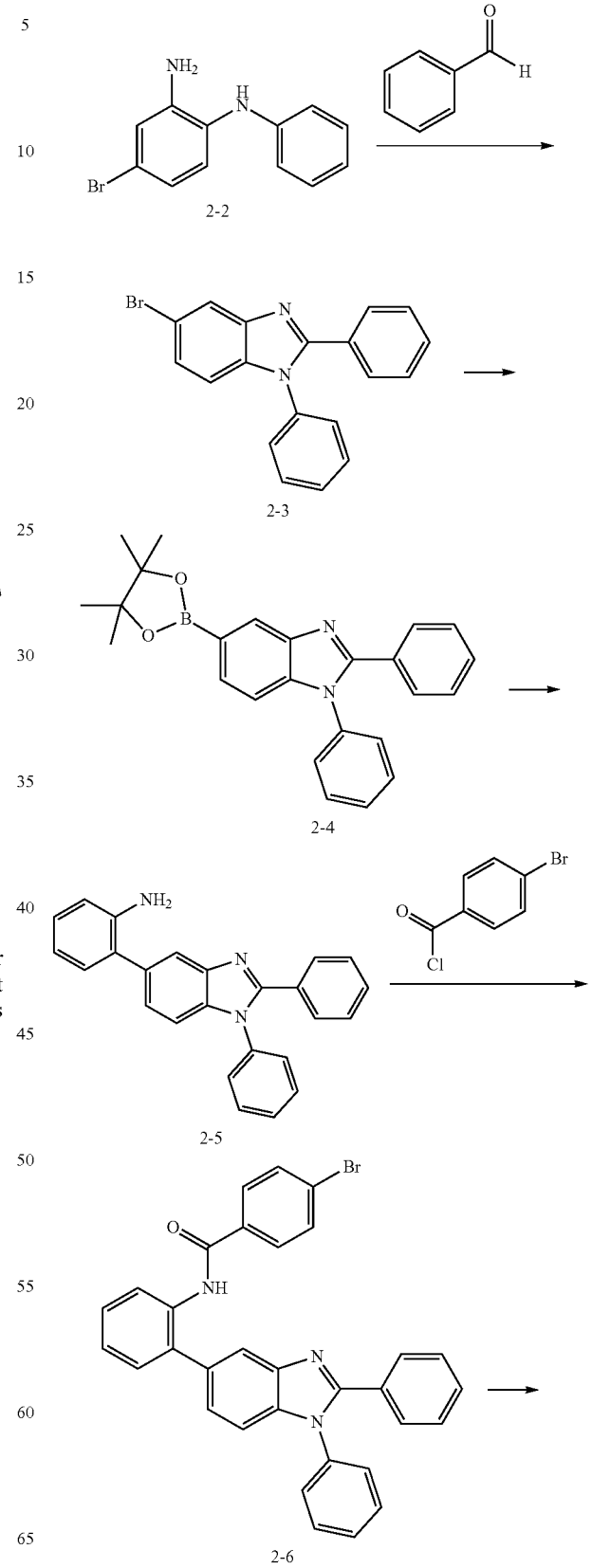

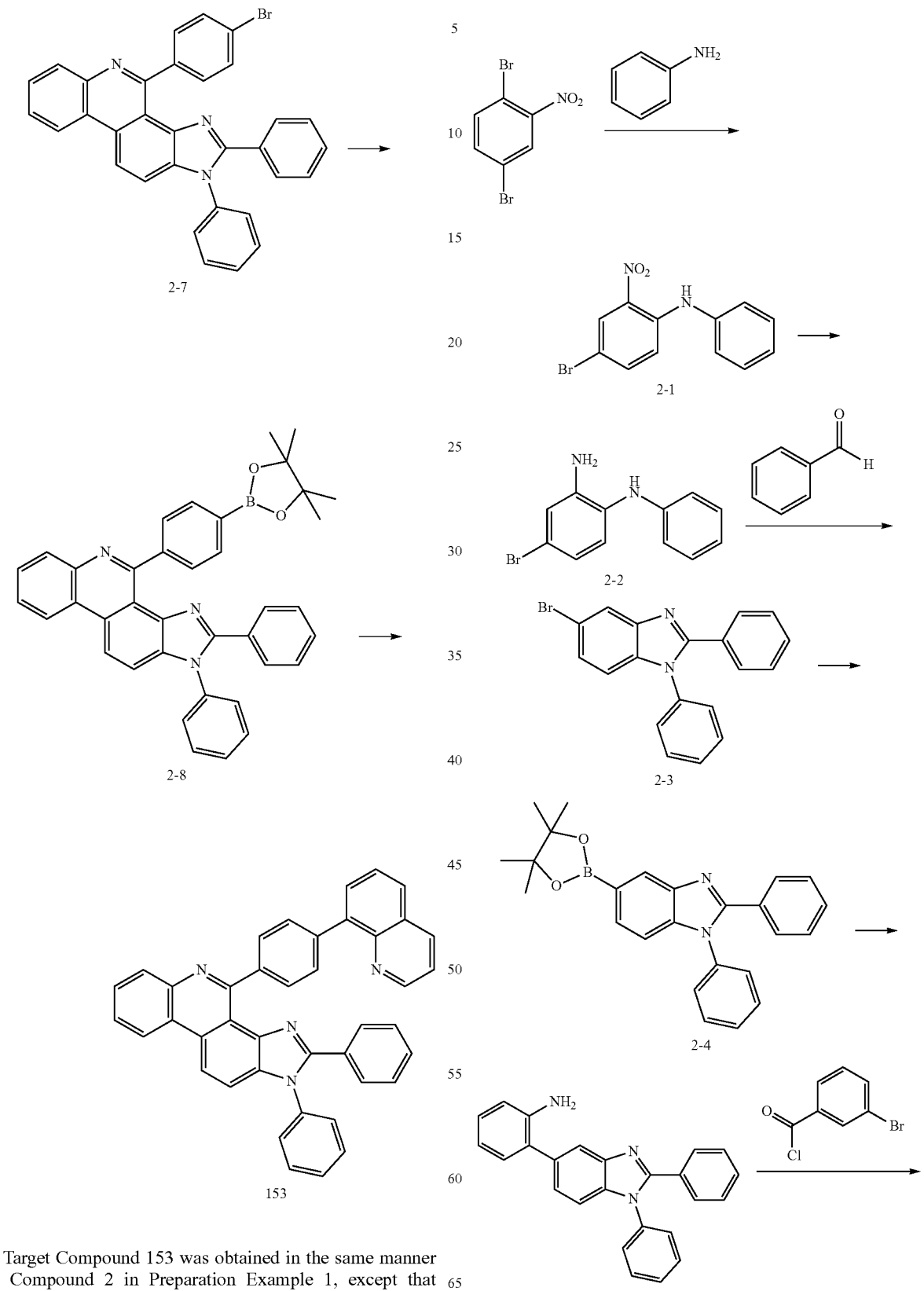
<Preparation Example 19> Preparation of Compound 154
Target Compound 153 was obtained in the same manner as Compound 2 in Preparation Example 1, except that 8-bromoquinoline was used instead of 9-bromo-10-phenylanthracene.

-continued

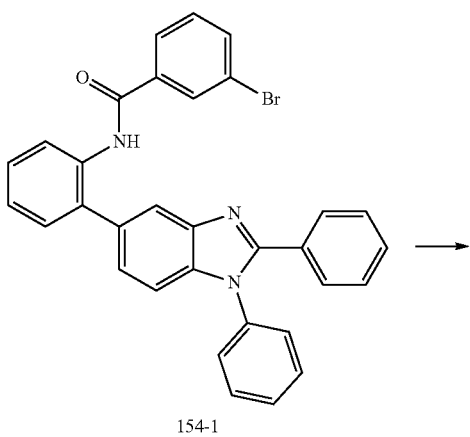
154-1

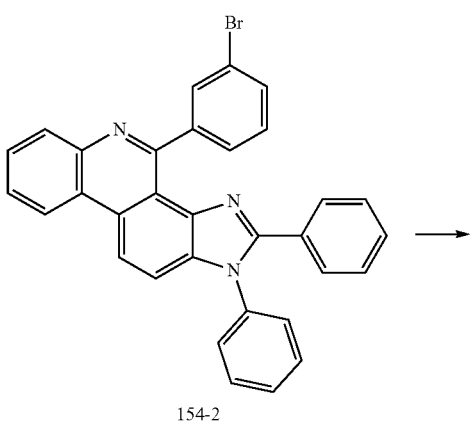
154-2

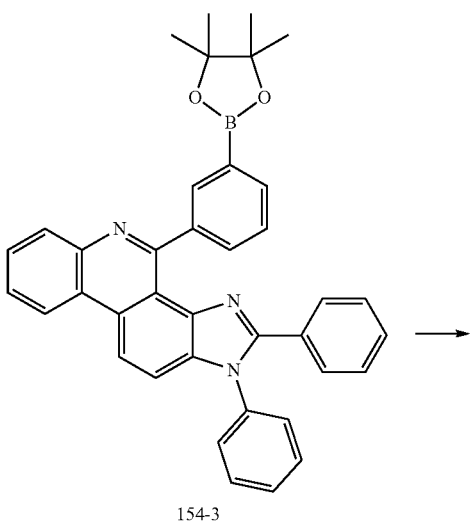
154-3

-continued

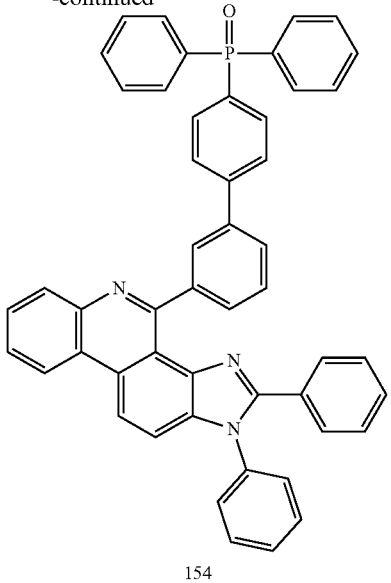
154

1) Preparation of Compound 154-1

After dissolving Compound 2-5 (30 g, 83.0 mmol) in THF, 3-bromobenzoyl chloride (16.5 ml, 1.5 eq) and TEA (34.5 ml, 3.0 eq.) were added thereto at 0° C., and the result was stirred for 2 hours at room temperature. After the reaction was completed, EA and distilled water were added to the reactor for solidification, and the produced solids were collected to obtain target Compound 154-1 (44 g, 97%).

2) Preparation of Compound 154-2

After dissolving Compound 154-1 (44 g, 80.8 mmol) in nitrobenzene, POCl₃ (7.5 ml, 1.0 eq.) was added thereto, and the result was stirred for 18 hours at 150° C. After the reaction was completed, the result was vacuum distilled to remove nitrobenzene, then cooled to room temperature, and extracted with distilled water and EA. The organic layer was dried with anhydrous MgSO₄, then the solvent was removed using a rotary evaporator, and the result was purified using column chromatography with dichloromethane and hexane as a developing solvent to obtain target Compound 154-2 (30 g, 71%).

3) Preparation of Compound 154-3

After dissolving Compound 154-2 (30 g, 57.0 mmol) in 1,4-dioxane, bis(pinacolato)diboron, Pd(dppf)Cl₂ and potassium acetate were added thereto, and the result was stirred for 2 hours at 110° C. After the reaction was completed, the result was extracted with distilled water and EA. The organic layer was dried with anhydrous MgSO₄, then the solvent was removed using a rotary evaporator, and target Compound 154-3 (29 g, 89%) was obtained without further purification.

4) Preparation of Compound 154

After adding (4-bromophenyl)diphenylphosphine oxide (5.5 g, 15.3 mmol), Pd(PPh₃)₄ (0.8 g, 0.71 mmol), K₂CO₃ (5.8 g, 42.3 mmol) and tolene/EtOH/H₂O to Compound 154-1 (8.0 g, 14.1 mmol), the result was stirred for 2 hours at 110° C. After the reaction was completed, the result was cooled to room temperature, and extracted with distilled water and EA. The organic layer was dried with anhydrous MgSO₄, then the solvent was removed using a rotary evaporator, and the result was purified using column chromatography with dichloromethane and hexane as a developing solvent to obtain target Compound 154 (8.5 g, 83%).

<Preparation Example 20> Preparation of Compound 155
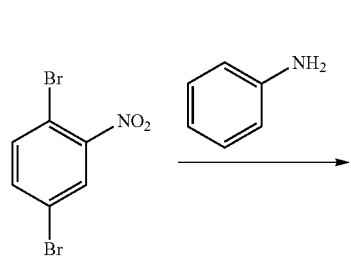
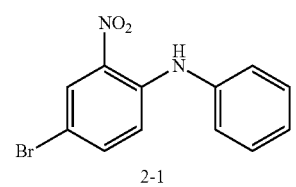
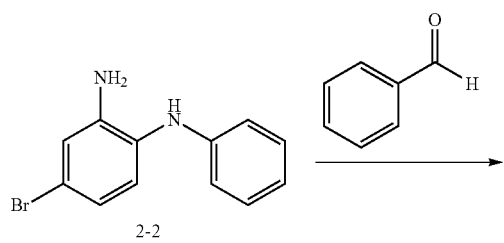
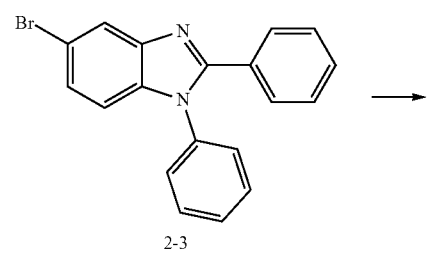
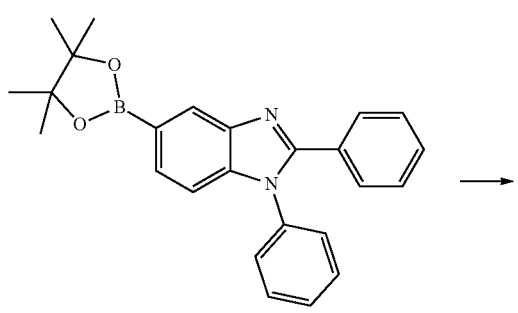
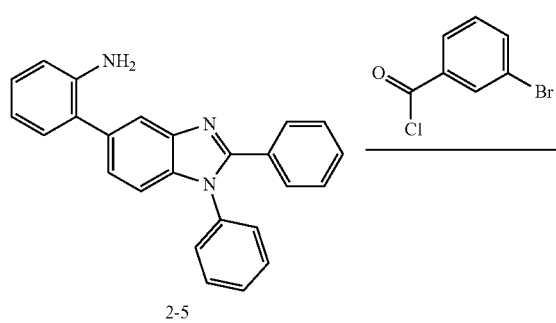
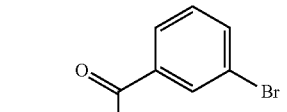
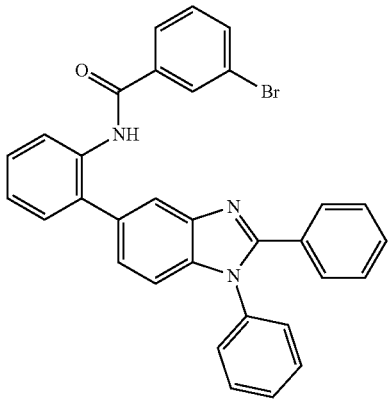
154-1
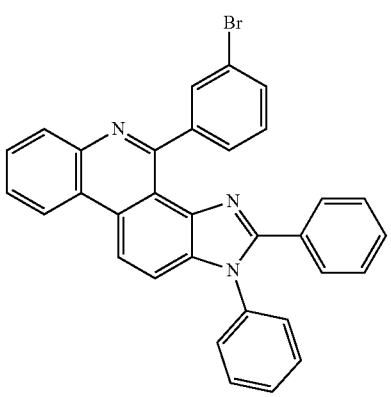
154-2
154-3

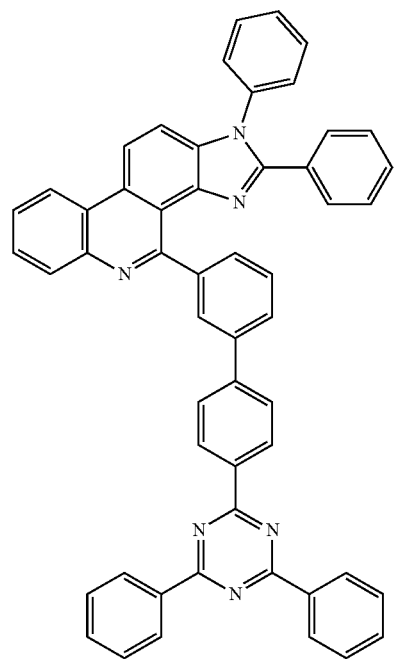
155
Target Compound 155 was obtained in the same manner as Compound 154 in Preparation Example 19, except that 2-bromo-4,6-diphenyl-1,3,5-triazine was used instead of (4-bromophenyl)diphenylphosphine oxide.
<Preparation Example 21> Preparation of Compound 156
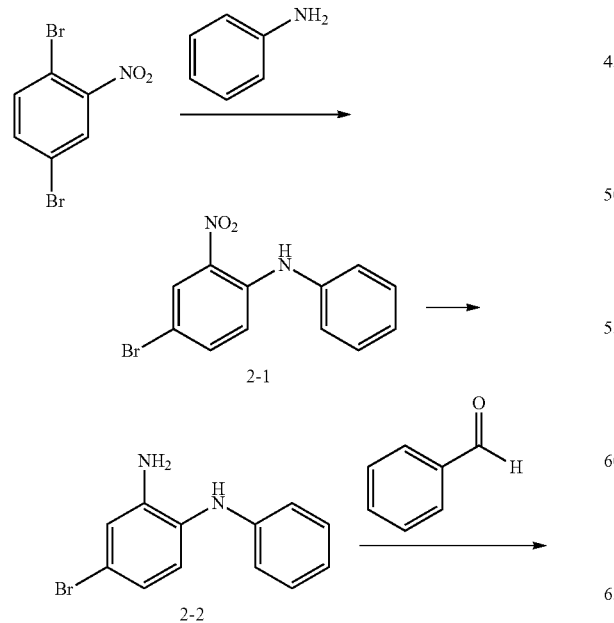
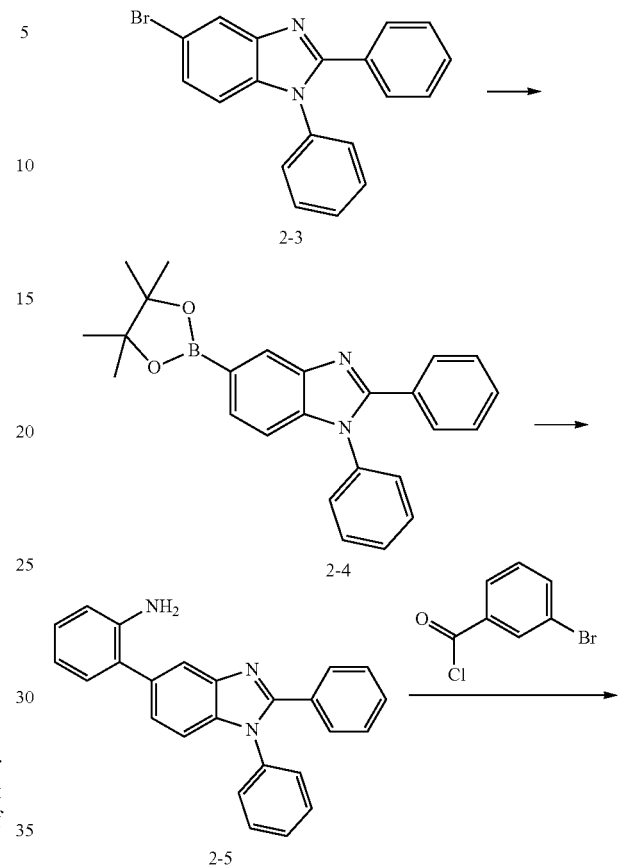
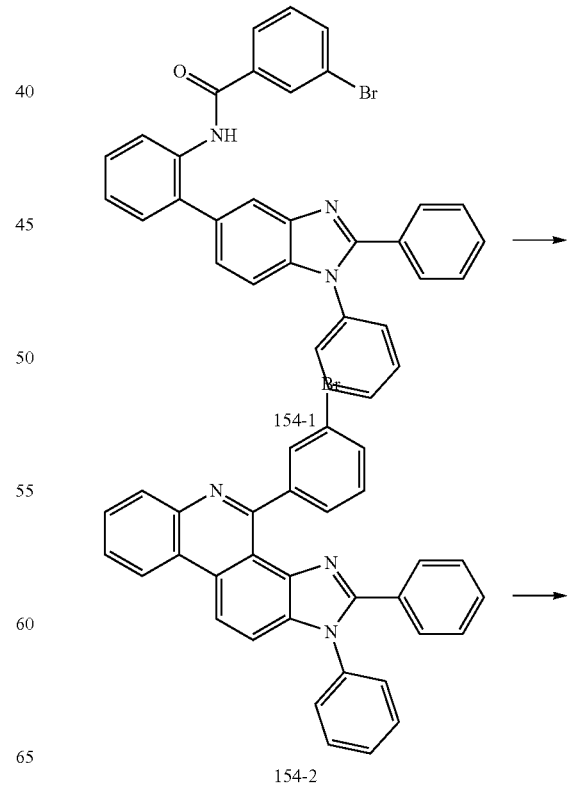

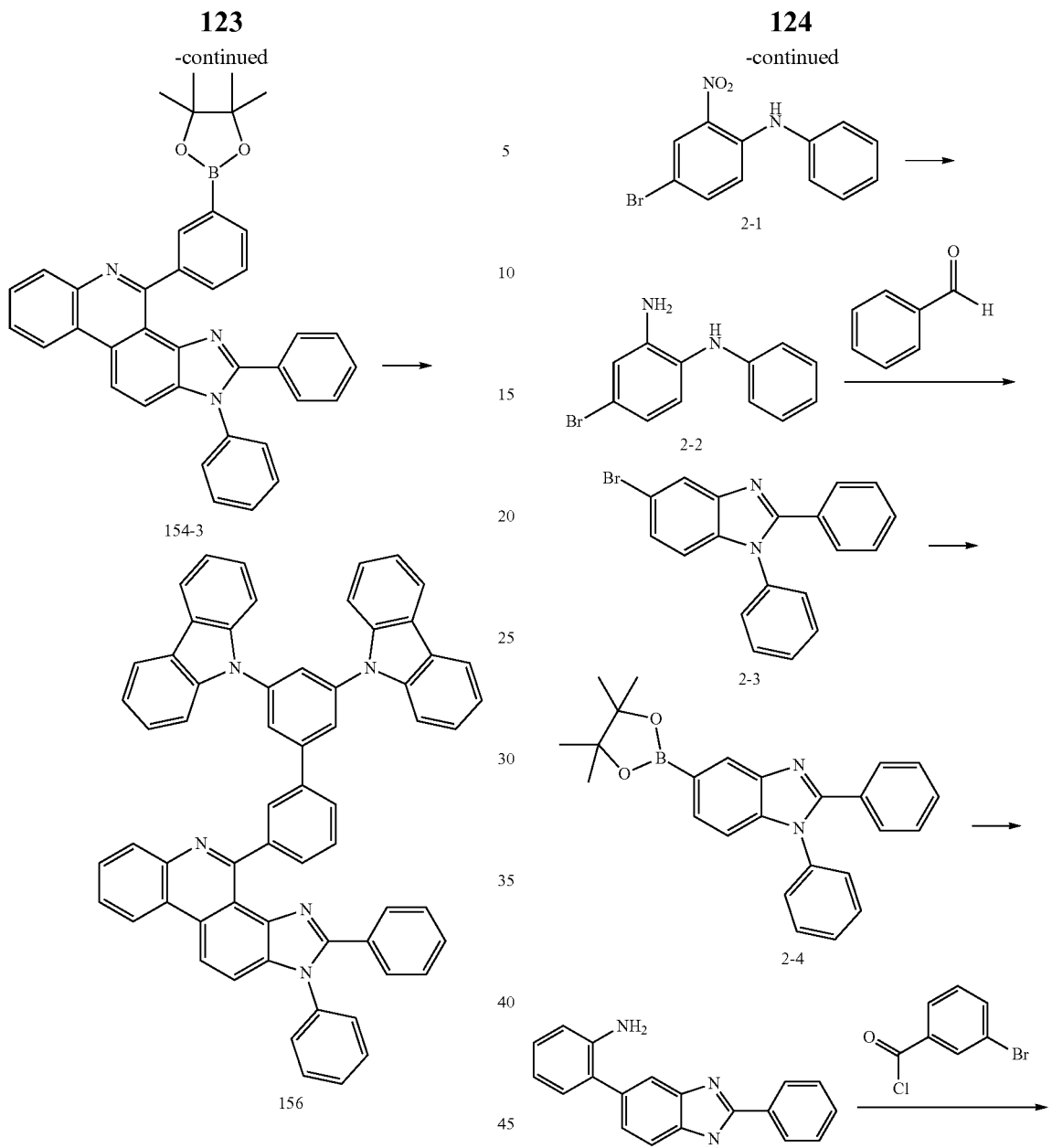
Target Compound 156 was obtained in the same manner as Compound 154 in Preparation Example 19, except that 9,9'-(5-bromo-1,3-phenylene)bis(9H-carbazole) was used instead of (4-bromophenyl)diphenylphosphine oxide.
<Preparation Example 22> Preparation of Compound 158
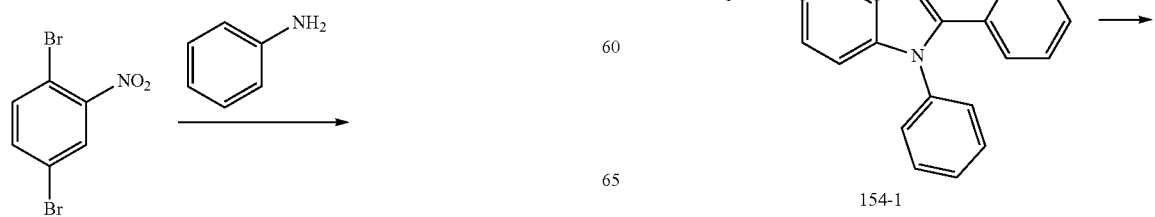

125
-continued
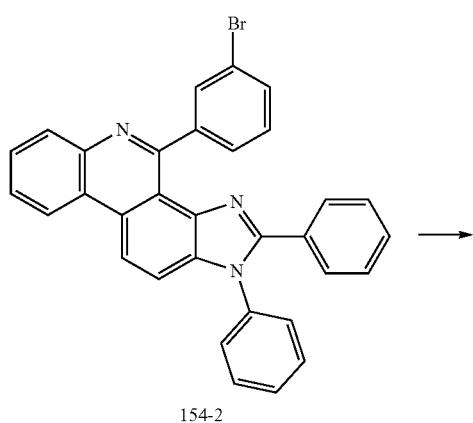
154-2
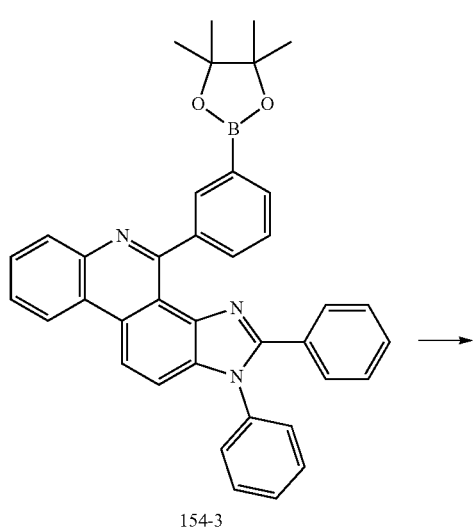
154-3
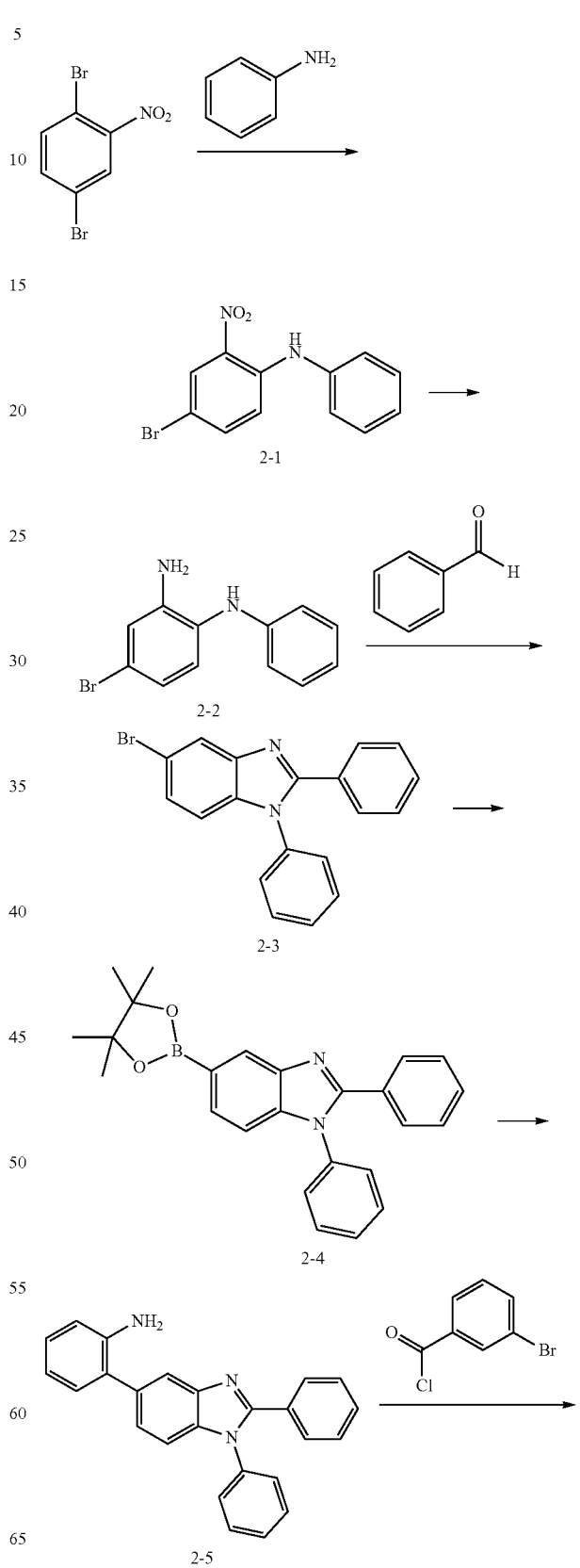
158
Target Compound 158 was obtained in the same manner as Compound 154 in Preparation Example 19, except that 4-chloro-2,6-diphenylpyrimidine was used instead of (4-bromophenyl)diphenylphosphine oxide.
126
<Preparation Example 23> Preparation of Compound 161

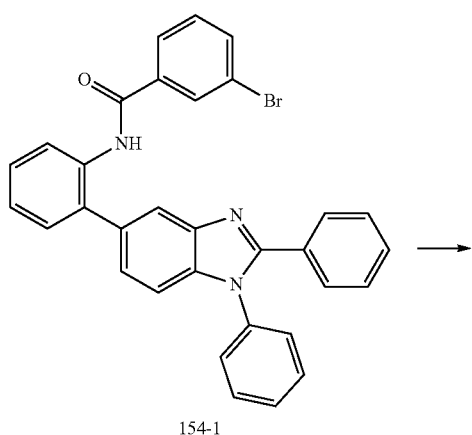
154-1
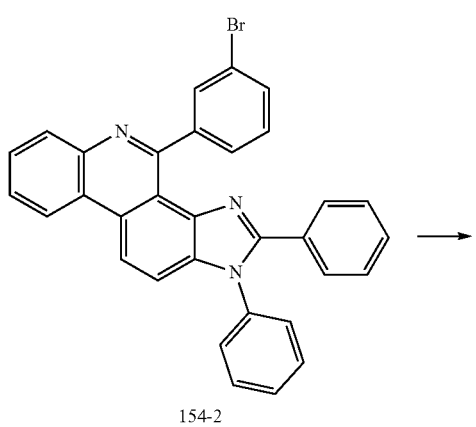
154-2
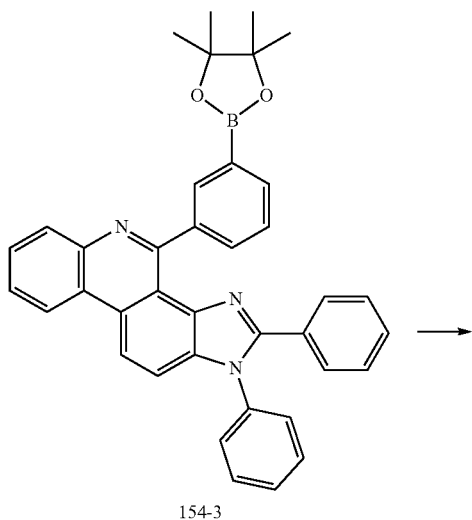
154-3
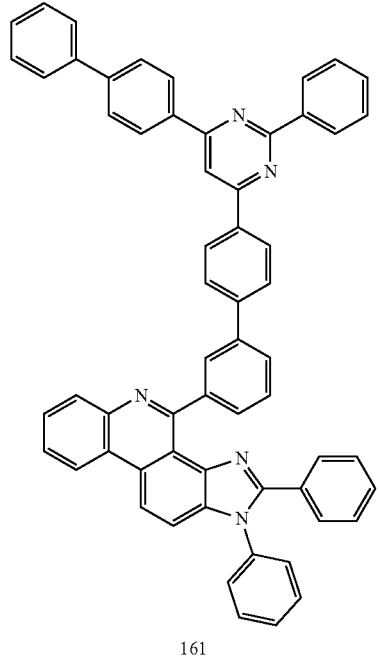
161
Target Compound 161 was obtained in the same manner as Compound 154 in Preparation Example 19, except that 4-([1,1'-biphenyl]-4-yl)-6-(4-chlorophenyl)-2-phenylpyrimidine was used instead of (4-bromophenyl)diphenylphosphine oxide.
<Preparation Example 24> Preparation of Compound 164
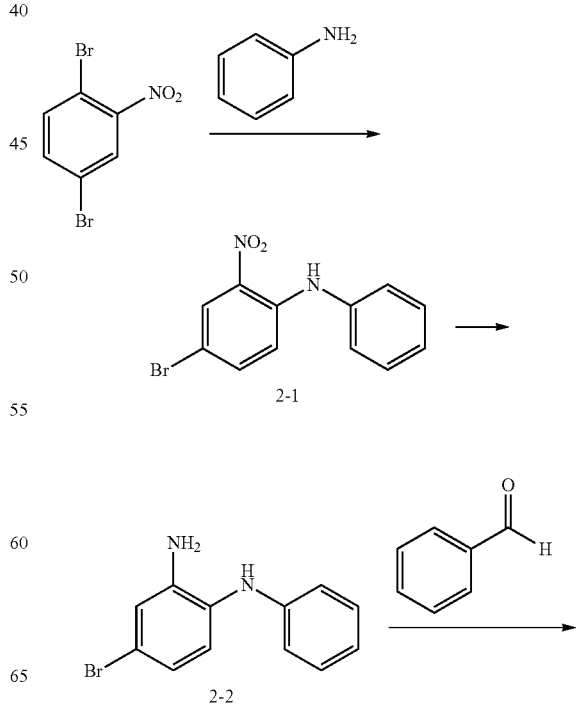
2-1
2-2

129
-continued
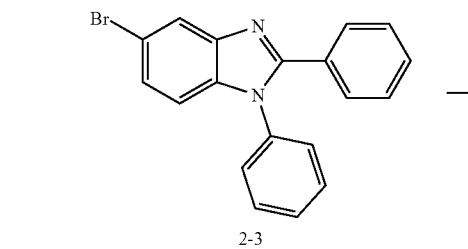
2-3
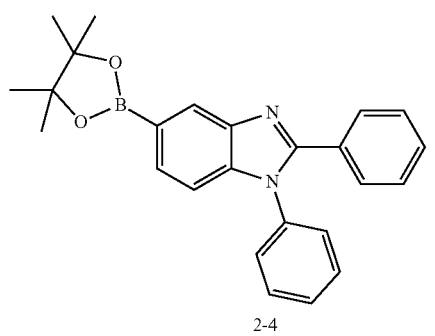
2-4
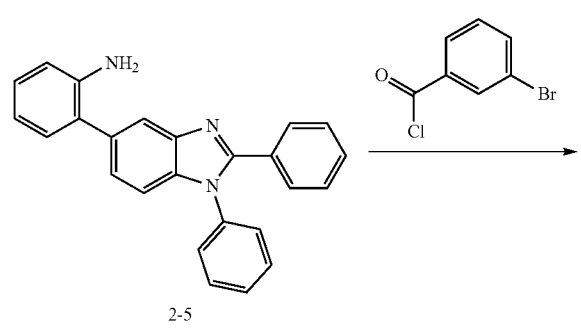
2-5
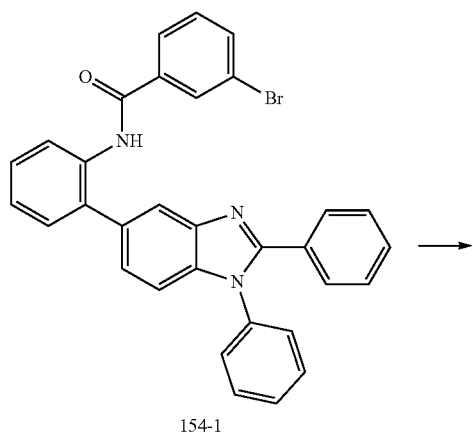
154-1
130
-continued
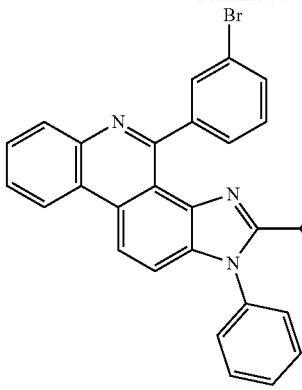
154-2
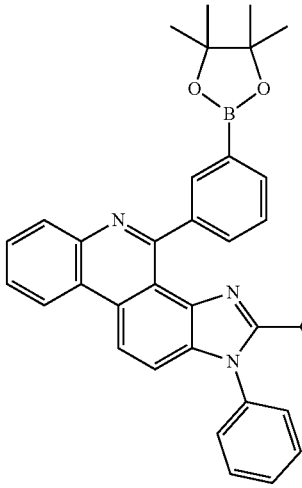
154-3
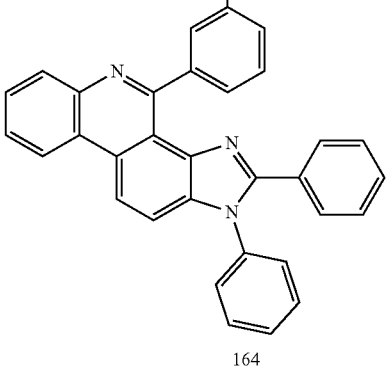
164
Target Compound 164 was obtained in the same manner as Compound 154 in Preparation Example 19, except that 2-(4-bromophenyl)-9-phenyl-1,10-phenanthroline was used instead of (4-bromophenyl)diphenylphosphine oxide.
<Preparation Example 25> Preparation of Compound 165
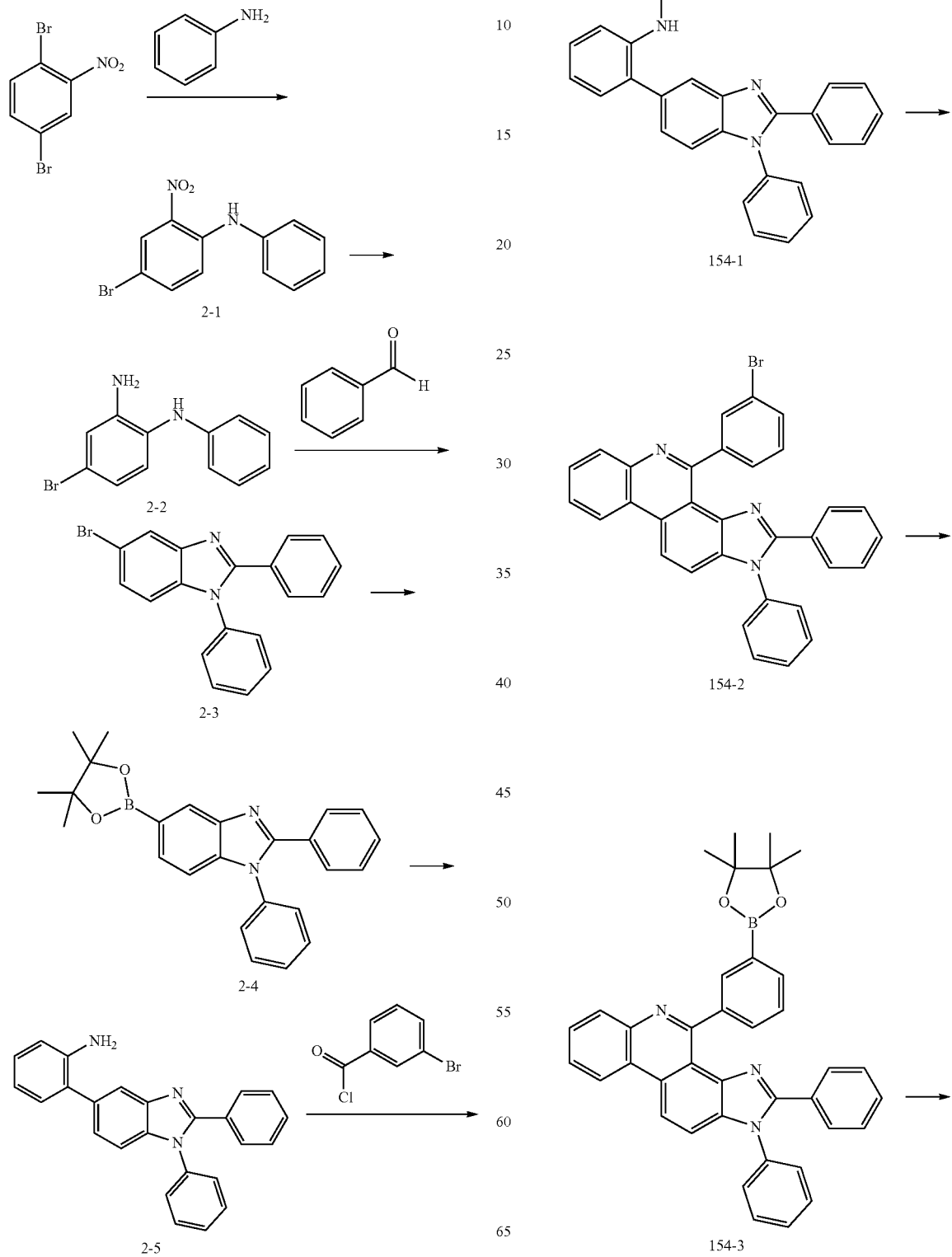

-continued

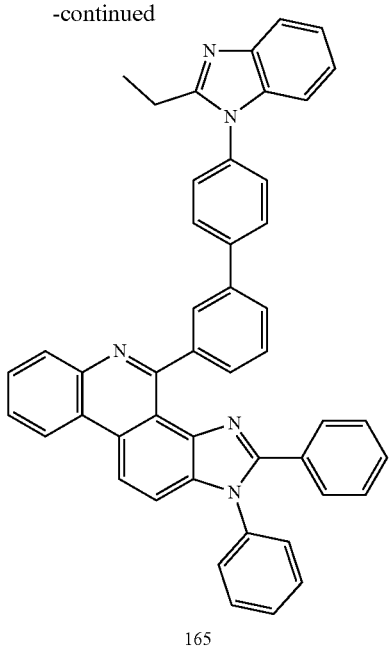

165

Target Compound 165 was obtained in the same manner as Compound 154 in Preparation Example 19, except that 1-(4-bromophenyl)-2-ethyl-1H-benzo[d]imidazole was used instead of (4-bromophenyl)diphenylphosphine oxide.

Compounds were prepared in the same manner as in the preparation examples, and the synthesis identification results are shown in Table 1 and Table 2.

TABLE 1

| NO | $^1$H NMR (CDCl$_3$, 300 Mz) |
|---|---|
| 2 | 7.25 (d, 2H), 7.37-7.38 (m, 6H), 7.41 (t, 1H), 7.48-7.50 (m, 5H), 7.55-7.57 (m, 3H), 7.62-7.65 (m, 3H), 7.70 (t, 1H), 7.83-7.85 (m, 2H), 7.94 (d, 1H), 8.20-8.21 (m, 5H), 8.28 (d, 2H), 8.69 (d, 2H) |
| 5 | 7.38 (d, 2H), 7.48-7.51 (m, 11H), 7.57 (d, 1H), 7.70 (t, 1H), 7.77 (m, 4), 7.83-7.85 (m, 2H), 7.94-7.96 (m, 3H), 8.20 (d, 1H), 8.28 (d, 2H), 8.36 (d, 2H) |
| 10 | 7.16-7.20 (m, 4H), 7.35-7.38 (m, 4H), 7.48-7.50 (m, 7H), 7.57-7.60 (m, 4H), 7.62 (t, 1H), 7.70 (t, 1H), 7.83-7.85 (m, 4H), 7.94 (m, 3H), 8.17-8.20 (m, 5H), 8.28 (d, 2H), 8.55 (d, 2H), 8.69 (d, 2H) |
| 11 | 7.38 (d, 2H), 7.48-7.50 (m, 11H), 7.57 (d, 1H), 7.62 (t, 1H), 7.70 (t, 1H), 7.83-7.85 (m, 2H), 7.94-7.96 (m, 3H), 8.20 (d, 1H), 8.28 (d, 2H), 8.36 (m, 4H), 8.69 (d, 2H) |
| 15 | 7.38 *d, 2H), 7.48-7.50 (m, 5H), 7.7 (d, 1H), 7.59-7.61 (m, 4H), 7.70 (t, 1H), 7.83-7.85 (m, 2H), 7.94-7.96 (m, 3H), 8.00 (d, 2H), 8.08 (d, 2H), 8.16-8.20 (m, 3H), 8.28 (d, 2H), 8.49 (d, 2H), 8.69 (d, 2H), 9.09 (s, 2H) |
| 25 | 7.38-7.41 (m, 3H), 7.48-7.50 (m, 8H), 7.55-7.57 (m, 3H), 7.62 (t, 1H), 7.70 (t, 1H), 7.75 (d, 2H), 7.83-7.85 (m, 4H), 7.94-7.96 (m, 5H), 8.20 (d, 1H), 8.23 (s, 1H), 8.28-8.30 (m, 4H), 8.69 (d, 2H) |
| 55 | 7.38-7.41 (m, 3H), 7.48-7.50 (m, 7H), 7.57-7.58 (m, 2H), 7.62 (t, 1H), 7.70 (t, 1H), 7.75 (d, 2H), 7.84-7.85 (m, 6H), 7.94 (d, 1H), 7.96 (d, 2H), 8.13 (d, 1H), 8.20 (d, 1H), 8.28 (d, 2H), 8.30 (d, 2H), 8.69 (d, 2H) |
| 70 | 7.25 (d, 2H), 7.38 *d, 2H), 7.48-7.50 (m, 10H), 7.57 (d, 1H), 7.62 (t, 1H), 7.65 (t, 4H), 7.70 (t, 1H), 7.80 (d, 4H), 7.83-7.85 (m, 2H), 7.94 (d, 1H), 8.20 (d, 1H), 8.28 (m, 2H), 8.35 (m, 2H), 8.69 (d, 2H) |
| 89 | 7.29 (d, 1H), 7.38 (d, 2H), 7.48-7.50 (m, 5H), 7.56-7.57 (m, 2H), 7.62 (t, 1H), 7.70 (t, 1H), 7.83-7.85 (m, 2H), 7.90 (d, 1H), 7.94 (d, 1H), 8.20 (m, 2H), 8.28 (m, 2H), 8.45 (d, 1H), 8.69 (m, 4H), 8.71 (d, 1H), 8.80 (d, 1H) |
| 94 | 7.25 (d, 2H), 7.37-7.38 (m, 3H), 7.48-7.50 (m, 8H), 7.57 (d, 1H), 7.62 (t, 1H), 7.70 (t, 1H), 7.73 (d, 1H), 7.83-7.85 (m, 2H), 7.94 (d, 1H), 8.14 (d, 2H), 8.20 (d, 1H), 8.28 *d, 2H), 8.37 (s, 1H), 8.43 (s, 1H), 8.69 (d, 2H) |
| 101 | 1.30 (t, 3H), 2.85 (1, 2H), 7.21 (t, 1H), 7.28 (t, 1H), 7.38 *d, 2H), 7.48-7.50 (m, 5H), 7.54-7.57 (m, 2H), 7.62 (t, 1H), 7.70 (t, 1H), 7.77-7.80 (m, 4H), 7.83-7.85 (m, 4H), 7.94 (d, 1H) |
| 104 | 7.25 (d, 2H), 7.38 (d, 2H), 7.48-7.57 (m, 8H), 7.62 (t, 1H), 7.70 (t, 1H), 7.83 (d, 1H), 7.85 (m, 3H), 7.94 (d, 1H), 7.96 (d, 2H), 8.02 (d, 1H), 8.18-8.20 (m, 2H), 8.28 (m, 2H), 8.69 (d, 2H) |
| 126 | 7.25 (d, 2H), 7.38 *d, 2H), 7.48-7.58 (m, 8H), 7.62 (t, 1H), 7.70 (t, 1H), 7.83-7.85 (m, 2H), 7.94 (d, 1H), 8.06-8.09 (m, 2H), 8.20 (m, 2H), 8.26-8.28 *m, 3H), 8.69 (d, 2H) |
| 131 | 7.38-7.40 (m, 5H), 7.48-7.50 (m, 5H), 7.55-7.57 (m, 1H), 7.60-7.63 (m, 5H), 7.70 (t, 1H), 7.83-7.85 (m, 4H), 7.94 (d, 1H), 7.97-7.99 (m, 3H), 8.06-8.09 (m, 2H), 8.20 (m, 2H), 8.28 (m, 2H), 8.69 (d, 2H) |
| 133 | 7.38 (d, 2H), 7.48-7.50 (m, 5H), 7.57 (d, 1H), 7.62 (t, 1H), 7.70 (t, 1H), 7.83-7.85 (m, 8H), 7.94 (d, 1H), 8.20 (d, 1H), 8.28 (m, 2H), 8.69 (d, 2H) |
| 136 | 6.90 (t, 1H), 7.14 (d, 1H), 7.38 (m, 3H), 7.48-7.50 (m, 5H), 7.57 (d, 1H), 7.62 (t, 1H), 7.70 (t, 1H), 7.83 (d, 1H), 7.85 (t, 1H), 7.94 (d, 1H), 8.20 (d, 1H), 8.28 (m, 2H), 8.37 (d, 1H), 8.69 (m, 4H) |
| 152 | 6.86 (t, 1H), 7.21 (t, 1H), 7.28 (m, 23H), 7.38 (d, 2H), 7.47-7.57 (m, 10H), 7.62 (t, 1H), 7.70 (t, 1H), 7.83-7.85 (m, 6H), 7.94 (d, 1H), 8.20 (d, 1H), 8.28-8.30 (m, 4H), 8.48 (d, 1H), 8.69 (d, 2H) |
| 153 | 7.25 (d, 2H), 7.38 (d, 2H), 7.48-7.50 (m, 6H), 7.62-7.64 (m, 2H), 7.70 (t, 1H), 7.83-7.85 (m, 2H), 7.94-7.96 (m, 2H), 8.05 (d, 1H), 8.28 (d, 2H), 8.55 (d, 1H), 8.69 (d, 2H), 8.87 (d, 1H) |
| 154 | 8.33~8.28 (m, 4H), 8.20 (d, 1H), 7.97-7.94 (m, 5H), 7.85-7.48 (m, 22H), 7.38 (d, 2H) |
| 155 | 8.36-8.28 (m, 8H), 8.20 (d, 1H), 7.96-7.94 (m, 3H), 7.85-7.83 (m, 2H), 7.73-7.48 (m, 16H), 7.38 (d, 2H), 7.25 (d, 2H) |
| 156 | 8.55 (d, 2H), 8.33-8.17 (m, 9H), 7.94 (d, 2H), 7.85-7.83 (m, 2H), 7.70-7.48 (m, 15H), 7.38-7.35 (m, 4H), 7.20-7.16 (m, 4H) |
| 158 | 8.35-8.20 (m, 8H), 7.94 (d, 4H), 7.85-7.83 (m, 2H), 7.73-7.48 (m, 15H), 7.38 (d, 2H) |
| 161 | 8.35-8.20 (m, 12H), 7.94 (d, 1H), 7.85-7.83 (m, 6H), 7.75-7.38 (m, 20H) |
| 164 | 8.71-8.69 (t, 4H), 8.33-8.20 (m, 8H), 7.94-7.83 (m, 6H), 7.73-7.48 (m, 13H), 7.38 (d, 2H), 7.29 (d, 2H) |
| 165 | 8.56 (d, 2H), 8.33-8.20 (m, 5H), 7.94 (d, 1H), 7.85-7.48 (m, 17H), 7.38 (d, 2H), 7.28-7.21 (m, 2H), 2.85 (q, 2H), 1.30 (t, 3H) |

TABLE 2

| Compound | FD-MS | Compound | FD-MS |
|---|---|---|---|
| 1 | m/z = 749.90 (C56H35N3 = 749.28) | 2 | m/z = 699.84 (C52H33N3 = 699.27) |
| 3 | m/z = 876.05 (C66H41N3 = 875.33) | 4 | m/z = 623.74 (C46H29N3 = 623.24) |
| 5 | m/z = 647.70 (C44H30N3OP = 647.21) | 6 | m/z = 723.80 (C50H34N3OP = 723.24) |
| 7 | m/z = 773.86 (C54H36N3OP = 773.26) | 8 | m/z = 773.86 (C54H36N3OP = 773.26) |

TABLE 2-continued

| Compound | FD-MS | Compound | FD-MS |
|---|---|---|---|
| 9 | m/z = 823.92 (C58H38N3OP = 823.28) | 10 | m/z = 854.01 (C62H39N5 = 853.32) |
| 11 | m/z = 678.78 (C47H30N6 = 678.25) | 12 | m/z = 680.76 (C45H28N8 = 680.24) |
| 13 | m/z = 680.76 (C45H28N8 = 680.24) | 14 | m/z = 680.76 (C45H28N8 = 680.24) |
| 15 | m/z = 778.90 (C55H34N6 = 778.28) | 16 | m/z = 778.90 (C55H34N6 = 778.28) |
| 17 | m/z = 754.88 (C53H34N6 = 754.28) | 18 | m/z = 804.94 (C57H36N6 = 804.30) |
| 19 | m/z = 677.79 (C48H31N5 = 677.26) | 20 | m/z = 679.77 (C46H29N7 = 679.25) |
| 21 | m/z = 679.77 (C46H29N7 = 679.25) | 22 | m/z = 679.77 (C46H29N7 = 679.25) |
| 23 | m/z = 777.91 (C56H35N5 = 777.29) | 24 | m/z = 777.91 (C56H35N5 = 777.29) |
| 25 | m/z = 753.89 (C54H35N5 = 753.29) | 26 | m/z = 829.99 (C60H39N5 = 829.32) |
| 27 | m/z = 753.89 (C54H35N5 = 753.29) | 28 | m/z = 829.99 (C60H39N5 = 829.32) |
| 29 | m/z = 753.89 (C54H35N5 = 753.29) | 30 | m/z = 854.01 (C62H39N5 = 853.32) |
| 31 | m/z = 854.01 (C62H39N5 = 853.32) | 32 | m/z = 906.08 (C66H43N5 = 905.35) |
| 33 | m/z = 906.08 (C66H43N5 = 905.35) | 34 | m/z = 829.99 (C60H39N5 = 829.32) |
| 35 | m/z = 829.99 (C60H39N5 = 829.32) | 36 | m/z = 803.95 (C58H37N5 = 803.30) |
| 37 | m/z = 677.79 (C48H31N5 = 677.26) | 38 | m/z = 679.77 (C46H29N7 = 679.25) |
| 39 | m/z = 679.77 (C46H29N7 = 679.25) | 40 | m/z = 679.77 (C46H29N7 = 679.25) |
| 41 | m/z = 777.91 (C56H35N5 = 777.29) | 42 | m/z = 777.91 (C56H35N5 = 777.29) |
| 43 | m/z = 753.89 (C54H35N5 = 753.29) | 44 | m/z = 829.99 (C60H39N5 = 829.32) |
| 45 | m/z = 753.89 (C54H35N5 = 753.29) | 46 | m/z = 829.99 (C60H39N5 = 829.32) |
| 47 | m/z = 753.89 (C54H35N5 = 753.29) | 48 | m/z = 854.01 (C62H39N5 = 853.32) |
| 49 | m/z = 854.01 (C62H39N5 = 853.32) | 50 | m/z = 829.99 (C60H39N5 = 829.32) |
| 51 | m/z = 906.08 (C66H43N5 = 905.35) | 52 | m/z = 829.99 (C60H39N5 = 829.32) |
| 53 | m/z = 906.08 (C66H43N5 = 905.35) | 54 | m/z = 880.04 (C64H41N5 = 879.34) |
| 55 | m/z = 727.85 (C52H33N5 = 727.27) | 56 | m/z = 651.76 (C46H29N5 = 651.24) |
| 57 | m/z = 727.85 (C52H33N5 = 727.27) | 58 | m/z = 701.81 (C50H31N5 = 701.26) |
| 59 | m/z = 701.81 (C50H31N5 = 701.26) | 60 | m/z = 803.95 (C58H37N5 = 803.30) |
| 61 | m/z = 727.85 (C52H33N5 = 727.27) | 62 | m/z = 803.95 (C58H37N5 = 803.30) |
| 63 | m/z = 777.91 (C56H35N5 = 777.29) | 64 | m/z = 777.91 (C56H35N5 = 777.29) |
| 65 | m/z = 803.95 (C58H37N5 = 803.30) | 66 | m/z = 727.85 (C52H33N5 = 727.27) |
| 67 | m/z = 803.95 (C58H37N5 = 803.30) | 68 | m/z = 777.91 (C56H35N5 = 777.29) |
| 69 | m/z = 777.91 (C56H35N5 = 777.29) | 70 | m/z = 753.89 (C54H35N5 = 753.29) |
| 71 | m/z = 906.08 (C66H43N5 = 905.35) | 72 | m/z = 906.08 (C66H43N5 = 905.35) |
| 73 | m/z = 854.01 (C62H39N5 = 853.32) | 74 | m/z = 854.01 (C62H39N5 = 853.32) |
| 75 | m/z = 829.99 (C60H39N5 = 829.32) | 76 | m/z = 829.99 (C60H39N5 = 829.32) |
| 77 | m/z = 829.99 (C60H39N5 = 829.32) | 78 | m/z = 803.95 (C58H37N5 = 803.30) |
| 79 | m/z = 803.95 (C58H37N5 = 803.30) | 80 | m/z = 651.76 (C46H29N5 = 651.24) |
| 81 | m/z = 727.85 (C52H33N5 = 727.27) | 82 | m/z = 727.85 (C52H33N5 = 727.27) |
| 83 | m/z = 727.85 (C52H33N5 = 727.27) | 84 | m/z = 803.95 (C58H37N5 = 803.30) |
| 85 | m/z = 803.95 (C58H37N5 = 803.30) | 86 | m/z = 727.85 (C52H33N5 = 727.27) |

TABLE 2-continued

| Compound | FD-MS | Compound | FD-MS |
|---|---|---|---|
| 87 | m/z = 803.95 (C58H37N5 = 803.30) | 88 | m/z = 803.95 (C58H37N5 = 803.30) |
| 89 | m/z = 625.72 (C44H27N5 = 625.23) | 90 | m/z = 701.81 (C50H31N5 = 701.26) |
| 91 | m/z = 701.81 (C50H31N5 = 701.26) | 92 | m/z = 639.75 (C45H29N5 = 639.24) |
| 93 | m/z = 639.75 (C45H29N5 = 639.24) | 94 | m/z = 639.75 (C45H29N5 = 639.24) |
| 95 | m/z = 639.75 (C45H29N5 = 639.24) | 96 | m/z = 591.70 (C41H29N5 = 591.24) |
| 97 | m/z = 667.80 (C47H33N5 = 667.27) | 98 | m/z = 667.80 (C47H33N5 = 667.27) |
| 99 | m/z = 715.84 (C51H33N5 = 715.27) | 100 | m/z = 715.84 (C51H33N5 = 715.27) |
| 101 | m/z = 667.80 (C47H33N5 = 667.27) | 102 | m/z = 667.80 (C47H33N5 = 667.27) |
| 103 | m/z = 591.70 (C41H29N5 = 591.24) | 104 | m/z = 656.80 (C45H28N4 = 656.20) |
| 105 | m/z = 706.85 (C49H30N4 = 706.22) | 106 | m/z = 656.80 (C45H28N4S = 656.20) |
| 107 | m/z = 656.80 (C45H28N4S = 656.20) | 108 | m/z = 656.80 (C45H28N4S = 656.20) |
| 109 | m/z = 676.82 (C49H32N4 = 676.26) | 110 | m/z = 752.92 (C55H36N4 = 752.29) |
| 111 | m/z = 678.80 (C47H30N6 = 678.25) | 112 | m/z = 678.80 (C47H30N6 = 678.25) |
| 113 | m/z = 678.80 (C47H30N6 = 678.25) | 114 | m/z = 754.90 (C53H34N6 = 754.28) |
| 115 | m/z = 754.90 (C53H34N6 = 754.28) | 116 | m/z = 754.90 (C53H34N6 = 754.28) |
| 117 | m/z = 601.71(C42H27N5 = 601.23) | 118 | m/z = 601.71(C42H27N5 = 601.23) |
| 119 | m/z = 601.71(C42H27N5 = 601.23) | 120 | m/z = 677.81 (C48H31N5 = 677.26) |
| 121 | m/z = 677.81 (C48H31N5 = 677.26) | 122 | m/z = 677.81 (C48H31N5 = 677.26) |
| 123 | m/z = 675.83 (C50H33N3 = 675.27) | 124 | m/z = 766.91 (C54H34N6 = 766.28) |
| 125 | m/z = 613.72 (C43H27N5 = 613.23) | 126 | m/z = 574.69 (C41H26N4 = 574.22) |
| 127 | m/z = 574.69 (C41H26N4 = 574.22) | 128 | m/z = 575.67 (C40H25N5 = 575.21) |
| 129 | m/z = 575.67 (C40H25N5 = 575.21) | 130 | m/z = 575.67 (C40H25N5 = 575.21) |
| 131 | m/z = 699.86 (C52H33N3 = 699.27) | 132 | m/z = 673.82 (C50H31N3 = 673.25) |
| 133 | m/z = 548.65 (C39H24N4 = 548.20) | 134 | m/z = 624.75 (C45H28N4 = 624.23) |
| 135 | m/z = 674.81 (C49H30N4 = 674.25) | 136 | m/z = 524.63 (C37H24N4 = 524.20) |
| 137 | m/z = 600.73 (C43H28N4 = 600.23) | 138 | m/z = 650.78 (47H30N4 = 650.25) |
| 139 | m/z = 650.78 (C47H30N4 = 650.25) | 140 | m/z = 755.88 (C52H33N7 = 755.28) |
| 141 | m/z = 908.08 (C64H41N7 = 907.34) | 142 | m/z = 856.01 (C60H37N7 = 855.31) |
| 143 | m/z = 856.01 (C60H37N7 = 855.31) | 144 | m/z = 754.90 (C53H34N6 = 754.28) |
| 145 | m/z = 831.00 (C59H38N6 = 830.32) | 146 | m/z = 754.90 (C53H34N6 = 754.28) |
| 147 | m/z = 831.00 (C59H38N6 = 830.32) | 148 | m/z = 804.96 (C57H36N6 = 804.30) |
| 149 | m/z = 831.00 (C59H38N6 = 830.32) | 150 | m/z = 728.86 (C51H32N6 = 728.27) |
| 151 | m/z = 639.76 (C45H29N5 = 639.24) | 152 | m/z = 715.86 (C51H33N5 = 715.27) |
| 153 | m/z = 574.69 (C41H26N4 = 574.22) | 154 | m/z = 723.80 (C50H34N3OP = 723.24) |
| 155 | m/z = 754.88 (C53H34N6 = 754.28) | 156 | m/z = 854.01 (C62H39N5 = 853.32) |
| 157 | m/z = 677.79 (C48H31N5 = 677.26) | 158 | m/z = 677.79 (C48H31N5 = 677.26) |
| 159 | m/z = 777.91 (C56H35N5 = 777.29) | 160 | m/z = 829.99 (C60H39N5 = 829.32) |

TABLE 2-continued

| Compound | FD-MS | Compound | FD-MS |
|---|---|---|---|
| 161 | m/z = 829.99 (C60H39N5 = 829.32) | 162 | m/z = 803.95 (C58H37N5 = 803.30) |
| 163 | m/z = 701.81 (C50H31N5 = 701.26) | 164 | m/z = 777.91 (C56H35N5 = 777.29) |
| 165 | m/z = 667.80 (C47H33N5 = 667.27) | 166 | m/z = 752.90 (C55H36N4 = 752.29) |
| 167 | m/z = 548.63 (C39H24N4 = 548.20) | | |

EXPERIMENTAL EXAMPLE

Experimental Example 1

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using W. After that, the substrate was transferred to a plasma cleaner (PT), and plasma treatment was carried out under vacuum for ITO work function and remaining film removal, and the substrate was transferred to a thermal deposition apparatus for organic deposition.

On the ITO transparent electrode (anode), organic materials were formed in a two-stack white organic light emitting device (WOLED) structure. As for the first stack, a hole transfer layer was formed first by thermal vacuum depositing TAPC to a thickness of 300 Å. After forming the hole transfer layer, a light emitting layer was thermal vacuum deposited thereon as follows. The light emitting layer was deposited to 300 Å by doping FIrpic in 8% as a blue phosphorescent dopant to TCz1, a host. An electron transfer layer was formed to 400 Å using TmPyPB, and then a charge generation layer was formed to 100 Å by doping $Cs_2CO_3$ in 20% to a compound described in the following Table 3.

As for the second stack, a hole injection layer was formed first by thermal vacuum depositing $MoO_3$ to a thickness of 50 Å. A hole transfer layer, a common layer, was formed by doping $MoO_3$ to TAPC in 20% and forming to 100 Å, and then depositing TAPC to 300 Å. After depositing a light emitting layer to 300 Å thereon by doping $Ir(ppy)_3$, a green phosphorescent dopant, in 8% to TCz1, a host, an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED device were vacuum sublimation purified under $10^{-6}$ torr to $10^{-8}$ torr by each material to be used in the OLED manufacture.

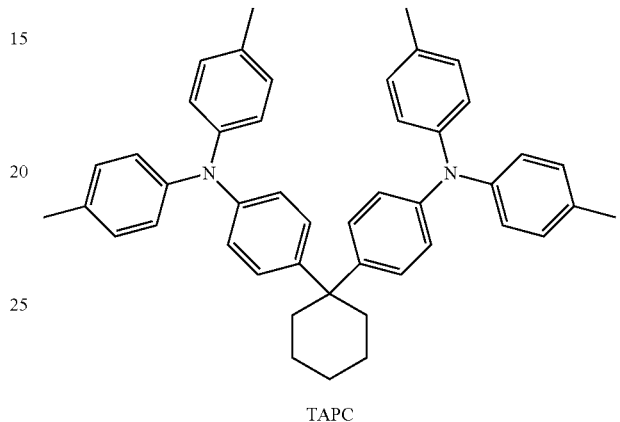

TAPC

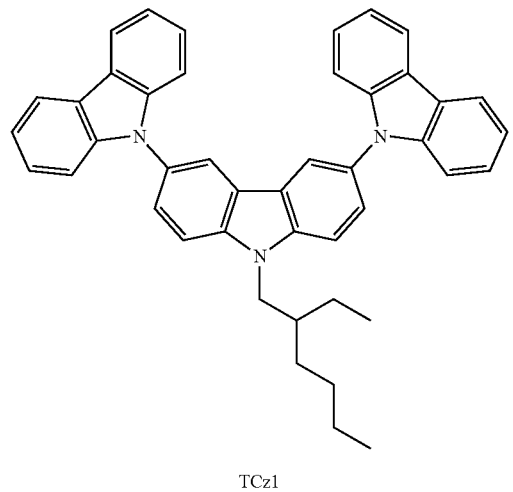

TCz1

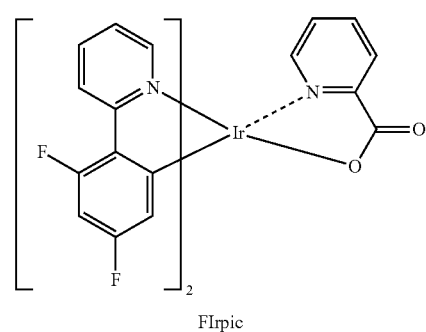

FIrpic

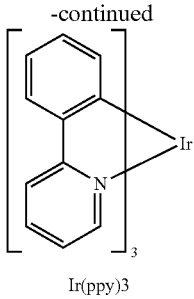

Ir(ppy)3

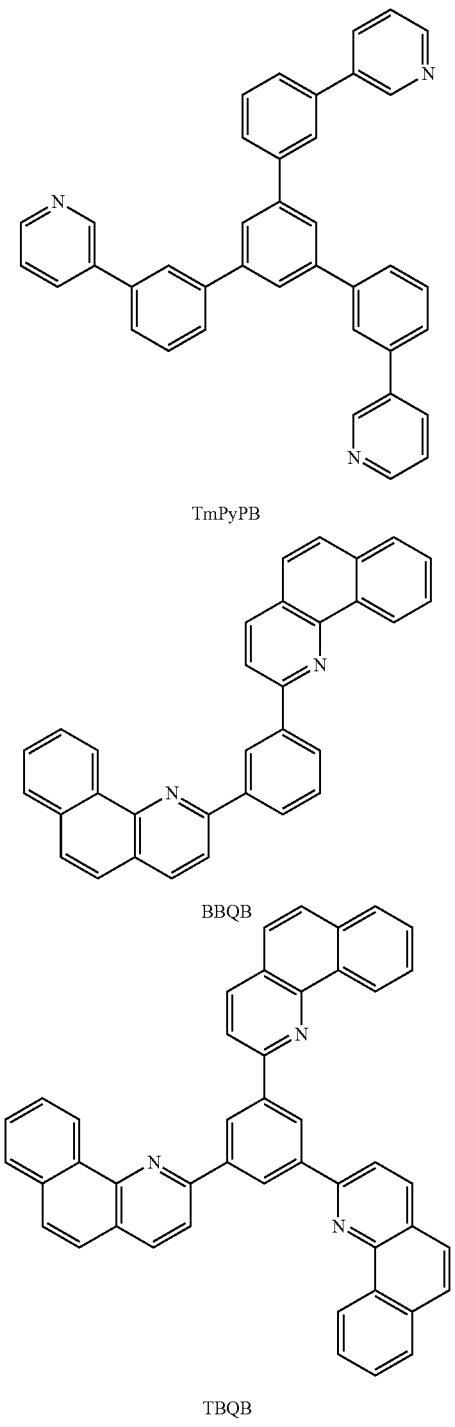

TmPyPB

BBQB

TBQB

2) Driving Voltage and Light Emission Efficiency of Organic Light Emitting Device For the organic light emitting devices manufactured as above, electroluminescent light emission (EL) characteristics were measured using M7000 manufactured by McScience Inc., and with the measurement results, $T_{95}$ when standard luminance was 3,500 cd/m² was measured using a lifetime test system (M6000) manufactured by McScience Inc. Results of measuring a driving voltage, light emission efficiency, external quantum efficiency and a color coordinate (CIE) of the white organic light emitting devices manufactured according to the present disclosure are as shown in Table 3.

TABLE 3

| | Compound | Driving Voltage (V) | Light Emission Efficiency (cd/A) | CIE (x, y) | Lifetime ($T_{95}$) |
|---|---|---|---|---|---|
| Example 1 | 2 | 7.78 | 59.95 | (0.218, 0.427) | 27 |
| Example 2 | 3 | 7.95 | 59.45 | (0.220, 0.431) | 28 |
| Example 3 | 4 | 7.92 | 59.88 | (0.200, 0.421) | 29 |
| Example 4 | 5 | 7.02 | 68.99 | (0.228, 0.436) | 41 |
| Example 5 | 10 | 7.08 | 69.74 | (0.243, 0.442) | 43 |
| Example 6 | 11 | 7.37 | 59.99 | (0.221, 0.433) | 47 |
| Example 7 | 15 | 7.41 | 67.13 | (0.233, 0.433) | 31 |
| Example 8 | 16 | 7.44 | 58.89 | (0.238, 0.438) | 33 |
| Example 9 | 17 | 7.07 | 70.01 | (0.225, 0.429) | 42 |
| Example 10 | 25 | 7.12 | 67.56 | (0.209, 0.415) | 44 |
| Example 11 | 26 | 7.00 | 69.89 | (0.231, 0.440) | 42 |
| Example 12 | 27 | 7.49 | 57.94 | (0.211, 0.419) | 37 |
| Example 13 | 28 | 7.66 | 58.26 | (0.209, 0.419) | 31 |
| Example 14 | 30 | 7.58 | 59.11 | (0.207, 0.409) | 38 |
| Example 15 | 34 | 7.50 | 56.66 | (0.208, 0.415) | 35 |
| Example 16 | 35 | 7.56 | 59.06 | (0.214, 0.420) | 33 |
| Example 17 | 43 | 7.21 | 69.56 | (0.224, 0.429) | 40 |
| Example 18 | 52 | 7.13 | 69.21 | (0.221, 0.434) | 42 |
| Example 19 | 55 | 7.45 | 56.45 | (0.212, 0.422) | 38 |
| Example 20 | 67 | 7.49 | 55.10 | (0.228, 0.418) | 38 |
| Example 21 | 70 | 7.54 | 56.89 | (0.231, 0.420) | 36 |
| Example 22 | 89 | 7.89 | 58.98 | (0.219, 0.411) | 35 |
| Example 23 | 90 | 7.80 | 59.11 | (0.210, 0.412) | 35 |
| Example 24 | 91 | 7.87 | 65.84 | (0.218, 0.421) | 30 |
| Example 25 | 94 | 8.00 | 59.21 | (0.209, 0.432) | 26 |
| Example 26 | 101 | 7.88 | 57.04 | (0.231, 0.418) | 37 |
| Example 27 | 104 | 7.39 | 63.38 | (0.243, 0.442) | 40 |
| Example 28 | 124 | 7.17 | 66.23 | (0.205, 0.411) | 49 |

TABLE 3-continued

| Compound | | Driving Voltage (V) | Light Emission Efficiency (cd/A) | CIE (x, y) | Lifetime ($T_{95}$) |
|---|---|---|---|---|---|
| Example 29 | 126 | 7.22 | 66.22 | (0.243, 0.442) | 32 |
| Example 30 | 131 | 7.80 | 55.88 | (0.209, 0.419) | 37 |
| Example 31 | 133 | 7.79 | 56.18 | (0.210, 0.420) | 35 |
| Example 32 | 136 | 7.69 | 54.20 | (0.231, 0.419) | 33 |
| Example 33 | 138 | 7.76 | 53.88 | (0.229, 0.424) | 35 |
| Example 34 | 141 | 7.51 | 54.99 | (0.229, 0.430) | 30 |
| Example 35 | 147 | 7.01 | 69.82 | (0.220, 0.440) | 43 |
| Example 36 | 151 | 7.56 | 56.88 | (0.231, 0.419) | 35 |
| Example 37 | 152 | 7.60 | 56.80 | (0.229, 0.423) | 36 |
| Example 38 | 153 | 7.77 | 56.67 | (0.230, 0.421) | 38 |
| Example 39 | 154 | 7.44 | 58.89 | (0.238, 0.438) | 79 |
| Example 40 | 155 | 6.89 | 72.21 | (0.225, 0.429) | 39 |
| Example 41 | 156 | 6.92 | 71.13 | (0.243, 0.442) | 40 |
| Example 42 | 158 | 7.00 | 69.89 | (0.231, 0.440) | 42 |
| Example 43 | 161 | 7.49 | 57.94 | (0.211, 0.419) | 42 |
| Example 44 | 164 | 7.58 | 62.31 | (0.210, 0.412) | 33 |
| Example 45 | 165 | 6.78 | 75.03 | (0.231, 0.418) | 34 |
| Comparative Example 1-1 | TmPyPB | 8.57 | 57.61 | (0.212, 0.433) | 24 |
| Comparative Example 1-2 | BBQB | 8.43 | 58.11 | (0.220, 0.429) | 27 |
| Comparative Example 1-3 | TBQB | 8.47 | 58.90 | (0.222, 0.430) | 28 |

As shown from the results of Table 3, the organic light emitting devices using the charge generation layer material of the 2-stack white organic light emitting device of the present disclosure had a low driving voltage and improved light emission efficiency compared to Comparative Examples 1. Particularly, it was identified that Compounds 5, 10, 11, 17, 25, 26, 43, 52, 124 and 147 were significantly excellent in all of driving, efficiency and lifetime.

The presumed reason for such results is that the compound of the present disclosure used as an N-type charge generation layer formed with an invented skeleton having proper length, strength and flat property and a proper heterocompound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifetime were improved.

Experimental Example 2

1) Manufacture of Organic Light Emitting Device

A transparent electrode ITO thin film obtained from glass for an OLED (manufactured by Samsung Corning Advanced Glass) was ultrasonic cleaned consecutively using trichloroethylene, acetone, ethanol and distilled water for 5 minutes each, placed in isopropanol and stored, and then used.

Next, the ITO substrate was installed in a substrate folder of vacuum deposition equipment, and the following 4,4',4"-tris(N,N-(2-naphthyl)-phenylamino)triphenyl amine (2-TNATA) was introduced to a cell in the vacuum deposition equipment.

2-TNATA

Subsequently, the chamber was exhausted until the degree of vacuum inside the chamber reached $10^{-6}$ torr, and then a current was applied to the cell to evaporate the 2-TNATA to deposit a hole injection layer having a thickness of 600 Å on the ITO substrate.

The following N,N'-bis(α-naphthyl)-N,N'-diphenyl-4,4'-diamine (NPB) was introduced to a different cell in the vacuum deposition equipment, a current was applied to the cell for evaporation to deposit a hole transfer layer having a thickness of 300 Å on the hole injection layer.

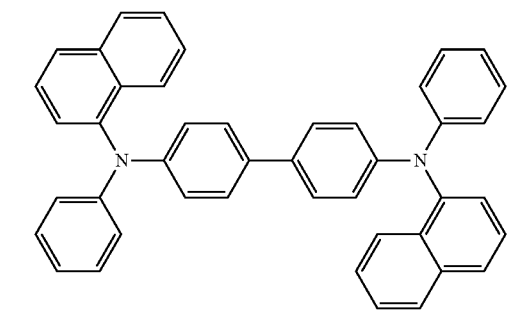

NPB

After forming the hole injection layer and the hole transfer layer as above, a blue light emitting material having a structure as follows was deposited thereon as a light emitting layer. Specifically, H1, a blue light emitting host material, was vacuum deposited to a thickness of 200 Å on one cell in the vacuum deposition equipment, and D1, a blue light emitting dopant material, was vacuum deposited thereon in 5% with respect to the host material.

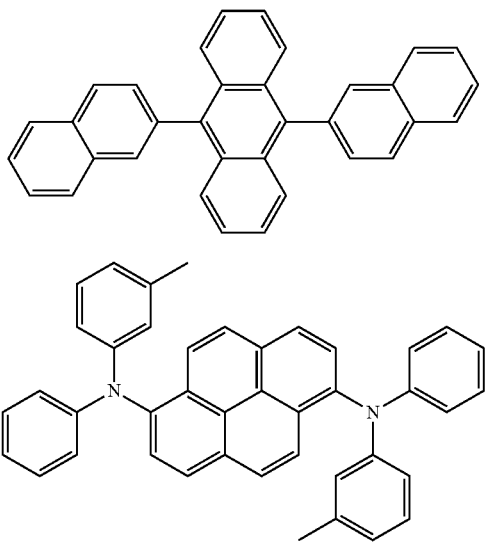

H1

D1

Subsequently, a compound of the following structural formula E1 was deposited to a thickness of 300 Å as an electron transfer layer.

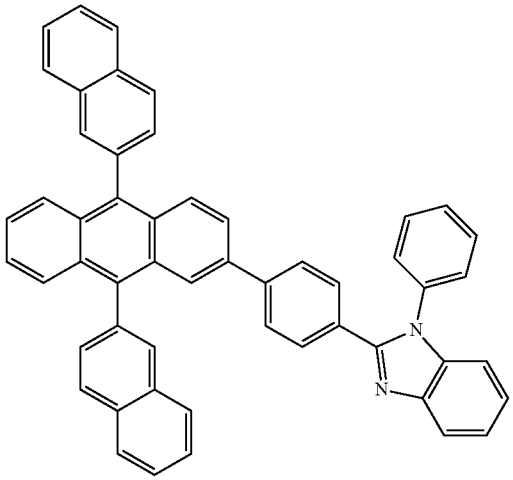

E1

As an electron injection layer, lithium fluoride (LiF) was deposited to a thickness of 10 Å, and an Al cathode was formed to a thickness of 1000 Å to manufacture an OLED device.

Meanwhile, all the organic compounds required to manufacture the OLED device were vacuum sublimation purified under $10^{-6}$ torr to $10^{-8}$ torr by each material to be used in the OLED manufacture.

OLED devices were manufactured in the same manner as in Experimental Example 2 except that compounds of the following Table 4 were used instead of Compound E1 as the electron transfer layer.

2) Driving Voltage and Light Emission Efficiency of Organic Light Emitting Device For the organic light emitting devices manufactured as above, electroluminescent light emission (EL) characteristics were measured using M7000 manufactured by McScience Inc., and with the measurement results, $T_{95}$ when standard luminance was 700 cd/m² was measured using a lifetime test system (M6000) manufactured by McScience Inc. Results of measuring a driving voltage, light emission efficiency, external quantum efficiency and a color coordinate (CIE) of the white organic light emitting devices manufactured according to the present disclosure are as shown in Table 4.

TABLE 4

| | Compound | Driving Voltage (V) | Light Emission Efficiency (cd/A) | CIE (x, y) | Lifetime ($T_{95}$) |
|---|---|---|---|---|---|
| Example 46 | 2 | 5.48 | 6.22 | (0.134, 0.101) | 38 |
| Example 47 | 3 | 5.44 | 6.25 | (0.134, 0.102) | 40 |
| Example 48 | 4 | 5.50 | 6.32 | (0.134, 0.101) | 33 |
| Example 49 | 5 | 4.72 | 6.53 | (0.134, 0.102) | 66 |
| Example 50 | 10 | 4.51 | 6.93 | (0.134, 0.100) | 40 |
| Example 51 | 11 | 4.56 | 6.88 | (0.134, 0.100) | 41 |
| Example 52 | 15 | 5.15 | 6.10 | (0.134, 0.103) | 39 |
| Example 53 | 16 | 5.20 | 6.15 | (0.134, 0.101) | 40 |
| Example 54 | 17 | 4.45 | 6.98 | (0.134, 0.100) | 40 |
| Example 55 | 25 | 4.50 | 6.99 | (0.134, 0.101) | 41 |
| Example 56 | 26 | 4.48 | 6.85 | (0.134, 0.099) | 40 |
| Example 57 | 27 | 5.07 | 6.24 | (0.134, 0.100) | 33 |
| Example 58 | 28 | 5.05 | 6.31 | (0.134, 0.100) | 31 |
| Example 59 | 30 | 5.09 | 6.22 | (0.134, 0.101) | 32 |
| Example 60 | 34 | 5.11 | 6.22 | (0.134, 0.103) | 36 |
| Example 61 | 35 | 5.11 | 6.20 | (0.134, 0.100) | 40 |
| Example 62 | 43 | 4.45 | 7.03 | (0.134, 0.100) | 33 |
| Example 63 | 52 | 4.41 | 6.95 | (0.134, 0.100) | 39 |
| Example 64 | 55 | 4.98 | 6.22 | (0.134, 0.100) | 40 |
| Example 65 | 67 | 5.02 | 6.34 | (0.134, 0.101) | 39 |
| Example 66 | 70 | 5.05 | 6.14 | (0.134, 0.101) | 40 |
| Example 67 | 89 | 5.44 | 6.22 | (0.134, 0.102) | 30 |
| Example 68 | 90 | 5.32 | 5.95 | (0.134, 0.101) | 29 |
| Example 69 | 91 | 5.40 | 6.13 | (0.134, 0.101) | 31 |
| Example 70 | 94 | 5.44 | 5.89 | (0.134, 0.100) | 32 |
| Example 71 | 101 | 5.39 | 6.01 | (0.134, 0.101) | 29 |
| Example 72 | 104 | 5.11 | 6.11 | (0.134, 0.100) | 40 |
| Example 73 | 124 | 4.44 | 7.14 | (0.134, 0.102) | 38 |

TABLE 4-continued

| | | | | | |
|---|---|---|---|---|---|
| Example 74 | 126 | 5.19 | 6.28 | (0.134, 0.102) | 40 |
| Example 75 | 131 | 5.24 | 6.10 | (0.134, 0.102) | 38 |
| Example 76 | 133 | 5.41 | 6.21 | (0.134, 0.101) | 39 |
| Example 77 | 136 | 5.33 | 6.19 | (0.134, 0.101) | 30 |
| Example 78 | 138 | 5.37 | 6.05 | (0.134, 0.100) | 28 |
| Example 79 | 141 | 5.10 | 6.21 | (0.134, 0.101) | 40 |
| Example 80 | 147 | 4.45 | 7.03 | (0.134, 0.100) | 40 |
| Example 81 | 151 | 5.05 | 6.23 | (0.134, 0.101) | 41 |
| Example 82 | 152 | 4.98 | 6.03 | (0.134, 0.101) | 35 |
| Example 83 | 153 | 5.40 | 6.21 | (0.134, 0.103) | 39 |
| Example 84 | 154 | 5.50 | 6.32 | (0.134, 0.101) | 61 |
| Example 85 | 155 | 4.14 | 7.31 | (0.134, 0.100) | 38 |
| Example 86 | 156 | 4.11 | 7.25 | (0.134, 0.100) | 37 |
| Example 87 | 158 | 4.56 | 6.88 | (0.134, 0.100) | 39 |
| Example 88 | 161 | 5.15 | 6.10 | (0.134, 0.103) | 41 |
| Example 89 | 164 | 5.05 | 6.22 | (0.134, 0.101) | 26 |
| Example 90 | 165 | 5.09 | 6.31 | (0.134, 0.101) | 28 |
| Comparative Example 2-1 | E1 | 5.56 | 5.91 | (0.134 0.100) | 28 |
| Comparative Example 2-2 | E2 | 6.01 | 4.97 | (0.134, 0.103) | 85 |
| Comparative Example 2-3 | E3 | 5.52 | 6.21 | (0.134, 0.101) | 29 |
| Comparative Example 2-4 | BBQB | 5.50 | 6.10 | (0.134, 0.101) | 30 |
| Comparative Example 2-5 | TBQB | 5.51 | 6.15 | (0.134, 0.102) | 29 |

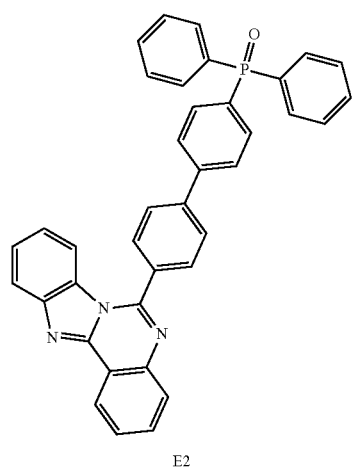 [SMILES: O=P(c1ccccc1)(c1ccccc1)c1ccc(-c2ccc(-c3nc4ccccc4c4nc5ccccc5n34)cc2)cc1]

E2

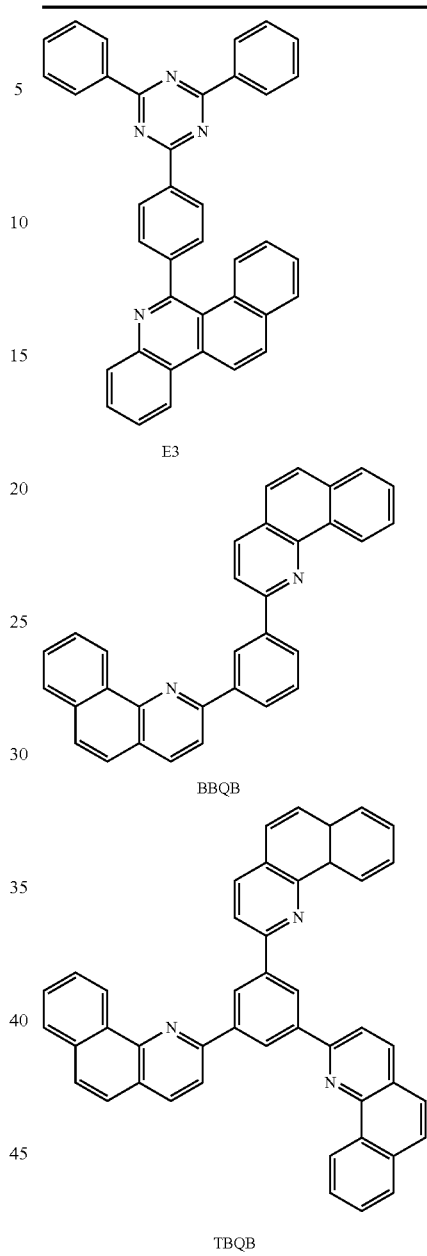

E3

BBQB

TBQB

As shown from the results of Table 4, the organic light emitting devices using the electron transfer layer material of the blue organic light emitting device of the present disclosure had a low driving voltage, and significantly improved light emission efficiency and lifetime compared to Comparative Examples 3. Particularly, it was identified that Compounds 5, 10, 11, 17, 25, 26, 43, 52, 124 and 147 were significantly excellent in all of driving, efficiency and lifetime.

The presumed reason for such results is that, when the invented compound having proper length, strength and flat property is used as an electron transfer layer, a compound in an excited state is produced by receiving electrons under a specific condition, and particularly, when the excited state is formed in the heteroskeleton site of the compound, excited energy moves to a stable state before the excited heteroskeleton site goes through a different reaction, and the relatively stabilized compound is capable of efficiently transferring electrons without compound decomposition or destruction. As a reference, it is considered that those having a stable state when excited are aryl or acene series compounds or multicyclic hetero-compounds. Accordingly, it is considered that the compound of the present disclosure enhances electron-transfer properties or improved stability resulting in excellency in all of driving, efficiency and lifetime.

The invention claimed is:

1. A hetero-cyclic compound represented by the following Chemical Formula 1:

[Chemical Formula 1]

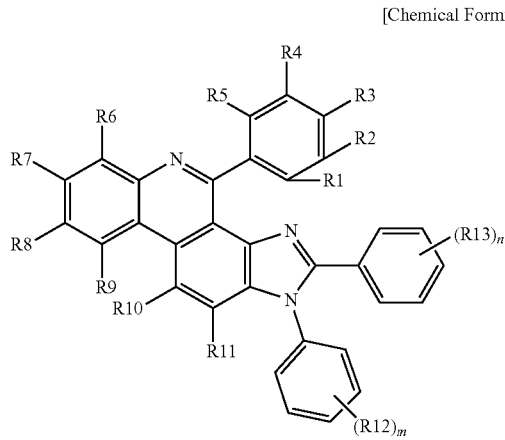

wherein, in Chemical Formula 1,
at least one of R1 to R5 is represented by -(L1)p-(Z1)q, and the rest are hydrogen or deuterium;
L1 is a direct bond; a substituted or unsubstituted $C_6$ to $C_{60}$ arylene group; or a $C_2$ to $C_{60}$ heteroarylene group;
Z1 is selected from the group consisting of —CN; a substituted or unsubstituted $C_6$ to $C_{60}$ aryl group; and a substituted or unsubstituted $C_2$ to $C_{60}$ heteroaryl group;
p is an integer of 1 to 4;
q is an integer of 1 to 4;
R6 to R13 are the same as or different from each other, and each independently selected from the group consisting of hydrogen; or deuterium; and
m and n are each independently an integer of 0 to 5.

2. The hetero-cyclic compound of claim 1, wherein R3 of R1 to R5 of Chemical Formula 1 is represented by -(L1)p-(Z1)q, and the rest are hydrogen, and
L1, Z1, p and q have the same definitions as in claim 1.

3. The hetero-cyclic compound of claim 1, wherein R1, R2, R4, R5, and R6 to R13 of Chemical Formula 1 are each independently hydrogen or deuterium.

4. The hetero-cyclic compound of claim 1, wherein R4 of R1 to R5 of Chemical Formula 1 is represented by -(L1)p-(Z1)q, and the rest are hydrogen, and
L1, Z1, p and q have the same definitions as in claim 1.

5. The hetero-cyclic compound of claim 1, wherein R1, R2, R3, R5, and R6 to R13 of Chemical Formula 1 are each independently hydrogen or deuterium.

6. The hetero-cyclic compound of claim 1, wherein Chemical Formula 1 is represented by any one of the following compounds:

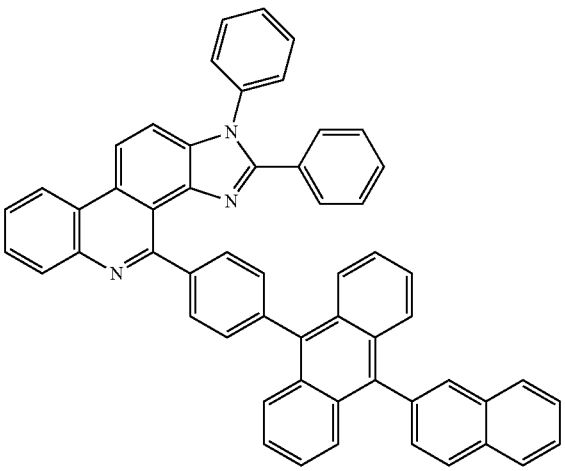

1

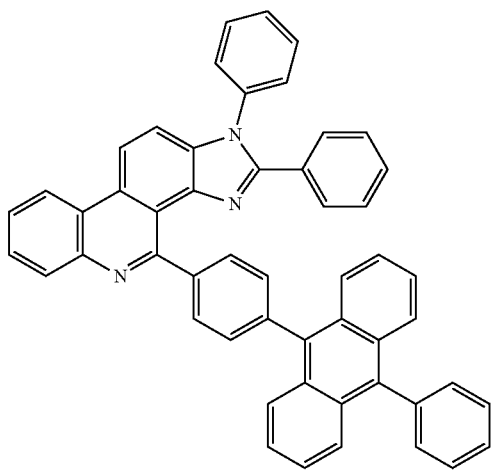

2

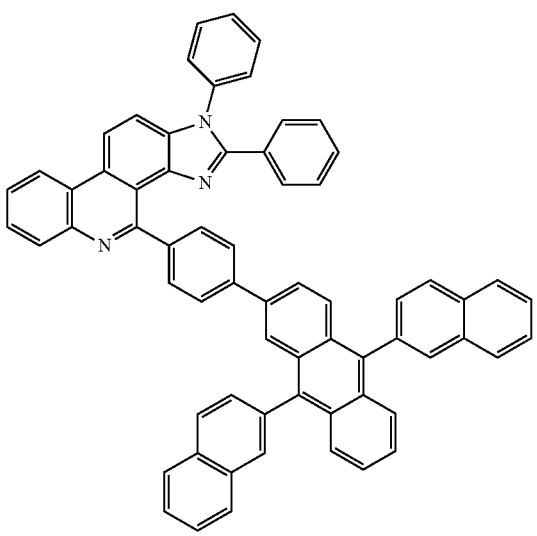

3

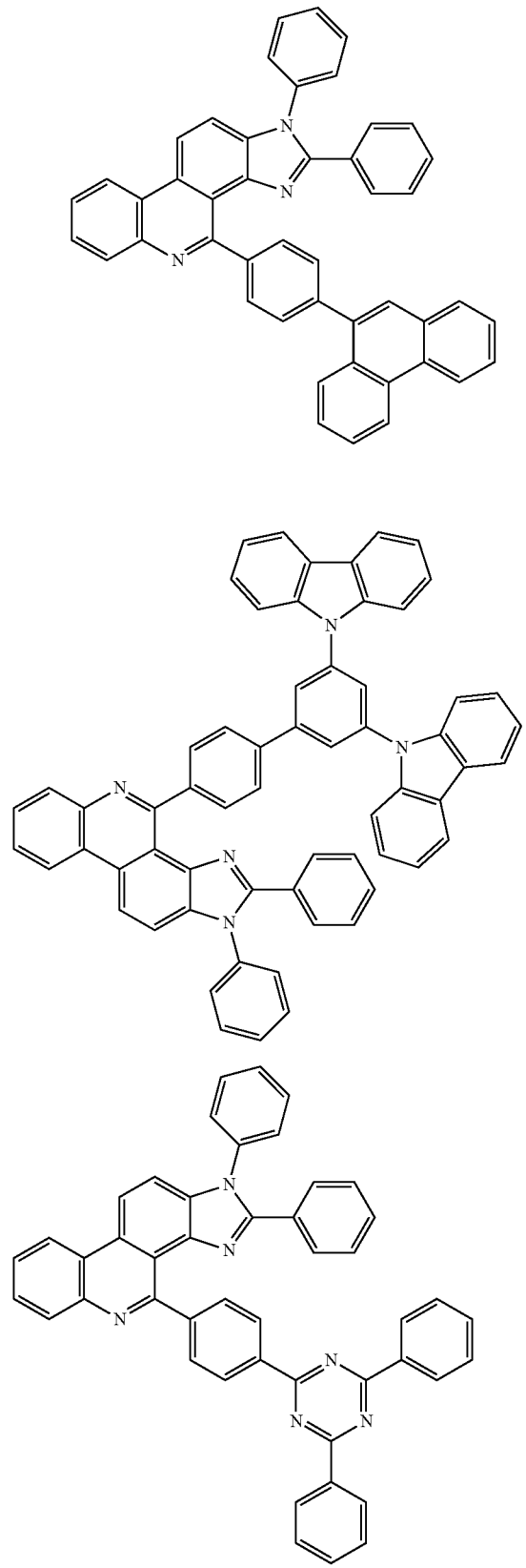
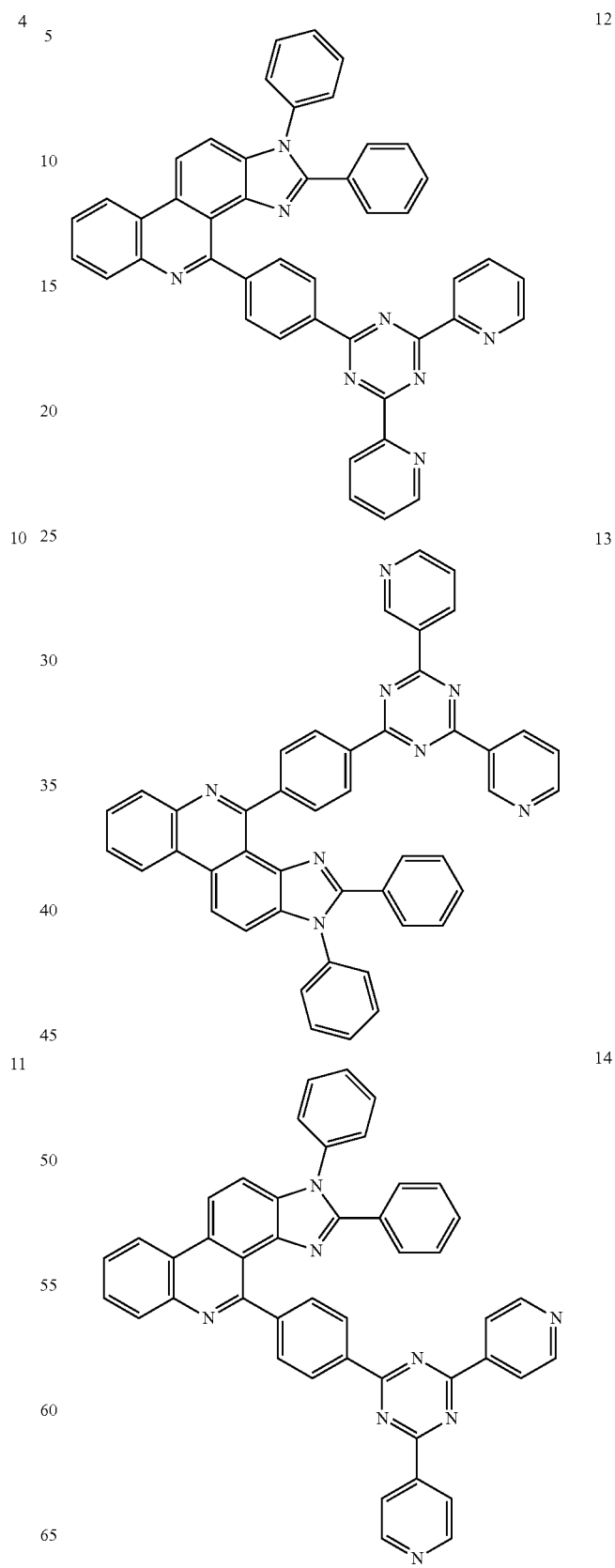

15
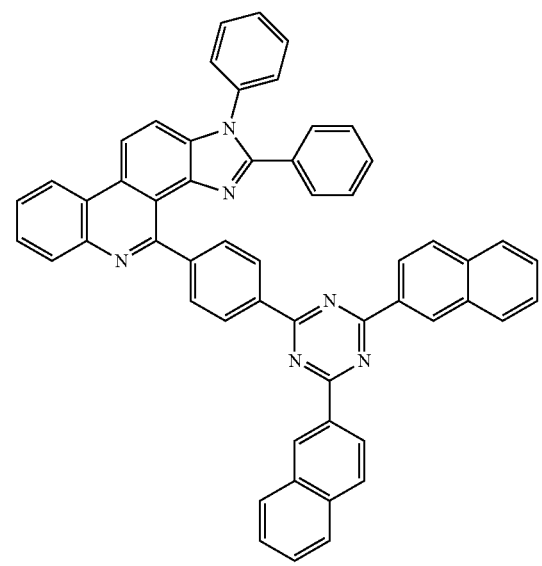
16
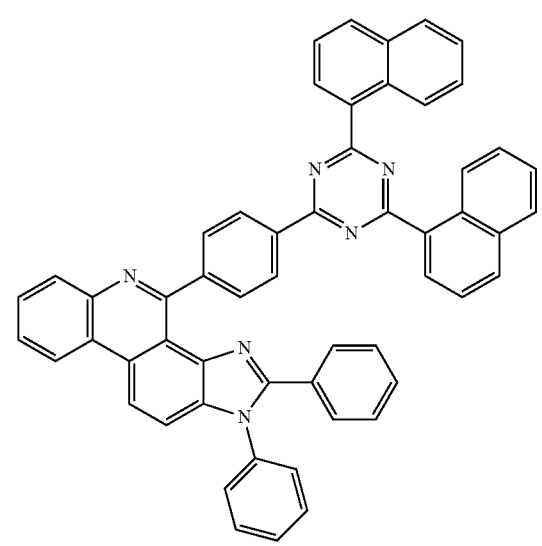
17
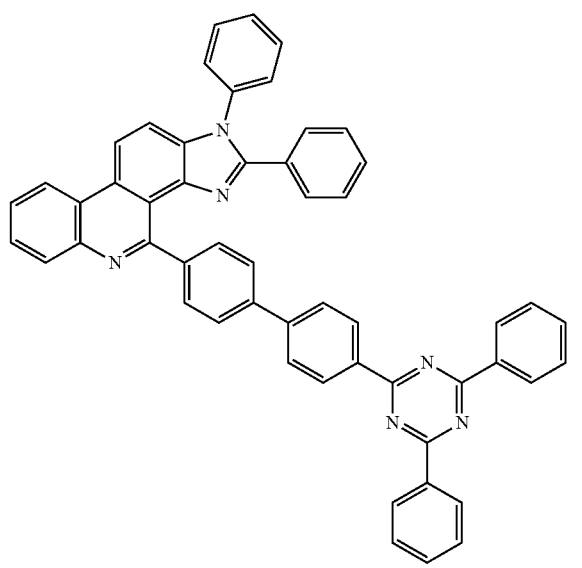
18
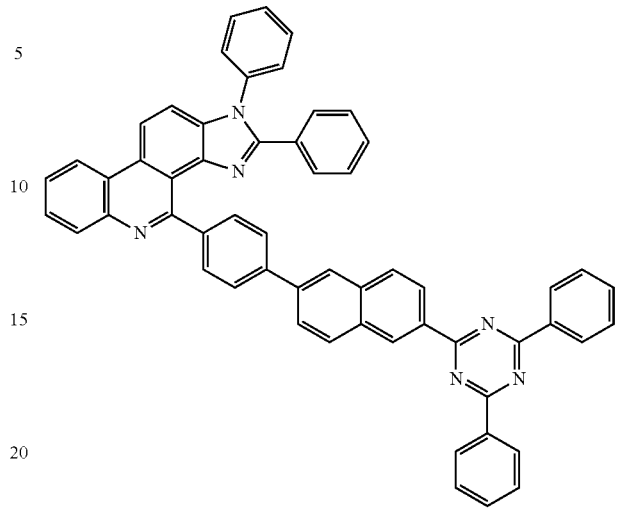
19
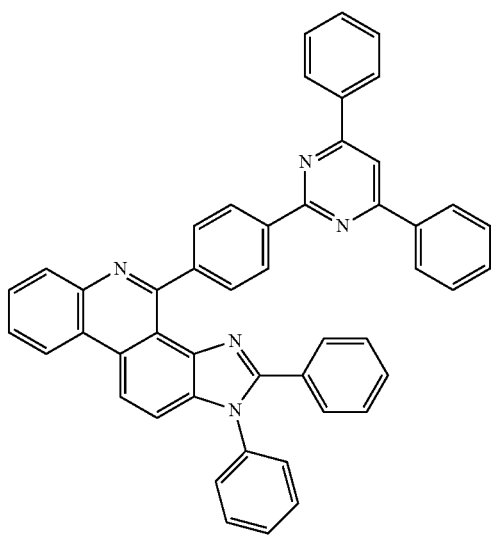
20
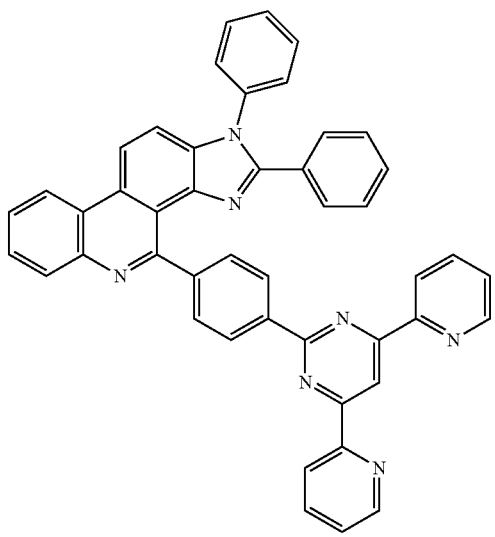

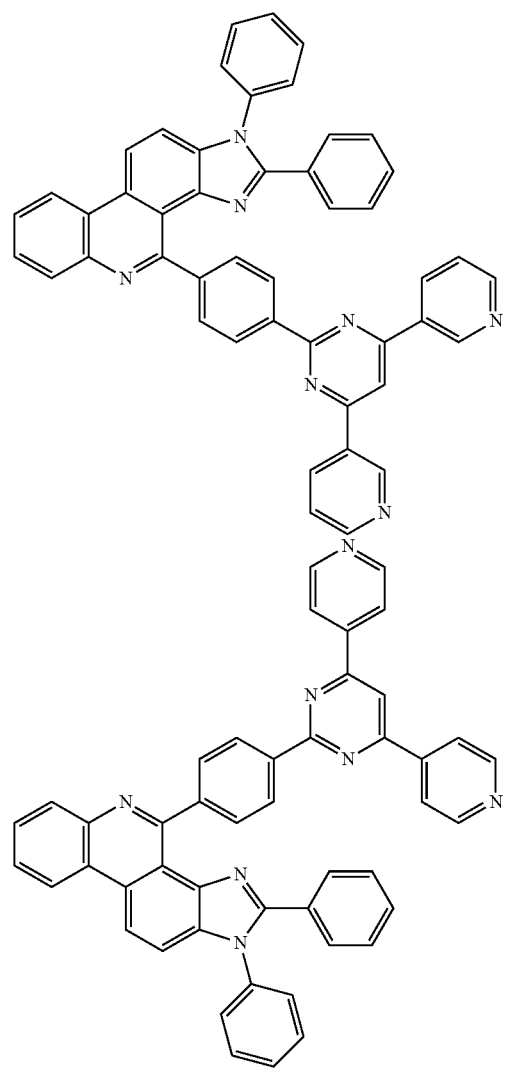
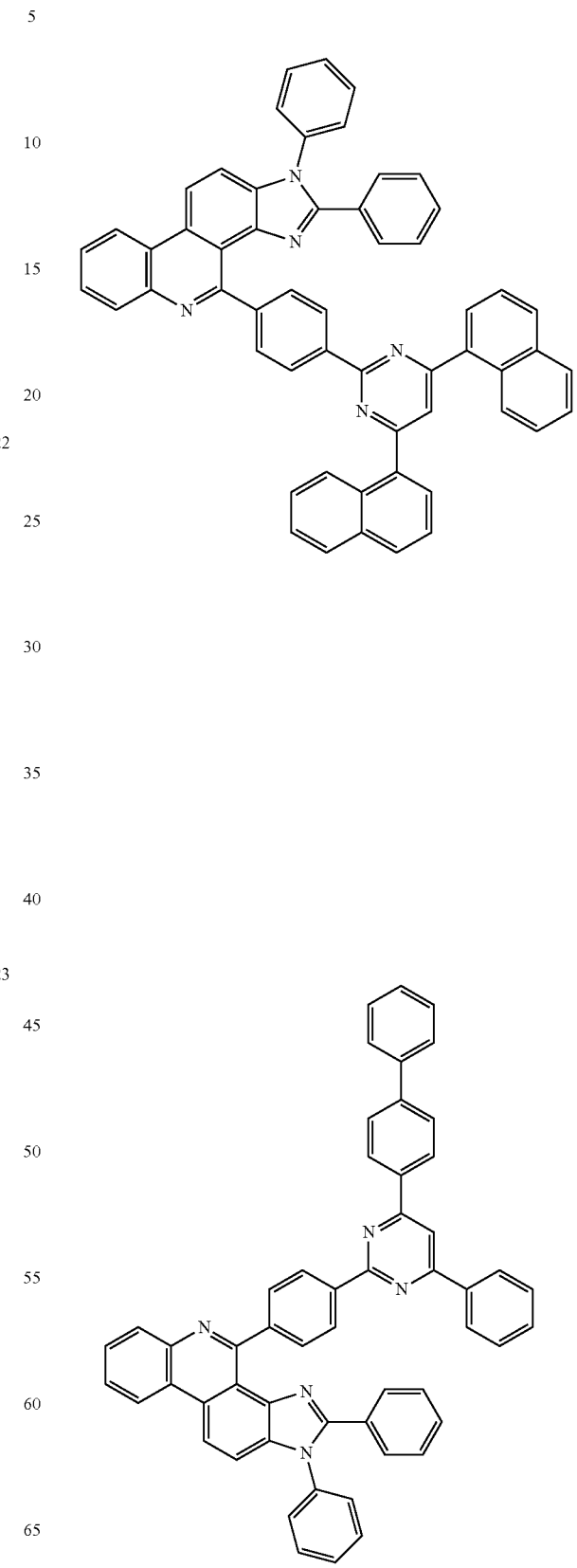

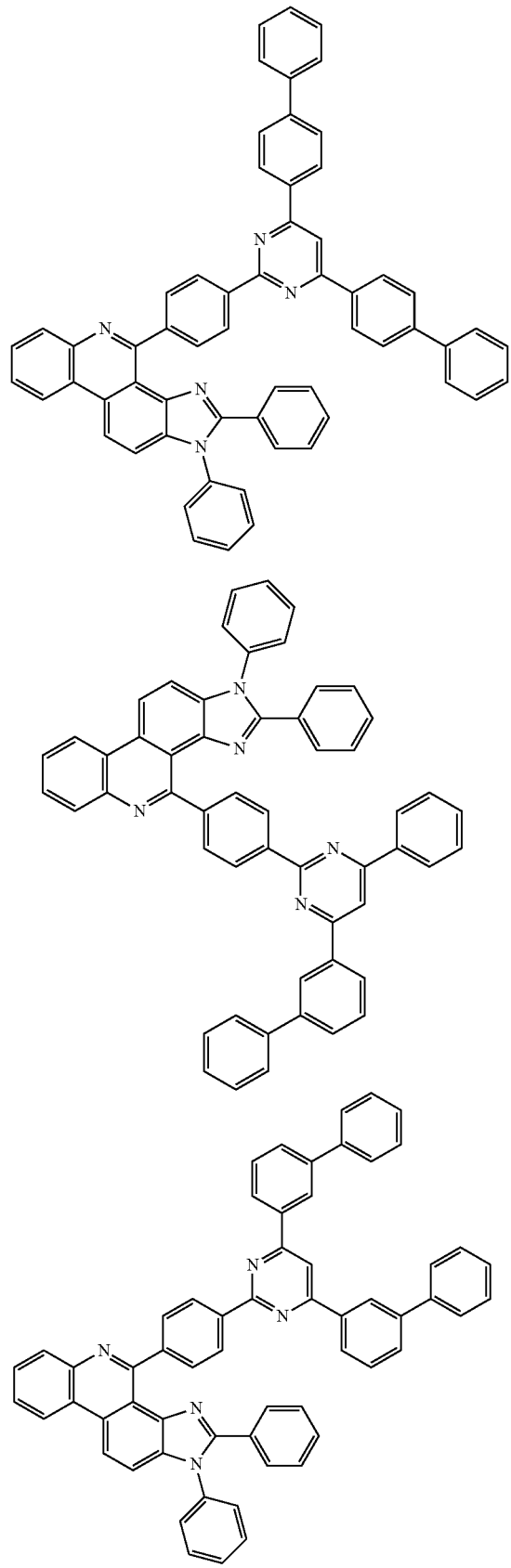
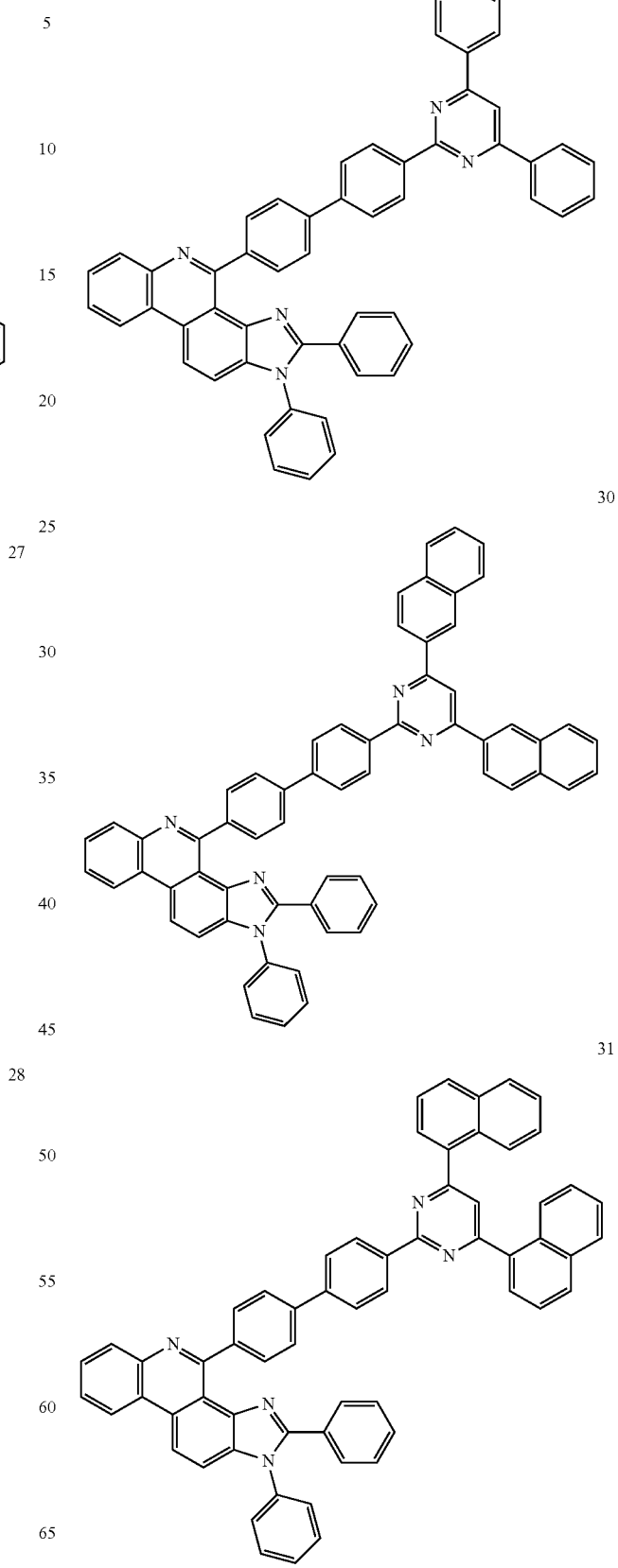

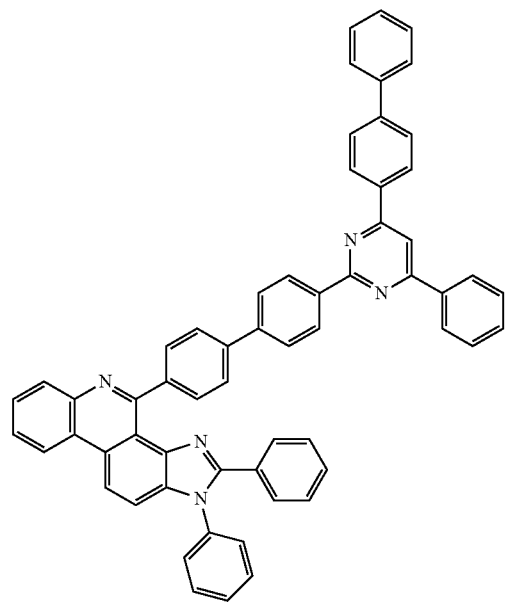
32
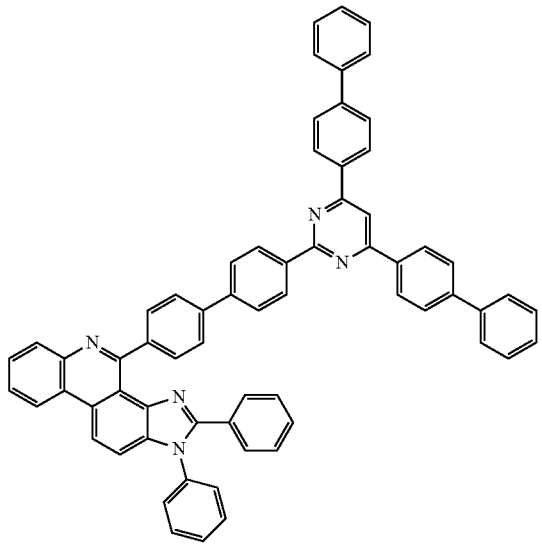
33
31
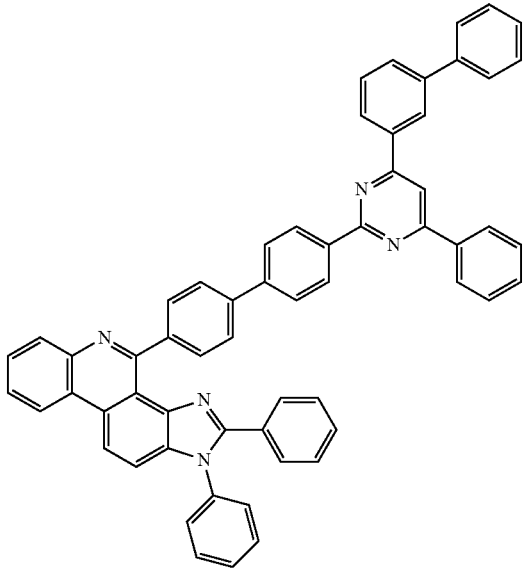
34
32
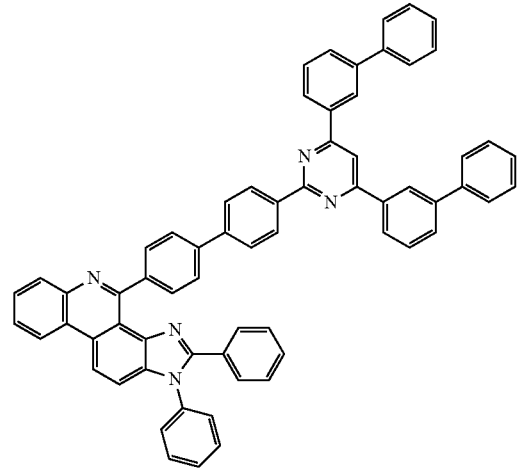
35

36
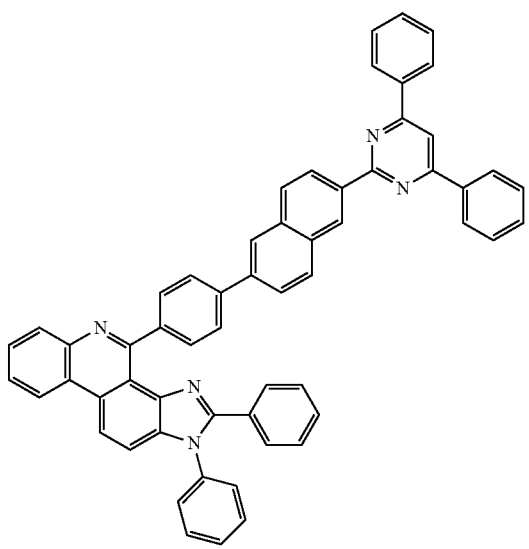
37
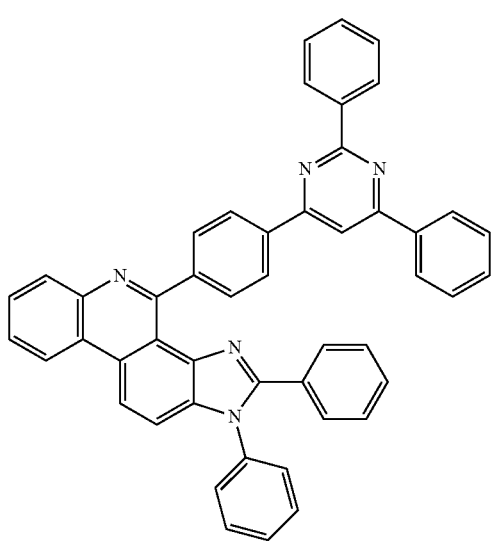
38
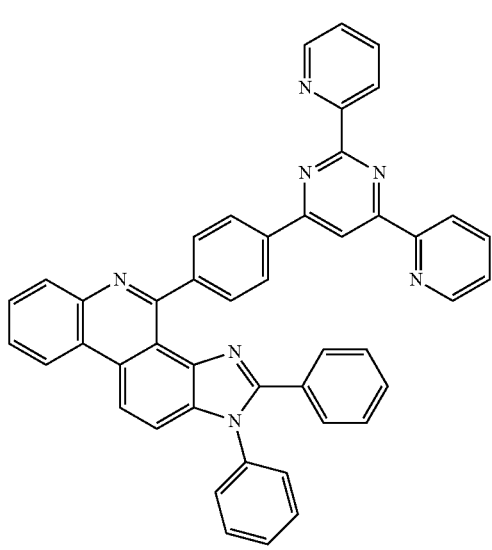
39
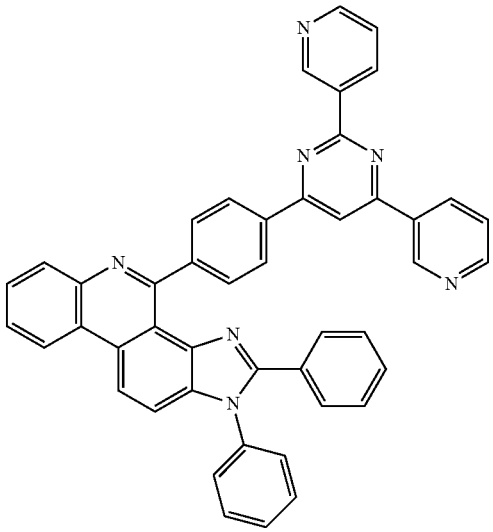
40
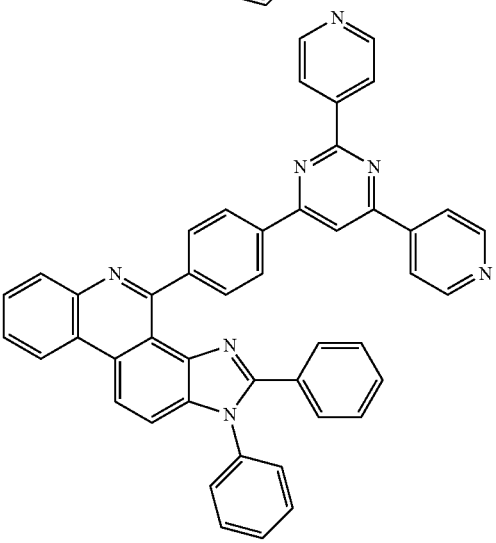
41
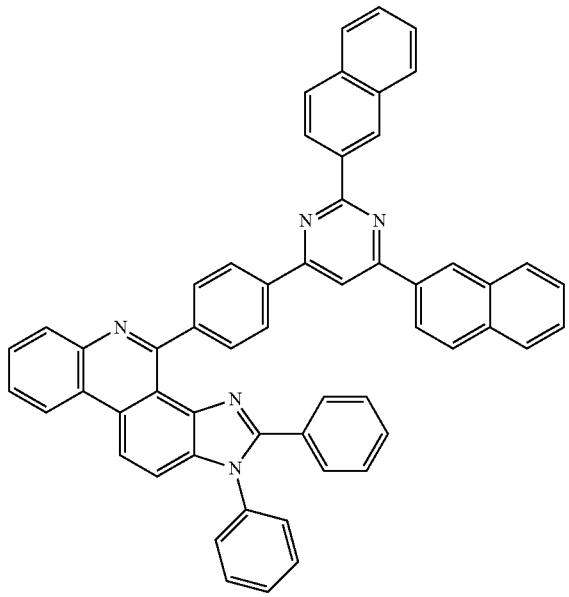

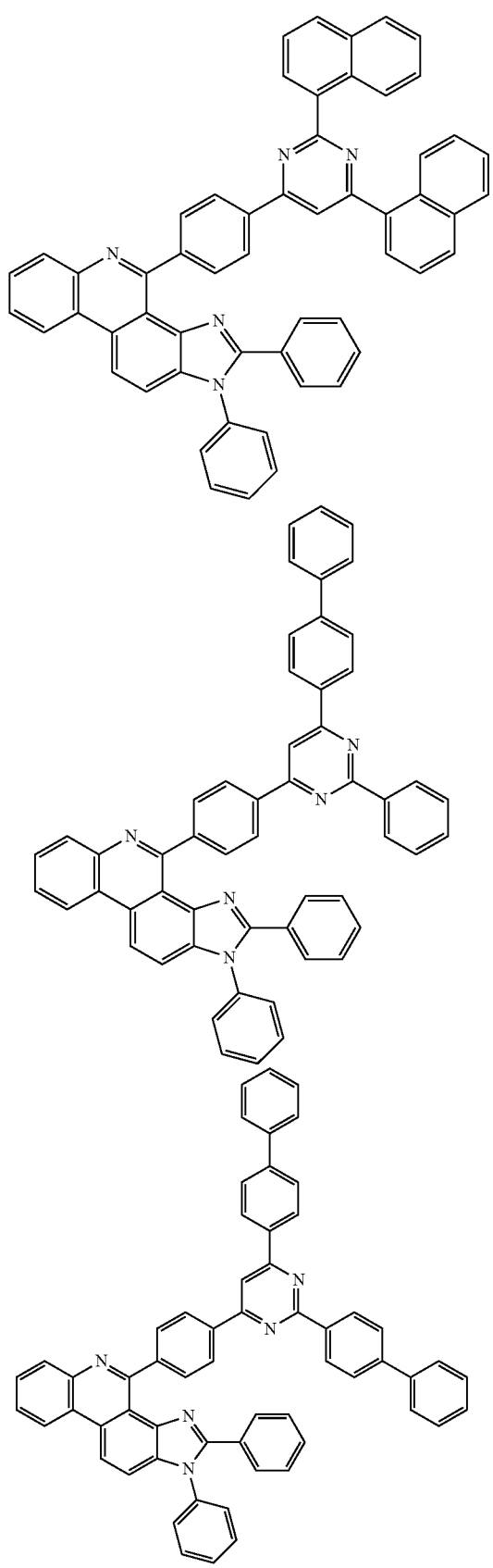
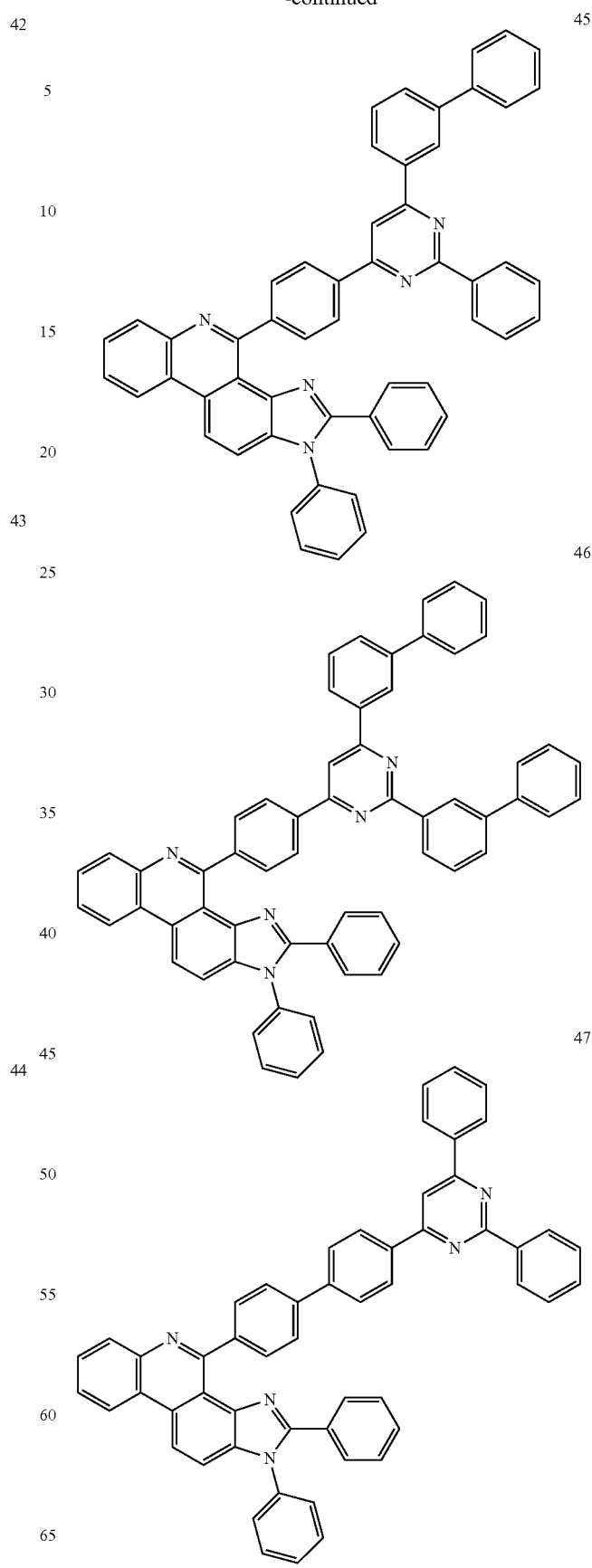

48
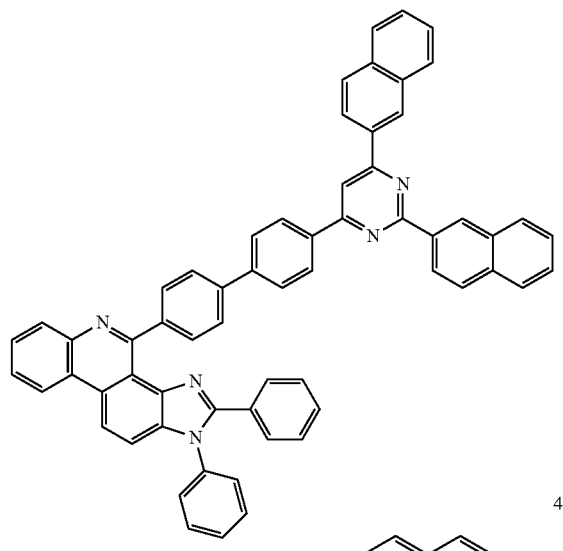
49
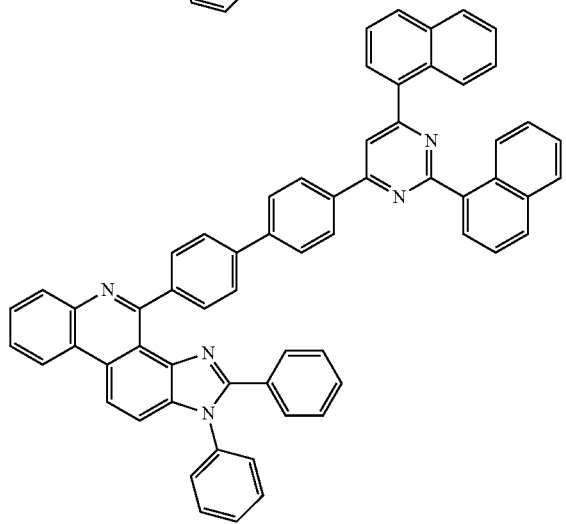
50
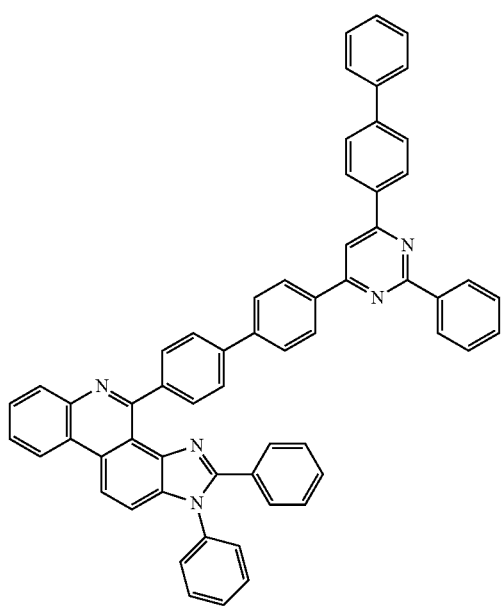
51
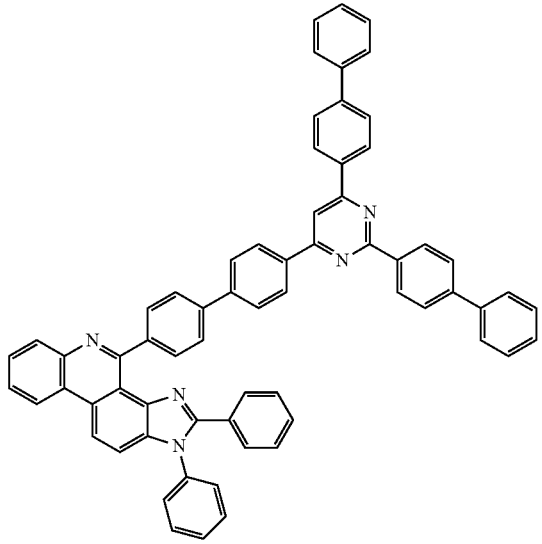
52
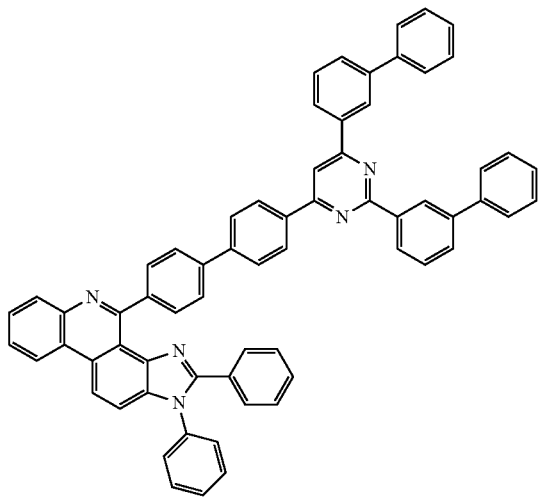
53

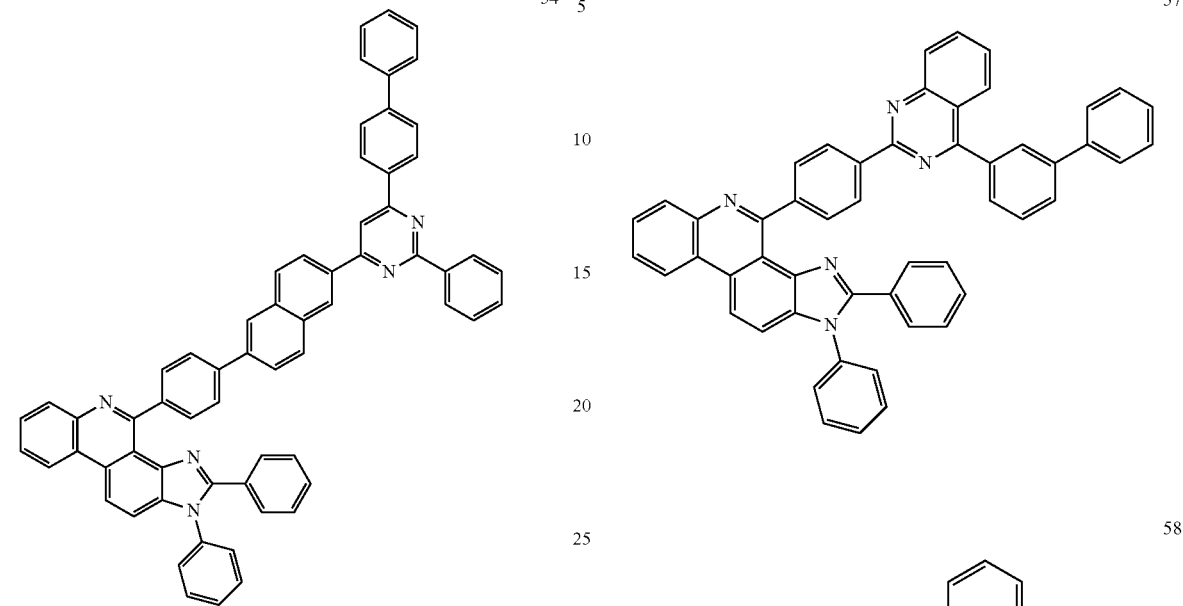
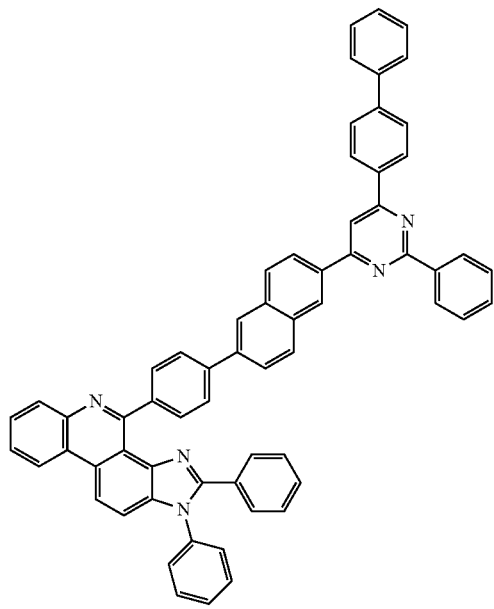
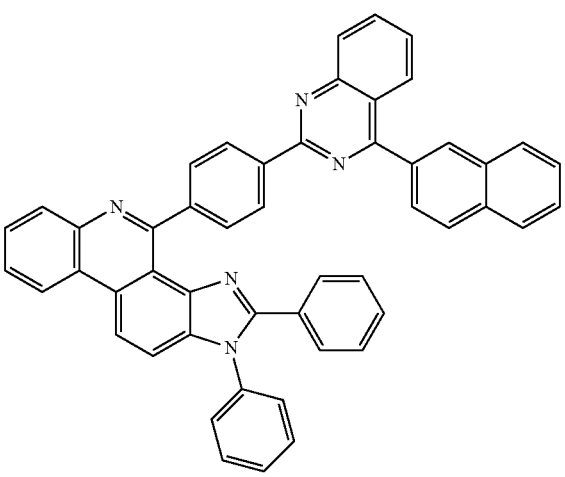
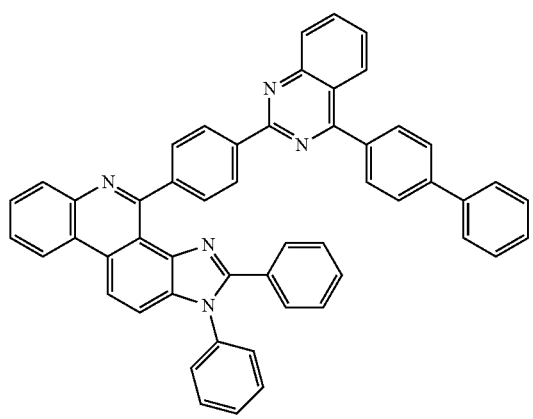
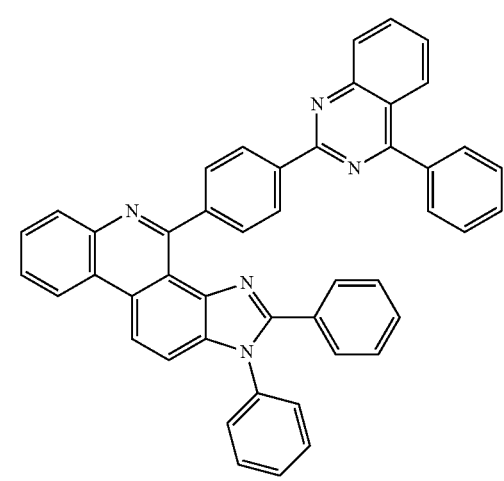

-continued
60
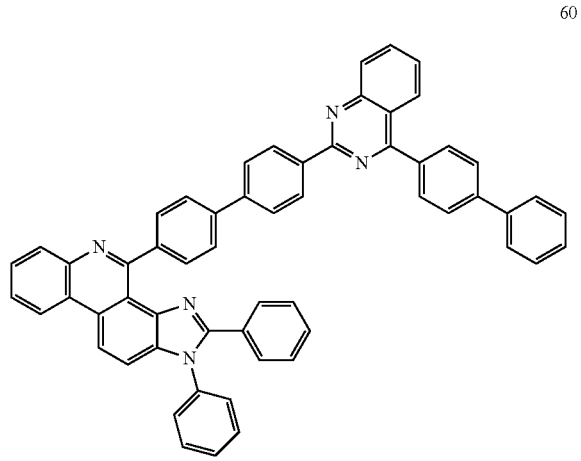
61
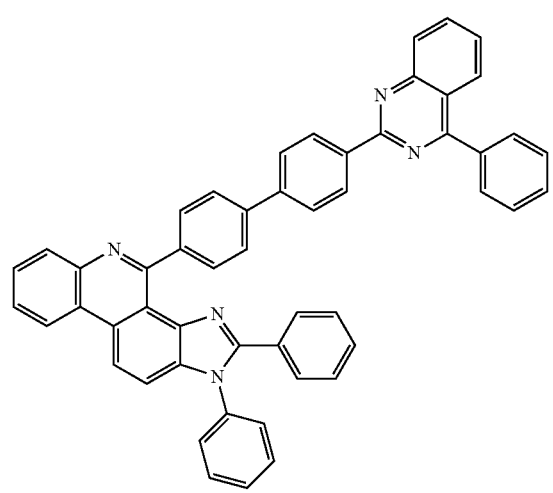
62
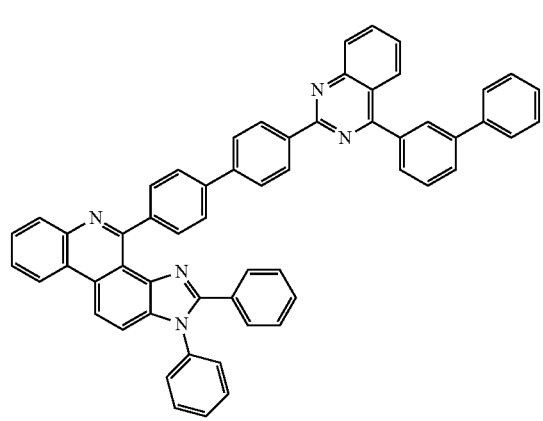
-continued
63
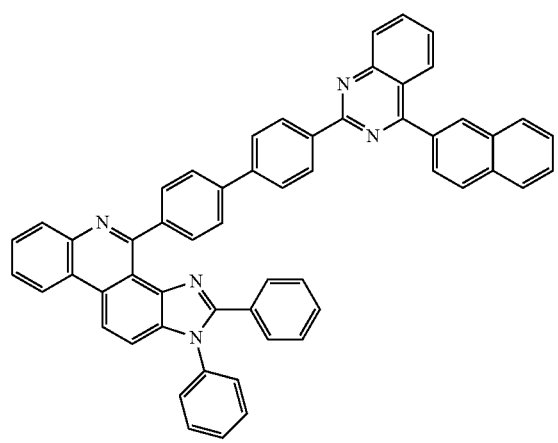
64
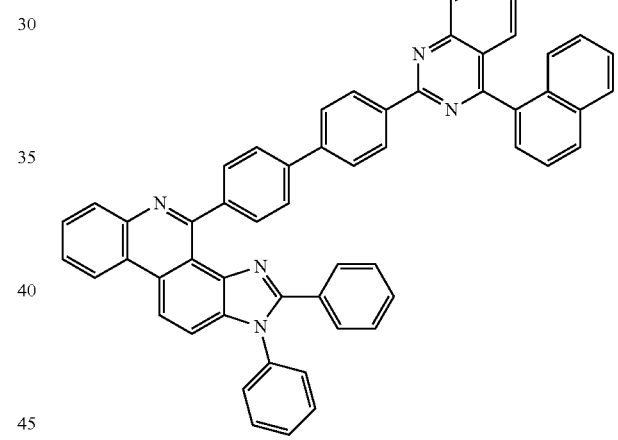
65
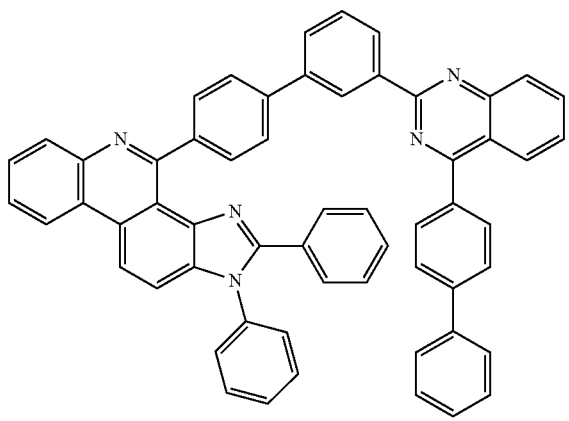

171
-continued
66
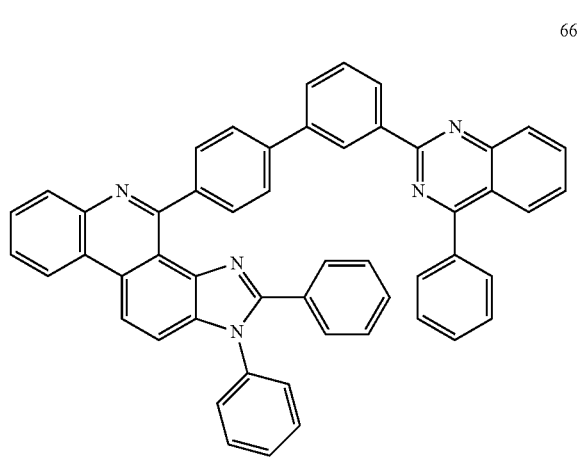
67
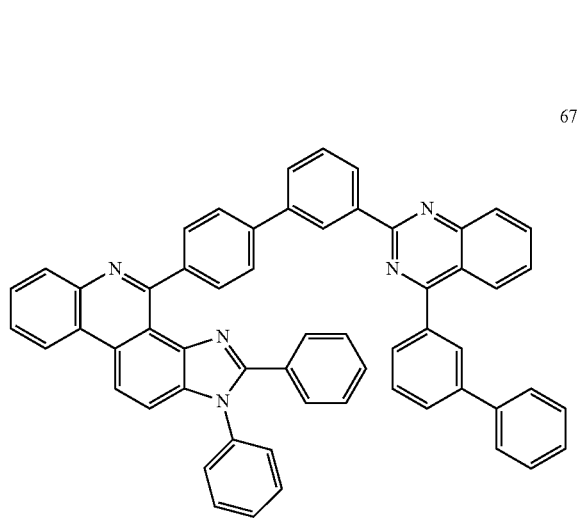
68
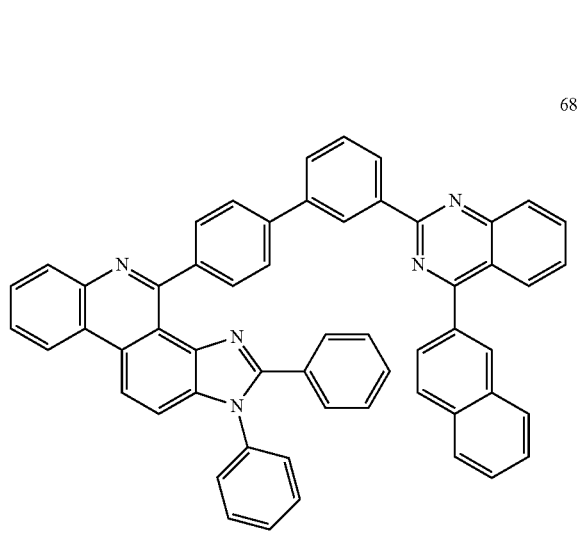
172
-continued
69
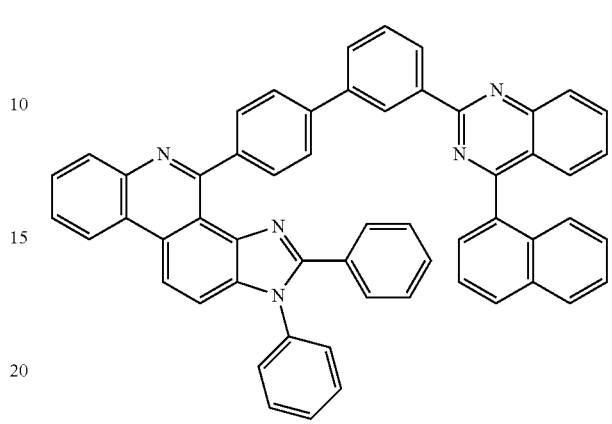
70
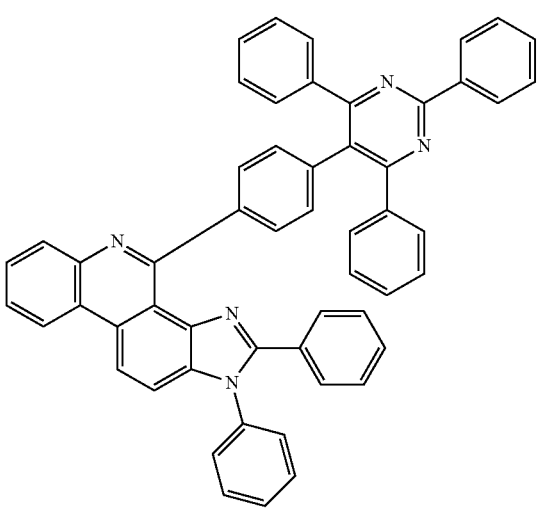
71
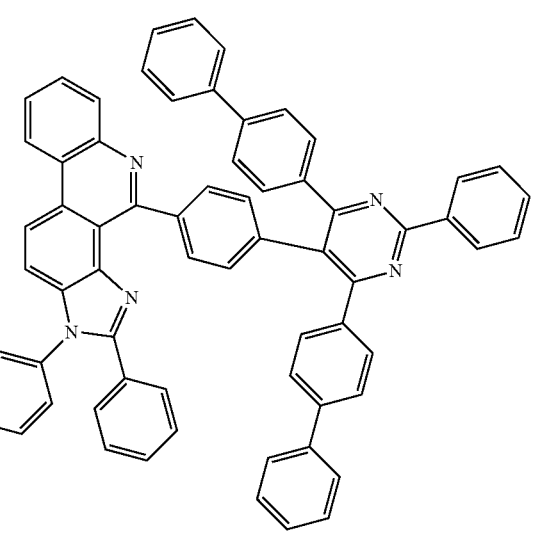

72
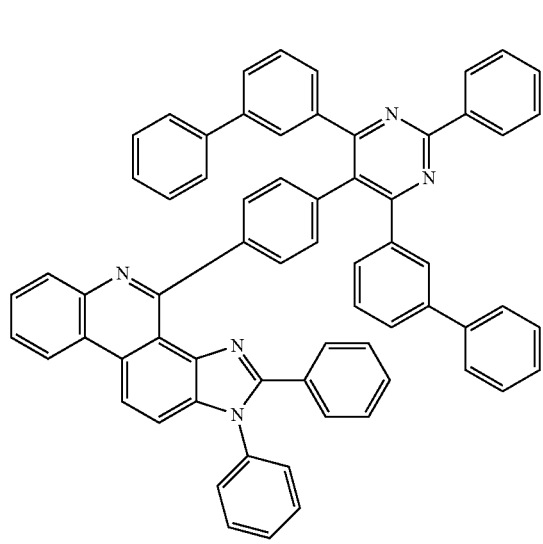
73
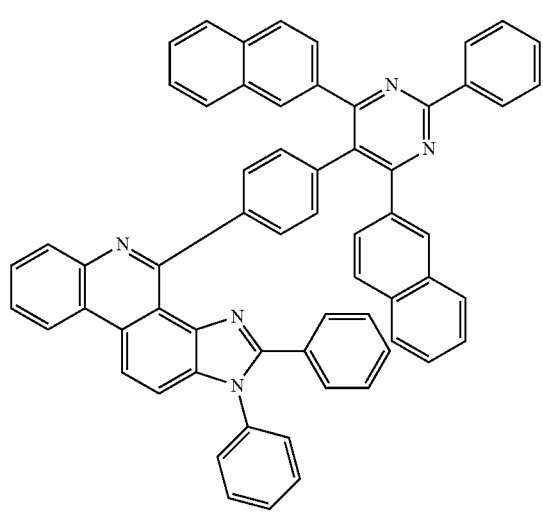
74
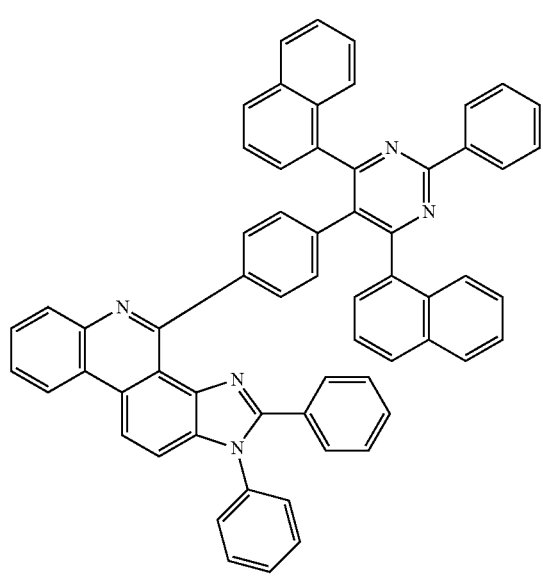
75
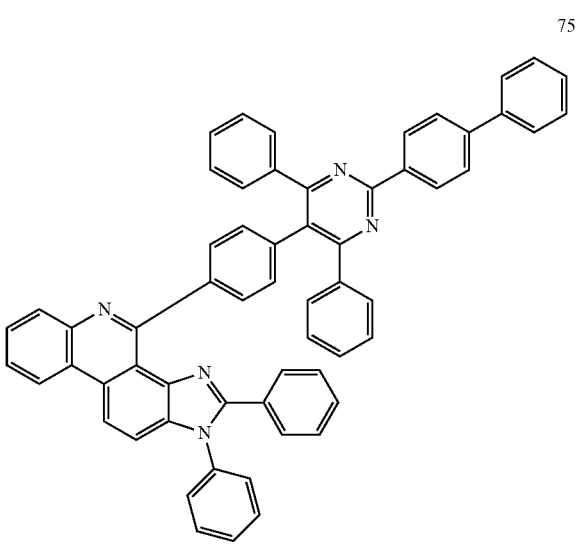
76
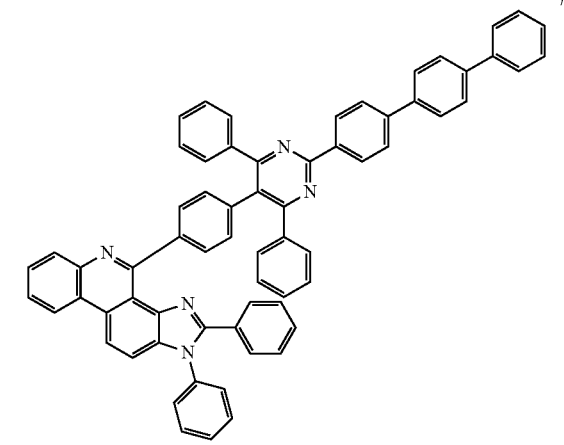
77
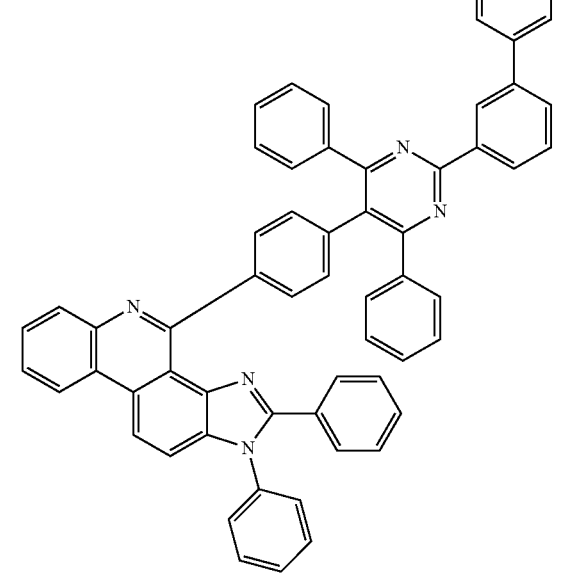

-continued
78
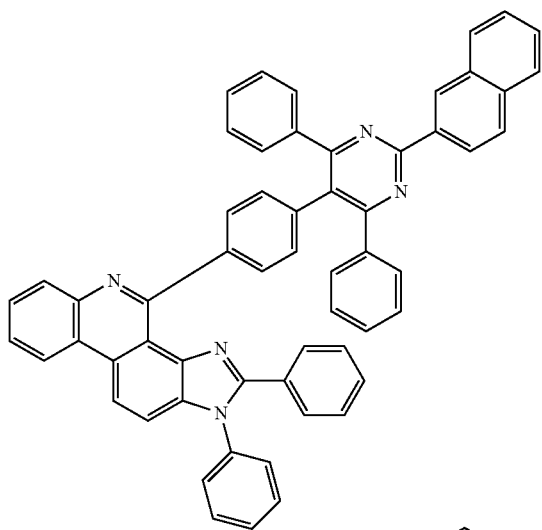
79
80
-continued
81
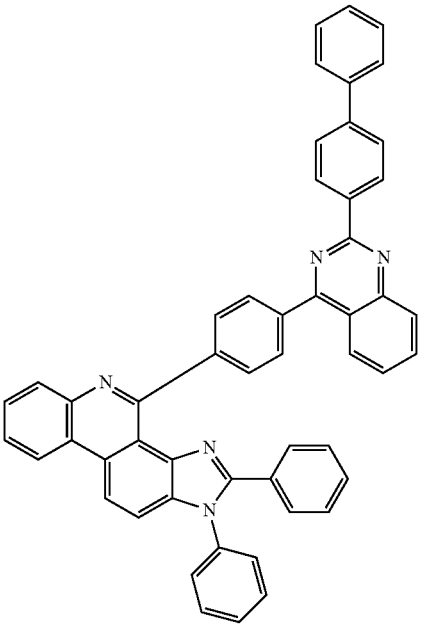
82

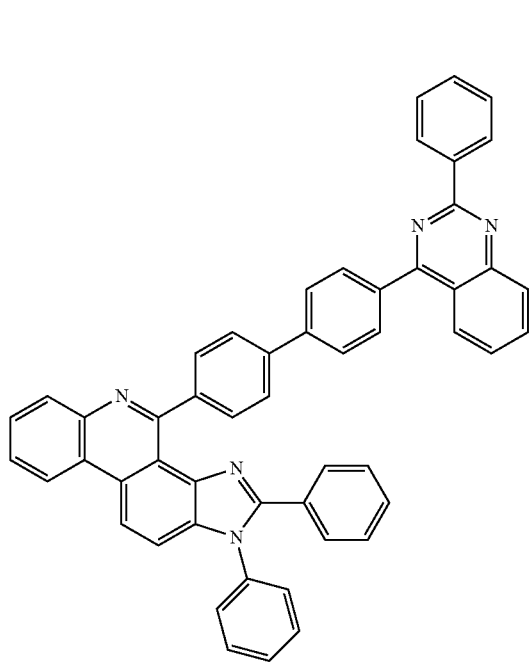
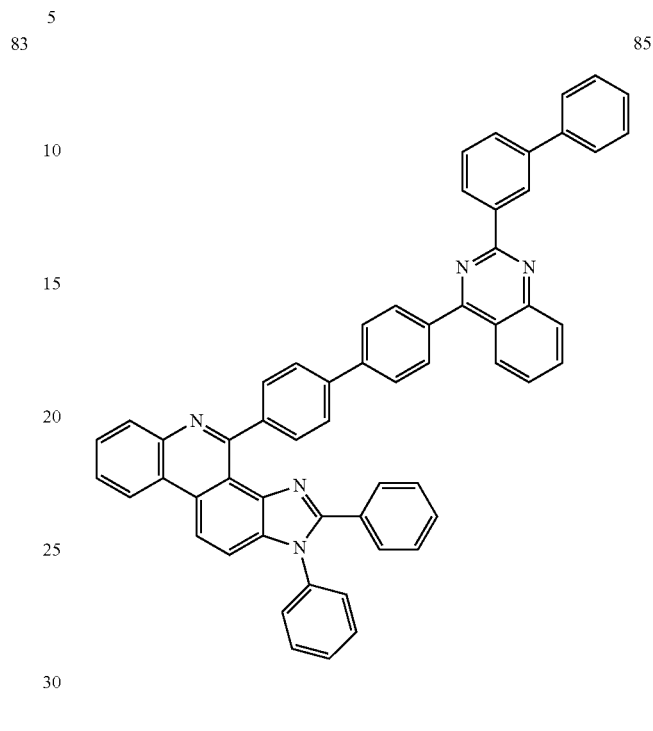

87
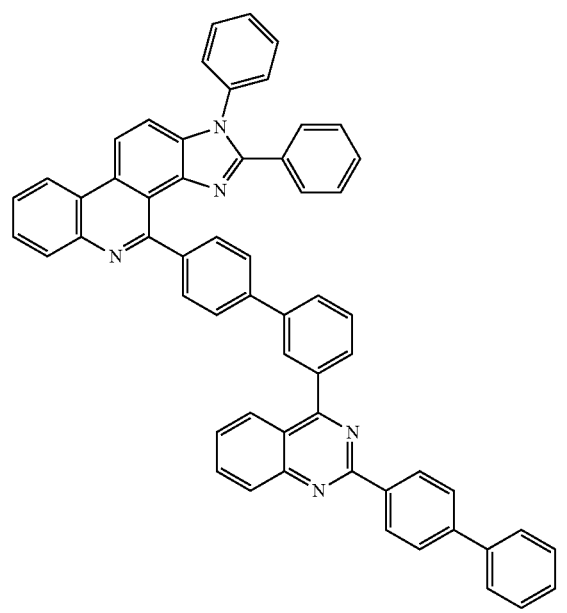
88
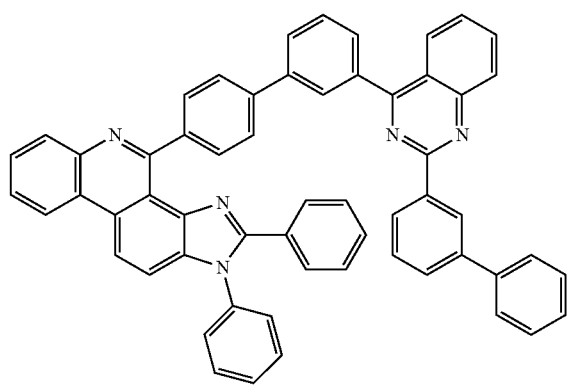
89
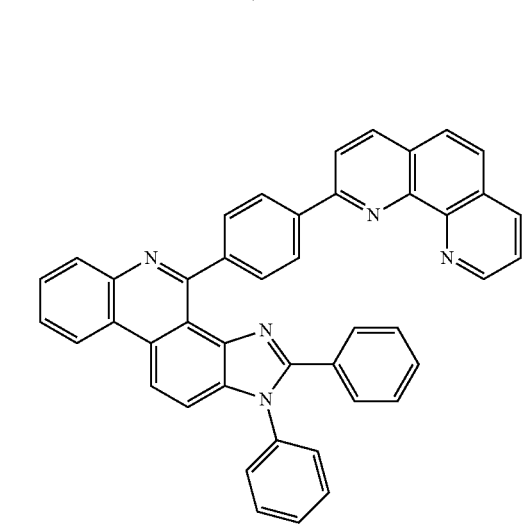
90
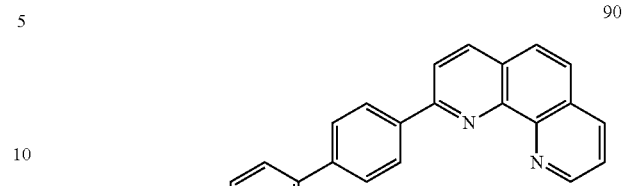
91
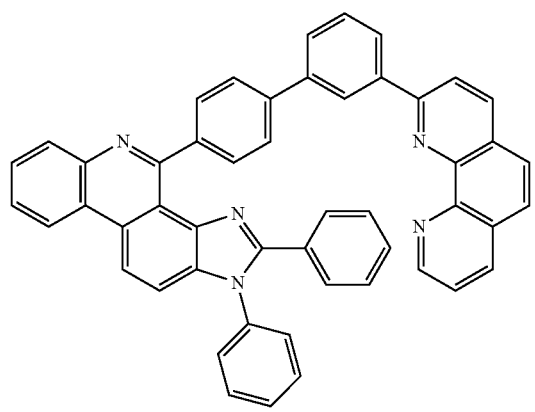
92
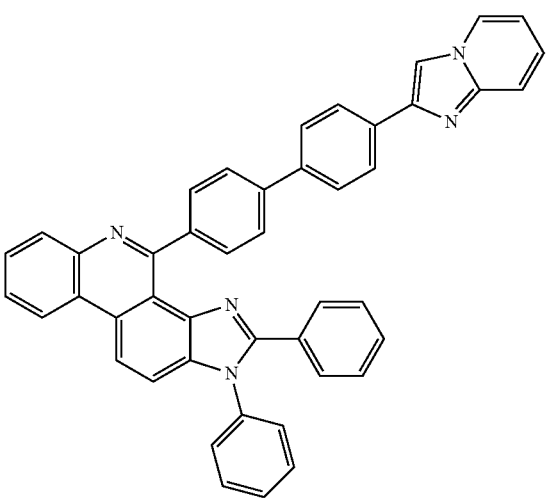

181
-continued
93
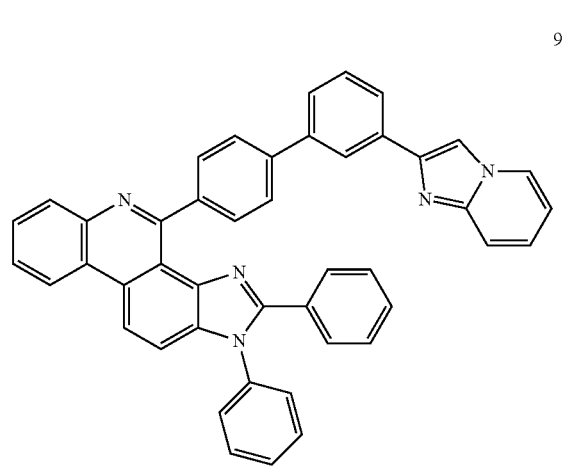
94
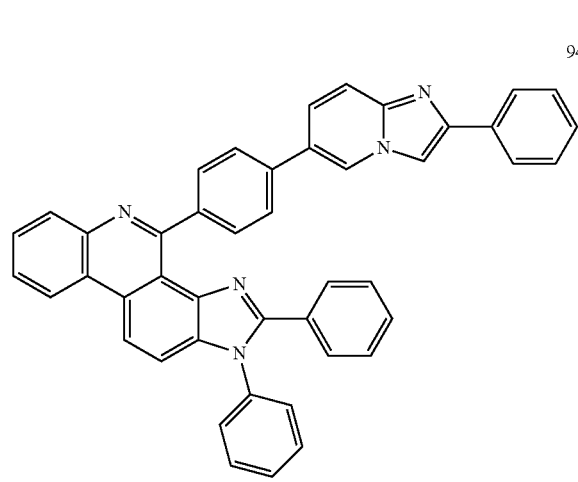
95
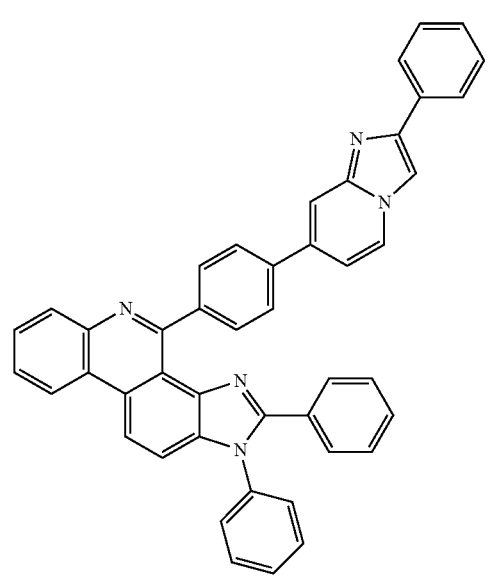
182
-continued
96
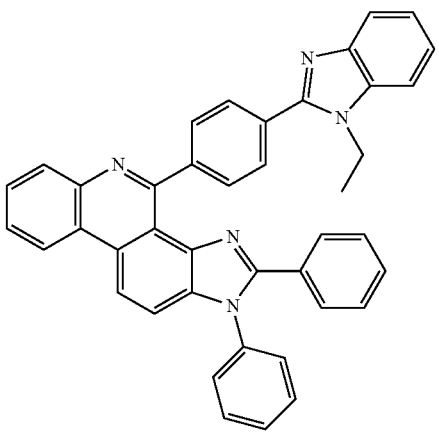
97
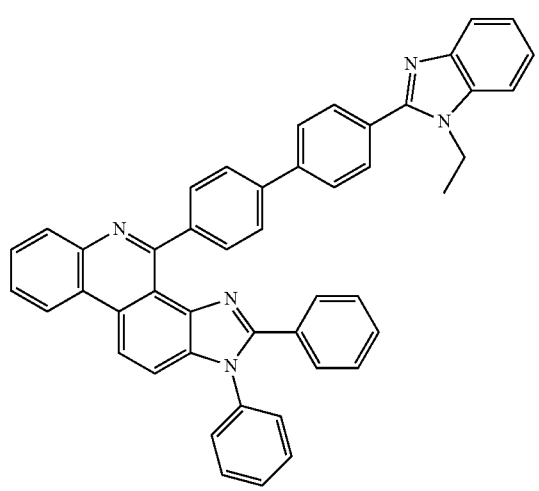
98
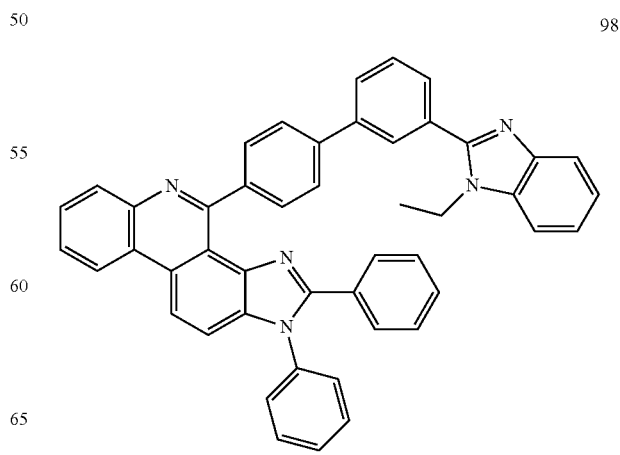

183
-continued
99
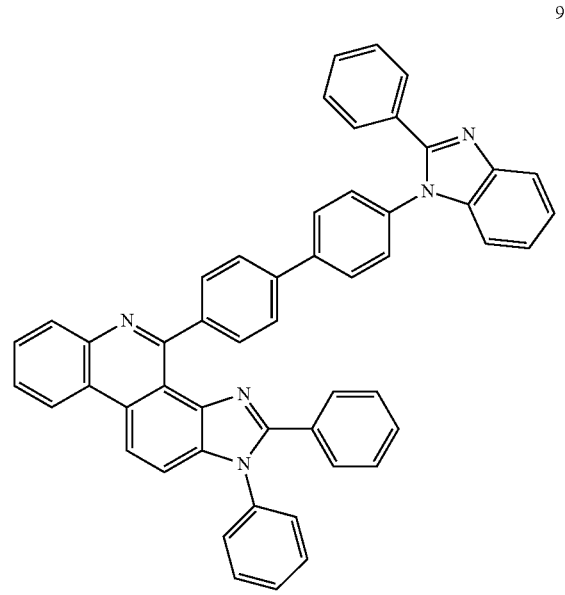
100
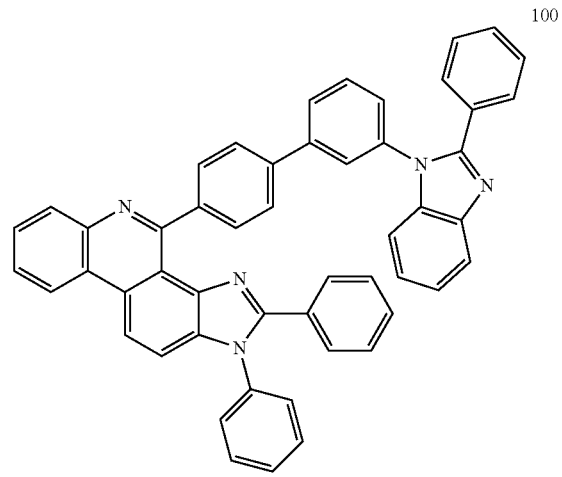
101
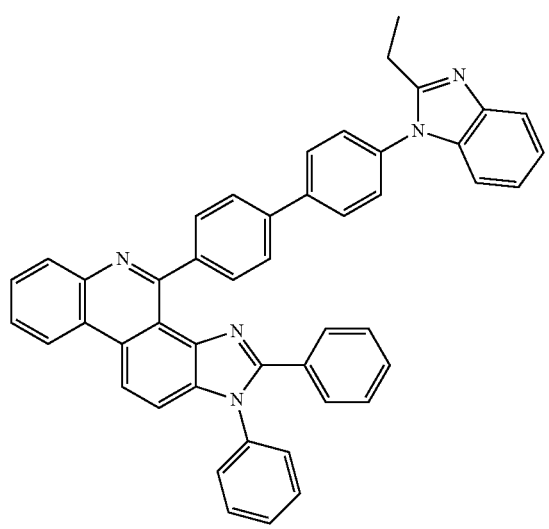
184
-continued
102
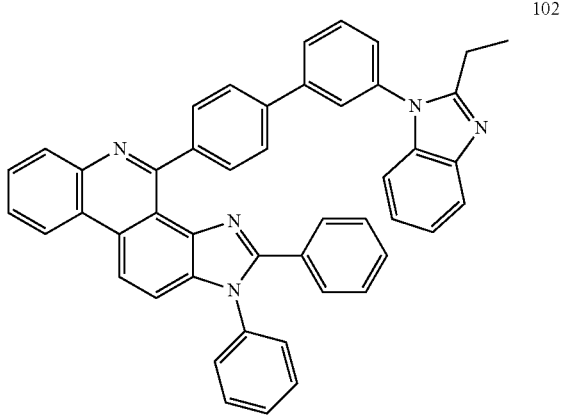
103
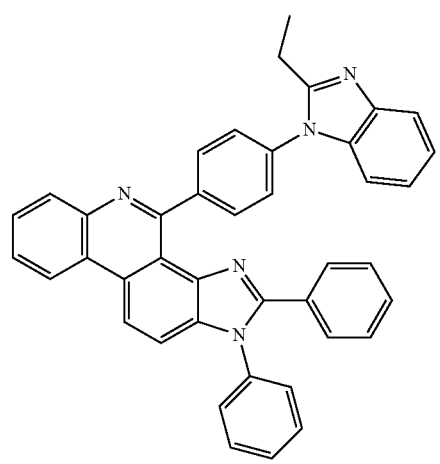
104
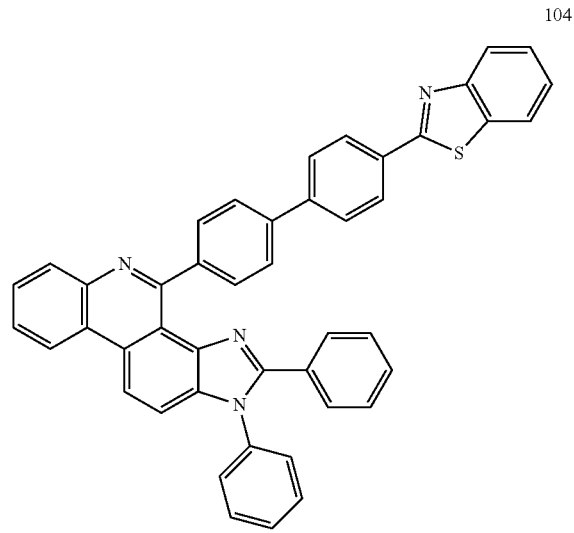

-continued
105
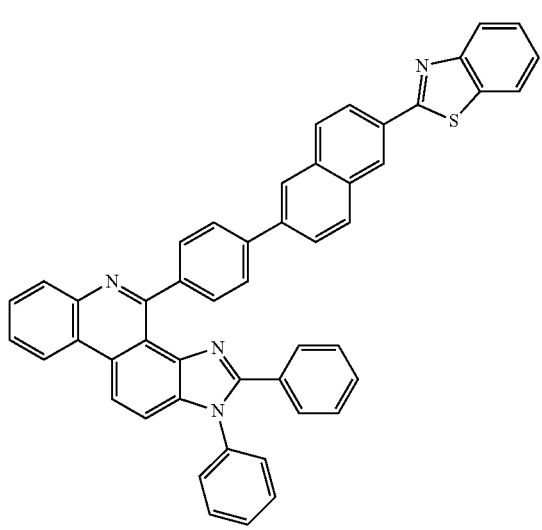
106
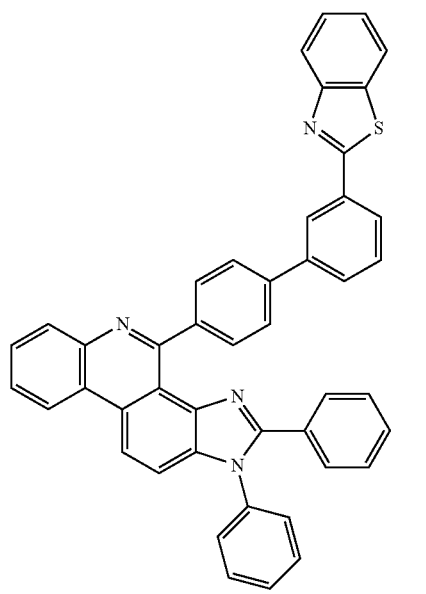
107
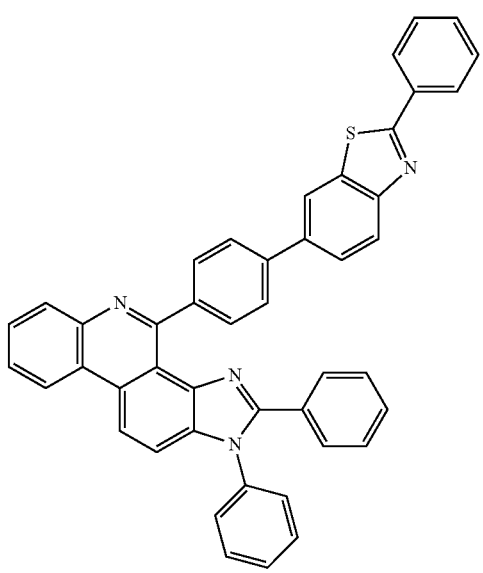
-continued
108
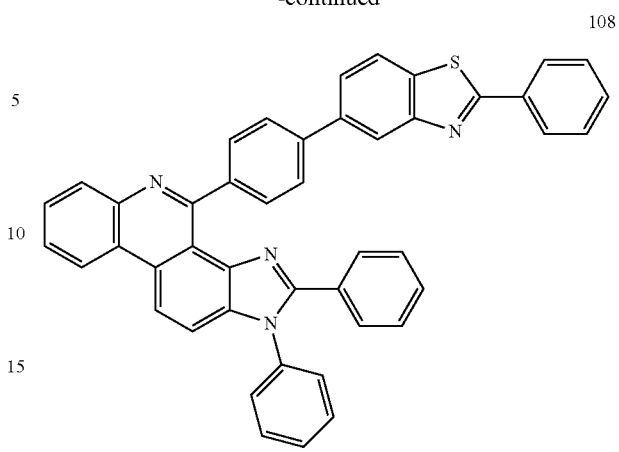
109
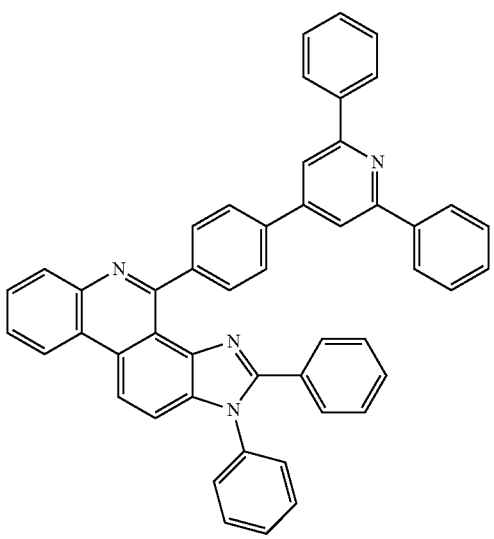
110
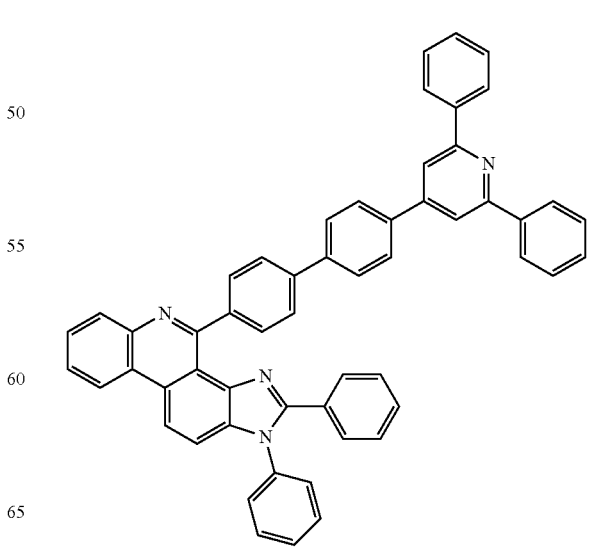

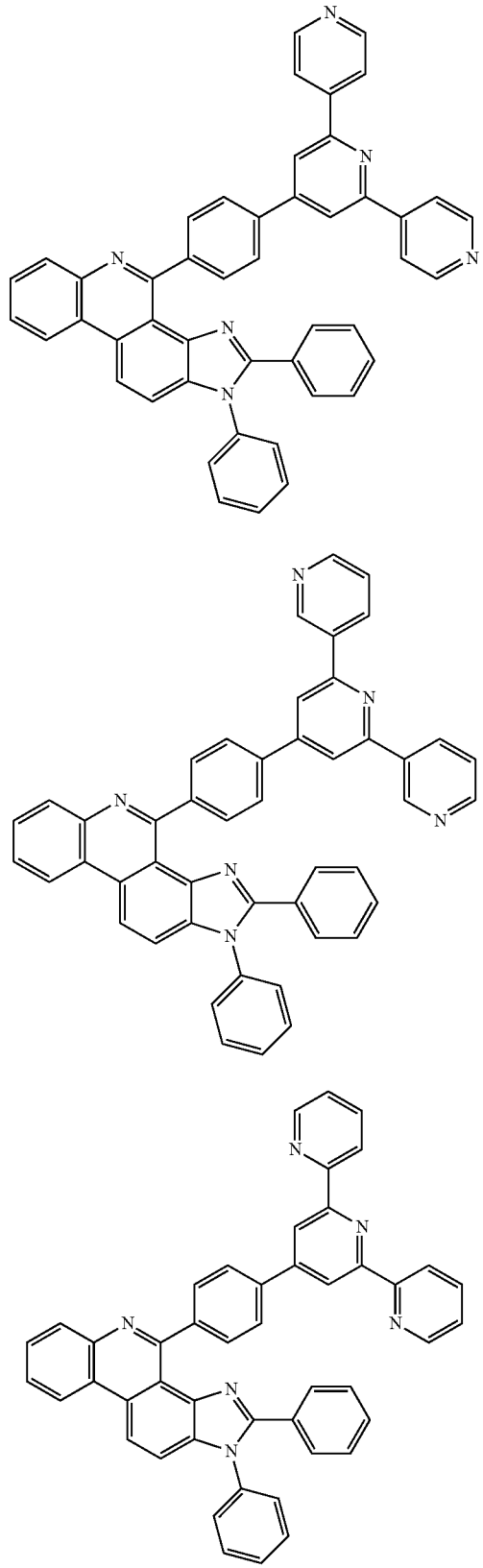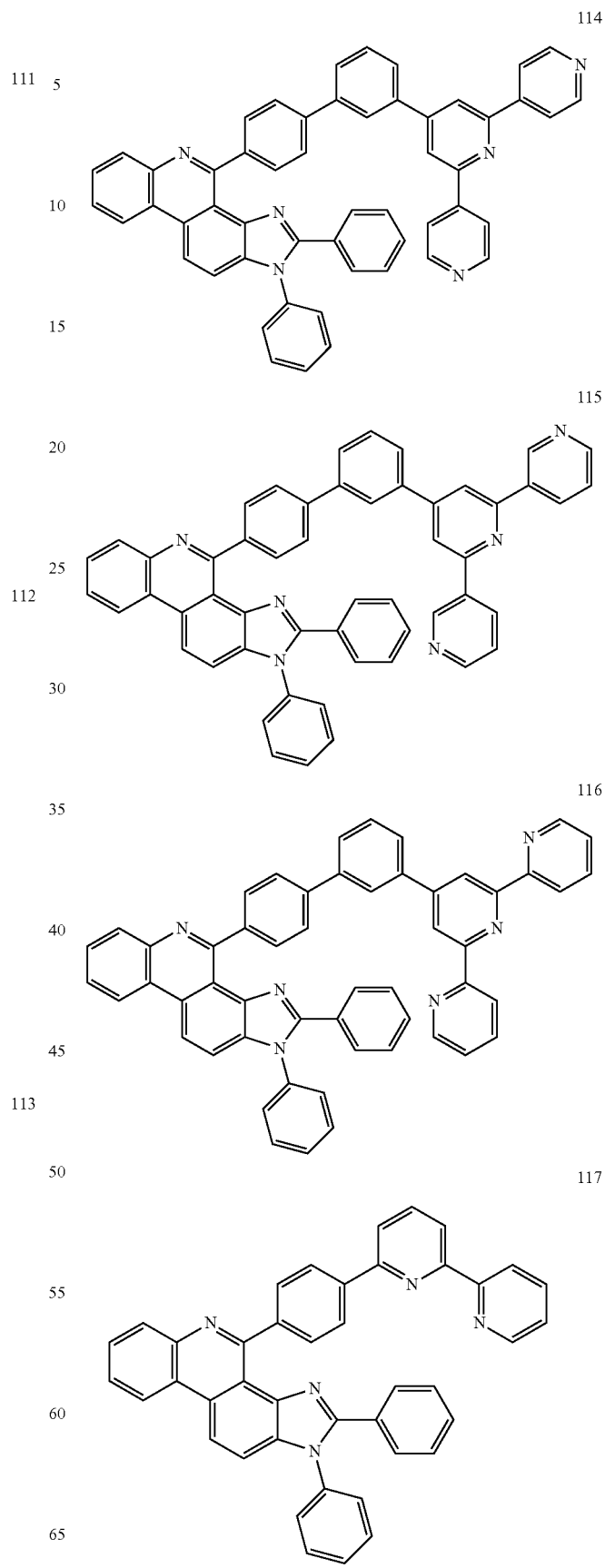

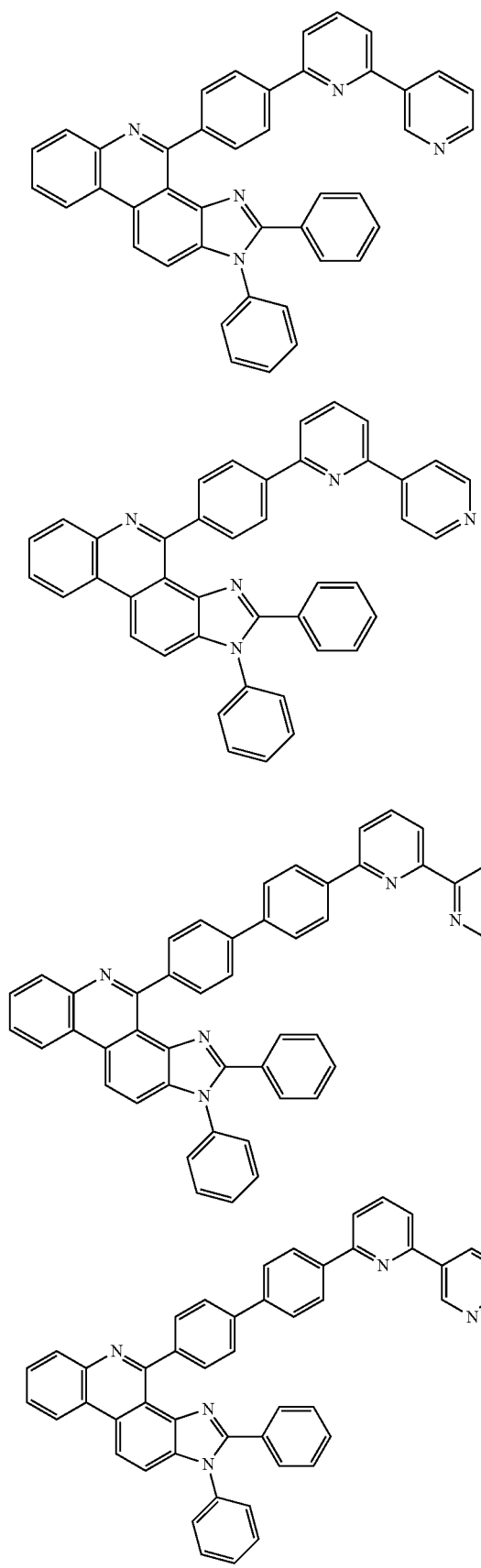
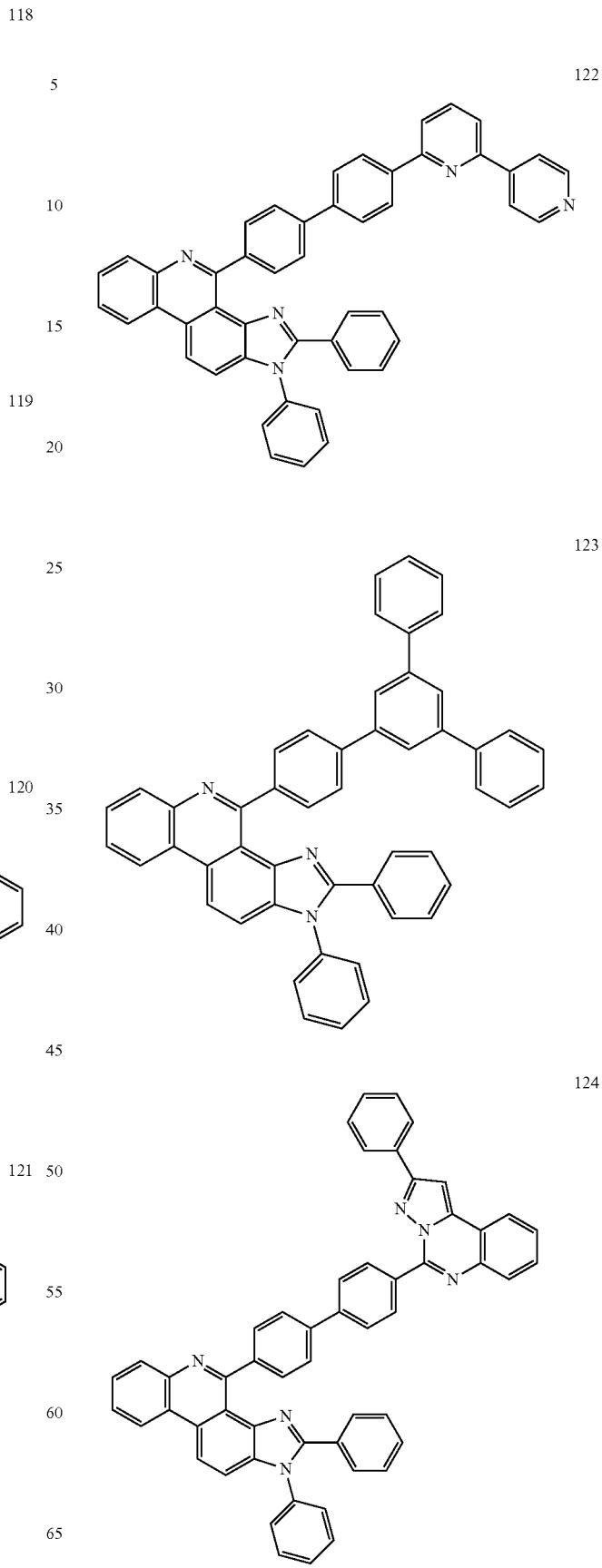

125
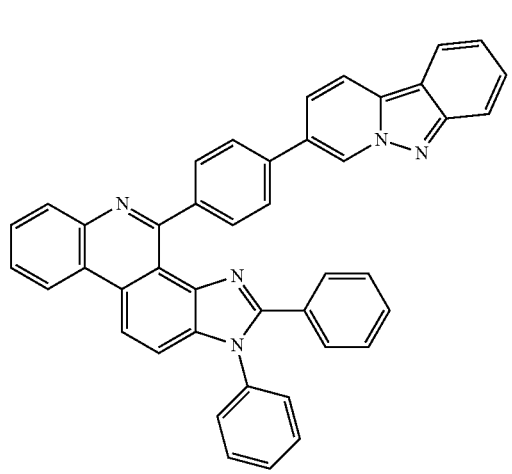
126
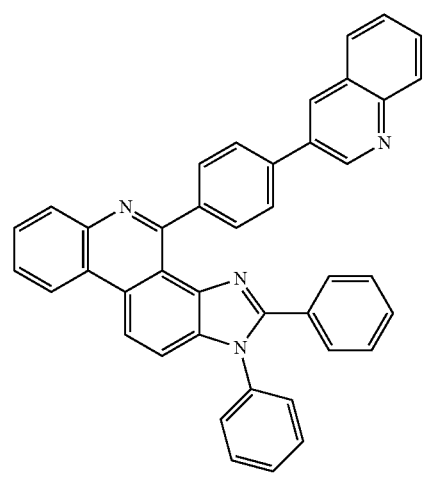
127
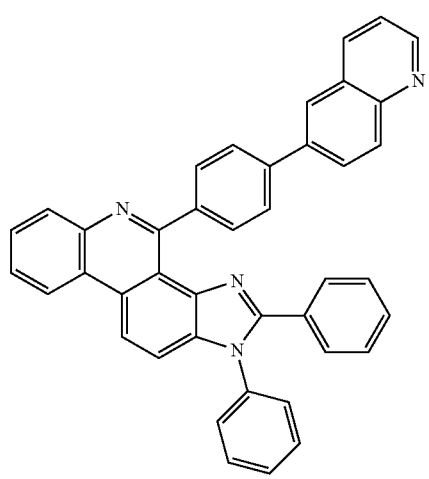
128
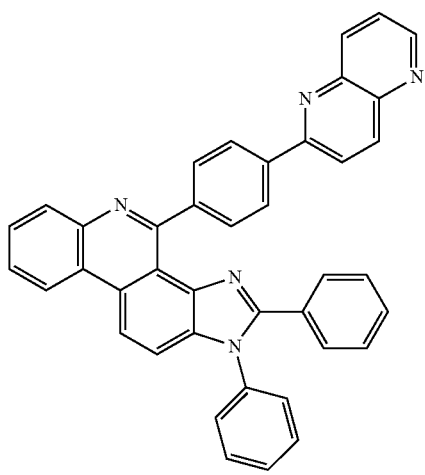
129
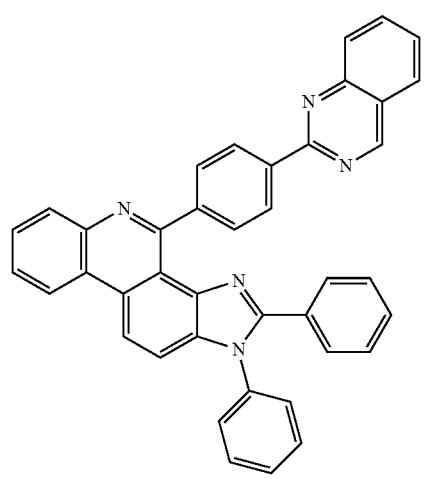
130
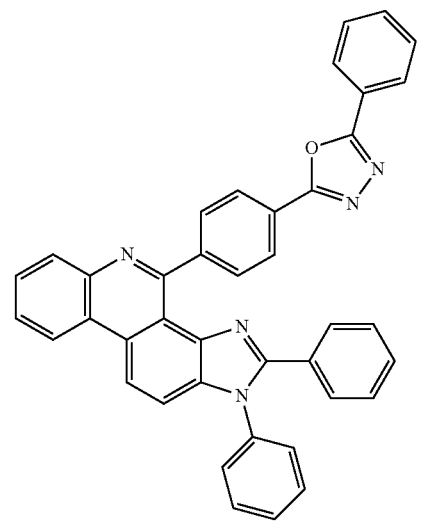

193
-continued
131
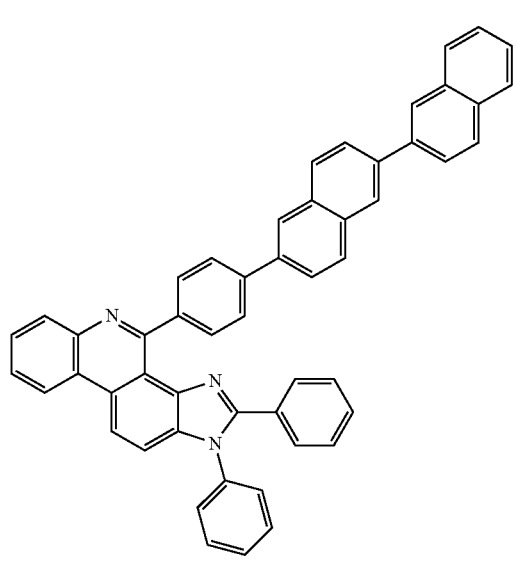
132
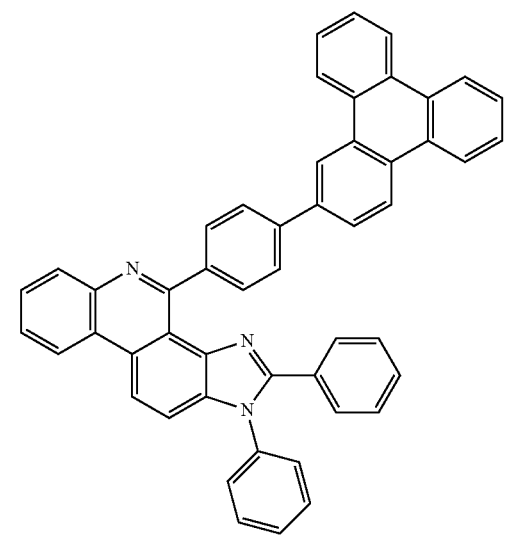
133
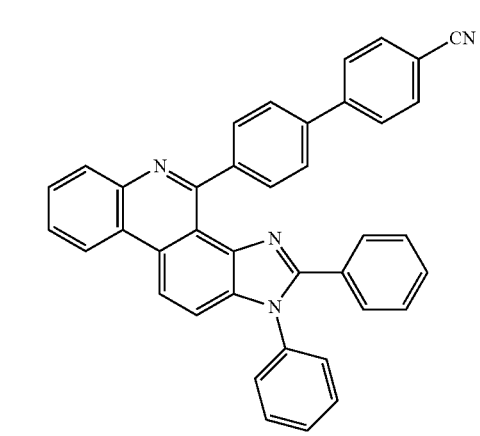
194
-continued
134
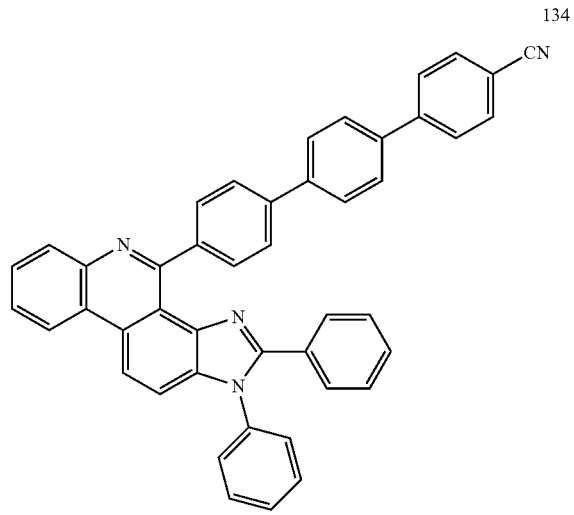
135
136
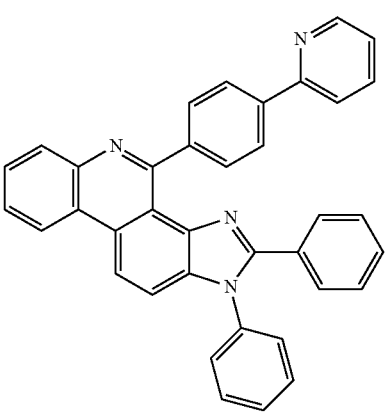

-continued
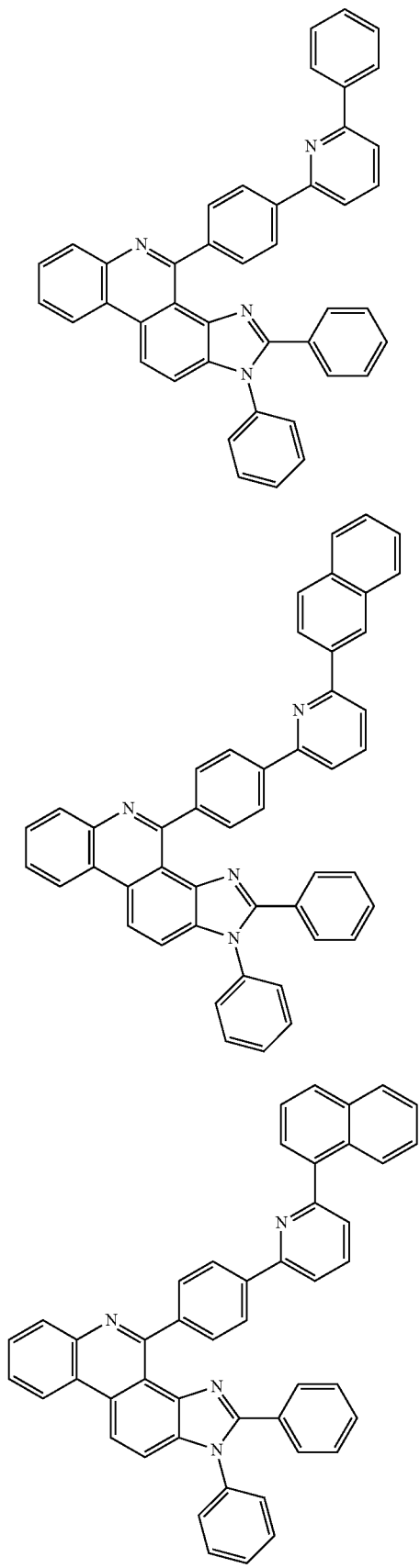
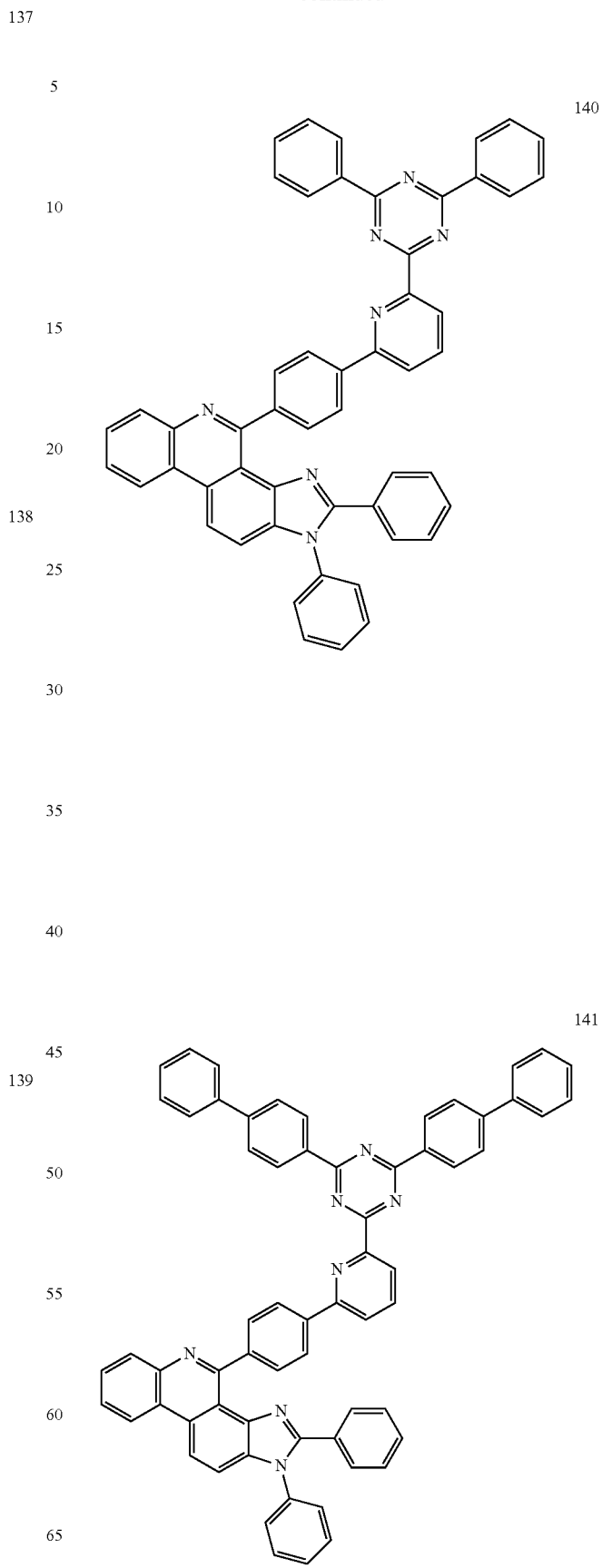

197
-continued
142
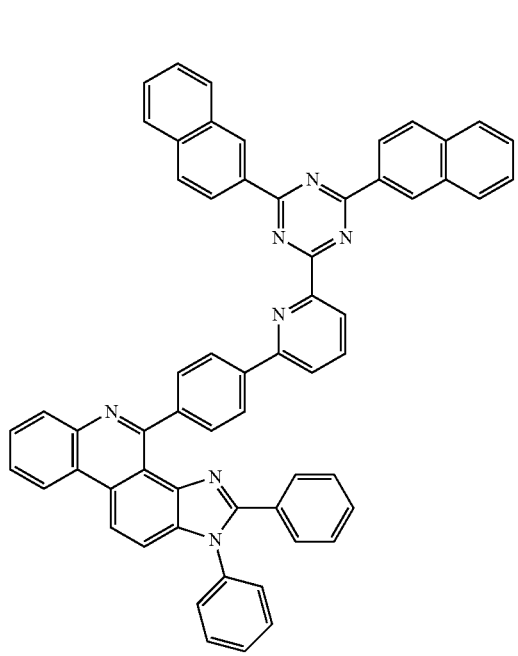
143
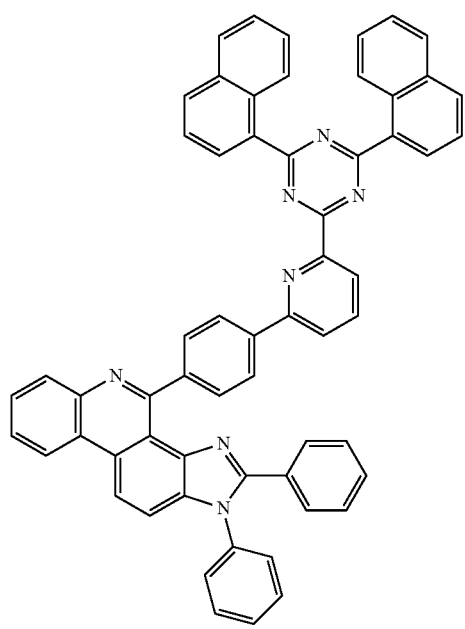
198
-continued
144
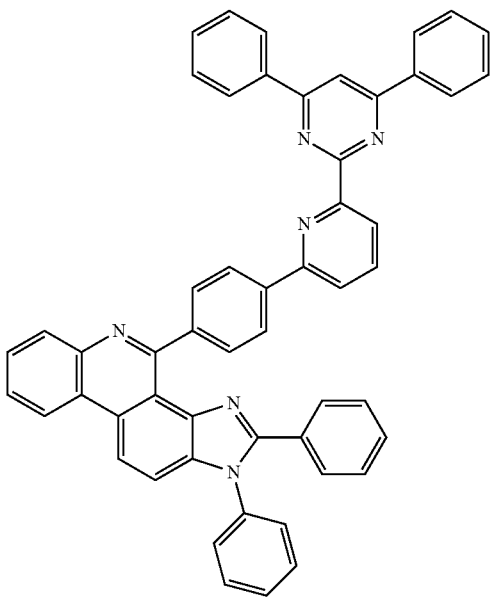
145
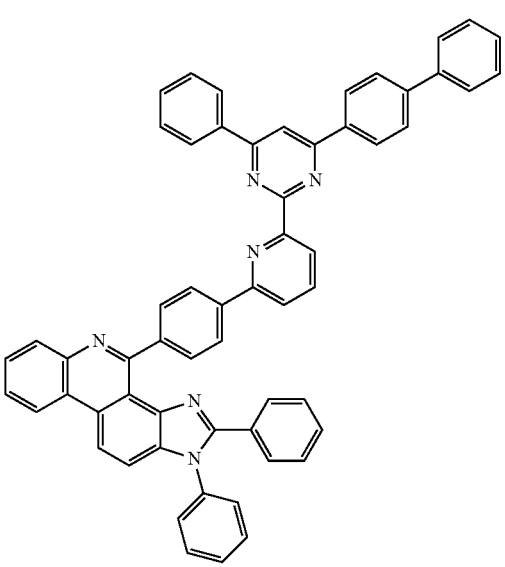

199
-continued
146
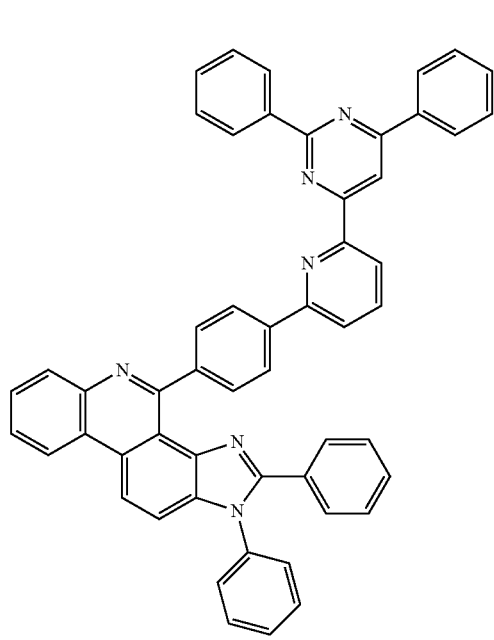
147
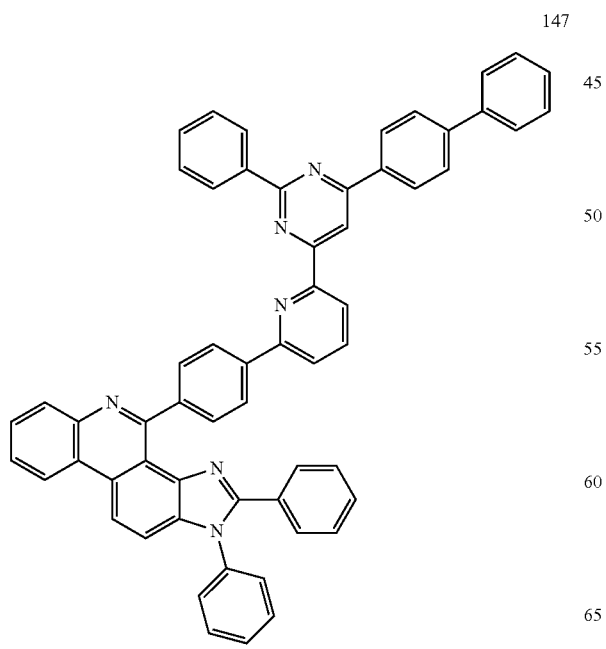
200
-continued
148
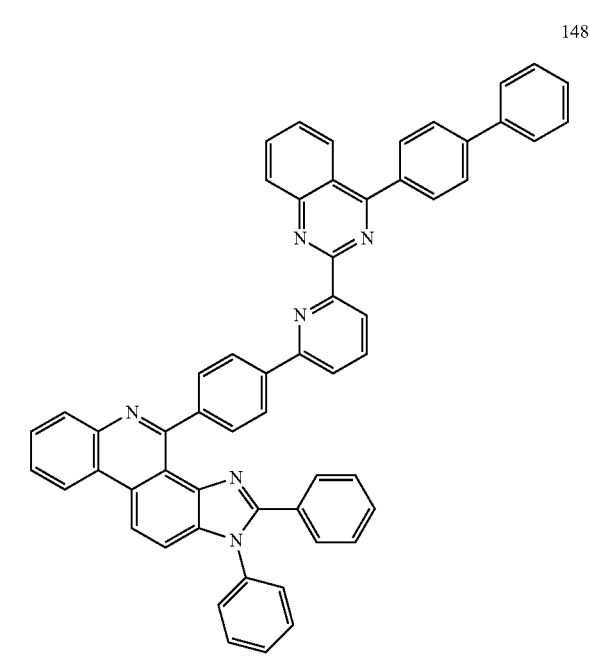
149
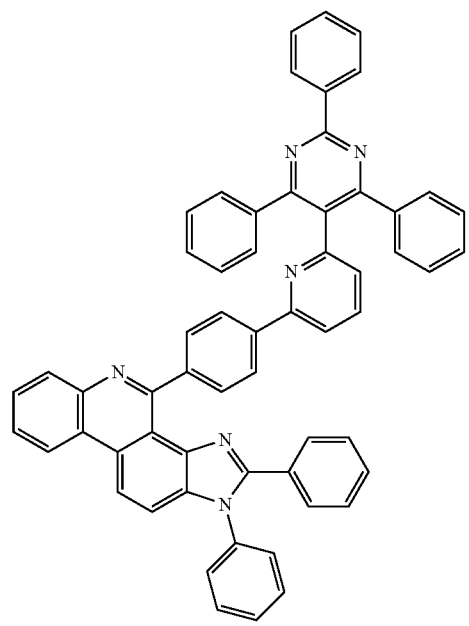

201
-continued
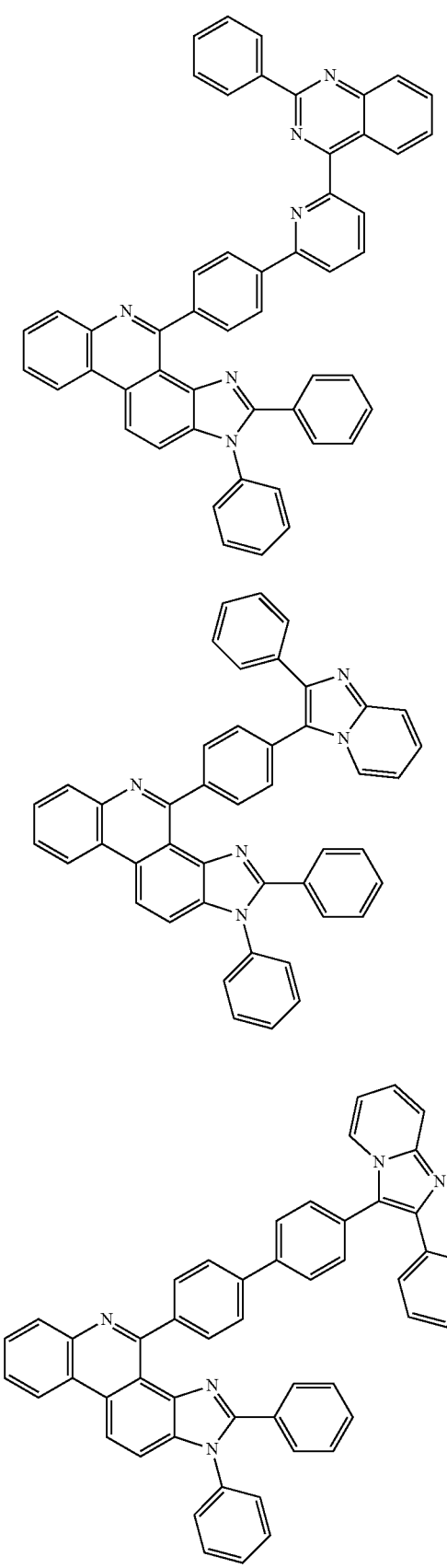
202
-continued
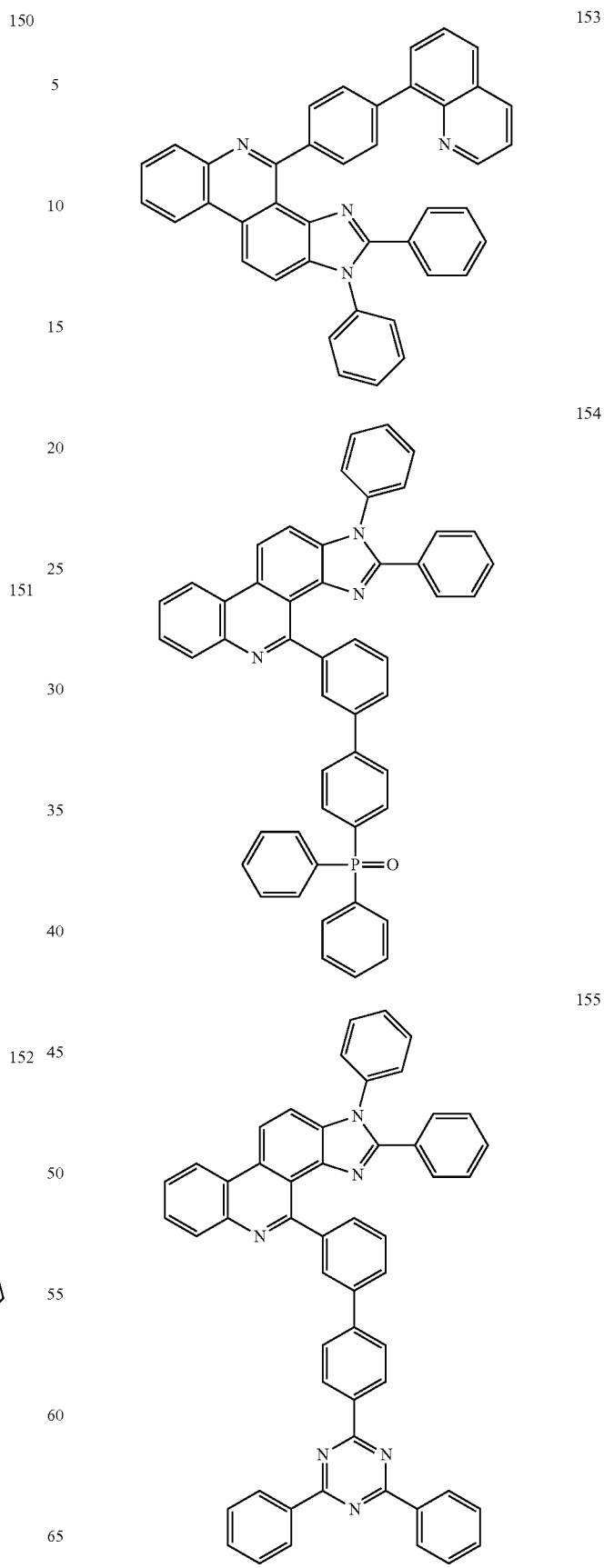

-continued
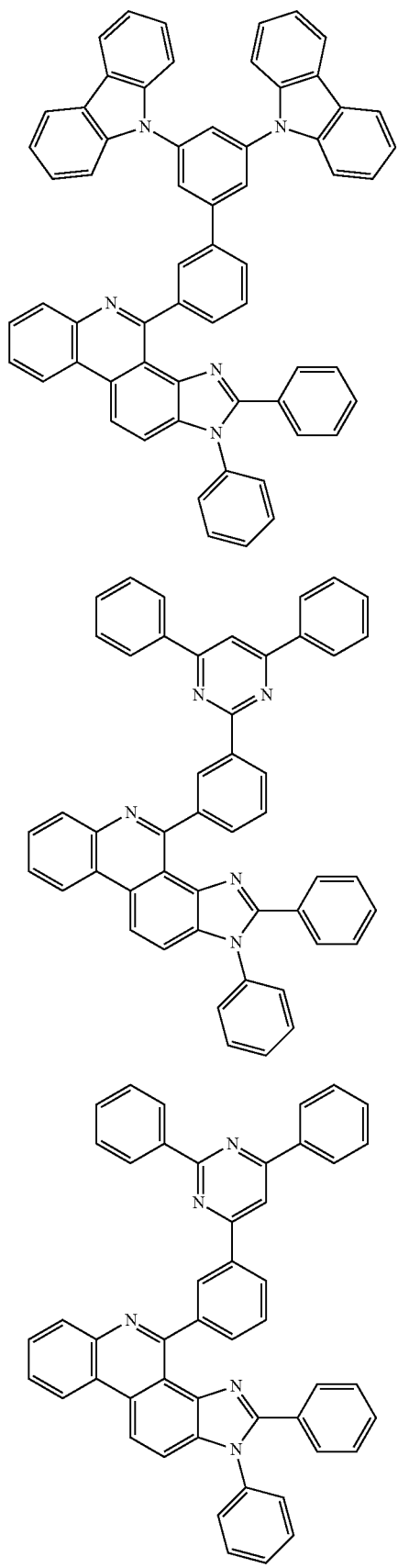
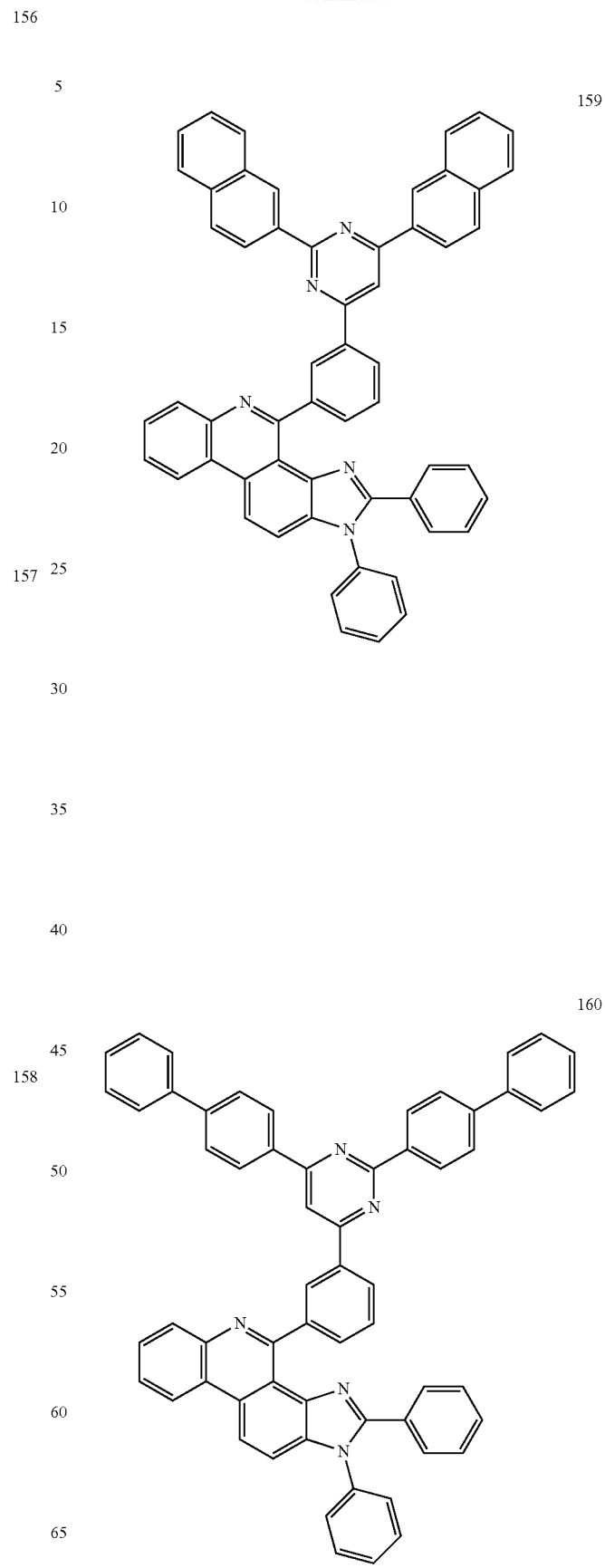

205
-continued
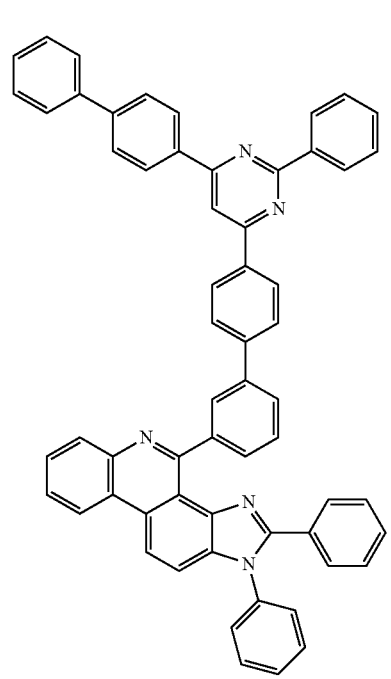
161
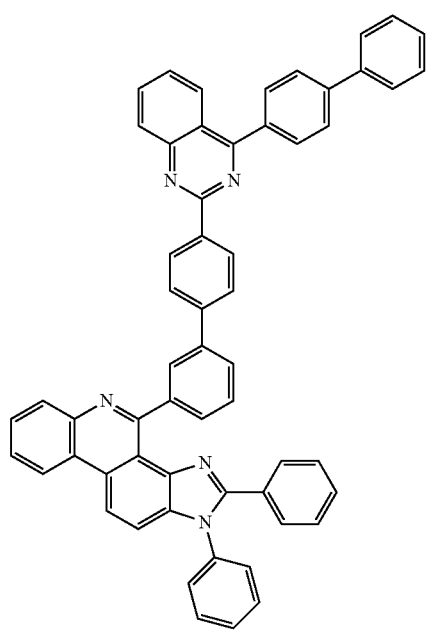
162
206
-continued
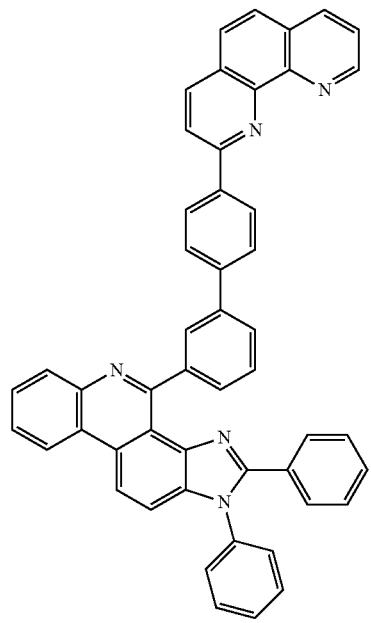
163
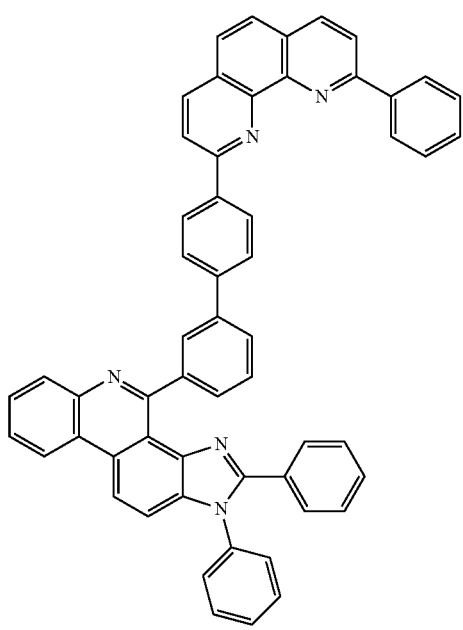
164

165

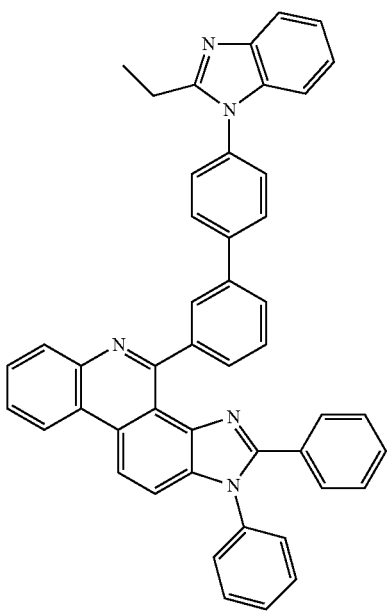

166

167

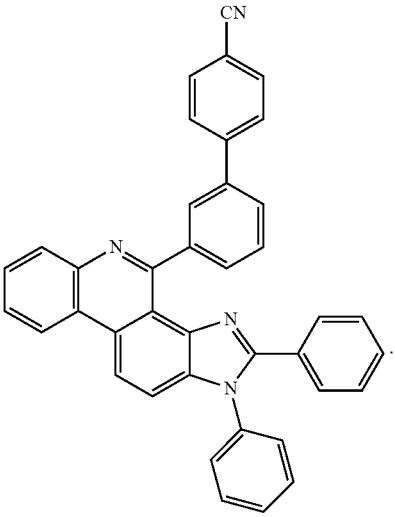

7. An organic light emitting device comprising:
an anode;
a cathode; and
one or more organic material layers provided between the anode and the cathode,
wherein one or more layers of the organic material layers comprise the hetero-cyclic compound of claim 1.

8. The organic light emitting device of claim 7, wherein the organic material layer comprises at least one of a hole blocking layer, an electron injection layer and an electron transfer layer, and at least one of the hole blocking layer, the electron injection layer and the electron transfer layer comprises the hetero-cyclic compound.

9. The organic light emitting device of claim 7, wherein the organic material layer comprises a light emitting layer, and the light emitting layer comprises the hetero-cyclic compound.

10. The organic light emitting device of claim 7, wherein the organic material layer comprises at least one of a hole injection layer, a hole transfer layer, and a layer carrying out hole injection and hole transfer at the same time, and at least one of the hole injection layer, the hole transfer layer, and the layer carrying out hole injection and hole transfer at the same time comprises the hetero-cyclic compound.

11. The organic light emitting device of claim 7, wherein the organic material layer comprises a charge generation layer, and the charge generation layer comprises the hetero-cyclic compound.

12. The organic light emitting device of claim 7 comprising:
an anode;
a first stack provided on the anode and comprising a first light emitting layer;
a charge generation layer provided on the first stack;
a second stack provided on the charge generation layer and comprising a second light emitting layer; and
a cathode provided on the second stack.

* * * * *